United States Patent
Small et al.

(10) Patent No.: US 9,334,203 B2
(45) Date of Patent: May 10, 2016

(54) OLIGOMERIZATION OF ALPHA OLEFINS USING METALLOCENE-SSA CATALYST SYSTEMS AND USE OF THE RESULTANT POLYALPHAOLEFINS TO PREPARE LUBRICANT BLENDS

(71) Applicant: Chevron Phillips Chemical Company LP, The Woodlands, TX (US)

(72) Inventors: Brooke L. Small, Kingwood, TX (US); Kenneth D. Hope, Kingwood, TX (US); Qing Yang, Bartlesville, OK (US); Albert P. Masino, Tulsa, OK (US); Max P. McDaniel, Bartlesville, OK (US); Richard M. Buck, Bartlesville, OK (US); William B. Beaulieu, Tulsa, OK (US); Eduardo J. Baralt, Kingwood, TX (US); Eric J. Netemeyer, Kingwood, TX (US); Bruce Kreischer, Kingwood, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 265 days.

(21) Appl. No.: 13/955,515

(22) Filed: Jul. 31, 2013

(65) Prior Publication Data

US 2013/0317265 A1 Nov. 28, 2013

Related U.S. Application Data

(62) Division of application No. 12/816,077, filed on Jun. 15, 2010, now Pat. No. 8,536,391.

(60) Provisional application No. 61/187,334, filed on Jun. 16, 2009.

(51) Int. Cl.
*C10M 107/00* (2006.01)
*C10M 171/00* (2006.01)
(Continued)

(52) U.S. Cl.
CPC . *C07C 2/30* (2013.01); *B01J 21/04* (2013.01); *B01J 21/12* (2013.01); *B01J 31/143* (2013.01);
(Continued)

(58) Field of Classification Search
CPC ............ C10M 107/10; C10N 2220/02; C10N 2220/021; C10N 2220/022; C10N 2220/023; C10N 2230/02
See application file for complete search history.

(56) References Cited

U.S. PATENT DOCUMENTS

| | | |
|---|---|---|
| 3,876,722 A | 4/1975 | Rossi et al. |
| 5,049,535 A | 9/1991 | Resconi et al. |

(Continued)

FOREIGN PATENT DOCUMENTS

| | | |
|---|---|---|
| EP | 1 164 146 A2 | 12/2001 |
| EP | 2196481 A1 | 6/2010 |

(Continued)

OTHER PUBLICATIONS

Qauijada, Raul et al., "Synthesis of Branched Polyethylene from Ethylene by Tandem Action of Iron and Zirconium Single Site Catalysts," Macromolecules, 34(8):2411-2417.
(Continued)

*Primary Examiner* — Pamela H Weiss
(74) *Attorney, Agent, or Firm* — Merchant & Gould P.C.

(57) ABSTRACT

This disclosure provides for alpha olefin oligomers and polyalphaolefins (or PAOs) and methods of making the alpha olefin oligomers and PAOs. This disclosure encompasses metallocene-based alpha olefin oligomerization catalyst systems, including those that include at least one metallocene and an activator comprising a solid oxide chemically-treated with an electron withdrawing anion. The alpha olefin oligomers and PAOs prepared with these catalyst systems can have a high viscosity index combined with a low pour point, making them particularly useful in lubricant compositions and as viscosity modifiers.

19 Claims, 11 Drawing Sheets

(51) Int. Cl.

| | | |
|---|---|---|
| *C10M 171/02* | (2006.01) | |
| *C07C 2/30* | (2006.01) | |
| *C08F 10/14* | (2006.01) | |
| *C10M 107/08* | (2006.01) | |
| *C10M 107/10* | (2006.01) | |
| *C10M 143/08* | (2006.01) | |
| *B01J 31/14* | (2006.01) | |
| *B01J 37/24* | (2006.01) | |
| *B01J 37/26* | (2006.01) | |
| *B01J 21/04* | (2006.01) | |
| *B01J 21/12* | (2006.01) | |
| C08F 4/659 | (2006.01) | |
| C08F 110/14 | (2006.01) | |
| B01J 27/053 | (2006.01) | |
| B01J 27/08 | (2006.01) | |

(52) U.S. Cl.
CPC *B01J 37/24* (2013.01); *B01J 37/26* (2013.01); *C08F 10/14* (2013.01); *C10M 107/08* (2013.01); *C10M 107/10* (2013.01); *C10M 143/08* (2013.01); *B01J 27/053* (2013.01); *B01J 27/08* (2013.01); *B01J 2231/20* (2013.01); *B01J 2531/48* (2013.01); *C08F 4/65912* (2013.01); *C08F 4/65916* (2013.01); *C08F 110/14* (2013.01); *C08F 2410/01* (2013.01); *C10G 2300/1088* (2013.01); *C10G 2300/302* (2013.01); *C10G 2300/304* (2013.01); *C10G 2300/703* (2013.01); *C10G 2400/22* (2013.01); *C10M 2205/026* (2013.01); *C10M 2205/028* (2013.01); *C10M 2205/0265* (2013.01); *C10M 2205/0285* (2013.01); *C10N 2220/021* (2013.01); *C10N 2220/022* (2013.01); *C10N 2220/023* (2013.01); *C10N 2220/028* (2013.01); *C10N 2220/032* (2013.01); *C10N 2230/02* (2013.01); *C10N 2230/10* (2013.01); *C10N 2230/34* (2013.01); *C10N 2230/74* (2013.01); *C10N 2270/00* (2013.01); *Y02P 20/52* (2015.11)

(56) References Cited

U.S. PATENT DOCUMENTS

| | | | |
|---|---|---|---|
| 5,177,276 A | 1/1993 | Beach et al. | |
| 5,329,031 A | 7/1994 | Miyake et al. | |
| 5,349,032 A | 9/1994 | Miyake et al. | |
| 5,416,179 A | 5/1995 | Welch et al. | |
| 5,543,373 A | 8/1996 | Winter et al. | |
| 5,741,868 A | 4/1998 | Winter et al. | |
| 5,756,609 A | 5/1998 | Cohen | |
| 5,831,106 A | 11/1998 | Langhauser et al. | |
| 5,840,947 A | 11/1998 | Kuber et al. | |
| 6,043,401 A | 3/2000 | Bagheri et al. | |
| 6,107,230 A | 8/2000 | McDaniel et al. | |
| 6,121,394 A | 9/2000 | Sugimoto et al. | |
| 6,153,549 A | 11/2000 | Hubscher et al. | |
| 6,169,051 B1 | 1/2001 | Mitani et al. | |
| 6,191,294 B1 | 2/2001 | Resconi et al. | |
| 6,239,059 B1 | 5/2001 | Saudemont et al. | |
| 6,255,417 B1 | 7/2001 | Oh et al. | |
| 6,265,339 B1 | 7/2001 | Bidell et al. | |
| 6,300,271 B1 | 10/2001 | McDaniel et al. | |
| 6,316,553 B1 | 11/2001 | McDaniel et al. | |
| 6,326,493 B1 | 12/2001 | Mitani et al. | |
| 6,365,763 B1 | 4/2002 | Winter et al. | |
| 6,376,415 B1 | 4/2002 | McDaniel et al. | |
| 6,395,666 B1 | 5/2002 | McDaniel et al. | |
| 6,395,948 B1 | 5/2002 | Hope et al. | |
| 6,423,660 B1 | 7/2002 | Albizzati et al. | |
| 6,444,604 B1 | 9/2002 | Albizzati et al. | |
| 6,444,607 B1 | 9/2002 | Gonioukh et al. | |
| 6,458,904 B1 | 10/2002 | Gonioukh et al. | |
| 6,524,987 B1 | 2/2003 | Collins et al. | |
| 6,524,988 B2 | 2/2003 | Speca | |
| 6,548,723 B2 | 4/2003 | Bagheri et al. | |
| 6,632,901 B2 | 10/2003 | McCullough | |
| 6,706,828 B2 | 3/2004 | DiMaio | |
| 6,720,396 B2 | 4/2004 | Bell et al. | |
| 6,750,302 B1 | 6/2004 | McDaniel et al. | |
| 6,774,194 B2 | 8/2004 | Albizzati et al. | |
| 6,831,141 B2 | 12/2004 | McDaniel et al. | |
| 6,858,767 B1 | 2/2005 | DiMaio et al. | |
| 6,878,785 B2 | 4/2005 | McDaniel et al. | |
| 6,936,667 B2 | 8/2005 | Jensen et al. | |
| 6,992,032 B2 | 1/2006 | McDaniel et al. | |
| 6,995,279 B2 | 2/2006 | Ushioda et al. | |
| 7,026,494 B1 | 4/2006 | Yang et al. | |
| 7,041,617 B2 | 5/2006 | Jensen et al. | |
| 7,109,277 B2 | 9/2006 | Hawley et al. | |
| 7,129,197 B2 * | 10/2006 | Song et al. | 508/591 |
| 7,129,306 B2 | 10/2006 | DiMaio | |
| 7,132,382 B2 | 11/2006 | McCullough | |
| 7,148,298 B2 | 12/2006 | Jensen et al. | |
| 7,163,906 B2 | 1/2007 | McDaniel et al. | |
| 7,199,073 B2 | 4/2007 | Martin et al. | |
| 7,226,886 B2 | 6/2007 | Jayaratne et al. | |
| 7,271,277 B2 | 9/2007 | Park et al. | |
| 7,285,513 B2 | 10/2007 | Kratzer et al. | |
| 7,294,599 B2 | 11/2007 | Jensen et al. | |
| 7,312,283 B2 | 12/2007 | Martin et al. | |
| 7,439,378 B2 | 10/2008 | Park et al. | |
| 7,468,451 B2 | 12/2008 | Guidotti et al. | |
| 7,470,758 B2 | 12/2008 | Jensen et al. | |
| 7,501,372 B2 | 3/2009 | Thorn et al. | |
| 7,517,939 B2 | 4/2009 | Yang et al. | |
| 7,527,686 B2 | 5/2009 | Yang et al. | |
| 7,547,811 B2 | 6/2009 | Kramer et al. | |
| 7,576,163 B2 | 8/2009 | Yang et al. | |
| 7,601,665 B2 | 10/2009 | McDaniel et al. | |
| 7,619,047 B2 | 11/2009 | Yang et al. | |
| 7,629,284 B2 | 12/2009 | Jensen et al. | |
| 7,652,160 B2 | 1/2010 | Yang et al. | |
| 7,828,957 B2 | 11/2010 | Yang et al. | |
| 8,143,467 B2 | 3/2012 | Patil et al. | |
| 8,536,391 B2 | 9/2013 | Small et al. | |
| 2003/0109377 A1 | 6/2003 | Chan et al. | |
| 2003/0130447 A1 | 7/2003 | Welch et al. | |
| 2003/0162651 A1 | 8/2003 | Collins et al. | |
| 2005/0137367 A1 * | 6/2005 | Kuchta et al. | 526/134 |
| 2005/0159300 A1 | 7/2005 | Jensen et al. | |
| 2005/0203261 A1 | 9/2005 | Sukhadia et al. | |
| 2006/0025299 A1 | 2/2006 | Miller et al. | |
| 2007/0043248 A1 | 2/2007 | Wu et al. | |
| 2007/0105711 A1 | 5/2007 | Goto et al. | |
| 2007/0225533 A1 | 9/2007 | Kramer et al. | |
| 2008/0242812 A1 | 10/2008 | Ruchatz et al. | |
| 2008/0281063 A9 | 11/2008 | Sukhadia et al. | |
| 2009/0042720 A1 | 2/2009 | Prades et al. | |
| 2009/0054713 A1 | 2/2009 | Matkovsky et al. | |
| 2009/0093657 A1 | 4/2009 | Buchanan et al. | |
| 2009/0281360 A1 * | 11/2009 | Knowles et al. | 585/12 |
| 2010/0292424 A1 * | 11/2010 | Wu et al. | 526/170 |
| 2010/0317904 A1 | 12/2010 | Small et al. | |
| 2011/0082323 A1 | 4/2011 | Small et al. | |

FOREIGN PATENT DOCUMENTS

| | | |
|---|---|---|
| JP | 2003/147009 A | 5/2003 |
| RU | 2287552 C2 | 11/2006 |
| WO | WO 89/12662 | 12/1989 |
| WO | WO 01/44317 A1 | 6/2001 |
| WO | WO 03/070670 A1 | 8/2003 |
| WO | WO 2006/052232 A1 | 5/2006 |
| WO | WO 2007/011459 | 1/2007 |
| WO | WO 2007011832 A1 * | 1/2007 |
| WO | WO 2007/111776 A1 | 10/2007 |
| WO | WO 2007/127465 A2 | 11/2007 |
| WO | WO 2008/010865 A2 | 1/2008 |
| WO | WO 2008/143802 A1 | 11/2008 |

(56) References Cited

FOREIGN PATENT DOCUMENTS

| WO | WO 2009/045300 A2 | 4/2009 |
| WO | WO 2009/045301 A2 | 4/2009 |
| WO | WO 2010/074233 A1 | 7/2010 |

OTHER PUBLICATIONS

Eisenhardt, A., et al., "A Water-Stable Constrained Geometry Catalysts for the Polymerization of Ethylene," Catalysis Communications, 5(11):653-657.

International Search Report and Written Opinion of PCT/US2010/051509, mailed Mar. 28, 2011, European Patent Office, 18 pages.
International Search Report dated Sep. 7, 2010 and Written Opinion for PCT/US2010/038681, International Search Authority/European Patent Office, 10 pages.
Naugalube® Apan; Material Safety Data Sheet; Version 1.5, Revision Date: Jan. 20, 2012; Print Date: Jun. 23, 2013; Chemtura Corporation; 10 pgs.

* cited by examiner

US 9,334,203 B2

OLIGOMERIZATION OF ALPHA OLEFINS USING METALLOCENE-SSA CATALYST SYSTEMS AND USE OF THE RESULTANT POLYALPHAOLEFINS TO PREPARE LUBRICANT BLENDS

CROSS REFERENCE TO RELATED APPLICATIONS

This application is a divisional application of co-pending U.S. patent application Ser. No. 12/816,077, filed Jun. 15, 2010, now U.S. Pat. No. 8,536,391, which claims priority to and the benefit of U.S. Provisional Patent Application No. 61/187,334, filed Jun. 16, 2009, the disclosures of which are hereby incorporated by reference in their entirety.

TECHNICAL FIELD OF THE INVENTION

This disclosure relates to the metallocene catalyzed oligomerization of alpha olefins to form alpha olefin oligomers and their hydrogenation to polyalphaolefins which have utility in synthetic lubricants and viscosity modifiers.

BACKGROUND OF THE INVENTION

Mono-1-olefins (alpha olefins), including ethylene, can be polymerized with catalyst systems employing titanium, zirconium, vanadium, chromium or other metals impregnated on a variety of support materials, often in the presence of activators. These catalyst systems can be useful for both the homopolymerization of ethylene and copolymerization of ethylene with comonomers such as propylene, 1-butene, 1-hexene, or higher alpha olefins. Because of the importance in this process for preparing functional materials, there exists a need and a constant search to develop new olefin polymerization catalysts, catalyst activation processes, and methods of making and using catalysts that will provide enhanced catalytic activities, selectivities, or new polymeric materials tailored to specific end uses.

One type of transition metal-based catalyst system utilizes metallocene compounds, often contacted with an activator such as methyl aluminoxane (MAO) to form an oligomerization catalyst. However, in order to achieve the desired high oligomerization activities, large amounts of expensive methyl aluminoxane typically are necessary to form the active metallocene catalysts. This feature has been an impediment to the commercialization of metallocene catalyst systems. Therefore improvements in catalyst systems and in methods of making the catalyst are needed to afford the desired oligomerization activities at reasonable commercial costs. Moreover, there remain important challenges in developing catalysts that can provide polymers or oligomers with the desired properties that can be tailored or maintained within a desired specification range.

SUMMARY OF THE INVENTION

This disclosure provides for alpha olefin oligomers, hydrogenated alpha olefin oligomers (also termed polyalphaolefins or PAOs throughout this disclosure), methods of making the alpha olefin oligomers, method of making hydrogenated alpha olefin oligomers, catalyst systems, and methods for preparing catalyst systems. In particular, this disclosure provides for alpha olefin homooligomers (or homopolymers), hydrogenated alpha olefin homooligomers, alpha olefin cooligomers (or copolymers), or hydrogenated alpha olefin cooligomers in which the alpha olefin monomers do not include ethylene. In the course of examining metallocene-based olefin polymerization catalysts, it was discovered that oligomerization of higher alpha olefins ($C_3$ and higher) could be effected using metallocenes and related catalyst components, in which the metallocenes can be employed along with an activator comprising a solid oxide chemically-treated with an electron withdrawing anion.

Alpha olefin oligomerization can be achieved by contacting an alpha olefin and a catalyst system, in which the catalyst system is a metallocene-based system. In an aspect, the catalyst system comprises a metallocene and an activator. In an aspect, the activator comprises a solid oxide chemically-treated with an electron withdrawing anion. In one aspect, the activator can be an aluminoxane (e.g. methyl aluminoxane (MAO) or modified methyl aluminoxane (MMAO)). In a further aspect, the resulting hydrogenated alpha olefin oligomers can be characterized as having a high viscosity index; alternatively, having a high viscosity index and a low pour point. Such features afford particular utility of these PAOs in lubricant compositions. Moreover, the methods disclosed herein provide for a process to adjust a viscosity or to select a desired viscosity range by regulating certain oligomerization or processing parameters. Yet another aspect of this disclosure provides for a PAO comprising monomer units derived from alpha olefins in which the alpha olefin monomers do not substantially include 1-decene. It has been discovered that the PAO comprising monomer units derived from alpha olefins which do not substantially include 1-decene do not have to be blended with a PAO comprising monomer units based upon 1-decene to afford PAOs having a high viscosity index and a low pour point. The first-pass economic advantages of this process for providing lubricant compositions are apparent.

According to an aspect of this disclosure, there is provided an oligomerization method, the method comprising:
a) contacting an alpha olefin monomer and a catalyst system, the catalyst system comprising at least one metallocene and a chemically-treated solid oxide; and
b) forming an oligomer product under oligomerization conditions.

According to one aspect of this disclosure, there is provided an oligomerization method, the method comprising:
a) contacting an alpha olefin monomer and a catalyst system, the catalyst system comprising
1) at least one metallocene;
2) at least one first activator comprising a chemically-treated solid oxide; and
3) at least one second activator; and
b) forming an oligomer product under oligomerization conditions.

In an embodiment, the chemically-treated solid oxide can be a fluorided silica-alumina. In an embodiment, the second activator can comprise organoaluminum compound. Further, the alpha olefin monomer and catalyst system can be contacted by the steps of simultaneously contacting the alpha olefin monomer, the metallocene, the first activator, and the second activator. Alternatively, the alpha olefin monomer and catalyst system can be contacted in any order, without limitation.

In one aspect, this disclosure provides for a polyalphaolefin having a 100° C. kinematic viscosity from 20 cSt to 1,200 cSt. In another aspect, this disclosure provides for a polyalphaolefin having a pour point less than −20° C. In some embodiments, this disclosure provides for a polyalphaolefin having a 100° C. kinematic viscosity from 20 cSt to 270 cSt and a pour point less than −30° C. Other useful properties such as Mw molecular weight, Mn molecular weight, polydispersity index, shear stability, crystallization properties, tacticity, and Bernoulli index (B) are described. In an aspect, the PAOs disclosed herein can comprise primarily head-to-tail oligomers. In an embodiment, the PAO disclosed herein can comprise head-to-tail oligomers in which there are less than 100 errors per 1000 alpha olefin monomers.

In an aspect, the alpha olefin monomer can comprise, singly or in any combination, a $C_3$ to $C_{70}$ normal alpha olefin; alternatively, a $C_4$ to $C_{20}$ normal alpha olefins. In an embodiment, the alpha olefin monomer can comprise 1-hexene, 1-octene, 1-decene, 1-dodecene, 1-tetradecene, or any combination thereof.

A lubricant composition comprising a polyalphaolefin composition prepared according to this disclosure is also provided. The lubricant composition can consist essentially of the PAO composition with or without additives, such as metal deactivators, detergents, dispersants, antioxidants, and the like.

This disclosure further provides for a method of producing a polyalphaolefin, the method comprising: a) contacting an alpha olefin monomer and a catalyst system comprising a metallocene; and b) forming an oligomer product under oligomerization conditions. The method of producing the polyalphaolefin can further comprise separating a reactor effluent to produce a heavy oligomer product and hydrogenating the heavy oligomer product to produce the polyalphaolefin. The catalyst system can further include an activator or a combination of activators; alternatively, the catalyst system can be substantially devoid of an activator. In some embodiments, the catalyst system can further comprise an activator. In some embodiments, the activator can be an alumoxane (for example methyl alumoxane or a modified methyl alumoxane), a trialkylaluminum compound, an alkylaluminum hydride compound, an alkylaluminum halide compound, an organozinc compound, an organomagnesium compound, an organolithium compound, an organoboron compound, an ionizing ionic compound, a borate compound, or an aluminate compound, or any combination thereof.

In one aspect, the activator can comprise a solid oxide chemically-treated with an electron withdrawing anion. In some embodiments, the solid oxide chemically-treated with an electron withdrawing anion can include fluorided alumina, chlorided alumina, sulfated alumina, fluorided silica-alumina, chlorided silica-alumina, fluorided silica-zirconia, or combinations thereof. Therefore, this disclosure encompasses a method of producing a polyalphaolefin, comprising:
   a) contacting an alpha olefin and a catalyst system comprising:
     a metallocene; and
     an activator comprising a solid oxide chemically-treated with an electron withdrawing anion; and
   b) forming an oligomer product under oligomerization conditions.

When a solid oxide chemically-treated with an electron withdrawing anion is employed as an activator, it can be used alone or in combination with additional activators. Examples of activators that can be used in combination with a chemically-treated solid oxide include, but are not limited to, an alumoxane (e.g. methyl alumoxane or a modified methyl alumoxane), a trialkylaluminum compound, an alkylaluminum hydride compound, an alkylaluminum halide compound, an organozinc compound, an organomagnesium compound, an organolithium compound, an organoboron compound, an ionizing ionic compound, a borate compound, or an aluminate compound, or any combination thereof.

A further aspect of this disclosure provides a method of producing an oligomer product, which can be further processed to a polyalphaolefin, in which any combination of alpha olefin monomer, metallocene, solid oxide, electron withdrawing anion, or any other any activator can be precontacted prior to their use in the catalytic process. In this aspect, any precontacting step or steps can be carried out for any length of time prior to the step of contacting the alpha olefin to be oligomerized and the catalyst system to initiate the alpha olefin oligomerization.

A wide range of metallocene compounds are suitable for use in the methods disclosed herein. The term "metallocene" is defined herein and is generally intended to include compounds that contain at least one pi-bonded $\eta^{x=5}$ ligand. Generally, the pi-bonded $\eta^{x=5}$ ligand can be a $\eta^5$-cyclopentadienyl, $\eta^5$-indenyl, $\eta^5$-fluorenyl, $\eta^5$-alkadienyl-, or $\eta^6$-boratabenzene-ligands. Pi-bonded $\eta^{x=5}$ ligands are also referred to as Group I ligands in this disclosure. Therefore, compounds that include only a single pi-bonded $\eta^{x=5}$ ligand are encompassed by the term "metallocene" as used in this disclosure. In an aspect, the metal of the metallocenes can comprise a Group 4, 5, or 6 metal. Suitable metallocenes can comprise a metal selected from titanium, zirconium, hafnium, vanadium, niobium, tantalum, chromium, molybdenum, or tungsten. Any substituent or substituents on the pi-bonded $\eta^{x=5}$ ligand that does not completely eliminate the activity of the resulting catalyst system is encompassed by this disclosure. Metallocenes of this disclosure can also contain Group II ligands that are exclusive of pi-bonded $\eta^{x=5}$ ligands. The non pi-bonded $\eta^{x=5}$ ligands can include formally monoanionic ligands that occupy a single coordinate site on the metal. These monoanionic ligands can include halides, hydrides, hydrocarbyl ligands, hydrocarboxy ligands, and aminyl ligands.

Suitable metallocenes include those that comprise multiple ligands. In some embodiments, the ligands of a metallocene containing multiple ligands can be unbridged; alternatively, the ligands of a metallocene containing multiple ligands can be connected by a linking group. For example, suitable metallocene compounds for use in the catalyst systems include metallocenes in which the metallocene contains two Group I ligands (pi-bonded $\eta^{x=5}$ ligands) that are connected by a linking group. Other suitable metallocenes include those in which a Group I ligand (pi-bonded $\eta^{x=5}$ ligand) can be connected by a linking group to a Group II ligand.

This disclosure also provides new catalyst systems for preparing an oligomer product (which can be further processed into polyalphaolefins), new methods for preparing catalyst systems, and methods for oligomerizing alpha olefins that result in improved productivity, without the need for using large excess concentrations of expensive activators such as methylaluminoxanes or modified methylaluminoxanes.

Additionally, this disclosure encompasses a process comprising contacting at least one monomer and the postcontacted catalyst system under oligomerization conditions to produce the oligomer. Thus, this disclosure provides methods for oligomerizing olefins using the catalyst systems prepared as described herein.

These and other embodiments and aspects of the alpha olefin oligomers and of the oligomerization process are described more fully in the Detailed Description and claims and further disclosure provided herein.

BRIEF DESCRIPTION OF THE FIGURES

FIG. 4 plots the dynamic viscosity (cP) versus temperature (° C.) of a series of hydrogenated oligomers produced using different metallocene oligomerization catalyst systems and a commercially available polyalphaolefins having a kinematic viscosity of 40 cSt at 100° C. Sample identification: A, hydrogenated 1-decene oligomers having a 100° C. kinematic viscosity of 41 cSt prepared using metallocene J (Example 8—Run 5); B, hydrogenated 1-octene oligomers having a 100° C. kinematic viscosity of 43.8 cSt prepared using metallocene N (Example 8—Run 6); C, hydrogenated 1-octene oligomers having a 100° C. kinematic viscosity of 37 cSt prepared using metallocene L (Example 8—Run 7); D, commercially available PAO 40; E, Blend B-2, blend of hydrogenated 1-octene oligomers having a 100° C. kinematic viscosity of 38.8 cSt. Refer to Tables 6 and 7 for sample preparation and properties.

FIG. 5 plots the dynamic viscosity (cP) versus temperature (° C.) of a series of hydrogenated oligomers produced using different metallocene oligomerization catalyst systems and commercially available polyalphaolefin having a kinematic viscosity of 100 cSt at 100° C. Sample identification: A, hydrogenated 1-octene oligomers having a 100° C. kinematic viscosity of 118 cSt prepared using metallocene J (Example 8—Run 10); B, hydrogenated 1-decene oligomers having a 100° C. kinematic viscosity of 100.5 cSt prepared using metallocene J (Example 8—Run 11); C, hydrogenated 1-octene oligomers having a 112.7° C. kinematic viscosity of 43.8 cSt prepared using metallocene B (Example 8—Run 12); D, commercially available PAO 100. Refer to Tables 6 and 7 for sample preparation and properties.

DETAILED DESCRIPTION OF THE INVENTION

General Description

Figure 1:
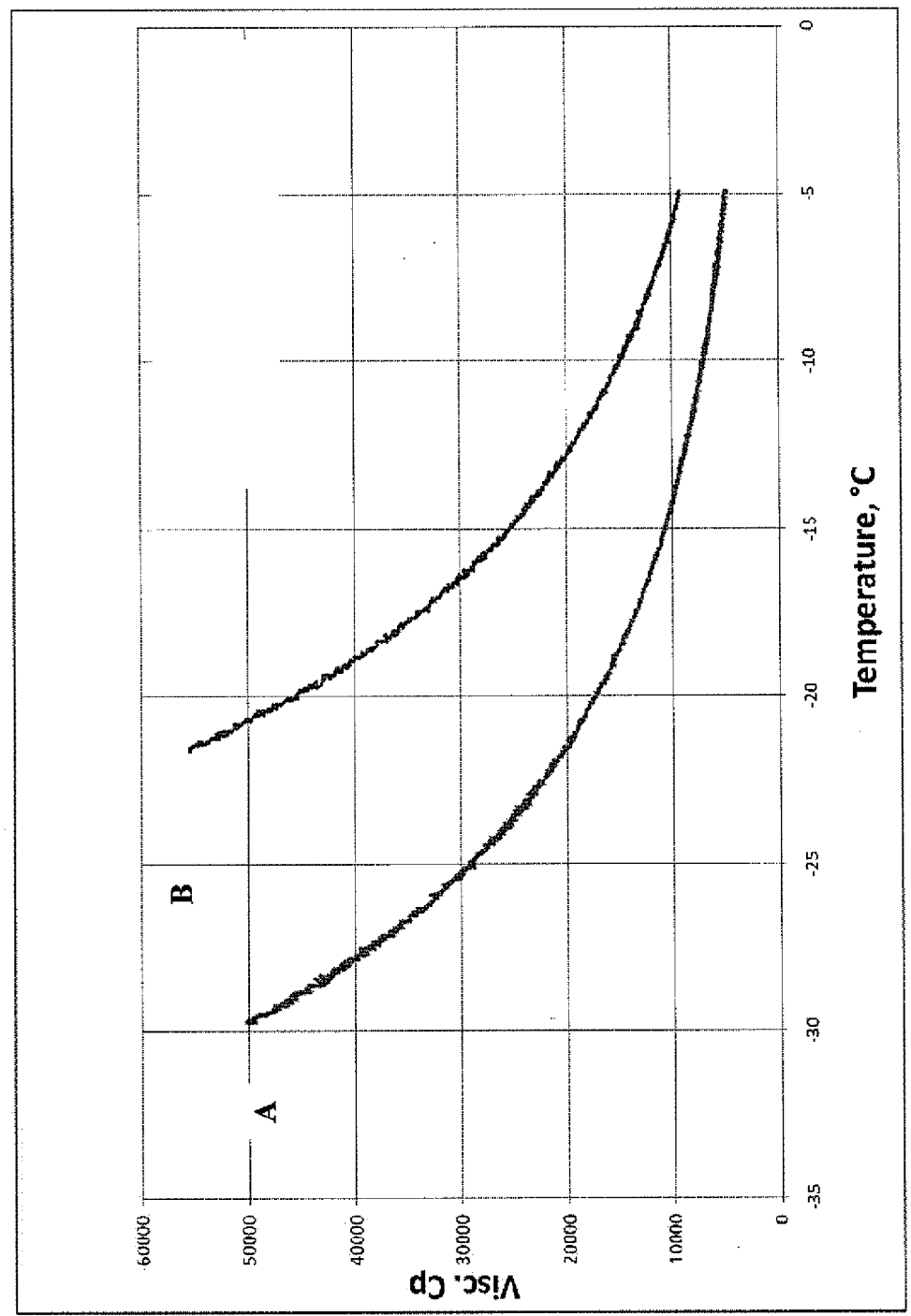
FIG. 1 provides a plot of the scanning Brookfield dynamic viscosity (cP) versus temperature (° C.) of a polyalphaolefin blend of hydrogenated 1-octene oligomers according to this disclosure, having a 100° C. kinematic viscosity of 38.8 cSt, compared to a commercially available PAO produced from 1-decene having nearly the same kinematic viscosity (PAO 40). Sample identification: A, Blend B-2, blend of hydrogenated 1-octene oligomers having a 100° C. kinematic viscosity of 38.8 cSt; B, commercially available PAO 40. Refer to Tables 6 and 7 for sample preparation and properties.

This disclosure provides for oligomers derived from alpha olefin (also referred to as alpha olefin oligomers), hydrogenated oligomer (also described throughout as polyalphaolefins or PAOs), methods of making the alpha olefin oligomers, methods for making PAOs, catalyst systems, and methods making catalyst systems. In particular, this disclosure encompasses oligomerizing one or more alpha olefins using a catalyst system that comprises a metallocene. The catalyst system can further comprise one or more activators. One type of activator that can be particularly useful is a solid oxide that has been chemically-treated with an electron withdrawing anion, which is fully described herein. The solid oxide that has been chemically-treated with an electron withdrawing anion can also be referred to throughout this disclosure as a chemically treated solid oxide (CTSO), a solid super acid (SSA), or an activator-support, and these terms are used interchangeably. Other activators can be used with the metallocenes in the catalyst system, either alone, in combination with the SSA, or in any combination with at least one other activator. Thus, by way of example, the catalyst system can comprise at least one metallocene, a first activator, and a second activator. In an aspect, the first activator can comprise, consist essentially of, or consist of, a chemically-treated solid oxide and the second activator can comprise, consist essentially of, or consist of, an organoaluminum compound. In a non-limiting embodiment, the chemically-treated solid oxide can be fluorided silica-alumina, and the second activator can be a trialkylaluminum compound (e.g. triethyl aluminum and/or triisobutyl aluminum).

These metallocene-based alpha olefin oligomerizations provide olefin oligomers and ultimately polyalphaolefins with particularly useful properties. The metallocene-based alpha olefin oligomerizations allow for variability in the properties of the oligomers and PAOs on the basis of the catalyst system and/or oligomerization conditions, among other factors described herein. For example, certain properties of the 1-octene homooligomers prepared according to this disclosure, and PAOs produced by hydrogenation the homooligomers, can be selected by adjusting the temperature at which the oligomerization is carried out. Moreover, this control extends to controlling product viscosity and pour point such that high value PAOs having 100° C. kinematic viscosities of 100 cSt and/or 40 cSt can be prepared.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of, apply only to feature class to which is utilized and it is possible to have different transitional terms or phrases utilized with different features within a claim. For example a method can comprise several recited steps (and other non-recited steps) but utilize a catalyst system preparation consisting of specific steps but utilize a catalyst system comprising recited components and other non-recited components. While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a metallocene" is meant to encompass one metallocene, or mixtures or combinations of more than one metallocene unless otherwise specified.

Groups of elements of the table are indicated using the numbering scheme indicated in the version of the periodic table of elements published in *Chemical and Engineering News,* 63(5), 27, 1985. In some instances a group of elements may be indicated using a common name assigned to the group; for example alkali metals for Group 1 elements, alkaline earth metals for Group 2 elements, transition metals for Group 3-12 elements, and halogens or halides for Group 17 elements.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g. a general reference to pentane includes n-pentane, 2-methyl-butane, and 2,2-dimethylpropane. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

In one aspect, a chemical "group" can be defined or described according to how that group is formally derived from a reference or "parent" compound, for example, by the number of hydrogen atoms that are formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials having three or more hydrogens atoms, as necessary for the situation, removed from an alkane. Throughout, the disclosure that a substituent, ligand, or other chemical moiety can constitute a particular "group" implies that the well-known rules of chemical structure and bonding are followed when that group is employed as described. By way of example, if a metallocene compound having the formula (eta-5-$C_5H_5)_2Zr(CH_3)(X)$ is described, and it is disclosed that X can be an "alkyl group," an "alkylene group," or an "alkane group," the normal rules of valence and bonding are followed. When describing a group as being "derived by," "derived from," "formed by," or "formed from," such terms are used in a formal sense and are not intended to reflect any specific synthetic methods or procedure, unless specified otherwise or the context requires otherwise. The bonding nomenclature "eta-5" is also written "$\eta^5$-" throughout.

Many groups are specified according to the atom that is bonded to the metal or bonded to another chemical moiety as a substituent, such as an "oxygen-bonded group," which is also called an "oxygen group." For example, an oxygen-bonded group includes species such as hydrocarboxy (—OR where R is a hydrocarbyl group), alkoxide (—OR where R is an alkyl group), aryloxide (—OAr where Ar is an aryl group), or substituted analogs thereof, which function as ligands or substituents in the specified location. Also, unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. Moreover, other identifiers or qualifying terms may be utilized to indicate the presence or absence of a particular substituent, a particular regiochemistry and/or stereochemistry, or the presence of absence of a branched underlying structure or backbone.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents as understood by one of ordinary skill in the art.

An "alpha olefin oligomer(s)," "alpha olefin oligomer product(s)," "oligomer product(s)," or "oligomerization product(s)," and similar terms are used to refer to the collection of alpha olefin dimers, alpha olefin trimers, and higher alpha olefin oligomers. Generally, the terms alpha olefin dimer, alpha olefin trimer, and higher alpha olefin oligomers (which can also be referred to as dimers, trimers, or heavy oligomers, respectively) refer to oligomerization products containing, 2, 3, or 4 or more units derived from the alpha olefin monomer, respectively. In any of dimers, trimers, and higher alpha olefin oligomers, the alpha olefin monomer units can be the same or can be different. The oligomer product in combination with residual monomer from preparing the oligomer product and any other material which exits the oligomerization reactor is termed the "oligomerization reactor effluent," "reactor effluent," or similar terms. Typically, alpha olefin oligomer and such terms are used to describe the oligomer product that is contained in the reactor effluent, and the term "heavy oligomer product" is used to describe the post-distillation oligomer product. In either case, the context and experimental details refer to whether the product has been distilled or not. Alpha olefin oligomer and heavy oligomer product and similar terms generally are not used to describe the post-hydrogenation samples, in which case polyalphaolefin (PAO) is the term used to define the hydrogenated alpha olefin oligomers. When referring to a fractionated (e.g. distilled) "alpha olefin oligomer(s)," "alpha olefin oligomer product(s)," "oligomer product(s)," or "oligomerization product(s)," the "alpha olefin oligomer(s)," "alpha olefin oligomer product(s)," "oligomer product(s)," or "oligomerization product(s)," may contain no more than 1 weight % residual alpha olefin monomer. However, the quantity of residual alpha olefin monomer can be specified to a value less than 1 weight percent. Moreover, when applied to an alpha olefin oligomer of a single carbon number, terms such as "alpha olefin oligomer" or "oligomer product" can be additionally described as such using terms such as "alpha olefin homooligomer," "homooligomer product," and the like. In should be noted that "alpha olefin homooligomer," "homooligomer product," and the like include impurity amounts of other alpha olefins, other olefins, and other materials that typically occur in any particular commercial sample of a single alpha olefin monomer that are not removed during the production of the single carbon number alpha olefin.

A "heavy oligomer product" is the product that results from removing some of the lower alpha olefin oligomers from the oligomer product within the oligomerization reactor effluent. In an aspect, the process utilized to remove some of the lower alpha olefin oligomers can be distillation. In other aspects, the process utilized to remove some of the lower alpha olefin oligomers can be purging or sparging. In other embodiment, the process to remove some of the lower alpha olefin oligomers may be distillation using a gas purge. When the material being distilled, purged, or sparged also contains some alpha olefin monomer (e.g. an oligomerization reactor effluent wherein not all of the alpha olefin monomer is converted to oligomer product), the distillation, purging, or sparging can also remove some or all of the alpha olefin monomer. Consequently, depending upon the oligomerization method and the fractionation method, the heavy oligomer product can contain less than some specified alpha olefin monomer (e.g. less than 1 weight percent). Generally, the process of removing some of the lower alpha olefin oligomers removes at least a portion of the alpha olefin monomer, the dimer, and/or the trimer to form the heavy oligomer product. It is noted that when the method utilized to remove some of the lower alpha olefin oligomers, by its nature, the method may also remove a portion of the higher olefin oligomers, and this point does not detract from the intent to remove a portion of the lower alpha olefin oligomers. In some cases, the term alpha olefin oligomer can be used to describe the reaction product both before and after distillation, in which case, reference to the context and experimental details can be made to determine whether the product has been distilled or not.

A "polyalphaolefin" (PAO) is a mixture of hydrogenated (or alternatively, substantially saturated) oligomers, containing units derived from an alpha olefin monomer (i.e. alpha olefin oligomers). Unless specified otherwise, the PAO can contain units derived from alpha olefin monomer units, which can be the same (hydrogenated or substantially saturated alpha olefin homooligomer) or can be different (hydrogenated or substantially saturated alpha olefin cooligomer). One having ordinary skill in the art will recognize that depending on the process utilized to produce the PAO, the as-produced alpha olefin oligomers can already be substantially saturated. For example, a process which is carried out in the presence of hydrogen can produce an olefin oligomer which may or may not require a separate hydrogenation step to provide a product with the desired properties. Generally, the alpha olefin monomer utilized to produce the polyalphaolefin can be any alpha olefin monomer described herein. One having ordinary skill in the art would recognize that the process(es) for producing the PAO can leave some hydrogenated monomer in the PAO (e.g. less than 1 weight %) and this quantity of hydrogenated monomer may be specified.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group that can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, and phosphines, and so forth. In one aspect, the hydrogen atom(s) removed to form the "organyl group," "organylene group," or "organic group" can be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), a N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" can be attached to a carbon atom not belonging to, and remote from, a functional group, for example, —CH$_2$C(O)CH$_3$, —CH$_2$NR$_2$, and the like. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, (among others known to those having ordinary skill in the art) as members. When bonded to a transition metal, an "organyl group," "organylene group," or "organic group" can be further described according to the usual $\eta^x$ (eta-x) nomenclature, in which x is an integer corresponding to the number of atoms which are coordinated to the transition metal or are expected to be coordinated to the transition metal, for example, according to the 18-electron rule.

The term "hydrocarbon" whenever used in this specification and claims refers to a compound containing only carbon and hydrogen. Other identifiers may be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be aliphatic or aromatic, acyclic or cyclic groups, and/or linear or branched. A "hydrocarbyl group," "hydrocarbylene group," and "hydrocarbon group" can include rings, ring systems, aromatic rings, and aromatic ring systems, which contain only carbon and hydrogen. When bonded to a transition metal, a "hydrocarbyl group," "hydrocarbylene group," and "hydrocarbon group" can be further described according to the usual $\eta^x$ (eta-x) nomenclature, in which x is an integer corresponding to the number of atoms which are coordinated to the transition metal or are expected to be coordinated to the transition metal, for example, according to the 18-electron rule. "Hydrocarbyl groups," "hydrocarbylene groups," and "hydrocarbon groups" include, by way of example, aryl, arylene, arene groups, alkyl, alkylene, alkane group, cycloalkyl, cycloalkylene, cycloalkane groups, aralkyl, aralkylene, and aralkane groups, respectively, among other groups as members.

An aliphatic compound is a class of acyclic or cyclic, saturated or unsaturated, carbon compounds, that excludes aromatic compounds. An "aliphatic group" is a generalized group formed by removing one or more hydrogen atoms (as necessary for the particular group) from carbon atom of an aliphatic compound. That is, an aliphatic compound is a non-aromatic organic compound. Aliphatic compounds and therefore aliphatic groups can contain organic functional group(s) and/or atom(s) other than carbon and hydrogen.

The term "alkane" whenever used in this specification and claims refers to a saturated hydrocarbon compound. Other identifiers may be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. A primary, secondary, and tertiary alkyl group are derived by removal of a hydrogen atom from a primary, secondary, tertiary carbon atom, respectively, of an alkane. The n-alkyl group derived by removal of a hydrogen atom from a terminal carbon atom of a linear alkane. The groups RCH$_2$ (R≠H), R$_2$CH(R≠H), and R$_3$C(R≠H) are primary, secondary, and tertiary alkyl groups, respectively.

A cycloalkane is a saturated cyclic hydrocarbon, with or without side chains, for example, cyclobutane. Other identifiers may be utilized to indicate the presence of particular groups in the cycloalkane (e.g. halogenated cycloalkane indicates that the presence of one or more halogen atoms replacing an equivalent number of hydrogen atoms in the cycloalkane). Unsaturated cyclic hydrocarbons having one endocyclic double or one triple bond are called cycloalkenes and cycloalkynes, respectively. Those having more than one such multiple bond are cycloalkadienes, cycloalkatrienes, and so forth. Other identifiers may be utilized to indicate the presence of particular groups in the cycloalkene, cycloalkadienes, cycloalkatrienes, and so forth.

A "cycloalkyl group" is a univalent group derived by removing a hydrogen atom from a ring carbon atom from a cycloalkane. For example, a 1-methylcyclopropyl group and a 2-methylcyclopropyl group are illustrated as follows.

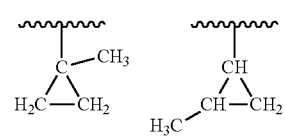

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. An "cycloalkane group" refers to a generalized group formed by removing one or more hydrogen atoms (as necessary for the particular group and at least one of which is a ring carbon) from a cycloalkane.

The term "alkene" whenever used in this specification and claims refers a linear or branched hydrocarbon olefin that has one carbon-carbon double bond and the general formula $C_nH_{2n}$. Alkadienes refer to a linear or branched hydrocarbon olefin having two carbon-carbon double bonds and the general formula $C_nH_{2n-2}$ and alkatrienes refer to linear or branched hydrocarbon olefins having three carbon-carbon and the general formula $C_nH_{2n-4}$. Alkenes, alkadienes, and alkatrienes can be further identified by the position of the carbon-carbon double bond(s). Other identifiers may be utilized to indicate the presence or absence of particular groups within an alkene, alkadiene, or alkatriene. For example, a haloalkene refers to an alkene having one or more hydrogen atoms replace with a halogen atom.

An "alkenyl group" is a univalent group derived from an alkene by removal of a hydrogen atom from any carbon atom of the alkene. Thus, "alkenyl group" includes groups in which the hydrogen atom is formally removed from an $sp^2$ hybridized (olefinic) carbon atom and groups in which the hydrogen atom is formally removed from any other carbon atom. For example and unless otherwise specified, 1-propenyl (—CH=CHCH$_3$), 2-propenyl [(CH$_3$)C=CH$_2$], and 3-propenyl (—CH$_2$CH=CH$_2$) groups are encompassed with the term "alkenyl group." Similarly, an "alkenylene group" refers to a group formed by formally removing two hydrogen atoms from an alkene, either two hydrogen atoms from one carbon atom or one hydrogen atom from two different carbon atoms. An "alkene group" refers to a generalized group formed by removing one or more hydrogen atoms (as necessary for the particular group) from an alkene. When the hydrogen atom is removed from a carbon atom participating in a carbon-carbon double bond, the regiochemistry of the carbon from which the hydrogen atom is removed, and regiochemistry of the carbon-carbon double bond can both be specified. Other identifiers may be utilized to indicate the presence or absence of particular groups within an alkene group. Alkene groups can also be further identified by the position of the carbon-carbon double bond.

The term "alkyne" whenever used in this specification and claims refers to a linear or branched hydrocarbon olefin that has one carbon-carbon triple bond and the general formula $C_nH_{2n-2}$. Alkadiynes refer to a hydrocarbon olefin having two carbon-carbon double bonds and the general formula $C_nH_{2n-6}$ and alkatriynes refer to hydrocarbon olefins having three carbon-carbon and the general formula $C_nH_{2n-10}$ Alkynes, alkadiynes, and alkatriynes can be further identified by the position of the carbon-carbon triple bond(s). Other identifiers may be utilized to indicate the presence or absence of particular groups within an alkene, alkadiene, or alkatriene. For example, a haloalkyne refers to an alkyne having one or more hydrogen atoms replace with a halogen atom.

An "alkynyl group" is a univalent group derived from an alkyne by removal of a hydrogen atom from any carbon atom of the alkyne. Thus, "alkynyl group" includes groups in which the hydrogen atom is formally removed from an sp hybridized (acetylenic) carbon atom and groups in which the hydrogen atom is formally removed from any other carbon atom. For example and unless otherwise specified, 1-propynyl (—C≡CCH$_3$) and 3-propynyl (HC≡CCH$_2$—) groups are all encompassed with the term "alkynyl group." Similarly, an "alkynylene group" refers to a group formed by formally removing two hydrogen atoms from an alkyne, either two hydrogen atoms from one carbon atom if possible or one hydrogen atom from two different carbon atoms. An "alkyne group" refers to a generalized group formed by removing one or more hydrogen atoms (as necessary for the particular group) from an alkyne. Other identifiers may be utilized to indicate the presence or absence of particular groups within an alkyne group. Alkyne groups can also be further identified by the position of the carbon-carbon triple bond.

The term "olefin" whenever used in this specification and claims refers to compound that has at least one carbon-carbon double bond that is not part of an aromatic ring or ring system. The term "olefin" includes aliphatic, aromatic, cyclic or acyclic, and/or linear and branched compounds having at least one carbon-carbon double bond that is not part of an aromatic ring or ring system unless specifically stated otherwise. The term "olefin," by itself, does not indicate the presence or absence of heteroatoms and/or the presence or absence of other carbon-carbon double bonds unless explicitly indicated. Olefins can also be further identified by the position of the carbon-carbon double bond. It is noted that alkenes, alkadienes, alkatrienes, cycloalkenes, cycloalkadienes, are members of the class of olefins. The olefin can be further identified by the position of the carbon-carbon double bond(s).

The term "alpha olefin" as used in this specification and claims refers to an olefin that has a double bond between the first and second carbon atom of a contiguous chain of carbon atoms. The term "alpha olefin" includes linear and branched alpha olefins unless expressly stated otherwise. In the case of branched alpha olefins, a branch may be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon monoolefin having a double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

The term "consists essentially of normal alpha olefin(s)" or variations thereof are used in the specification and claims to refer to commercially available normal alpha olefin product(s). The commercially available normal alpha olefin product can contain non-normal alpha olefin impurities such as vinylidenes, internal olefins, branched alpha olefins, paraffins, and diolefins, among other impurities, which are not removed during the normal alpha olefin production process. One of ordinary skill in the art will recognize that the identity and quantity of the specific impurities present in the commercial normal alpha olefin product will depend upon the source of commercial normal alpha olefin product. Additionally, when applied to a normal alpha olefin of a single carbon number, the term "consists essentially of a normal alpha olefin(s)" also includes small quantities (e.g. less than 5, 4, 3, 2, or 1 weight %) of olefins having a different carbon number than the recited normal alpha olefin carbon number which are not removed during the production of the single carbon number normal alpha olefin production process. Consequently, the term "consists essentially of normal alpha olefins" and its variants is not intended to limit the amount/quantity of the non-linear alpha olefin components (or in relation to carbon number the amount of a non-recited carbon number) any more stringently than the amounts/quantities present in a particular commercial normal alpha olefin product, unless explicitly stated. One source of commercially available alpha olefins products are those produced by the oligomerization of ethylene. A second source of commercially available alpha olefin products are those which are produced, and optionally isolated from, Fischer-Tropsch synthesis streams. One source of commercially available normal alpha olefin products produced by ethylene oligomerization which can be utilized as an olefin feedstock is Chevron Phillips Chemical Company LP, The Woodlands, Tex., USA. Other sources of commercially available normal alpha olefin products produced by ethylene oligomerization which can be utilized as an olefin feedstock include Inneos Oligomers (Feluy, Belgium), Shell Chemicals Corporation (Houston, Tex., USA or London, United Kingdom), Idemitsu Kosan (Tokyo, Japan), and Mitsubishi Chemical Corporation (Tokyo, Japan), among others. One source of commercially available normal alpha olefin products produced, and optionally isolated from Fisher-Tropsch synthesis streams includes Sasol (Johannesburg, South Africa), among others.

An "aromatic group" refers to a generalized group formed by removing one or more hydrogen atoms (as necessary for the particular group and at least one of which is an aromatic ring carbon atom) from an aromatic compound. Thus, an "aromatic group" as used herein refers to a group derived by removing one or more hydrogen atoms from an aromatic compound, that is, a compound containing a cyclically conjugated hydrocarbon that follows the Hückel (4n+2) rule and containing (4n+2) pi-electrons, where n is an integer from 1 to about 5. Aromatic compounds and hence "aromatic groups" can be monocyclic or polycyclic unless otherwise specified. Aromatic compounds include "arenes" (hydrocarbon aromatic compounds) and "heteroarenes," also termed "hetarenes" (heteroaromatic compounds formally derived from arenes by replacement of one or more methine (—C═) carbon atoms by trivalent or divalent heteroatoms, in such a way as to maintain the continuous pi-electron system characteristic of aromatic systems and a number of out-of-plane pi-electrons corresponding to the Hückel rule (4n+2)). While arene compounds and heteroarene compounds are mutually exclusive members of the group of aromatic compounds, a compound that has both an arene group and a heteroarene group that compound generally is considered a heteroarene compound. Aromatic compounds, arenes, and heteroarenes can be mono- or polycyclic unless otherwise specified. Examples of arenes include, but are not limited to, benzene, naphthalene, and toluene, among others. Examples of heteroarenes include, but are not limited to, furan, pyridine, and methylpyridine, among others. When bonded to a transition metal, an aromatic group can be further described according to the usual $\eta^x$ (eta-x) nomenclature, in which x is an integer corresponding to the number of atoms which are coordinated to the transition metal or are expected to be coordinated to the transition metal, for example, according to the 18-electron rule. As disclosed herein, the term "substituted" can be used to describe an aromatic group wherein any non-hydrogen moiety formally replaces a hydrogen in that group, and is intended to be non-limiting.

An "aryl group" is a group derived from the formal removal of a hydrogen atom from an aromatic hydrocarbon ring carbon atom from an arene compound. One example of an "aryl group" is ortho-tolyl (o-tolyl), the structure of which is shown here.

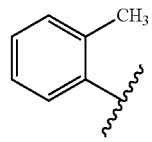 [SMILES: *c1ccccc1C]

Similarly, an "arylene group" refers to a group formed by removing two hydrogen atoms (at least one of which is from an aromatic hydrocarbon ring carbon) from an arene. An "arene group" refers to a generalized group formed by removing one or more hydrogen atoms (as necessary for the particular group and at least one of which is an aromatic hydrocarbon ring carbon) from an arene. However, if a group contains both arene and heteroarene moieties its classification depends upon the particular moiety from which the hydrogen atom was removed, that is, an arene group if the removed hydrogen came from a carbon atom of an aromatic hydrocarbon ring or ring system and a heteroarene group if the removed hydrogen came from a carbon atom of a heteroaromatic ring or ring system. When bonded to a transition metal, an "aryl group," "arylene group," and "arene group" can be further described according to the usual $\eta^x$ (eta-x) nomenclature, in which x is an integer corresponding to the number of atoms which are coordinated to the transition metal or are expected to be coordinated to the transition metal, for example, according to the 18-electron rule.

A "heterocyclic compound" is a cyclic compound having at least two different elements as ring member atoms. For example, heterocyclic compounds can comprise rings containing carbon and nitrogen (for example, tetrahydropyrrole), carbon and oxygen (for example, tetrahydrofuran), or carbon and sulfur (for example, tetrahydrothiophene), among others. Heterocyclic compounds and heterocyclic groups can be either aliphatic or aromatic. When bonded to a transition metal, a heterocyclic compound can be further described according to the usual $\eta^x$ (eta-x) nomenclature, in which x is an integer corresponding to the number of atoms which are coordinated to the transition metal or are expected to be coordinated to the transition metal, for example, according to the 18-electron rule.

A "heterocyclyl group" is a univalent group formed by removing a hydrogen atom from a heterocyclic ring or ring system carbon atom of a heterocyclic compound. By specifying that the hydrogen atom is removed from a heterocyclic ring or ring system carbon atom, a "heterocyclyl group" is distinguished from a "cycloheteryl group," in which a hydrogen atom is removed from a heterocyclic ring or ring system heteroatom. For example, a pyrrolidin-2-yl group illustrated below is one example of a "heterocyclyl group," and a pyrrolidin-1-yl group illustrated below is one example of a "cycloheteryl" group."

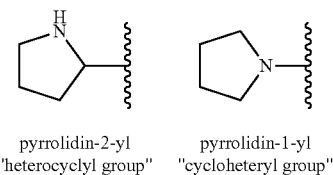

pyrrolidin-2-yl "heterocyclyl group"  pyrrolidin-1-yl "cycloheteryl group"

Similarly, a "heterocyclylene group" or more simply, a "heterocyclene group," refers to a group formed by removing two hydrogen atoms from a heterocyclic compound, at least one of which is from a heterocyclic ring or ring system carbon. Thus, in a "heterocyclylene group," at least one hydrogen is removed from a heterocyclic ring or ring system carbon atom, and the other hydrogen atom can be removed from any other carbon atom, including for example, the same heterocyclic ring or ring system carbon atom, a different heterocyclic ring or ring system ring carbon atom, or a non-ring carbon atom. A "heterocyclic group" refers to a generalized group formed by removing one or more hydrogen atoms (as necessary for the particular group and at least one of which is a heterocyclic ring carbon atom) from a heterocyclic compound. When bonded to a transition metal, a "heterocyclyl group," "heterocyclylene group," and "heterocyclic group" can be further described according to the usual $\eta^x$ (eta-x) nomenclature, in which x is an integer corresponding to the number of atoms which are coordinated to the transition metal or are expected to be coordinated to the transition metal, for example, according to the 18-electron rule.

A "cycloheteryl group" is a univalent group formed by removing a hydrogen atom from a heterocyclic ring or ring system heteroatom of a heterocyclic compound, as illustrated. By specifying that the hydrogen atom is removed from a heterocyclic ring or ring system heteroatom and not from a ring carbon atom, a "cycloheteryl group" is distinguished from a "heterocyclyl group" in which a hydrogen atom is removed from a heterocyclic ring or ring system carbon atom. Similarly, a "cycloheterylene group" refers to a group formed by removing two hydrogen atoms from an heterocyclic compound, at least one of which is removed from a heterocyclic ring or ring system heteroatom of the heterocyclic compound; the other hydrogen atom can be removed from any other atom, including for example, a heterocyclic ring or ring system ring carbon atom, another heterocyclic ring or ring system heteroatom, or a non-ring atom (carbon or heteroatom). A "cyclohetero group" refers to a generalized group formed by removing one or more hydrogen atoms (as necessary for the particular group and at least one of which is from a heterocyclic ring or ring system heteroatom) from a heterocyclic compound. When bonded to a transition metal, a "cycloheteryl group," "cycloheterylene group," and "cyclohetero group" can be further described according to the usual $\eta^x$ (eta-x) nomenclature, in which x is an integer corresponding to the number of atoms which are coordinated to the transition metal or are expected to be coordinated to the transition metal, for example, according to the 18-electron rule.

A "heteroaryl group" is a class of "heterocyclyl group" and is a univalent group formed by removing a hydrogen atom from a heteroaromatic ring or ring system carbon atom of a heteroarene compound. By specifying that the hydrogen atom is removed from a ring carbon atom, a "heteroaryl group" is distinguished from an "arylheteryl group," in which a hydrogen atom is removed from a heteroaromatic ring or ring system heteroatom. For example, an indol-2-yl group illustrated below is one example of a "heteroaryl group," and an indol-1-yl group illustrated below is one example of an "arylheteryl" group."

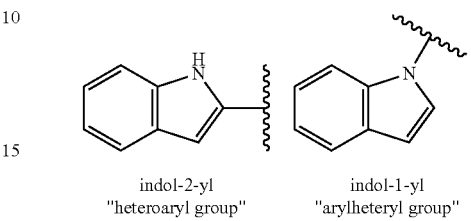

indol-2-yl "heteroaryl group"  indol-1-yl "arylheteryl group"

Similarly, a "heteroarylene group" refers to a group formed by removing two hydrogen atoms from a heteroarene compound, at least one of which is from a heteroarene ring or ring system carbon atom. Thus, in a "heteroarylene group," at least one hydrogen is removed from a heteroarene ring or ring system carbon atom, and the other hydrogen atom can be removed from any other carbon atom, including for example, a heteroarene ring or ring system carbon atom, or a non-heteroarene ring or ring system atom. A "heteroarene group" refers to a generalized group formed by removing one or more hydrogen atoms (as necessary for the particular group and at least one of which is a heteroarene ring or ring system carbon atom) from a heteroarene compound. When bonded to a transition metal, a "heteroaryl group," "heteroarylene group," and "heteroarene group" can be further described according to the usual $\eta^x$ (eta-x) nomenclature, in which x is an integer corresponding to the number of atoms which are coordinated to the transition metal or are expected to be coordinated to the transition metal, for example, according to the 18-electron rule.

An "arylheteryl group" is a class of "cycloheteryl group" and is a univalent group formed by removing a hydrogen atom from a heteroaromatic ring or ring system heteroatom of a heteroaryl compound, as illustrated. By specifying that the hydrogen atom is removed from of a heteroaromatic ring or ring system heteroatom and not from a heteroaromatic ring or ring system carbon atom, an "arylheteryl group" is distinguished from a "heteroaryl group" in which a hydrogen atom is removed from a heteroaromatic ring or a ring system carbon atom. Similarly, an "arylheterylene group" refers to a group formed by removing two hydrogen atoms from an heteroaryl compound, at least one of which is removed from a heteroaromatic ring or ring system heteroatom of the heteroaryl compound; the other hydrogen atom can be removed from any other atom, including for example, a heteroaromatic ring or ring system ring carbon atom, another heteroaromatic ring or ring system heteroatom, or a non-ring atom (carbon or heteroatom) from a heteroaromatic compound. An "arylhetero group" refers to a generalized group formed by removing one or more hydrogen atoms (as necessary for the particular group and at least one of which is from a heteroaromatic ring or ring system) heteroatom from a heteroarene compound. When bonded to a transition metal, an "arylheteryl group," "arylheterylene group," and "arylhetero group" can be further described according to the usual $\eta^x$ (eta-x) nomenclature, in which x is an integer corresponding to the number of atoms which are coordinated to the transition metal or are expected to be coordinated to the transition metal, for example, according to the 18-electron rule.

An "organoheteryl group" is a univalent group containing carbon, which are thus organic, but which have their free valence at an atom other than carbon. Thus, organoheteryl and organyl groups are complementary and mutually exclusive. Organoheteryl groups can be cyclic or acyclic, and/or aliphatic or aromatic, and thus encompasses aliphatic "cycloheteryl groups" such as pyrrolidin-1-yl, aromatic "arylheteryl groups" such as indol-1-yl, and acyclic groups such as organylthio, trihydrocarbylsilyl, and aryloxide, among others. Similarly, an "organoheterylene group" is a divalent group containing carbon and at least one heteroatom having two free valences, at least one of which is at a heteroatom. An "organohetero group" is a generalized group containing carbon and at least one heteroatom having one or more free valences (as necessary for the particular group and at least one of which is at a heteroatom) from an organohetero compound. When bonded to a transition metal, an "organoheteryl group," an "organoheterylene group," or an "organohetero group" can be further described according to the usual $\eta^x$ (eta-x) nomenclature, in which x is an integer corresponding to the number of atoms which are coordinated to the transition metal or are expected to be coordinated to the transition metal, for example, according to the 18-electron rule.

An "aralkyl group" is an aryl-substituted alkyl group having a free valance at a non-aromatic carbon atom, for example, a benzyl group. Similarly, an "aralkylene group" is an aryl-substituted alkylene group having two free valances at a single non-aromatic carbon atom or a free valence at two non-aromatic carbon atoms while an "aralkane group" is a generalized is an aryl-substituted alkane group having one or more free valances at a non-aromatic carbon atom(s). A "heteroaralkyl group" is a heteroaryl-substituted alkyl group having a free valence at a non-heteroaromatic ring or ring system carbon atom. Similarly a "heteroaralkylene group" is a heteroaryl-substituted alkylene group having a two free valances at a single non-heteroaromatic ring or ring system carbon atom or a free valence at two non-heteroaromatic ring or ring system carbon atoms while a "heteroaralkane group" is a generalized aryl-substituted alkane group having one or more free valances at a non-heteroaromatic ring or ring system carbon atom(s).

A "halide" has its usual meaning. Examples of halides include fluoride, chloride, bromide, and iodide.

An "oxygen group," also called an "oxygen-bonded group," is a chemical moiety having at least one free valence on an oxygen atom. Exemplary "oxygen groups" include, but are not limited to, hydroxy (—OH), —OR, —OC(O)R, —OSiR$_3$, —OPR$_2$, —OAlR$_2$, —OSiR$_2$, —OGeR$_3$, —OSnR$_3$, —OSO$_2$R, —OSO$_2$OR, —OBR$_2$, —OB(OR)$_2$, —OAlR$_2$, —OGaR$_2$, —OP(O)R$_2$, —OAs(O)R$_2$, —OAlR$_2$, and the like, including substituted analogs thereof. In one aspect, each R can be independently a hydrocarbyl group; e.g. each R can be independently alkyl, cycloalkyl, aryl, aralkyl, substituted alkyl, substituted cycloalkyl, substituted aryl, or substituted aralkyl. In an "oxygen group" having more than one free valency, the other free valencies can be on atom(s) other than oxygen, for example carbon, in accord with the rules of chemical structure and bonding.

A "sulfur group," also called a "sulfur-bonded group," is a chemical moiety having at least one free valence on a sulfur atom. Exemplary "sulfur group(s)" include, but are not limited to, —SH, —SR, —SCN, —S(O)R, —SO$_2$R, and the like, including substituted analogs thereof. In one aspect, each R can be independently a hydrocarbyl group; e.g. each R can be independently alkyl, cycloalkyl, aryl, aralkyl, substituted alkyl, substituted cycloalkyl, substituted aryl, or substituted aralkyl. In a "sulfur group" having more than one free valency, the other free valencies can be on atom(s) other than sulfur, for example carbon, in accord with the rules of chemical structure and bonding.

A "nitrogen group," also called a "nitrogen-bonded group," is a chemical moiety having at least one free valence on a nitrogen atom. Exemplary "nitrogen groups" include, but are not limited to, an aminyl group (—NH$_2$), an N-substituted aminyl group (—NRH), an N,N-disubstituted aminyl group (—NR$_2$), a hydrazido group (—NHNH$_2$), an N$^1$-substituted hydrazido group (—NRNH$_2$), an N$^2$-substituted hydrazido group (—NHNRH), an N$^2$,N$^2$-disubstituted hydrazido group (—NHNR$_2$), a nitro group (—NO$_2$), an azido group (—N$_3$), an amidyl group (—NHC(O)R), an N-substituted amido group (—NRC(O)R), and the like, including substituted analogs thereof. In one aspect, each R can be independently a hydrocarbyl group; e.g. each R can be independently alkyl, cycloalkyl, aryl, aralkyl, substituted alkyl, substituted cycloalkyl, substituted aryl, or substituted aralkyl. In a "nitrogen group" having more than one free valency, the other free valencies can be on any atom(s) in the group in accord with the rules of chemical structure and bonding, including atoms other than nitrogen, for example, carbon.

A "phosphorus group," also called a "phosphorus-bonded group," is a chemical moiety having at least one free valence on a phosphorus atom. Exemplary "phosphorous groups" include, but are not limited to, —PH$_2$, —PHR, —PR$_2$, —P(O)R$_2$, —P(OR)$_2$, —P(O)(OR)$_2$, —P(NR$_2$)$_2$, —P(O)(NR$_2$)$_2$, and the like, including substituted analogs thereof. In one aspect, each R can be independently a hydrocarbyl group; e.g. each R can be independently alkyl, cycloalkyl, aryl, aralkyl, substituted alkyl, substituted cycloalkyl, substituted aryl, or substituted aralkyl. In a "phosphorus group" having more than one free valency, the other free valencies can be on any atom(s) in the group in accord with the rules of chemical structure and bonding, including atoms other than phosphorus, for example, carbon.

An "arsenic group," also called an "arsenic-bonded group," is a chemical moiety having a free valence on an arsenic atom. Exemplary "arsenic groups" include, —AsH$_2$, —AsHR, —AsR$_2$, —As(O)R$_2$, —As(OR)$_2$, —As(O)(OR)$_2$, and the like, including substituted analogs thereof. In one aspect, each R can be independently a hydrocarbyl group; e.g. each R can be independently alkyl, cycloalkyl, aryl, aralkyl, substituted alkyl, substituted cycloalkyl, substituted aryl, or substituted aralkyl. In an "arsenic group" having more than one free valency, the other free valencies can be on any atom(s) in the group in accord with the rules of chemical structure and bonding, including atoms other than phosphorus, for example, carbon.

A "silicon group," also called a "silicon-bonded group," is a generalized chemical moiety having at least one free valence on a silicon atom. A "silyl group" is a chemical moiety having at least one free valence on a silicon atom. Exemplary "silyl groups" include, but are not limited to, —SiH$_3$, —SiH$_2$R, —SiHR$_2$, —SiR$_3$, —SiR$_2$OR, —SiR(OR)$_2$, —Si(OR)$_3$ and the like. In one aspect, each R can be independently a hydrocarbyl group; e.g. each R can be independently alkyl, cycloalkyl, aryl, aralkyl, substituted alkyl, substituted cycloalkyl, substituted aryl, or substituted aralkyl. In a "silicon group" having more than one free valency, the other free valencies can be on any atom(s) in the group in accord with the rules of chemical structure and bonding, including atoms other than silicon, for example, carbon.

A "germanium group," also called or a "germanium-bonded group," is a generalized chemical moiety having at least free valence on a germanium atom. A "germanyl group" is a chemical moiety having at least one free valence on a germanium atom. Exemplary "germanyl groups" include, but are not limited to, —GeH$_3$, —GeH$_2$R, —GeHR$_2$, —GeR$_3$, —GeR$_2$OR, —GeR(OR)$_2$, —Ge(OR)$_3$ and the like. In one aspect, each R can be independently a hydrocarbyl group; e.g. each R can be independently alkyl, cycloalkyl, aryl, aralkyl, substituted alkyl, substituted cycloalkyl, substituted aryl, or substituted aralkyl. In a "germanium group" having more than one free valency, the other free valencies can be on any atom(s) in the group in accord with the rules of chemical structure and bonding, including atoms other than germanium, for example, carbon.

A "tin group," also called a "tin-bonded group," is a generalized chemical moiety having at least one free valence on a tin atom. A "stannyl group" is a chemical moiety having a one free valence on a tin atom. Exemplary "stannyl groups" include, but is not limited to, —SnH$_3$, —SnH$_2$R, —SnHR$_2$, —SnR$_3$ and —Sn(OR)$_3$. In one aspect, each R can be independently a hydrocarbyl group; e.g. each R can be independently alkyl, cycloalkyl, aryl, aralkyl, substituted alkyl, substituted cycloalkyl, substituted aryl, or substituted aralkyl. In a "tin group" having more than one free valency, the other free valencies can be on any atom(s) in the group in accord with the rules of chemical structure and bonding, including atoms other than tin, for example, carbon.

A "lead group," also called a "lead-bonded group," is a chemical moiety having a free valence on a lead atom. Exemplary "lead groups" include, but are not limited to, —PbH$_3$, —PbH$_2$R, —PbHR$_2$, —PbR$_3$ and —Pb(OR)$_3$. In one aspect, each R can be independently a hydrocarbyl group; e.g. each R can be independently alkyl, cycloalkyl, aryl, aralkyl, substituted alkyl, substituted cycloalkyl, substituted aryl, or substituted aralkyl. In a "lead group" having more than one free valency, the other free valencies can be on any atom(s) in the group in accord with the rules of chemical structure and bonding, including atoms other than lead, for example, carbon.

A "boron group," also called a "boron-bonded group," is a generalized chemical moiety having at least one free valence on a boron atom. A "boronyl group" is a chemical moiety having at least one free valence on a boron atom. Exemplary "boronyl groups" include, but are not limited to, —BH$_2$, —BHR, —BR$_2$, —BR(OR), —B(OR)$_2$, and the like. In one aspect, each R can be independently a hydrocarbyl group; e.g. each R can be independently alkyl, cycloalkyl, aryl, aralkyl, substituted alkyl, substituted cycloalkyl, substituted aryl, or substituted aralkyl. In a "boron group" having more than one free valency, the other free valencies can be on any atom(s) in the group in accord with the rules of chemical structure and bonding, including atoms other than boron, for example, carbon.

An "aluminum group," also called an "aluminum-bonded group," is a generalized chemical moiety having at least one free valence on an aluminum atom. An "aluminyl group" is a chemical moiety having at least one free valence on an aluminum atom. Exemplary "aluminyl groups" include, but are not limited to, —AlH$_2$, —AlHR, —AlR$_2$, —AlR(OR), —Al(OR)$_2$, and the like. In one aspect, each R can be independently a hydrocarbyl group; e.g. each R can be independently alkyl, cycloalkyl, aryl, aralkyl, substituted alkyl, substituted cycloalkyl, substituted aryl, or substituted aralkyl. In an "aluminium group" having more than one free valency, the other free valencies can be on any atom(s) in the group in accord with the rules of chemical structure and bonding, including atoms other than aluminum, for example, carbon.

For each of the specific groups in which the free valence is situated on a heteroatom (non-carbon atom), such as the "oxygen group," "sulfur group," "nitrogen group," "phosphorus group," "arsenic group," "silicon group," "germanium group," "tin group," "lead group," "boron group," "aluminum group," and the like, such groups can include a general "R" moiety. In each instance, R can be independently a organyl group; alternatively, a hydrocarbyl group; alternatively, an alkyl group; alternatively, an aliphatic group; alternatively, a cycloalkyl group; alternatively, an alkenyl group; alternatively, an alkynyl group; alternatively, an aromatic group; alternatively, an aryl group; alternatively, a heterocyclyl group; alternatively, a cycloheteryl group; alternatively, a heteroaryl group; alternatively, an arylheteryl group; alternatively, an organoheteryl group; alternatively, an aralkyl group; alternatively, a heteroaralkyl group; or alternatively, a halide.

An "organoaluminum compound," is used to describe any compound that contains an aluminum-carbon bond. Thus, organoaluminum compounds include, but are not limited to, hydrocarbyl aluminum compounds such as trihydrocarbyl-, dihydrocarbyl-, or monohydrocarbylaluminum compounds; hydrocarbylaluminum halide compounds; hydrocarbylalumoxane compounds; and aluminate compounds which contain an aluminum-organyl bond such as tetrakis(p-tolyl)aluminate salts.

A "discernable crystallization" is determined by thermal analysis using a differential scanning calorimeter (DSC). A "discernable crystallization" is determined using ASTM D 3418, using two heating scans with an interceding cooling scan. While referred to as a crystallization the term also encompasses a discernable melting as determined by thermal analysis using a differential scanning calorimeter (DSC). The sample is cooled to −60° C. and held at −60° C. for 5 minutes before each heating scan. The first heating scan and second heating scans are conducted with a heating rate of 10° C./min from −60° C. to 100° C. The interceding cooling scan is conducted at rate of 10° C./min 100° C. to −60° C. The DSC is performed using a flow rate of 20 cc/min (cubic centimeters per minute) of nitrogen. The crystallization temperature (if present) or melting temperature (if present), and crystallization enthalpy (if present) or melting enthalpy (if present) is taken to be the temperature and enthalpy of the DSC crystallization transition or DSC melting transition, respectively, of the second heating scan and can be represented by an endotherm or an exotherm.

A "solid super acid" or "SSA" is synonymous with a solid oxide chemically-treated with an electron withdrawing anion, or a "chemically treated solid oxide." An SSA is a solid activator that derives from a solid oxide chemically-treated with an electron withdrawing anion as provided herein.

The term "substantially optically pure" is used to indicate a mixture of enantiomers having an enantiomeric excess of greater than or equal to 99.5%.

Terms that refer to the "substantial absence" of one particular alpha olefin from a sample of a different alpha olefin, for example, the statement that a PAO is derived from an alpha olefin sample in which the alpha olefin monomers "do not substantially include 1-decene," is intended to reflect a commercially-available sample of the subject alpha olefin monomer. By way of example, commercial samples of 1-octene and 1-dodecene can include up to about 1 weight percent of 1-decene, and such samples of 1-octene and 1-dodecene are encompassed in the characterization that such samples "do not include substantially amounts of 1-decene" or "are substantially 1-decene-free" and the like. Thus, the non-1-decene alpha olefin monomers used herein can include quantities of 1-decene found in commercially available alpha olefins.

The term "precontacted" is used herein to describe a first mixture of catalyst components that are contacted for a first period of time prior to the first mixture being used to form a "postcontacted" or second mixture of catalyst components that are contacted for a second period of time. For example, a precontacted mixture can describe a mixture of metallocene compound, olefin monomer, and organoaluminum compound, before this mixture is contacted with the chemically treated solid oxide and optionally additional organoaluminum compound. Thus, "precontacted" describes components that are used to contact each other, but prior to contacting with additional components in the second, postcontacted mixture. Accordingly, this disclosure can occasionally distinguish between a component used to prepare the precontacted mixture and that component after the mixture has been prepared. For example, according to this description, it is possible for the precontacted organoaluminum compound, once it is contacted with the metallocene and the olefin monomer, to have reacted to form at least one different chemical compound, formulation, or structure from the distinct organoaluminum compound used to prepare the precontacted mixture. In this case, the precontacted organoaluminum compound or component is described as comprising an organoaluminum compound that was used to prepare the precontacted mixture.

Similarly, the term "postcontacted" is used herein to describe a second mixture of catalyst components that are contacted for a second period of time, and one constituent of which is the "precontacted" or first mixture of catalyst components that were contacted for a first period of time. For example, a postcontacted mixture can describe a mixture of first metallocene compound, first metallocene compound, olefin monomer, organoaluminum compound, and chemically treated solid oxide, formed from contacting the precontacted mixture of a portion of these components with any additional components added to make up the postcontacted mixture. In this example, the additional component added to make up the postcontacted mixture is the chemically treated solid oxide, and optionally can include an organoaluminum compound the same or different from the organoaluminum compound used to prepare the precontacted mixture, as described herein. Accordingly, this disclosure can also occasionally distinguish between a component used to prepare the postcontacted mixture and that component after the mixture has been prepared.

The term "metallocene" as used herein is an organometallic coordination compound between a metal compound and at least one pi-bonded $\eta^{x \geq 5}$ ligand; eg. $\eta^{x \geq 5}$-hydrocarbyl, $\eta^{x \geq 5}$-arene, $\eta^{x \geq 5}$-heteroarene, $\eta^{x \geq 5}$-heterocyclic, $\eta^{x \geq 5}$-organyl, or $\eta^{x \geq 5}$-organoheteryl group or moiety that is aromatic (for example, $\eta^5$-cycloalkadienyl-type) or conjugated with (4n+2) pi-electrons, where n is an integer, usually either 1 or 2 (for example, $\eta^5$-alkadienyl-type). In this aspect, the IUPAC definition (IUPAC Compendium of Chemical Terminology, $2^{nd}$ Edition (1997)) of a "metallocene" is much more limiting than the definition of a "metallocene" used herein; therefore the IUPAC definition for "metallocene" is not used herein. In this disclosure, such ligands can be referred to as Group I ligands, and compounds that contain at least one such ligand are referred to as metallocenes. For example, a metallocene can contain at least one pi-bonded $\eta^{x \geq 5}$ ligand; e.g. $\eta^5$-cycloalkadienyl-type or $\eta^5$-alkadienyl-type ligand, for example, $\eta^5$-cyclopentadienyl, $\eta^5$-indenyl, $\eta^5$-fluorenyl, $\eta^5$-alkadienyl-, $\eta^6$-boratabenzene-ligand, and the like. Thus, a metallocene is indicated as containing an $\eta^{x \geq 5}$ moiety according to the usual $\eta^x$ (eta-x) nomenclature, in which x is an integer corresponding to the number of atoms which are coordinated to the transition metal or are expected to be coordinated to the transition metal, for example, according to the 18-electron rule.

The term "linking group" is used to describe the entire chemical moiety that connects two groups (for example, a Group I ligand with another ligand in the molecule, either another Group I ligand or a Group II ligand). The "linking group" includes a "bridge" having "bridging atom(s)." The bridge comprises the smallest number of contiguous atoms (bridging atoms) required to traverse the connection between the linked ligands (e.g. the Group I ligand and the other ligand it is connected to). Generally, the linking group and the bridge can comprise any atom; for example, the bridge can comprise C, Si, Ge, Sn, or any combination thereof. The linking group can be saturated, or the linking group can be unsaturated. By way of example, in the metallocene illustrated here, the "linking group" is the entire hydrocarbylene group $C(CH_3)$ $CH_2CH_2CH=CH_2$, whereas the "bridge" or the "bridging atom" is a single carbon atom. Thus, the so-called "constrained-geometry" metallocene catalysts are encompassed within the metallocenes of the catalyst composition of this disclosure.

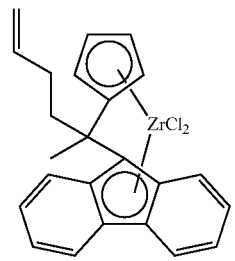

In some instances, reference can be made to "cyclic groups." Unless otherwise specified, "cyclic groups" include aromatic and aliphatic groups having a ring structure, including homocyclic and heterocyclic groups.

Alpha Olefin Oligomer, Heavy Oligomer Product, and Polyalphaolefin—Structure and Properties An "alpha olefin oligomer" or "oligomer product" are terms used to refer to the collection of alpha olefin dimers, alpha olefin trimers, and higher alpha olefin oligomers that arise from the oligomerization reaction. "Heavy oligomer product" refers to the product that results from removing some of the lower alpha olefin oligomers and/or monomers from the oligomer product within the oligomerization reactor effluent. For example, "heavy oligomer product" can refer to the post-separation collection of alpha olefin dimers, alpha olefin trimers, and higher alpha olefin oligomers. "Polyalphaolefin" (PAO) is the term used to describe hydrogenated (e.g. hydrogenated heavy olefin product) or substantially saturated alpha olefin oligomers. Thus, a polyalphaolefin (PAO) is a mixture of hydrogenated (or alternatively, substantially saturated) alpha olefin oligomers containing units derived from an alpha olefin monomer. The alpha olefin oligomer and the polyalphaolefins (PAOs) prepared according to this disclosure can have properties that can be selected over a range of possible values. These properties can be achieved using the methods and catalyst systems disclosed herein. The properties of the PAOs prepared according to this disclosure can also have properties which depend upon the amount (e.g. weight percent) of hydrogenated alpha olefin monomers, hydrogenated alpha olefin dimers, hydrogenated trimers, and/or hydrogenated higher oligomers present in the PAO (or alternatively, the amount of saturated alpha olefin monomers, saturated alpha olefin dimers, saturated trimers, and/or saturated higher oligomers). Thus, the term "hydrogenated" as applied to alpha olefin monomers, dimers, and higher oligomers is used herein to reflect that either the as-prepared oligomers (oligomer product or the heavy oligomer product) have been hydrogenated, either as a separate step or in the oligomerization step to some extent.

Generally, an alpha olefin oligomer refers to the collection of alpha olefin oligomers including dimers, trimers, and/or higher olefin oligomers (containing 4 or more alpha olefin monomer units). The alpha olefin monomers used to produce the dimers, trimers, and higher olefin oligomers in the oligomerization reaction, can be the same or can be different. An oligomerization reactor effluent can include the alpha olefin oligomer product, remaining non-oligomerized alpha olefin monomer, solvent, and/or catalyst system component, among other components. In an aspect, the reactor effluent can be processed to provide an alpha olefin oligomer product which can include all or a portion of the alpha olefin oligomer product and/or alpha olefin monomer utilized to form the alpha olefin oligomer. Depending on the method utilized to process the reactor effluent, the alpha olefin oligomer can contain residual alpha olefin monomer (typically less than 1 weight percent—other amounts are described herein and can be utilized without limitation). In this aspect, the alpha olefin oligomers can be described by the alpha olefin monomer(s) utilized to form the oligomers, the amount of alpha olefin monomer units found in the alpha olefin oligomer, the quantity of dimers in the alpha olefin oligomer, the quantity of trimers found in the alpha olefin oligomers, the quantity of the higher oligomers found in the alpha olefin oligomer, Mw, Mn, a 100° C. kinematic viscosity, a 40° C. kinematic viscosity, viscosity index, pour point, flash point, fire point, Noack volatility, errors in head-to-tail addition. These features of the alpha olefin oligomer are independently described herein and the alpha olefin oligomers can be described utilizing any combination of alpha olefin monomer utilized to form the oligomers described herein, the amount of alpha olefin monomer units found in the alpha olefin oligomer described herein, the quantity of dimers in the alpha olefin oligomer described herein, the quantity of trimers found in the alpha olefin oligomers described herein, the quantity of the higher oligomers found in the alpha olefin oligomer described herein, Mw described herein, Mn described herein, 100° C. kinematic viscosity described herein, viscosity index described herein, pour point described herein, flash point described herein, fire point described herein, Noack volatility described herein, and or errors in head-to-tail addition described herein. Generally, these features can also be applied, in any combination and without limitation, to any fraction of alpha olefin oligomer described herein (e.g., heavy oligomer product). In some embodiments, the alpha olefin oligomer can be separated (e.g. by distillation) to produce a heavy oligomer product. Depending upon the separation method utilized, the separation method can remove at least a portion of the alpha olefin monomer, dimers, and/or trimers. Additionally, depending upon the separation method utilized, the fractionation method may not remove all of the alpha olefin monomer and the heavy oligomer product can have an alpha olefin monomer content. In some embodiments, the residual alpha olefin monomer content of the separated alpha olefin oligomer can be specified as any value provided herein.

In a non-limiting embodiment, the collection of alpha olefin monomer and alpha olefin oligomer product exiting the reactor (i.e. reactor effluent) can comprise: a) less than 15 weight % alpha olefin monomer, b) less than 20 weight % dimers, and c) greater than 60 weight % higher oligomers. In other embodiments, the collection of alpha olefin monomer and alpha olefin oligomer product exiting the reactor (i.e. reactor effluent) can comprise: a) less than 12.5 weight % alpha olefin monomer, b) less than 15 weight % dimers, and c) greater than 65 weight % higher oligomers. In some non-limiting embodiments, an alpha olefin oligomer product can be produced from an alpha olefin monomer consisting essentially of a $C_8$ normal alpha olefin. Other embodiments are readily apparent from the present disclosure.

In a non-limiting embodiment, an oligomer product can comprise, a) less than 20 weight % dimers, and b) greater than 70 weight % higher oligomers and having, i) a 100° C. kinematic viscosity of at least 15 cSt, and ii) a viscosity index greater than 150. In a non-limiting embodiment, an oligomer product can be produced from an alpha olefin monomer consisting essentially of a $C_8$ normal alpha olefin and can comprise a) less than 15 weight % dimers, and b) greater than 75 weight % higher oligomers; and having, i) a 100° C. kinematic viscosity from 30 cSt to 50 cSt, and ii) a viscosity index from 150 to 260. In a non-limiting embodiment, an oligomer product can be produced from an alpha olefin monomer consisting essentially of a $C_8$ normal alpha olefin and can comprise, a) less than 12 weight % dimers, and b) greater than 75 weight % higher oligomers; and having i) a 100° C. kinematic viscosity from 80 cSt to 140 cSt, and ii) a viscosity index from 150 to 260. Other embodiments are readily apparent from the present disclosure.

In an non-limiting embodiment, an oligomer product obtained by separating a reactor effluent (e.g. heavy oligomer product, or any other) can have a residual alpha olefin monomer content of less than 1 weight %; alternatively, less than 0.8 weight %; alternatively, less than 0.6 weight %; alternatively, less than 0.5 weight % t; alternatively, less than 0.4 weight %; alternatively, less than 0.3 weight %; alternatively, less than 0.2 weight %; or alternatively, less than 0.1 weight %.

In a non-limiting embodiment, a heavy oligomer product can comprise: a) less than 1 weight % alpha olefin monomer, b) less than 3 weight % dimers, and c) greater than 80 weight % higher oligomers; and having, i) a 100° C. kinematic viscosity of at least 15 cSt, and ii) a viscosity index greater than 150. In some non-limiting embodiments, a heavy oligomer product can be produced from an alpha olefin monomer consisting essentially of a $C_8$ normal alpha olefin, the alpha olefin oligomer product comprising: a) less than 0.5 weight % alpha olefin monomer, b) less than 1.5 weight % dimers, and c) greater than 88 weight % higher oligomers; and having, i) a 100° C. kinematic viscosity from 30 cSt to 50 cSt, and ii) a viscosity index from 150 to 260. In another non-limiting embodiment, a heavy oligomer product can be produced from an alpha olefin monomer consisting essentially of a $C_8$ normal alpha olefin, the alpha olefin oligomer product comprising: a) less than 0.4 weight % alpha olefin monomer, b) less than 1.5 weight % dimers, and c) greater than 88 weight % higher oligomers; and having, i) a 100° C. kinematic viscosity from 80 cSt to 140 cSt, and ii) a viscosity index from 150 to 260. Other embodiments of the heavy oligomer product are readily apparent from the present disclosure.

In a further aspect, the PAO can be described by the alpha olefin monomer(s) utilized to form the PAO, the amount of alpha olefin monomer units found in the PAO, the amount of hydrogenated monomer found in the PAO, the quantity of hydrogenated dimers in the PAO, the quantity of hydrogenated trimers found in the PAO, the quantity of the hydrogenated higher oligomers found in the PAO, Mw, Mn, a 100° C.

kinematic viscosity, a 40° C. kinematic viscosity, viscosity index, pour point, flash point, fire point, Noack volatility, RPVOT test result, errors in head-to-tail addition, tacticity, Bernoulli index, Markov number, a shear stability as measured by ASTM D6278-07, polydispersity index, and/or the presence or absence of a discernable crystallization. These features of the PAO are independently described herein and the PAO can be described utilizing any combination of the alpha olefin monomer utilized to form the PAO described herein, the amount of alpha olefin monomer units found in the PAO described herein, the amount of hydrogenated monomer found in the PAO described herein, quantity of hydrogenated dimers in the PAO described herein, the quantity of hydrogenated trimers found in the PAO described herein, the quantity of the hydrogenated higher oligomers found in the PAO described herein, Mw described herein, Mn described herein, 100° C. kinematic viscosity described herein, viscosity index described herein, pour point described herein, flash point described herein, fire point described herein, Noack volatility described herein, RPVOT test result, errors in head-to-tail addition described herein, tacticity described herein, Bernoulli index described herein, and/or the presence or absence of discernable crystallization described herein.

By way of example, in a non-limiting embodiment, a polyalphaolefin (PAO) derived from hydrogenating a heavy oligomer product can have Bernoulli index less 1.65; or alternatively, within a range of 1.1±0.4. In another non-limiting embodiment, the polyalphaolefin can have no discernable crystallization above −40° C. as determined differential scanning calorimetry using ASTM D 3418. In a further non-limiting example, the polyalphaolefin can have a pour point from −30° C. to −90° C., the polyalphaolefin can have a RPVOT as measured by ASTM D2272 in the presence of 0.5 weight % of Naugalube® APAN antioxidant of at least 2,100 minutes, the polyalphaolefin can have Bernoulli index less 1.65 or within a range of 1.1±0.4, or any combination of these properties. Other embodiments can be readily discerned from the present disclosure.

In an aspect, the alpha olefin oligomers, any fraction of alpha olefin oligomers, and/or polyalphaolefins which can be produced according to the methods described herein can be produced using an olefin monomer comprising an alpha olefin; alternatively, a normal alpha olefin. In an embodiment, the olefin monomer can comprise at least 60 weight percent, 70 weight percent, 75 weight percent, 80 weight percent, 82.5 weight percent, 85 weight percent, 87.5 weight percent, 90 weight percent, 91, weight percent, 92 weight percent, 93 weight percent, 94, weight percent, 95 weight percent, 96 weight percent, 97 weight percent, or 98 weight percent alpha olefin. In some embodiments, the olefin monomer can comprise at least 60 weight percent, 70 weight percent, 75, weight percent, 80 weight percent. 82.5 weight percent, 85 weight percent, 87.5 weight percent, 90 weight percent, 91, weight percent, 92 weight percent, 93 weight percent, 94, weight percent, 95 weight percent, 96 weight percent, 97 weight percent, or 98 weight percent normal alpha olefin. Generally, the alpha olefin of the olefin monomer can be any alpha olefin or normal alpha olefin (single or blend) described herein.

A wide range of alpha olefin monomers can be oligomerized according to the methods provided herein. For example, the methods described here are applicable to alpha olefin monomers as small as propylene and as large as the waxes having 70 or 75 carbon atoms. In an aspect and in any embodiment described herein, the alpha olefin oligomer, any fraction of the alpha olefin oligomers, and/or the PAO can be produced from an alpha olefin monomer comprising, or consisting essentially of, a $C_3$ to $C_{70}$ alpha olefin; alternatively, a $C_3$ to $C_{40}$ alpha olefin; alternatively, a $C_4$ to $C_{20}$ alpha olefin; alternatively, a $C_5$ to $C_{18}$ alpha olefin; alternatively, a $C_6$ to $C_{16}$ alpha olefin; or alternatively, a $C_8$ to $C_{12}$ alpha olefin. In an embodiment, the alpha olefin oligomers, any fraction of the alpha olefin oligomers, and/or the PAO can be produced from an alpha olefin monomer comprising, or consisting essentially of, a $C_6$ alpha olefin, a $C_8$ alpha olefin, a $C_{10}$ alpha olefin, a $C_{12}$ alpha olefin, a $C_{14}$ alpha olefin, a $C_{16}$ alpha olefin, or any combination thereof; alternatively, a $C_8$ alpha olefin, a $C_{10}$ alpha olefin, a $C_{12}$ alpha olefin, or any combination thereof; alternatively, a $C_6$ alpha olefin; alternatively, a $C_8$ alpha olefin; alternatively, a $C_{10}$ alpha olefin; alternatively, a $C_{12}$ alpha olefin; alternatively, a $C_{14}$ alpha olefin; alternatively, a $C_{16}$ alpha olefin; or alternatively, a $C_{18}$ alpha olefin. In a further aspect and in any suitable embodiment described herein, the alpha olefin oligomers, any fraction of the alpha olefin oligomers, and/or the PAO can be produced from an alpha olefin monomer comprising, or consisting essentially of, a $C_3$ to $C_{70}$ normal alpha olefin; alternatively, a $C_3$ to $C_{40}$ normal alpha olefin; alternatively, a $C_4$ to $C_{20}$ normal alpha olefin; alternatively, a $C_5$ to $C_{18}$ normal alpha olefin; alternatively, a $C_6$ to $C_{16}$ normal alpha olefin; or alternatively, a $C_8$ to $C_{12}$ normal alpha olefin. In an embodiment, the alpha olefin oligomers, any fraction of the alpha olefin oligomers, and/or the PAO can be produced from an alpha olefin monomer comprising, or consisting essentially of, a $C_6$ normal alpha olefin, a $C_8$ normal alpha olefin, a $C_{10}$ normal alpha olefin, a $C_{12}$ normal alpha olefin, a $C_{14}$ normal alpha olefin, a $C_{16}$ normal alpha olefin, or any combination thereof; alternatively, a $C_8$ normal alpha olefin, a $C_{10}$ normal alpha olefin, a $C_{12}$ normal alpha olefin, or any combination thereof; alternatively, a $C_6$ normal alpha olefin; alternatively, a $C_6$ normal alpha olefin; alternatively, a $C_8$ normal alpha olefin; alternatively, a $C_{10}$ normal alpha olefin; alternatively, a $C_{12}$ normal alpha olefin; alternatively, a $C_{14}$ normal alpha olefin; alternatively, a $C_{16}$ normal alpha olefin; or alternatively, a $C_{18}$ normal alpha olefin.

In an aspect and any embodiment described herein, the alpha olefin oligomers, any fraction of the alpha olefin oligomers, and/or the PAO can be produced from an alpha olefin monomer comprising, or consisting essentially of, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, or any combination thereof; alternatively, 1-hexene, 1-heptene, 1-octene, 1-nonene, 1-decene, 1-undecene, 1-dodecene, 1-tridecene, 1-tetradecene, 1-pentadecene, 1-hexadene, or any combination thereof; alternatively, 1-octene, 1-nonene, 1-decene, 1-undecene, 1-dodecene, or any combination thereof. In some embodiments, the alpha olefin oligomers, any fraction of the alpha olefin oligomers, and/or the PAO can be produced from an alpha olefin monomer comprising, or consisting essentially of, 1-hexene, 1-octene, 1-decene, 1-dodecene, 1-tetradecene, 1-hexadecene, or any combination thereof; alternatively, 1-octene, 1-decene, 1-dodecene, or any combination thereof. In other embodiments, the alpha olefin oligomers, any fraction of the alpha olefin oligomers, and/or the PAO can be produced from an alpha olefin monomer comprising, or consisting essentially of, 1-pentene; alternatively, 1-hexene; alternatively, 1-heptene; alternatively, 1-octene; alternatively, 1-nonene; alternatively, 1-decene; alternatively, 1-undecene; alternatively, 1-dodecene; alternatively, 1-tridecene; alternatively, 1-tetradecene; alternatively, 1-pentadecene; alternatively, 1-hexadecene; alternatively, 1-heptadecene; or alternatively, 1-octadecene.

In an aspect and any embodiment described herein, the alpha olefin oligomers, any fraction of the alpha olefin oligomers, and/or the PAO can be produced from an alpha olefin monomer comprising, or consisting essentially of, an alpha olefin having the formula $CH_2=CH(CH_2)_nCH_3$, wherein n can be an integer from 1 to 17; alternatively, having the formula $CH_2=CH(CH_2)_nCH_3$, wherein n can be an integer from 2 to 15; alternatively, having the formula $CH_2=CH(CH_2)_nCH_3$, wherein n can be an integer from 3 to 13; alternatively, having the formula $CH_2=CH(CH_2)_nCH_3$, wherein n can be an integer from 5 to 9; or alternatively, having the formula $CH_2=CH(CH_2)_nCH_3$. In some embodiments, the alpha olefin oligomers, any fraction of the alpha olefin oligomers, and/or the PAO can be produced from an alpha olefin monomer comprising, or consisting essentially of, an alpha olefin having the formula $CH_2=CH(CH_2)_nCH_3$, wherein n can be 3; alternatively, an alpha olefin having the formula $CH_2=CH(CH_2)_nCH_3$, wherein n can be 5; alternatively, an alpha olefin having the formula $CH_2=CH(CH_2)_nCH_3$, wherein n can be 7; alternatively, an alpha olefin having the formula $CH_2=CH(CH_2)_nCH_3$, wherein n can be 9; alternatively, an alpha olefin having the formula $CH_2=CH(CH_2)_nCH_3$, wherein n can be 11; alternatively, an alpha olefin having the formula $CH_2=CH(CH_2)_nCH_3$, wherein n can be 13; or alternatively, an alpha olefin having the formula $CH_2=CH(CH_2)_nCH_3$, wherein n can be 15.

In an aspect, the alpha olefin oligomers, any fraction of the alpha olefin oligomers, and/or the PAO which can be produced according to the methods described herein can be produced using an olefin monomer comprising, or consisting essentially of, a blend of alpha olefins; or alternatively, a blend of normal alpha olefins. Generally, the olefin monomer can be a blend of any alpha olefin described herein; or alternatively, any normal alpha olefin, described herein. In a embodiment, the blend of alpha olefins can comprise at least at least 50 weight percent, at least 60 weight percent, 70 weight percent, 75 weight percent, 80 weight percent, 85 weight percent, 90 weight percent, 92.5 weight percent, or 95 weight percent of any carbon number range of alpha olefins described herein; alternatively, of any combination of single carbon numbered alpha olefins described herein; or alternatively, of any single carbon numbered normal alpha olefin described herein. In some non-limiting embodiments, the blend of normal alpha olefins can comprise at least at least 50 weight percent, at least 60 weight percent, 70 weight percent, 75 weight percent, 80 weight percent, 85 weight percent, 90 weight percent, 92.5 weight percent, or 95 weight percent of any carbon numbered range of normal alpha olefins described herein; alternatively, any combination of single carbon numbered normal alpha olefins described herein; or alternatively, any single numbered normal alpha olefin described herein.

In another aspect, the alpha olefin oligomers, any fraction of the alpha olefin oligomers, and/or the PAO which can be produced according to the methods described herein can be produced using an alpha olefin monomer comprising, or consisting essentially of, a blend of normal alpha olefins. Generally, the blend of alpha olefins can be a blend of any alpha olefin described herein. In an embodiment, blend of alpha olefin can comprise at least 50 weight percent, at least 60 weight percent, 70 weight percent, 75 weight percent, 80 weight percent, 85 weight percent, 90 weight percent, 92.5 weight percent, or 95 weight percent of any carbon number range of alpha olefins described herein; alternatively, any combination of any single carbon numbered alpha olefin described herein; or alternatively, any single numbered alpha olefin described herein. In yet another aspect, the alpha olefin oligomers, any fraction of the alpha olefin oligomers, and/or the PAO which can be produced according to the methods described herein can be produced using a normal alpha olefin monomer comprising, or consisting essentially of, a blend of normal alpha olefins. Generally, the blend of normal alpha olefins can be a blend of any normal alpha olefin described herein. In an embodiment, blend of normal alpha olefin can comprise at least 50 weight percent, at least 60 weight percent, 70 weight percent, 75 weight percent, 80 weight percent, 85 weight percent, 90 weight percent, 92.5 weight percent, or 95 weight percent of any carbon number range of normal alpha olefins described herein; alternatively, any combination of any single carbon numbered normal alpha olefin described herein; or alternatively, any single numbered normal alpha olefin described herein.

In a non-limiting example, the olefin monomer can comprise a blend of alpha olefin comprising at least 80 weight percent of $C_6$ to $C_{16}$ alpha olefins; alternatively, at least 60 weight percent of a $C_6$ alpha olefin and $C_{14}$ alpha olefin; alternatively, at least 90 weight percent of a $C_8$ to $C_{12}$ normal alpha olefin; alternatively, at least 85 weight percent of 1-hexene, 1-decene, and 1-tetradecene; alternatively, at least 75 weight percent 1-octene; or alternatively, at least 75 weight percent of a normal alpha olefin consisting essentially of 1-octene. In some non-limiting embodiments, the single carbon numbered alpha olefin which can be utilized in an alpha olefin blend can consist essentially of a $C_6$ alpha olefin; alternatively, a $C_8$ alpha olefin; alternatively, a $C_{10}$ alpha olefin; alternatively, a $C_{12}$ alpha olefin; alternatively, a $C_{14}$ alpha olefin; or alternatively, a $C_{16}$ alpha olefin. In other non-limiting embodiments, the single carbon numbered normal alpha olefin which can be utilized in an alpha olefin blend or normal alpha olefin blend can consist essentially of a $C_6$ normal alpha olefin; alternatively, a $C_8$ normal alpha olefin; alternatively, a $C_{10}$ normal alpha olefin; alternatively, a $C_{12}$ normal alpha olefin; alternatively, a $C_{14}$ normal alpha olefin; or alternatively, a $C_{16}$ normal alpha olefin. Other potential blends which can be utilized as olefin monomer, alpha olefin, or normal alpha olefin monomer are readily apparent from the present disclosure.

As described, the alpha olefin oligomers, any fraction of the alpha olefin oligomers, and/or the polyalphaolefin of any aspect or embodiment can be produced by oligomerizing an alpha olefin. The alpha olefin oligomers produced in the oligomerization comprise units derived from the alpha olefin monomers. One having ordinary skill in the art will recognize that a catalyst system utilized to form the alpha olefin oligomers can isomerize the alpha olefin monomer to a non-alpha olefin (e.g. an internal olefin). Alternatively or additionally, the alpha olefin feedstock can contain quantities of non-alpha olefins. Depending upon the catalyst system utilized, the non-alpha olefins can be incorporated into the alpha olefin oligomer (and such that the polyalphaolefin can contain alpha olefin monomer units in combination with internal olefin monomer units). In some instances the catalyst system may limit the extent of alpha olefin isomerization and/or limit the quantity of non-alpha olefins incorporated into the alpha olefin oligomer. Consequently, one feature of the alpha olefin oligomers, any fraction of the alpha olefin oligomers, and/or the polyalphaolefin can be the percentage of alpha olefin units in the alpha olefin oligomer, fraction of alpha olefin oligomers and/or PAO. Thus, in any disclosed embodiment, the alpha olefin oligomers, any fraction of the alpha olefin oligomers, and/or the polyalphaolefin described herein can comprise at least 70 percent alpha olefin monomer units; alternatively, at least 75 percent alpha olefin monomer units; alternatively, at least 80 percent alpha olefin monomer units; alternatively, at least 85 percent alpha olefin monomer units; alternatively, at least 90 percent alpha olefin monomer units; alternatively, at least 95 percent alpha olefin monomer units; alternatively, at least 98 percent alpha olefin monomer units; or alternatively, at least 99 percent alpha olefin monomer units. In a further aspect, the alpha olefin oligomers, any fraction of the alpha olefin oligomers, and/or the polyalphaolefin according to any embodiment can consist essentially of alpha olefin monomer units. Generally, the alpha olefin can be any alpha olefin described herein.

In an aspect, the collection of alpha olefin monomer and alpha olefin oligomer product in the reactor effluent, the alpha olefin product, or a fraction of the alpha olefin oligomer product according to this disclosure can comprise less than 20 weight % alpha olefin monomer; alternatively, less than 17.5 weight % alpha olefin monomer; alternatively, less than 15 weight % alpha olefin monomer; alternatively, less than 12.5 weight % alpha olefin monomer; alternatively, less than 10 weight % alpha olefin monomer; alternatively, less than 9 weight % alpha olefin monomer; alternatively, less than 8 weight % alpha olefin monomer; alternatively, less than 7 weight % alpha olefin monomer; alternatively, less than 6 weight % alpha olefin monomer; alternatively, less than 5 weight % alpha olefin monomer; alternatively, less than 4 weight % alpha olefin monomer; alternatively, less than 3 weight % alpha olefin monomer; alternatively, less than 2 weight % alpha olefin monomer; alternatively, less than 1 weight % alpha olefin monomer; alternatively, less than 0.8 weight % alpha olefin monomer; alternatively, less than 0.6 weight % alpha olefin monomer; alternatively, less than 0.5 weight % alpha olefin monomer; alternatively, less than 0.4 weight % alpha olefin monomer; alternatively, less than 0.3 weight % alpha olefin monomer; alternatively, less than 0.2 weight % alpha olefin monomer; or alternatively, less than 0.1 weight % alpha olefin monomer. In some embodiments, the alpha olefin monomer content may be referred to as residual alpha olefin monomer (e.g. a separated reactor effluent or separated olefin oligomer, among others) and can utilize any alpha olefin monomer value content described herein. In an aspect, the collection of alpha olefin monomer and alpha olefin oligomer product, the alpha olefin product, or a fraction of the alpha olefin oligomer product according to this disclosure can comprise less than 20 weight % dimers; alternatively, less than 19 weight % dimers; alternatively, less than 18 weight % dimers; alternatively, less than 17 weight % dimers; alternatively, less than 16 weight % dimers; alternatively, less than 15 weight % dimers; alternatively, less than 14 weight % dimers; alternatively, less than 13 weight % dimers; alternatively, less than 12 weight % dimers; alternatively, less than 11 weight % dimers; alternatively, less than 10 weight % dimers; alternatively, less than 9 weight % dimers; alternatively, less than 8 weight % dimers; alternatively, less than 7 weight % dimers; alternatively, less than 6 weight % dimers; alternatively, less than 5 weight % dimers; alternatively, less than 4 weight % dimers; less than 3 weight % dimers; less than 2.5 weight % dimers; alternatively, less than 2 weight % dimers; alternatively, less than 1.75 weight % dimers; alternatively, less than 1.5 weight % dimers; alternatively, less than 1.25 weight % dimers; alternatively, less than 1 weight % dimers; alternatively, less than 0.9 weight % dimers; alternatively, less than 0.8 weight % dimers; alternatively, less than 0.7 weight % dimers; alternatively, less than 0.6 weight % dimers; alternatively, less than 0.5 weight % dimers; alternatively, less than 0.4 weight % dimers; or alternatively, less than 0.3 weight % dimers. In a further aspect, the collection of alpha olefin monomer and alpha olefin oligomer product, the alpha olefin product, or a fraction of the alpha olefin oligomer product according to this disclosure can comprise less than 20 weight % trimers; alternatively, less than 17.5 weight % trimers; alternatively, less than 15 weight % trimers; alternatively, less than 12.5 weight % trimers; alternatively, less than 10 weight % trimers; less than 7.5 weight % trimers; alternatively, less than 5 weight % trimers; alternatively, less than 4 weight % trimers; alternatively, less than 3 weight % trimers; 2 weight % trimers; alternatively, less than 1.75 weight % trimers; alternatively, less than 1.5 weight % trimers; alternatively, less than 1.25 weight % trimers; alternatively, less than 1 weight % trimers; alternatively, less than 0.9 weight % trimers; alternatively, less than 0.8 weight % trimers; alternatively, less than 0.7 weight % trimers; alternatively, less than 0.6 weight % trimers; alternatively, less than 0.5 weight % trimers; alternatively, less than 0.4 weight % trimers; alternatively, less than 0.3 weight % trimers; alternatively, less than 0.2 weight % trimers; or alternatively, less than 0.1 weight % trimers. In a further aspect, the collection of alpha olefin monomer and alpha olefin oligomer product, the alpha olefin product, or a fraction of the alpha olefin oligomer product according to this disclosure can comprise at least 50 weight % higher oligomers; alternatively, at least 55 weight % higher oligomers; alternatively, at least 60 weight % higher oligomers; alternatively, at least 62.5 weight % higher oligomers; alternatively, at least 65 weight % higher oligomers; alternatively, at least 67.5 weight % higher oligomers; alternatively, at least 70 weight % higher oligomers; alternatively, at least 72.5 weight % higher oligomers; alternatively, at least 75 weight % higher oligomers; alternatively, at least 77.5 weight % higher oligomers; alternatively, at least 80 weight % higher oligomers; at least 82.5 weight % higher oligomers; alternatively, at least 85 weight % higher oligomers; alternatively, at least 86 weight % higher oligomers; alternatively, at least 87 weight % higher oligomers; alternatively, at least 88 weight % higher oligomers; alternatively, at least 89 weight % higher oligomers; alternatively, at least 90 weight % higher oligomers; alternatively, at least 91 weight % higher oligomers; alternatively, at least 92 weight % higher oligomers; alternatively, at least 93 weight % higher oligomers; alternatively, at least 94 weight % higher oligomers; or alternatively, at least 95 weight % higher oligomers. Moreover, any appropriate combination of these alpha olefin oligomer weight percentage features can be utilized to describe a fraction of the alpha olefin oligomer as provided herein. Generally, the weight percent of alpha olefin monomers, dimers, trimers, and higher oligomers of the collection of alpha olefin monomer and alpha olefin oligomer product satisfy the formula monomer+dimer+trimer+higher oligomer=100. Generally, the weight percent of dimers, trimers, and higher oligomers of the alpha olefin product or a fraction of the alpha olefin oligomer product satisfy the formula dimers+trimers+higher oligomers=100. However, when desired or necessary for clarity, the amount of monomer (residual monomer) may be stated (e.g. when referring to a fractionated reactor effluent, among other compositions) and in this instance the weight percent of alpha olefin monomers, dimers, trimers, and higher oligomers satisfy the formula monomers+dimers+trimers+higher oligomers=100.

In an aspect, the heavy oligomer product can comprise less than 1 weight % alpha olefin monomer; alternatively, less than 0.8 weight % alpha olefin monomer; alternatively, less than 0.6 weight % alpha olefin monomer; alternatively, less than 0.5 weight % alpha olefin monomer; alternatively, less than 0.4 weight % alpha olefin monomer; alternatively, less than 0.3 weight % alpha olefin monomer; alternatively, less than 0.2 weight % alpha olefin monomer; or alternatively, less than 0.1 weight % alpha olefin monomer. In some embodiments, the alpha olefin monomer content of the heavy oligomer product may be referred to as residual alpha olefin monomer and can utilize any alpha olefin monomer value described. In another aspect, the heavy oligomer product or a fraction of the heavy oligomer product according to this disclosure can comprise less than 10 weight % dimers; alternatively, less than 9 weight % dimers; alternatively, less than 8 weight % dimers; alternatively, less than 7 weight % dimers; alternatively, less than 6 weight % dimers; alternatively, less than 5 weight % dimers; alternatively, less than 4.5 weight % dimers; alternatively, less than 4 weight % dimers; alternatively, less than 3 weight % dimers; alternatively, less than 2.5 weight % dimers; alternatively, less than 2 weight % dimers; alternatively, less than 1.75 weight % dimers; alternatively, less than 1.5 weight % dimers; alternatively, less than 1.25 weight % dimers; alternatively, less than 1 weight % dimers; alternatively, less than 0.9 weight % dimers; alternatively, less than 0.8 weight % dimers; alternatively, less than 0.7 weight % dimers; alternatively, less than 0.6 weight % dimers; alternatively, less than 0.5 weight % dimers; alternatively, less than 0.4 weight % dimers; alternatively, less than 0.3 weight % dimers; alternatively, less than 0.2 weight % dimers; or alternatively, less than 0.1 weight % dimers. In another aspect the, the heavy oligomer product or a fraction of the heavy oligomer product can comprise less than 20 weight % trimers; alternatively, less than 17.5 weight % trimers; alternatively, less than 15 weight % trimers; alternatively, less than 12.5 weight % trimers; alternatively, less than 10 weight % trimers; less than 7.5 weight % trimers; alternatively, less than 5 weight % trimers; alternatively, less than 4 weight % trimers; alternatively, less than 3 weight % trimers; 2 weight % trimers; alternatively, less than 1.75 weight % trimers; alternatively, less than 1.5 weight % trimers; alternatively, less than 1.25 weight % trimers; alternatively, less than 1 weight % trimers; alternatively, less than 0.9 weight % trimers; alternatively, less than 0.8 weight % trimers; alternatively, less than 0.7 weight % trimers; alternatively, less than 0.6 weight % trimers; alternatively, less than 0.5 weight % trimers; alternatively, less than 0.4 weight % trimers; alternatively, less than 0.3 weight % trimers; alternatively, less than 0.2 weight % trimers; or alternatively, less than 0.1 weight % trimers. In yet another aspect, the heavy oligomer product or a fraction of the heavy oligomer product can comprise at least 80 weight % higher oligomers; at least 82.5 weight % higher oligomers; alternatively, at least 85 weight % higher oligomers; alternatively, at least 86 weight % higher oligomers; alternatively, at least 87 weight % higher oligomers; alternatively, at least 88 weight % higher oligomers; alternatively, at least 89 weight % higher oligomers; alternatively, at least 90 weight % higher oligomers; alternatively, at least 91 weight % higher oligomers; alternatively, at least 92 weight % higher oligomers; alternatively, at least 93 weight % higher oligomers; alternatively, at least 94 weight % higher oligomers; or alternatively, at least 95 weight % higher oligomers. Moreover, any appropriate combination of these heavy oligomer weight percentage features can be utilized to describe a fraction of the heavy oligomer as provided herein. Generally, the weight percent of alpha olefin monomer, dimers, trimers, and higher oligomers of the heavy oligomer product satisfy the formula monomers+dimers+trimers+higher oligomers=100. In some instances, it may be desired only to refer to the heavy oligomer composition in terms of the oligomers and in this instance the weight percent of dimers, trimers, and higher oligomers of the heavy oligomer product satisfy the formula dimers+trimers+higher oligomers=100.

In an aspect, the PAO provided according to this disclosure, can comprise less than 1 weight % hydrogenated alpha olefin monomer; alternatively, less than 0.8 weight % hydrogenated alpha olefin monomer; alternatively, less than 0.6 weight % hydrogenated alpha olefin monomer; alternatively, less than 0.5 weight % hydrogenated alpha olefin monomer; alternatively, less than 0.4 weight % hydrogenated alpha olefin monomer; alternatively, less than 0.3 weight % hydrogenated alpha olefin monomer; alternatively, less than 0.2 weight % hydrogenated alpha olefin monomer; or alternatively, less than 0.1 weight % hydrogenated alpha olefin monomer. In another aspect, the PAO prepared according to this disclosure can comprise less than 10 weight % hydrogenated dimers; alternatively, less than 9 weight % hydrogenated dimers; alternatively, less than 8 weight % hydrogenated dimers; alternatively, less than 7 weight % hydrogenated dimers; alternatively, less than 6 weight % hydrogenated dimers; alternatively, less than 5 weight % hydrogenated dimers; alternatively, less than 4 weight % hydrogenated dimers; alternatively, less than 4.5 hydrogenated dimers; alternatively, less than 3.5 hydrogenated dimers; alternatively, less than 3 weight % hydrogenated dimers; less than 2.5 weight % hydrogenated dimers; alternatively, less than 2 weight % hydrogenated dimers; alternatively, less than 1.75 weight % hydrogenated dimers; alternatively, less than 1.5 weight % hydrogenated dimers; alternatively, less than 1.25 weight % hydrogenated dimers; alternatively, less than 1 weight % hydrogenated dimers; alternatively, less than 0.9 weight % hydrogenated dimers; alternatively, less than 0.8 weight % hydrogenated dimers; alternatively, less than 0.7 weight % hydrogenated dimers; alternatively, less than 0.6 weight % hydrogenated dimers; alternatively, less than 0.5 weight % hydrogenated dimers; alternatively, less than 0.4 weight % hydrogenated dimers; alternatively, less than 0.3 weight % hydrogenated dimers; alternatively, less than 0.2 weight % hydrogenated dimers; or alternatively, less than 0.1 weight % hydrogenated dimers. In another aspect, the PAO according to this disclosure can comprise less than 20 weight % hydrogenated trimers; alternatively, less than 17.5 weight % hydrogenated trimers; alternatively, less than 15 weight % hydrogenated trimers; alternatively, less than 12.5 weight % hydrogenated trimers; alternatively, less than 10 weight % hydrogenated trimers; less than 7.5 weight % hydrogenated trimers; alternatively, less than 5 weight % hydrogenated trimers; alternatively, less than 4 weight % hydrogenated trimers; alternatively, less than 3 weight % hydrogenated trimers; 2 weight % hydrogenated trimers; alternatively, less than 1.75 weight % hydrogenated trimers; alternatively, less than 1.5 weight % hydrogenated trimers; alternatively, less than 1.25 weight % hydrogenated trimers; alternatively, less than 1 weight % hydrogenated trimers; alternatively, less than 0.9 weight % hydrogenated trimers; alternatively, less than 0.8 weight % hydrogenated trimers; alternatively, less than 0.7 weight % hydrogenated trimers; alternatively, less than 0.6 weight % hydrogenated trimers; alternatively, less than 0.5 weight % hydrogenated trimers; alternatively, less than 0.4 weight % hydrogenated trimers; alternatively, less than 0.3 weight % hydrogenated trimers; alternatively, less than 0.2 weight % hydrogenated trimers; or alternatively, less than 0.1 weight % hydrogenated trimers. In a further aspect, the PAO according to this disclosure can comprise at least 80 weight % hydrogenated higher oligomers; at least 82.5 weight % hydrogenated higher oligomers; alternatively, at least 85 weight % hydrogenated higher oligomers; alternatively, at least 86 weight % hydrogenated higher oligomers; alternatively, at least 87 weight % hydrogenated higher oligomers; alternatively, at least 88 weight % hydrogenated higher oligomers; alternatively, at least 89 weight % hydrogenated higher oligomers; alternatively, at least 90 weight % hydrogenated higher oligomers; alternatively, at least 91 weight % hydrogenated higher oligomers; alternatively, at least 92 weight % hydrogenated higher oligomers; alternatively, at least 93 weight % hydrogenated higher oligomers;

alternatively, at least 94 weight % hydrogenated higher oligomers; or alternatively, at least 95 weight % hydrogenated higher oligomers. Moreover, any appropriate combination of these features can be utilized to describe PAO described herein. Generally, the weight percent of hydrogenated alpha olefin monomers, hydrogenated dimers, hydrogenated trimers, and hydrogenated higher oligomers of the PAO satisfy the formula monomer+dimer+trimer+higher oligomer=100. In some instances, it may be desired only to refer to the PAO in terms of the oligomers and in these instances the weight percent of hydrogenated dimers, hydrogenated trimers, and hydrogenated higher oligomers of the PAO satisfy the formula dimers+trimers+higher oligomers=100. When referring the PAO, hydrogenated monomers, hydrogenated dimers, hydrogenated trimers, and hydrogenated higher olefins can also be referenced as saturated monomers, saturated dimers, saturated trimers, and saturated higher oligomers (respectively) and that any number associated with hydrogenated monomers, hydrogenated dimers, hydrogenated trimers, and hydrogenated higher olefins can be applied to the respective saturated alternative.

In an aspect, this disclosure provides that the alpha olefin oligomers, a fraction of the alpha olefin oligomers, the heavy oligomer product, and/or the PAO can have an Mw at least 400; alternatively, at least 500; alternatively, at least 600; alternatively, at least 700; alternatively, at least 800; alternatively, at least 900; alternatively, at least 1,000; alternatively, at least 1,250; alternatively, at least 1,500; alternatively, at least 1,750; alternatively, at least 2,000; alternatively, at least 2,250; alternatively, at least 2,500; alternatively, at least 2,750; alternatively, at least 3,000; alternatively, at least 3,500; alternatively, at least 4,000; alternatively, at least 4,500; alternatively, at least 5,000; alternatively, at least 5,500; alternatively, at least 6,000; alternatively, at least 6,500; alternatively, at least 7,000; alternatively, at least 7,500; alternatively, at least 8,000; alternatively, at least 8,500; alternatively, at least 9,000; alternatively, at least 9,500; alternatively, at least 10,000; alternatively, at least 11,000; alternatively, at least 12,000; alternatively, at least 13,000; alternatively, at least 14,000; alternatively, at least 15,000; alternatively, at least 16,000; alternatively, at least 17,000; alternatively, at least 18,000; alternatively, at least 19,000; alternatively, at least 20,000; alternatively, at least 22,500; alternatively, at least 25,000; or alternatively, at least 30,000. Unless specified otherwise, the alpha olefin oligomers, fraction of the alpha olefin oligomers, and/or the PAOs of this disclosure can have an upper limit of Mw of 60,000; alternatively, 55,000; alternatively, 50,000; alternatively, 47,500; alternatively, 45,000; alternatively, 42,500; alternatively, 40,000; alternatively, 37,500; alternatively, 35,000; alternatively, 32,500; alternatively, 30,000; alternatively, 27,500; alternatively, 25,000; alternatively, 22,500; alternatively, 20,000; alternatively, 19,000; alternatively, 18,000; alternatively, 17,000; alternatively, 16,000; alternatively, 15,000; alternatively, 14,000; alternatively, 13,000; alternatively, 12,000; alternatively, 11,000; alternatively, 10,000; alternatively, 9,000; alternatively, 8,500; alternatively, 8,000; alternatively, 7,500; alternatively, 7,000; alternatively, 6,500; alternatively, 6,000; alternatively, 5,500; alternatively, 5,000; alternatively, 4,500; alternatively, 4,000; alternatively, 3,000; alternatively, 2,750; alternatively, 2,500; alternatively, 2,000; alternatively, 1,750; alternatively, 1,500; alternatively, 1,250; alternatively, 1,000. In an aspect, the alpha olefin oligomers, a fraction of the alpha olefin oligomers, the heavy oligomer product, and/or the PAOs of this disclosure can have Mw ranging from any lower PAO Mw disclosed herein to any maximum PAO Mw disclosed herein. In a non-limiting embodiments, the alpha olefin oligomers, a fraction of the alpha olefin oligomers, the heavy oligomer product, and/or the PAO of this disclosure can have an Mw ranging from 1,500 to 15,000; alternatively, ranging from 2,000 to 12,500; or alternatively, 2,500 to 10,000. In some non-limiting embodiments, a PAO of this disclosure can have an Mw ranging from 2,000 to 4,500; alternatively, ranging from 2,500 to 4,000; or alternatively, 2,750 to 3,750. In other non-limiting embodiments, a PAO of this disclosure can have an Mw ranging from 3,500 to 6,000; alternatively, ranging from 4,000 to 5,500; alternatively, 4,250 to 5,250.

In an aspect, this disclosure provides that the alpha olefin oligomers, a fraction of the alpha olefin oligomers, the heavy oligomer product, and/or the PAO can have an Mn at least 400; alternatively, at least 500; alternatively, at least 600; alternatively, at least 700; alternatively, at least 800; alternatively, at least 900; alternatively, at least 1,000; alternatively, at least 1,250; alternatively, at least 1,500; alternatively, at least 1,750; alternatively, at least 2,000; alternatively, at least 2,250; alternatively, at least 2,500; alternatively, at least 2,750; alternatively, at least 3,000; alternatively, at least 3,500; alternatively, at least 4,000; alternatively, at least 4,500; alternatively, at least 5,000; alternatively, at least 5,500; alternatively, at least 6,000; alternatively, at least 6,500; alternatively, at least 7,000; alternatively, at least 7,500; alternatively, at least 8,000; alternatively, at least 8,500; alternatively, at least 9,000; alternatively, at least 9,500; alternatively, at least 10,000; alternatively, at least 11,000; alternatively, at least 12,000; alternatively, at least 13,000; alternatively, at least 14,000; alternatively, at least 15,000; alternatively, at least 16,000; alternatively, at least 17,000; alternatively, at least 18,000; alternatively, at least 19,000; alternatively, at least 20,000; alternatively, at least 22,500; alternatively, at least 25,000; or alternatively, at least 30,000. Unless specified otherwise, the alpha olefin oligomers, fraction of the alpha olefin oligomers, and/or the PAOs of this disclosure can have an upper limit of Mn of 60,000; alternatively, 55,000; alternatively, 50,000; alternatively, 47,500; alternatively, 45,000; alternatively, 42,500; alternatively, 40,000; alternatively, 37,500; alternatively, 35,000; alternatively, 32,500; alternatively, 30,000; alternatively, 27,500; alternatively, 25,000; alternatively, 22,500; alternatively, 20,000; alternatively, 19,000; alternatively, 18,000; alternatively, 17,000; alternatively, 16,000; alternatively, 15,000; alternatively, 14,000; alternatively, 13,000; alternatively, 12,000; alternatively, 11,000; alternatively, 10,000; alternatively, 9,000; alternatively, 8,500; alternatively, 8,000; alternatively, 7,500; alternatively, 7,000; alternatively, 6,500; alternatively, 6,000; alternatively, 5,500; alternatively, 5,000; alternatively, 4,500; alternatively, 4,000; alternatively, 3,000; alternatively, 2,750; alternatively, 2,500; alternatively, 2,000; alternatively, 1,750; alternatively, 1,500; alternatively, 1,250; alternatively, 1,000. In an aspect, the alpha olefin oligomers, a fraction of the alpha olefin oligomers, the heavy oligomer product, and/or the PAOs of this disclosure can have Mw ranging from any lower PAO Mn disclosed herein to any maximum PAO Mw disclosed herein. In a non-limiting embodiments, the alpha olefin oligomers, a fraction of the alpha olefin oligomers, the heavy oligomer product, and/or the PAO of this disclosure can have an Mw ranging from 1,500 to 15,000; alternatively, ranging from 2,000 to 12,500; or alternatively, 2,500 to 10,000. In some non-limiting embodiments, a PAO of this disclosure can have a Mn ranging from 2,000 to 4,500; alternatively, ranging from 2,500 to 4,000; or alternatively, 2,750 to 3,750. In other non-limiting embodiments, a PAO of this disclosure have a Mn ranging from 3,500 to 6,000; alternatively, ranging from 4,000 to 5,500; alternatively, 4,250 to 5,250.

The methods described here have the ability to produce alpha olefin oligomers, fraction of alpha olefin oligomers, heavy oligomer product, and/or PAO having a wide range of 100° C. kinematic viscosities and/or 40° C. kinematic viscosities. For example, materials having 100° C. kinematic viscosities over 1,000 cSt, are accessible using the catalyst systems and/or methods provided herein. In an aspect of this disclosure provides that the alpha olefin oligomers, a fraction of the alpha olefin oligomer, heavy oligomer product, and/or the PAO can have a 100° C. kinematic viscosity of at least 15 cSt; alternatively, at least 20 cSt; alternatively, at least 25 cSt; alternatively, at least 35 cSt; alternatively, at least 45 cSt; alternatively, at least 55 cSt; alternatively, at least 65 cSt; alternatively, at least 75 cSt; alternatively, at least 85 cSt; alternatively, at least 95 cSt; alternatively, at least 105 cSt; alternatively, at least 115 cSt; alternatively, at least 125 cSt; alternatively, at least 135 cSt; alternatively, at least 145 cSt; alternatively, at least 155 cSt; alternatively, at least 165 cSt; alternatively; alternatively, at least 175 cSt; alternatively, at least 200 cSt; alternatively, alternatively, at least 225 cSt; alternatively, at least 250 cSt; alternatively, at least 270 cSt; alternatively, at least 300 cSt; alternatively, at least 350 cSt; alternatively, at least 400 cSt; alternatively, at least 500 cSt; alternatively, at least 600 cSt; alternatively, at least 700 cSt; alternatively, at least 800 cSt; alternatively, at least 900 cSt; alternatively, at least 1000 cSt; alternatively, at least 1100 cSt; or alternatively, at least 1200 cSt. In an aspect of this disclosure provides that the alpha olefin oligomers, a fraction of the alpha olefin oligomer, heavy oligomer product, and/or the PAO can have a 40° C. kinematic viscosity of at least 120 cSt; alternatively, at least 130 cSt; alternatively, at least 140 cSt; alternatively, at least 150 cSt; alternatively, at least 160 cSt; alternatively, at least 170 cSt; alternatively, at least 180 cSt; alternatively, at least 190 cSt; alternatively, at least 200 cSt; alternatively, at least 225 cSt; alternatively, at least 250 cSt; alternatively, at least 270 cSt; alternatively, at least 300 cSt; alternatively, at least 350 cSt; alternatively, at least 400 cSt; alternatively, at least 500 cSt; alternatively, at least 600 cSt; alternatively, at least 700 cSt; alternatively, at least 800 cSt; alternatively, at least 900 cSt; alternatively, at least 1000 cSt; alternatively, at least 1100 cSt; alternatively, at least 1200 cSt; alternatively, at least 1300 cSt; alternatively, at least 1400 cSt; alternatively, at least 1500 cSt; alternatively, at least 1600 cSt; alternatively, at least 1700 cSt; alternatively, at least 1800 cSt; alternatively, at least 1900 cSt; or alternatively, at least 2000 cSt. In some embodiments, alpha olefin oligomers, a fraction of the alpha olefin oligomer, heavy oligomer product, and/or the PAO can have a 100° C. kinematic viscosity from 15 to 1,500, alternatively, from 15 to 1,250; alternatively, from 15 to 1,000; alternatively, from 15 to 750; alternatively, from 15 to 500; alternatively, 15 cSt to 250 cSt; alternatively, from 20 cSt to 225 cSt; alternatively, from 25 cSt to 55 cSt; alternatively, from 30 cSt to 50 cSt; alternatively, from 32 cSt and 48 cSt; alternatively, from 35 cSt to 45 cSt; alternatively, from 40 cSt to 80 cSt; alternatively, from 45 cSt to 75 cSt; alternatively, from 50 cSt and 70 cSt; alternatively, from 60 cSt to 100 cSt; alternatively, from 65 cSt to 95 cSt; alternatively, from 70 cSt and 90 cSt; alternatively, from 80 cSt to 140 cSt; alternatively, from 80 cSt to 120 cSt; alternatively, from 85 cSt to 115 cSt; alternatively, from 90 cSt and 110 cSt; alternatively, from 100 cSt to 140 cSt; alternatively, from 105 cSt to 135 cSt; alternatively, from 110 cSt and 130 cSt; alternatively, from 120 cSt to 180 cSt; alternatively, from 130 cSt to 170 cSt; alternatively, from 140 cSt and 160 cSt; alternatively, from 150 cSt to 210 cSt; alternatively, from 160 cSt to 200 cSt; alternatively, from 150 cSt and 190 cSt; alternatively, from 180 cSt to 240 cSt; alternatively, from 190 cSt to 230 cSt; alternatively, from 200 cSt and 220 cSt; alternatively, from 200 cSt to 300 cSt; alternatively, from 220 cSt to 280 cSt; alternatively, from 235 to 265; alternatively, from 250 cSt to 350 cSt; alternatively, from 270 cSt to 330 cSt; alternatively, 285 cSt to 315 cSt; alternatively, from 300 cSt to 400 cSt; alternatively, from 320 cSt to 380 cSt; alternatively, from 335 cSt to 365 cSt; alternatively, from 350 cSt to 450 cSt; alternatively, from 370 cSt to 430 cSt; alternatively, 385 cSt to 415 cSt; alternatively, from 400 cSt to 500 cSt; alternatively, from 420 cSt to 480 cSt; alternatively, from 435 cSt to 465 cSt; alternatively, from 450 cSt to 550 cSt; alternatively, from 470 cSt to 530 cSt; alternatively, 485 cSt to 515 cSt; alternatively, from 500 cSt to 700 cSt; alternatively, from 540 cSt to 660 cSt; alternatively, from 570 cSt to 630 cSt; alternatively, from 600 cSt to 800 cSt; alternatively, from 640 cSt to 760 cSt; alternatively, 670 cSt to 740 cSt; alternatively, from 700 cSt to 900 cSt; alternatively, from 740 cSt to 860 cSt; alternatively, from 770 cSt to 830 cSt; alternatively, from 800 cSt to 1,000 cSt; alternatively, from 840 cSt to 960 cSt; alternatively, 870 cSt to 940 cSt; alternatively, from 900 cSt to 1,100 cSt; alternatively, from 940 cSt to 1,060 cSt; or alternatively, from 970 cSt to 1,030 cSt. In some embodiments, alpha olefin oligomers, a fraction of the alpha olefin oligomer, heavy oligomer product, and/or the PAO can have a 40° C. kinematic viscosity from 120 cSt to 2000 cSt. Alternatively, and in any embodiment described herein, the polyalphaolefins prepared by this disclosure can have a 40° C. kinematic viscosity from 150 cSt to 1750 cSt; or alternatively, from 200 cSt to 1500 cSt.

Yet another aspect of this disclosure provides that the alpha olefin oligomers, a fraction of the alpha olefin oligomer, heavy oligomer product, and/or the PAO can have a viscosity index greater than 150; alternatively, greater than 155; alternatively, greater than 160; alternatively, greater than 165; alternatively, greater than 170; alternatively, greater than 175; alternatively, greater than 180; alternatively, greater than 185; alternatively, greater than 190; or alternatively, greater than 200. In a further aspect, this disclosure the alpha olefin oligomers, a fraction of the alpha olefin oligomer, heavy oligomer product, and/or the PAO can have a viscosity index from 150 to 260; alternatively, from 155 to 245; alternatively, from 160 to 230; or alternatively, 165 to 220.

According to still another aspect, this disclosure provides that the alpha olefin oligomers, a fraction of the alpha olefin oligomer, heavy oligomer product, and/or the PAO can have a pour point less than 0° C.; alternatively, less than −10° C.; alternatively, less than −20° C.; alternatively, less than −30° C.; alternatively, less than −35° C.; alternatively, less than −40° C.; alternatively, less than −45° C.; alternatively, less than −50° C.; or alternatively, less than −55° C. Further, the alpha olefin oligomers, a fraction of the alpha olefin oligomer, heavy oligomer product, and/or the PAO according to this disclosure can have a pour point from 0° C. to −100° C.; alternatively, from −10° C. to −95° C.; alternatively, from −20° C. to −90° C.; alternatively, from −30° C. to −90° C.; alternatively, from −35° C. to −90° C.; alternatively, from −40° C. to −90° C.; alternatively, from −45° C. to −90° C.; alternatively, from −50° C. to −85° C.; or alternatively, from −55° C. to −80° C.

In an embodiment, this disclosure provides that the alpha olefin oligomers, a fraction of the alpha olefin oligomer, heavy oligomer product, and/or the PAO can have a flash point greater than 200° C.; alternatively, greater than 225° C.; alternatively, greater than 250° C.; or alternatively, greater than 275° C. In some embodiments, this disclosure provides that the alpha olefin oligomers, a fraction of the alpha olefin oligomer, heavy oligomer product, and/or the PAO can have a fire point greater than 200° C.; alternatively, greater than 225° C.; alternatively, greater than 250° C.; or alternatively, greater than 275° C. In other embodiments, the alpha olefin oligomers, a fraction of the alpha olefin oligomer, heavy oligomer product, and/or the PAO can have a Noack volatility less than 8 weight %; alternatively, less than 8 weight %; alternatively, less than 7 weight %; alternatively, less than 6 weight %; alternatively, less than 5 weight %; alternatively, less than 4.5 weight %; alternatively, less than 4 weight %; alternatively, less than 3.5 weight %; alternatively, less than 3 weight %; alternatively, less than 2.5 weight %; alternatively, less than 2 weight %; alternatively, less than 1.5 weight %; or alternatively, less than 1 weight %.

In an aspect, the oligomerization methods described herein can produce alpha olefin oligomers by reacting the alpha olefin monomers in a predominately stereoregular head-to-tail fashion. In some embodiments, the alpha olefin oligomers, any fraction of the alpha olefin oligomers (e.g. the heavy oligomer product), and/or PAO comprises, or alternatively consists essentially of, head-to-tail oligomers. In any aspect or disclosed embodiment, the alpha olefin oligomers, any fraction of the alpha olefin oligomers, heavy oligomer product, and/or the PAO can comprise head-to-tail oligomers, wherein there are less than 100 errors per 1000 alpha olefin monomers; alternatively, less than 80 errors per 1000 alpha olefin monomers; alternatively, less than 60 errors per 1000 alpha olefin monomers; or alternatively, less than 40 errors per 1000 alpha olefin monomers. Generally, the number of errors (non-head-to-tail additions) can be determined by relative $^1$H NMR or $^{13}$C NMR peak intensities.

The polyalphaolefin described herein can have advantageous properties relating to it oxidative stability. One test for oxidative stability is the RPVOT test as measured by ASTM D2272. In an aspect, the polyalphaolefin can have a RPVOT as measured by ASTM D2272 in the presence of 0.5 weight % of Naugalube® APAN antioxidant of at least 2,000 minutes; alternatively, 2,100 minutes; alternatively, 2,150 minutes; alternatively, 2,200 minutes; alternatively, 2,250 minutes; alternatively, 2,300 minutes; alternatively, 2,400 minutes; alternatively, 2,500 minutes; alternatively, 2,750 minutes; or alternatively, 3,000 minutes.

In still a further aspect and in any of the embodiments disclosed herein, this disclosure provides that the polyalphaolefin can be described by tacticity according to the percentage of mr (heterotactic) triads, mm (isotactic) triads, and/or rr (syndiotactic) triads present in the PAO. In an aspect, the PAO can have a percentage of mr (heterotactic) triads between 20% and 70%; alternatively, between 25% and 65%; alternatively, between 30% and 60%; alternatively, between 35% and 55%; or alternatively, between 40% and 50%. In another aspect, the PAO can have a percentage of mm (isotactic) triads between 10% and 55%; alternatively, between 15% and 50%; alternatively, between 20% and 45%; or alternatively, between 25% and 45%. In another aspect, the PAO can have a percentage of mm (isotactic) triads between 25% and 60%, as determined by relative $^1$H NMR or $^{13}$C NMR peak intensities; alternatively, between 30% and 55%; alternatively, between 32% and 50%; alternatively, between 35% and 48%; or alternatively, between 38% and 45%. In another aspect, the PAO can have a percentage of rr (syndiotactic) triads between 5% and 40%; alternatively, between 7.5% and 35%; alternatively, between 10% and 30%; or alternatively, between 12.5% and 25%. In another aspect, the PAO can have a percentage of rr (syndiotactic) triads between 2% and 35%, as determined by relative $^1$H NMR or $^{13}$C NMR peak intensities; alternatively, between 5% and 30%; alternatively, between 8% and 25%; alternatively, between 10% and 20%; or alternatively, between 12% and 18%. Generally, the percentage of triads satisfy the formula mm triads+mr triads+rr triad=100. Generally, the percentage of mm triads, mr triads and rr triads can be determined using $^1$H NMR or $^{13}$C NMR peak intensities as described by per Il Kim, Jia-Min Zhou and Hoeil Chung, "Higher α-Olefin Polymerization by Zr Complex", J. of *Polymer Science Part A: Polymer Chemistry*, Vol. 38, 1687-1697 (2000).

One useful measure of oligomer tacticity is the Bernoulli index (B), which is defined as $B=4[mm][rr]/[mr]^2$, where [mm], [rr], and [mr] represent the percentage of isotactic triads, syndiotactic triads, and heterotactic triads, respectively. In this aspect and in any of the embodiments disclosed herein, this disclosure PAO can have a Bernoulli index less than 3; alternatively, less than 2.5; alternatively, less than 2; alternatively, less than 1.75; alternatively, less than 1.7; alternatively, less than 1.65; alternatively, less than 1.6; alternatively, less than 1.55; alternatively, less than 1.5; alternatively, less than 1.45; alternatively, less than 1.4; alternatively, less than 1.35; alternatively, less than 1.3; alternatively, less than 1.25; alternatively, less than 1.25; or alternatively, less than 1.15. According to still another aspect, this disclosure provides this polyalphaolefin can have a Bernoulli index within a range of 1.4±0.25; alternatively, 1.4±0.2; alternatively, within a range of 1.4±0.15; alternatively, within a range of 1.4±0.10; alternatively, within a range of 1.3±0.3; alternatively, within a range of 1.3±0.25; alternatively, within a range of 1.3±0.2; alternatively, within a range of 1.3±0.15; alternatively, within a range of 1.4±0.1; alternatively, within a range of 1.2±0.35; alternatively, within a range of 1.2±0.3; alternatively, within a range of 1.2±0.25; alternatively, within a range of 1.2±0.2; alternatively, within a range of 1.2±0.15; alternatively, within a range of 1.1±0.40; alternatively, within a range of 1.1±0.3; alternatively, within a range of 1.1±0.2; or alternatively, within a range of 1.1±0.15. Further, any combinations of the individual features described here can be provided in the PAO prepared as described herein. Moreover, the polyalphaolefin disclosed in any embodiment can have a shear stability as a reduction in viscosity of less than 1 percent, as determined according to ASTM D6278-07. Alternatively, the polyalphaolefins prepared according to this disclosure can also have a shear stability as a reduction in viscosity of less than 0.75 percent; alternatively, less than 0.5; or alternatively, less than 0.25.

In further characterization, the polyalphaolefin disclosed in any embodiment herein can have a polydispersity index (PDI) from 1.4 to 3, as determined from Mn and Mw obtained from gel permeation chromatography. Alternatively, the polyalphaolefins prepared according to this disclosure can also have a polydispersity index (PDI) from 1.5 to 2.8; alternatively, a polydispersity index of from 1.6 to 2.6; alternatively, a polydispersity index of from 1.7 to 2.5; alternatively, a polydispersity index of from 1.8 to 2.3; or alternatively, a polydispersity index of from 1.9 to 2.1.

In another embodiment, the PAO can have the feature of having an absence of a discernable crystallization. Generally, a discernable crystallization" is determined by thermal analysis using a differential scanning calorimeter (DSC) as described herein. In yet another embodiment, the PAO can have the feature of having an absence of a discernable crystallization above −40° C. as determined differential scanning calorimetry using ASTM D 3418.

As described herein, the PAO can be described using any combination of the alpha olefin monomer utilized to form the PAO, the amount of alpha olefin monomer units found in the PAO, the amount of hydrogenated monomer found in the PAO, quantity of hydrogenated dimers in the PAO, the quantity of hydrogenated trimers found in the PAO, the quantity of the hydrogenated higher oligomers found in the PAO, Mw, Mn, a 100° C. kinematic viscosity, a 40° C. kinematic viscosity, viscosity index, pour point, RPVOT test result, errors in head-to-tail addition, tacticity, Bernoulli index, a shear stability as measured by ASTM D6278-07, polydispersity index, and/or the presence or absence of a discernable crystallization. In a non-limiting embodiment, this disclosure provides a PAO produced from an alpha olefin monomer comprising a $C_4$ to $C_{20}$ normal alpha olefin, the PAO comprising: a) less than 1 weight % hydrogenated alpha olefin monomer, b) less than 3 weight % hydrogenated dimers, and c) greater than 80 weight % hydrogenated higher oligomers; and having i) a 100° C. kinematic viscosity of at least 15 cSt, ii) a viscosity index greater than 150, and iii) a pour point less than 0° C. Other embodiments of the PAO are readily discerned based upon the present disclosure.

In another non-limiting aspect, this disclosure provides for a PAO produced from an alpha olefin monomer consisting essentially of a $C_8$ normal alpha olefin, the PAO comprising a) less than 0.4 weight % hydrogenated alpha olefin monomer, b) less than 1.5 weight % hydrogenated dimers, and c) greater than 88 weight % hydrogenated higher oligomers; and having i) a 100° C. kinematic viscosity from 30 cSt to 50 cSt, ii) a viscosity index from 150 to 260, and iii) a pour point less than −30° C. In some embodiments, polyalphaolefin can have a RPVOT as measured by ASTM D2272 in the presence of 0.5 weight % of Naugalube® APAN antioxidant of at least 2,100 minutes. In other embodiments, the polyalphaolefin also can be further characterized by having a Bernoulli index less than 1.65; or alternatively, within a range of 1.4±0.25. In yet other embodiments, this PAO can be characterized as having no discernable crystallization as determined differential scanning calorimetry using ASTM D 3418. Other embodiments of the PAO are readily discerned based upon the present disclosure.

In yet another non-limiting embodiment, this disclosure provides for a PAO produced from an alpha olefin monomer consisting essentially of a $C_8$ normal alpha olefin, the PAO comprising a) less than 0.5 weight % hydrogenated alpha olefin monomer, b) less than 1 weight % hydrogenated dimers, and c) greater than 88 weight % hydrogenated higher oligomers; and having i) a 100° C. kinematic viscosity from 80 cSt to 140 cSt, ii) a viscosity index from 150 to 260, and iii) a pour point less than −30° C. In some embodiment, the polyalphaolefin can have a RPVOT as measured by ASTM D2272 in the presence of 0.5 weight % of Naugalube® APAN antioxidant of at least 2,000 minutes. In other embodiments, the polyalphaolefin can have a Bernoulli index less than 3; or alternatively, 1.1±0.4. In yet another embodiment, the PAO can have no discernable crystallization as determined differential scanning calorimetry using ASTM D 3418. Other embodiments of the PAO are readily discerned based upon the present disclosure.

In an embodiment, the alpha olefin oligomers can be an alpha olefin oligomer produced by any alpha olefin oligomer production method described herein. In some embodiments, the heavy oligomer product can be a heavy oligomer product produced by any heavy oligomer production method described herein. In yet another embodiment, the PAO can be a PAO produced by any PAO production method described herein.

Lubricant Compositions

This disclosure also provides new synthetic lubricants comprising a PAO as described herein, and/or prepared according to the method described in this disclosure. The PAOs described herein and/or produced according to the methods of this disclosure can also have utility in lubricant compositions and as viscosity modifiers. The PAOs described herein and/or produced according to the methods can be used as sole base oil or utilized in combination with another base oil (for example, a mineral oil and/or another polyalphaolefin). The lubricant compositions utilizing the PAOs described herein and/or produced according to the methods of this disclosure can be utilized in combination with various additives. The lubricant composition or viscosity modifier can consist essentially of the PAO described herein and/or produced according to the methods of this disclosure without additives. Alternatively, the lubricant composition or viscosity modifier can comprise any PAO described herein and/or produced according to the methods and any additive described herein. Additives that can be utilized with any PAO described herein include, but are not limited to, metal deactivators, detergents, dispersants, antioxidants, and the like.

While not intending to be bound by theory, in some aspects, the PAOs prepared according to this disclosure can be characterized as having a high viscosity index combined with a relatively low pour point among other properties. These features can have particular utility in lubricant compositions and are desirable for viscosity modifiers. In this aspect, any of the PAO described herein and/or PAOs prepared according to this disclosure can be used as a base oil in a lubricant composition or as a viscosity modifier. In an embodiment, the PAO described herein and/or PAOs prepared according to this disclosure can be utilized as the sole base oil or in mixture with other base oils. In an embodiment, the PAO described herein and/or PAOs prepared according to this disclosure can be utilized combination with various additives. For example, any PAO described herein and/or PAOs prepared according to this disclosure can be used as a base oil in a lubricant composition or a viscosity modifier; alternatively, used as a base oil in a lubricant composition; or alternatively, used as a viscosity modifier. In an embodiment, the lubricant composition or viscosity modifier composition can comprise any PAO described herein and/or PAOs prepared according to this disclosure and at least one additive. In an embodiment, the at least one additive can be a metal deactivator, a detergent, a dispersant (e.g. borated or non-borated dispersant), a viscosity index improver, a viscosity modifier, an antioxidant, a corrosion inhibitor, a pour point depressant, a seal swelling agent, a demulsifier, an antifoam agent, a polysulfide component, an oil of lubricating viscosity, a phosphorus-containing acid, a phosphorus-containing salt, a phosphorus-containing ester, or any combination thereof.

In some embodiments, metal deactivators which can be utilized include, but are not limited to, derivatives of benzotriazoles ("benzotriazole-based compounds"), 1,2,4-triazoles, benzimidazoles, 2-alkyldithiobenzimidazoles, 2-alkyldithiobenzothiazoles, 2-(N,N-dialkyldithiocarbamoyl) benzothiazoles, 2,5-bis(alkyl-dithio)-1,3,4-thiadiazoles, 2,5-bis(N,N-dialkyldithiocarbamoyl)-1,3,4-thiadiazoles, 2-alkyldithio-5-mercapto thiadiazoles, and any combinations thereof. For example, in one aspect the metal deactivator is a derivative of benzotriazole. In one embodiment the metal deactivator is a 2,5-bis(alkyl-dithio)-3,4-thiadiazole. The metal deactivator can be used alone or in combination with other metal deactivators in the lubricant compositions. Hydrocarbyl derivatives of benzotriazole can contain hydrocarbyl substitutions any of the substitutable ring positions, for example, at the 1-, 4-, 5-, 6-, or 7-positions, or combinations of these positions for multiple substituents. The hydrocarbyl groups typically are $C_1$ to $C_{30}$ hydrocarbyl groups; alternatively, $C_1$ to $C_{15}$ hydrocarbyl groups; alternatively, $C_1$ to $C_{10}$ hydrocarbyl groups; or alternatively, $C_1$ to $C_7$ hydrocarbyl groups. Hydrocarbyl groups are described herein and may be utilized without limitation to further described the derivatives of benzotriazole containing hydrocarbyl groups. In one embodiment the metal deactivator is tolyltriazole. In one aspect, suitable metal deactivators that are useful in the lubricant compositions of this disclosure are provided in U.S. Patent Application Publication Number 20040259743, which is incorporated herein by reference in pertinent part.

In an embodiments, a suitable metal deactivators can be, but is not limited to, a 2,5-bis(alkyl-dithio)-1,3,4-thiadiazole. The alkyl groups of 2,5-bis(alkyl-dithio)-1,3,4-thiadiazole can be $C_1$ to $C_{30}$ alkyl groups; alternatively, $C_2$ to $C_{25}$ alkyl groups; alternatively, $C_3$ to $C_{20}$ alkyl groups; or alternatively, $C_4$ to $C_{15}$ alkyl groups. Alkyl groups are described herein and may be utilized without limitation to further describe the 2,5-bis(alkyl-dithio)-1,3,4-thiadiazoles. In some embodiments, the 2,5-bis(alkyl-dithio)-1,3,4-thiadiazole can be, but is not limited to, 2,5-bis(tert-octyldithio)-1,3,4-thiadiazole 2,5-bis(tert-nonyldithio)-1,3-,4-thiadiazole, 2,5-bis(tert-decyldithio)-1,3,4-thiadiazole, 2,5-bis(tert-undecyldithio)-1,3,4-thiadiazole, 2,5-bis(tert-dodecyldithio)-1,3,4-thiadiazole, 2,5-bis(tert-tridecyldithio)-1,3,4-thiadiazole, 2,5-bis(tert-tetradecyldithio)-1,3,4-thiadiazole, 2,5-bis(tert-pentadecyldithio)-1,3,4-thiadiazole, 2,5-bis(tert-hexadecyldithio)-1,3,4-thiadiazole-, 2,5-bis(tert-heptadecyldithio)-1,3,4-thiadiazole, 2,5-bis(tert-octadecyldithio)-1,3,4-thiadiazole, 2,5-bis(tert-nonadecyldi-thio)-1,3,4-thiadiazole, 2,5-bis(tert-eicosyldithio)-1,3,4-thiadiazole, and mixtures thereof. In other embodiments, the metal deactivator can be 2,5-bis(tert-nonyldithio)-1,3,4-thiadiazole. The metal deactivator can be present in the composition in the range from 0.0001 to 5 weight percent of the lubricant composition; alternatively, from 0.0003 to 1.5 weight percent of the lubricant composition; alternatively, from 0.0005 to 0.5 weight percent of the lubricant composition; or alternatively, from 0.001 to 0.2 weight percent of the lubricant composition. Also by way of example, other suitable metal deactivators include but are not limited to, gallic acid ester-based compounds. In one aspect, for example, the metal deactivator can be benzotriazole, tolyltriazole, or a combination thereof. In another aspect, a suitable metal deactivator is IRGAMET™ 39, manufactured by Ciba Specialty Chemicals Corporation.

Detergents that can be used in the subject lubricant compositions include but are not limited to, metal-containing (or "metallic") detergents. Metallic detergents can include an oil-soluble neutral or overbased salt of alkali or alkaline earth metal with one or more of the following acidic substances (or any combinations thereof): (1) a sulfonic acid, (2) a carboxylic acid, (3) a salicylic acid, (4) an alkyl phenol, (5) a sulfurized alkyl phenol, and (6) an organic phosphorus acid characterized by at least one direct carbon-to-phosphorus linkage. Organic phosphorus acids can include those prepared by the treatment of an olefin polymer (e.g., polyisobutylene having a molecular weight of around 1,000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. In a further aspect, detergents that can be used in the lubricant compositions of this disclosure include oil-soluble neutral and overbased sulfonates, phenates, sulfurized phenates, thiophosphonates, salicylates, and naphthenates and other oil-soluble carboxylates of a metal, particularly the alkali or alkaline earth metals; alternatively, an alkali earth metal; or alternatively, an alkaline earth metal. In some embodiments, the metal can be lithium, sodium, potassium, magnesium, calcium, or barium; alternatively, lithium, sodium, or potassium; alternatively, magnesium, calcium, or barium; alternatively, lithium; alternatively, sodium; alternatively, potassium; alternatively, magnesium; alternatively, calcium; or alternatively, barium.

In an aspect, any detergent utilized in a lubricant composition or viscosity modifier composition including any PAO described herein and/or PAOs prepared according to this disclosure can be an alkali metal detergent, an alkaline earth metal detergent, an overbased detergent containing a metal compound of Mg, Be, Sr, Na, Ca and K, or any combination thereof; alternatively, an alkali earth metal detergent; alternatively, an alkaline earth metal detergent; or alternatively, an overbased detergent containing a metal compound of Mg, Be, Sr, Na, Ca and K. In some embodiments, the detergent can comprise an overbased calcium detergent. In some embodiments, any detergent utilized in a lubricant composition or viscosity modifier composition including any PAO described herein and/or PAOs prepared according to this disclosure can be a phenate, a carboxylate, a sulfonate, a salicylate, a salixarate, a calixarate, a saliginen, or any combination thereof.

As used in connection with metallic detergents, the term "overbased" is used to designate metal salts in which the metal is present in stoichiometrically larger amounts than the organic radical. The commonly employed methods for preparing the overbased salts involve heating a mineral oil solution of an acid with a stoichiometric excess of a metal neutralizing agent such as the metal oxide, hydroxide, carbonate, bicarbonate, or sulfide, and filtering the resultant product. The use of a "promoter" in the neutralization step to aid the incorporation of a large excess of metal likewise is known. Examples of compounds useful as the promoter include phenolic substances (e.g. phenol, naphthol, alkyl phenol, thiophenol, sulfurized alkylphenol, and condensation products of formaldehyde with a phenolic substance), alcohols (e.g. methanol, 2-propanol, octanol, 2-ethoxyethanol, diethylene glycol ethyl ether, ethylene glycol, stearyl alcohol, and cyclohexyl alcohol), and amines (e.g. aniline, phenylene diamine, phenothiazine, phenyl-beta-naphthylamine, and dodecylamine). For example, one method for preparing the basic salts comprises mixing an acid with an excess of a basic alkaline earth metal neutralizing agent and at least one alcohol promoter, and carbonating the mixture at an elevated temperature such as 60° C. to 200° C.

Examples of suitable metal-containing detergents include, but are not limited to, neutral and overbased salts of such substances as neutral sodium sulfonate, an overbased sodium sulfonate, a sodium carboxylate, a sodium salicylate, a sodium phenate, a sulfurized sodium phenate, a lithium sulfonate, a lithium carboxylate, a lithium salicylate, a lithium phenate, a sulfurized lithium phenate, a calcium sulfonate, a calcium carboxylate, a calcium salicylate, a calcium phenate, a sulfurized calcium phenate, a magnesium sulfonate, a magnesium carboxylate, a magnesium salicylate, a magnesium phenate, a sulfurized magnesium phenate, a potassium sulfonate, a potassium carboxylate, a potassium salicylate, a potassium phenate, a sulfurized potassium phenate, a zinc sulfonate, a zinc carboxylate, a zinc salicylate, a zinc phenate, and a sulfurized zinc phenate. Further examples include a calcium, lithium, sodium, potassium, and magnesium salt of a hydrolyzed phosphosulfurized olefin having 10 to 2,000 carbon atoms or of a hydrolyzed phosphosulfurized alcohol and/or an aliphatic-substituted phenolic compound having 10 to 2,000 carbon atoms. Even further examples include a calcium, lithium, sodium, potassium, and magnesium salt of an aliphatic carboxylic acid and an aliphatic substituted cycloaliphatic carboxylic acid and many other similar alkali and alkaline earth metal salts of oil-soluble organic acids. A mixture of a neutral or an overbased salt of two or more different alkali and/or alkaline earth metals can be used. Likewise, a neutral and/or an overbased salt of mixtures of two or more different acids can also be used.

As is well known, overbased metal detergents are generally regarded as containing overbasing quantities of inorganic bases, generally in the form of micro dispersions or colloidal suspensions. Thus the term "oil-soluble" as applied to metallic detergents is intended to include metal detergents wherein inorganic bases are present that are not necessarily completely or truly oil-soluble in the strict sense of the term, inasmuch as such detergents when mixed into base oils behave much the same way as if they were fully and totally dissolved in the oil. Collectively, the various metallic detergents referred to herein above, are sometimes called neutral, basic, or overbased alkali metal or alkaline earth metal-containing organic acid salts.

Oil-soluble neutral and overbased metallic detergents and alkaline earth metal-containing detergents and the methods for the production are described in U.S. Pat. Nos. 2,001,108, 2,081,075, 2,095,538, 2,144,078, 2,163,622, 2,270,183, 2,292,205, 2,335,017, 2,399,877, 2,416,281, 2,451,345, 2,451,346, 2,485,861, 2,501,731, 2,501,732, 2,585,520, 2,671,758, 2,616,904, 2,616,905, 2,616,906, 2,616,911, 2,616,924, 2,616,925, 2,617,049, 2,695,910, 3,178,368, 3,367,867, 3,496,105, 3,629,109, 3,865,737, 3,907,691, 4,100,085, 4,129,589, 4,137,184, 4,184,740, 4,212,752, 4,617,135, 4,647,387, and 4,880,550, among other patents.

The metallic detergents utilized in this disclosure can, if desired, be oil-soluble boronated neutral and/or overbased alkali of alkaline earth metal-containing detergents. Methods for preparing boronated metallic detergents are described in U.S. Pat. Nos. 3,480,548, 3,679,584, 3,829,381, 3,909,691, 4,965,003, and 4,965,004, among other patents. Additional detergents generally useful in the lubricant formulation also include "hybrid" detergents formed with mixed surfactant systems, e.g., phenate/salicylates, sulfonate/phenates, sulfonate/salicylates, sulfonates/phenates/salicylates, as described in U.S. Pat. Nos. 6,153,565, 6,281,179, 6,429,178, and 6,429,179, among other patents.

The detergent can be present in the lubricant composition in any desired or effective amount. In an aspect, the lubricant composition can comprise from 0.01% to 0.8% by weight relative to the total weight of the lubricating composition; alternatively, from 0.05% to 0.6% by weight relative to the total weight of the lubricating composition; alternatively, from 0.09% to 0.4% by weight relative to the total weight of the lubricating composition. In an aspect, the additive composition can comprise from 0.06% to 5% by weight by weight relative to the total weight of the lubricating composition; alternatively, from 0.30% to 3.6% by weight relative to the total weight of the lubricating composition; alternatively, from 0.54% to 2.38% by weight relative to the total weight of the additive composition. However, one of ordinary skill in the art would understand that any amount can be used in the subject lubricant compositions.

In an aspect and by way of example, dispersants that are suitable for use in the subject lubricant compositions include but are not limited to, basic nitrogen-containing ashless dispersants. Suitable ashless dispersants, include, but are not limited to hydrocarbyl succinimides, hydrocarbyl succinamides, mixed ester/amides of hydrocarbyl-substituted succinic acids (e.g. those formed by reacting a hydrocarbyl-substituted succinic acylating agent stepwise or with a mixture of alcohols and amines, and/or with amino alcohols), Mannich condensation products (e.g. those formed from hydrocarbyl-substituted phenols, formaldehyde and polyamines), and amine dispersants formed by reacting high molecular weight aliphatic or alicyclic halides with amines (e.g. polyalkylene polyamines). Combinations or mixtures of any of these dispersants can also be used.

Methods of preparing such dispersants are known and are found as follows. For example, hydrocarbyl-substituted succinimides and succinamides and methods for their preparation are described in U.S. Pat. Nos. 3,018,247, 3,018,250, 3,018,291, 3,172,892, 3,185,704, 3,219,666, 3,272,746, 3,361,673, and 4,234,435, among other patens. Mixed ester-amides of hydrocarbyl-substituted succinic acid are described, for example, in U.S. Pat. Nos. 3,576,743, 4,234, 435, and 4,873,009, among other patents. Mannich dispersants, which are condensation products of hydrocarbyl-substituted phenols, formaldehyde and polyamines are described, for example, in U.S. Pat. Nos. 3,368,972, 3,413,347, 3,539, 633, 3,697,574, 3,725,277, 3,725,480, 3,726,882, 3,798,247, 3,803,039, 3,985,802, 4,231,759, and 4,142,980, among other patents. Amine dispersants and methods for their production from high molecular weight aliphatic or alicyclic halides and amines are described, for example, in U.S. Pat. Nos. 3,275,554, 3,438,757, 3,454,555, and 3,565,804, among other patents.

In an aspect and in general, amines containing basic nitrogen or basic nitrogen and additionally one or more hydroxyl groups, including amines of the types described in U.S. Pat. No. 4,235,435 can be used in the formation of dispersants suitable for use herein. The amines can be polyamines such as polyalkylene polyamines, hydroxy-substituted polyamines and polyoxyalkylene polyamines. Polyalkylene polyamines include diethylene triamine, triethylene tetramine, tetraethylene pentamine, pentaethylene hexamine, and dipropylene triamine. Pure polyethylene polyamines can be used, as well as mixtures of linear, branched and cyclic polyethylene polyamines having an average in the range of 2 to 7 nitrogen atoms per molecule, such as 3 to 5 nitrogen atoms per molecule. Hydroxy-substituted amines include, but are not limited to, N-hydroxyalkyl-alkylene polyamines such as N-(2-hydroxyethyl)ethylene diamine, N-(2-hydroxyethyl) piperazine, and N-hydroxyalkylated alkylene diamines of the type described in U.S. Pat. No. 4,873,009. Polyoxyalkylene polyamines typically include polyoxyethylene and polyoxypropylene diamines and triamines having average molecular weights in the range of 200 to 2500.

In an aspect, the at least one dispersant can contain hydrocarbyl substituents such as olefinic hydrocarbons. A non-limiting example of suitable olefinic hydrocarbons includes isobutene. The isobutylene utilized can be a stream containing isobutylene made by cracking a hydrocarbon stream to produce a hydrocarbon mixture consisting essentially of $C_4$ hydrocarbons. For example, thermocracking processes (streamcracker) produce $C_4$ cuts comprising $C_4$ paraffins and $C_4$ olefins, with a major component being isobutene. Butadiene and acetylene are substantially removed from the stream by additional selective hydrogenation or extractive distillation techniques. The resulting stream is referred to as "raffinate I" and is suitable for polyisobutylene (PIB) synthesis and has the following typical composition: 44-49% of isobutene, 24-28% of 1-butene, 19-21% of 2-butene, 6-8% of n-butane, 2-3% of isobutane. The components of the raffinate I stream can vary depending on operating conditions. The raffinate I stream can be purified to provide an essentially pure isobutene product, that is, a product consisting essentially of isobutene.

Antioxidants that can be used in the subject lubricant compositions include but are not limited to, amine-based antioxidants, phenol-based antioxidants, and sulfur-based antioxidants. Amine-based antioxidants include but are not limited to, monoalkyldiphenylamine-based compounds (e.g. monooctyldiphenylamine and mononon yldiphenylamine), dialkyldiphenylamine-based compounds (e.g. 4,4'-dibutyldiphenylamine, 4,4'-dipentyldiphenylamine, 4,4'-dihexyldiphenylamine, 4,4'-diheptyldiphenylamine, 4,4'-dioctyldiphenylamine, and 4,4'-dinonyldiphenylamine), polyalkyldiphenylamine-based compounds (e.g. tetrabutyldiphenylamine, tetrahexyldiphenylamine, tetraoctyldiphenylamine, and tetranonyldiphenylamine), and naphthylamine-based compounds (e.g. alpha-naphthylamine, phenyl-alpha-naphthylamine, butylphenyl-alpha-naphthylamine, pentylphenyl-alpha-naphthylamine, hexylphenyl-alpha-naphthylamine, heptylphenyl-alpha-naphthylamine, octylphenyl-alpha-naphthylamine, and nonylphenyl-alpha-naphthylamine). Phenol-based antioxidants include but are not limited to, monophenol-based compounds (e.g 2,6-di-tert-butyl-4-methylphenol and 2,6-di-tert-butyl-4-ethylphenol), and diphenol-based compounds (e.g. 4,4'-methylenebis (2,6-di-tert-butylphenol) and 2,2'-methylenebis(4-ethyl-6-tert-butylphenol)). Sulfur-based antioxidants include but are not limited to, phenothiazine, pentaerythritol-tetrakis(3-laurylthiopropionate), bis(3,5-tert-butyl-4-hydroxybenzyl)sulfide, thiodiethylenebis(3-(3,5-di-tert-butyl-4-hydroxyphenyl))propionate, and 2,6-di-tert-butyl-4-(4,6-bis(octylthio)-1,3,5-triazine-2-methylamino)phen-ol. In an aspect, each of these antioxidants can be used alone or in any combination or two or more.

In an aspect, any demulsifier utilized in a lubricant composition or viscosity modifier composition including any PAO described herein and/or PAOs prepared according to this disclosure can be a derivative of propylene oxide, a derivative of ethylene oxide, a polyoxyalkylene alcohol, an alkyl amine, an alkoxylated amino alcohol, an alkoxylated diamine, an alkoxylated polyamines polyethylene glycol, polyethylene oxide, polypropylene oxide, a glycolic monooleate, an overbased calcium sulfonate, a 1-(2-hydroxyethyl)-2-alkenyl imidazolines wherein the alkenyl group contains from 8 to 25 carbon atoms, a fatty acid alkylamine contact product, a solution of alkoxylated alkylphenol formaldehyde resin, an alkoxylated polyglycol, or any combination thereof. In an embodiment, any alkoxylated compound utilized as a demulsifier can be an alkoxylate of ethylene oxide, a substituted ethylene oxide (e.g. propylene oxide), polyene oxide, or any combination thereof.

In an aspect, any polysulfide component utilized in a lubricant composition or viscosity modifier composition including any PAO described herein and/or PAOs prepared according to this disclosure can be olefin sulfide, an oligomeric sulfur species, a dialkyl trisulfide compound, a dialkyl tetrasulfide compound, a substituted thiadiazole, a 2-(NN-dialkyldithiocarbamoyl)benzothiazole, a 2,5-bis(alkyldithio)-1,3,4-thiadiazole, a 2,5-bis(tert-nonyldithio)-1,3,4 thiadiazole, a 2,5-bis(NN-dialkyldithiocarbamoyl)-1,3,4-thiadiazole, a 2-alkyldithio-5-mercapto thiadiazole, a sulfurized methyl ester of oleic acid, a sulfurized alkylphenol, a sulfurized dipentene, a sulfurized dicyclopentadiene, a sulfurized terpene, a sulfurized Diels-Alder adduct, a phosphosulfurized hydrocarbon, or any combination thereof.

In an aspect, any foam inhibitor utilized in a lubricant composition or viscosity modifier composition including any PAO described herein and/or PAOs prepared according to this disclosure can be a copolymer of ethyl acrylate and 2-ethylhexylacrylate, a polymer comprising vinyl acetate monomer, a polyethylene glycol, a polyethylene oxide a polypropylene oxide, a (ethylene oxide-propylene oxide) polymer, silicones of polyacetate, a silicone of dimethyl silicone, a polysiloxane, a polyacrylate a polyethylacrylate, a poly-2-ethylhexylacrylate, a polyvinylacetate, a 2-ethylhexylacrylate/ethylacrylate copolymer, a polydimethyl/siloxane, or any combination thereof.

In an aspect, any phosphorus-containing acid, phosphorus-containing salt, or phosphorus-containing ester utilized in a lubricant composition or viscosity modifier composition including any PAO described herein and/or PAOs prepared according to this disclosure can be zinc dialkyldithiophosphate, zinc di-(amyl)dithiophosphate, zinc di-(1,3-dimethylbutyl)dithiophosphate, zinc di-(heptyl)dithiophosphate, zinc di-(octyl)dithiophosphate di-(2-ethylhexyl)dithiophosphate, zinc di-(nonyl)dithiophosphate, zinc di-(decyl)dithiophosphate, zinc di-(dodecyl)dithiophosphate, zinc di(dodecylphenyl)dithiophosphate, zinc di-(heptylphenyl)dithiophosphate, dialkyldithiophosphoric acid esters and amine salts thereof, amine salts of phosphites, amine salts of phosphorus-containing carboxylic esters, amine salts of phosphorus-containing ethers, amine salts of phosphorus-containing amides, partially esterified phosphoric acid, zinc dialkyldithiophosphate derived from mixture of amyl alcohol and isobutyl alcohol, zinc dialkyldithiophosphate derived from mixture of 2-ethylhexyl alcohol and isopropyl alcohol, zinc dialkyldithiophosphate derived from mixture of 4-methyl-2-pentanol and isopropyl alcohol, or any combination thereof.

Catalyst System and Catalyst System Components

This disclosure encompasses a catalyst system, a method of making the catalyst system, an oligomerization method using the catalyst system, and a method of producing a polyalphaolefin using the catalyst system. The disclosed catalyst system generally comprises a metallocene component and an activator component. For example, the catalyst system can comprise at least one metallocene and at least one activator; alternatively, the catalyst system can comprise at least one metallocene, at least one first activator, and at least one second activator. This disclosure further encompasses an oligomerization method comprising: a) contacting an alpha olefin monomer and a catalyst system comprising a metallocene, and b) forming an oligomer product under oligomerization conditions. In an embodiment, the oligomerization can comprise: a) contacting an alpha olefin monomer and a catalyst system comprising a metallocene, b) forming an oligomer product under oligomerization conditions, and c) separating a reactor effluent comprising the oligomer product to provide a heavy oligomer product. In some embodiments, the catalyst system can comprise a metallocene and an activator; or alternatively, a metallocene and a combination of activators. In other embodiments, the catalyst system can comprise a metallocene, a first activator, and a second activator. In other embodiments, or the catalyst system can be substantially devoid of an activator.

Generally, the alpha olefin monomer, the catalyst system, metallocene, activator (first, second, or other), the oligomer product, oligomerization conditions, and heavy oligomer product are independent elements of the oligomerization method and are independently described herein. The oligomerization method and any process which incorporates the oligomerization method can be described utilizing any combination of alpha olefin monomer described herein, catalyst system described herein, metallocene described herein, activator (first, second, or other) described herein, oligomer product described herein, oligomerization conditions described herein, and heavy oligomer product described herein.

When an activator is used in the catalyst system, the activator (first, second, or other) can comprise a solid oxide chemically-treated with an electron withdrawing anion; alternatively, the activator (first, second, or other) can comprise an alumoxane. In some embodiments, the catalyst system can comprise a metallocene, a first activator comprising a solid oxide chemically-treated with an electron withdrawing anion, and a second activator. In other embodiments, the catalyst system can comprise a metallocene, a first activator comprising an alumoxane, and a second activator.

Any number of precontacting or postcontacting steps can be employed in which any selection of catalyst system components and/or the alpha olefin monomer can be precontacted and/or postcontacted prior to the step of forming alpha olefin oligomer product under oligomerization conditions. In any aspect or embodiment of the oligomerization method disclosed herein can utilize any combination of alpha olefin monomer, metallocene, activator, solid oxide, or electron withdrawing anion, or any other activator or combination of activators which can be precontacted for any length of time prior to the step of contacting the alpha olefin and the catalyst system. Each of the components that can be used in the catalyst system is described independently herein.

In an aspect and any embodiment described herein, the oligomerization method(s) described herein can be incorporated into a process of producing a polyalphaolefin. In an non-limiting embodiment, the process to produce a polyalphaolefin comprises: a) contacting an alpha olefin monomer and a catalyst system comprising a metallocene, b) forming an oligomer product under oligomerization conditions, c) separating a reactor effluent comprising the oligomer product to provide a heavy oligomer product, and d) hydrogenating the heavy oligomer product to provide a polyalphaolefin.

Metallocenes

In one aspect, the present disclosure provides a catalyst system comprising a metallocene. In an embodiment, a combination of metallocenes can be employed in the catalysts system. When multiple metallocenes are utilized, the metallocene may be referred to herein as a first metallocene (or metallocene compound) and a second metallocene (or metallocene compound). In another aspect, two different metallocenes can be used simultaneously in an oligomerization process to produce the alpha olefin product.

Throughout this disclosure, metallocenes are described generally as comprising a Group I ligand, a Group II ligand, and a group 4, 5, or 6 metal; alternatively, a Group I ligand, a Group II ligand, and a group 4 metal; alternatively, a Group I ligand, a Group II ligand, and a group 5 metal; or alternatively, a Group I ligand, a Group II ligand, and a group 6 metal. In an aspect, the metal of the metallocene can be Ti, Zr, Hf, V, Nb, Ta, Cr, Mo, or W. In another aspect, the metal of the metallocene can be titanium, zirconium, hafnium, vanadium, niobium, tantalum, chromium, molybdenum, or tungsten; alternatively, titanium, zirconium, hafnium, or vanadium; alternatively, titanium, zirconium, or hafnium; alternatively, titanium; alternatively, zirconium; alternatively, hafnium; or alternatively, vanadium.

In an aspect, the Group I ligands of the metallocene are pi-bonded $\eta^{x \geq 5}$ ligands. The pi-bonded $\eta^{x \geq 5}$ ligands which can be utilized as a Group I ligand of the present disclosure include $\eta^5$-cycloalkadienyl-type ligands, $\eta^5$-cycloalkadienyl-type ligand analogs, and $\eta^5$-alkadienyl-type ligands as utilized in "open metallocenes." In an embodiment, a metallocene which can be utilized in any aspect or embodiment of the present disclosure contains at least one $\eta^5$-cycloalkadienyl-type or $\eta^5$-alkadienyl-type ligand. In some embodiments, the Group I ligand can be $\eta^5$-cyclopentadienyl, $\eta^5$-indenyl, $\eta^5$-fluorenyl, $\eta^5$-alkadienyl-, $\eta^6$-boratabenzene-ligand, and their substituted analogs. Other aspects and embodiments of the Group I ligands are described herein and can be utilized without limitation to describe the metallocene with can be utilized in any aspect or embodiment disclosed herein. Regarding the bonding of the unsaturated ligand to the metal in a metallocene, such a ligand can be indicated as containing a ligand bound according to the usual $\eta^x$ (eta-x) nomenclature, in which x is an integer corresponding to the number of atoms which are coordinated to the transition metal or are expected to be coordinated to the transition metal, for example, according to the 18-electron rule. The Group I ligands can be substituted or unsubstituted.

According to a further aspect, the Group I ligands can comprise at least one heterocyclic ring that is fused to a $\eta^5$-cycloalkadienyl-type or $\eta^5$-alkadienyl-type ligand. In some embodiments, for example, the Group I ligand can be a $\eta^5$-cyclopentadienyl ligand, a $\eta^5$-indenyl ligand, or similar Group I ligands, including their substituted analogs, to which a heterocyclic moiety is fused. Examples of fused heterocyclic moieties include, but are not limited to, pyrrole, furan, thiophene, phosphole, imidazole, imidazoline, pyrazole, pyrazoline, oxazole, oxazoline, isoxazole, isoxazoline, thiazole, thiazoline, isothiozoline, and the like, including partially saturated analogs of these rings.

In an aspect, the Group II ligands of the metallocene are the ligands that are not $\eta^{x \geq 5}$ bonded ligands and are prototypically sigma-bonded ligands and those pi-bonded ligands that are bound to the metal in an $\eta^{x < 5}$ bonding mode. Therefore, the $\eta^{x < 5}$-bonded ligands encompass the typical sigma-bonded halide, sigma-bonded hydride, sigma-bonded hydrocarbyl ligands (e.g. alkyl and alkenyl ligands, among others), and $\eta^{x < 5}$ "pi-bonded" ligands such as $\eta^2$-alkene, $\eta^3$-allyl, $\eta^4$-alkadienyl, and the like, which are bound to the metal in an $\eta^{x < 5}$ bonding mode. Thus, the Group II ligand of the metallocenes of this disclosure include those sigma-bonded ligands and some pi-bonded ligands in the metallocene that are not the $\eta^5$-cycloalkadienyl-type ligands and are not the other pi-bonded $\eta^{x \geq 5}$ ligands typically associated with defining a metallocene compound. Examples and alternative embodiments of Group II ligands are provided herein.

In an aspect, the metallocene can comprise two Group I ligands. In this aspect, and in any embodiment, the metallocene can comprise two Group I ligands, wherein the two Group I ligands are connected by a linking group; or alternatively, wherein the two Group I ligands are separate (not connected or unlinked). Because a linking group is considered a substituent on a Group I ligand, a linked Group I ligand can be further substituted with other, non-linking substituents or can be unsubstituted with the exception of the linking group. Thus, the Group I ligands can be linked and further substituted, linked but not further substituted, not linked but substituted with non-linking ligands, or not linked and not further substituted; alternatively, the Group I ligands can be linked and further substituted; alternatively, the Group I ligands can be linked but not further substituted; alternatively, the Group I ligands may not be linked but substituted with non-linking ligands; or alternatively, the Group I ligands may not be linked and not further substituted. Also in any embodiment, the metallocene can comprise a Group I ligand and at least one Group II ligand, where the Group I ligand and a Group II ligand are connected by a linking group; or alternatively, where the Group I ligand the Group II ligands are separate not connected by a linking group.

In an aspect, and in any embodiment, the metallocene can have the formula $X^{21}X^{22}X^{23}X^{24}M^1$. In this aspect, $X^{21}$, $X^{22}$, $X^{23}$, $X^{24}$, and $M^1$ are independently described herein and can be utilized in any combination to described the metallocene having the formula $X^{21}X^{22}X^{23}X^{24}M^1$. In some embodiments, $M^1$ can be a group 4, 5, or 6 metal; alternatively, a group 4 metal; alternatively, a group 5 metal; or alternatively, a group 6 metal. In other embodiments, $M^1$ can be Ti, Zr, Hf, V, Nb, Ta, Cr, Mo, or W; alternatively, Ti, Zr, or Hf; alternatively, V, Nb, or Ta; alternatively, Cr, Mo, or W; alternatively, Ti, Zr, Hf, or V; alternatively, Ti, Zr, or Hf; alternatively, Ti; alternatively, Zr; alternatively, Hf; or alternatively, V. In an embodiment, $X^{21}$ is a Group I ligand, $X^{22}$ is a Group I ligand or a Group II ligand, and $X^3$ and $X^4$ independently are Group II ligands; alternatively, $X^{21}$ and $X^{22}$ independently are Group I ligands not connected by a linking group, and $X^{23}$ and $X^{24}$ independently are Group II ligands; alternatively, $X^{21}$ and $X^{22}$ independently are Group I ligands connected by a linking group, and $X^{23}$ and $X^{24}$ independently are Group II ligands; or alternatively, $X^{21}$ is a Group I ligand and $X^{22}$, $X^{23}$, and $X^{24}$ independently are substituted or an unsubstituted hydrocarbyl group having from 1 to 20 carbon atoms. In an embodiment, any substituent on $X^{21}$, $X^{22}$, $X^{23}$, and $X^{24}$ can be independently a halide, a $C_1$ to $C_{20}$ hydrocarboxide group, an $C_1$ to $C_{20}$ aliphatic group, a $C_1$ to $C_{20}$ heterocyclic group, a $C_6$ to $C_{20}$ aromatic group, a $C_1$ to $C_{20}$ heteroaromatic group, an amido group, an $C_1$ to $C_{20}$ N-hydrocarbylamido group, a $C_1$ to $C_{20}$ N,N-dihydrocarbylamido group, a $C_1$ to $C_{20}$ hydrocarbylthiolate group, or a $C_3$ to $C_{30}$ trihydrocarbylsiloxy group.

In a non-limiting embodiment, the metallocene can have the formula:

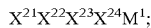

wherein:
$M^1$ is selected from titanium, zirconium, hafnium, vanadium, niobium, tantalum, chromium, molybdenum, or tungsten;
$X^{21}$ is a Group I ligand;
$X^{22}$ is a Group I ligand or a Group II ligand; and
$X^{23}$ and $X^{24}$ are independently selected from a Group II ligand. In some embodiments $X^{21}$ and $X^{22}$ are connected by a linking group. In other embodiments, $X^{21}$ and $X^{22}$ are not connected by a linking group.

In some non-limiting embodiments, the metallocene can have the formula:

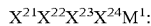

wherein:
$M^1$ is selected independently from Ti, Zr, or Hf;
$X^{21}$ and $X^{22}$ are Group I ligands connected by a linking group; and
$X^{23}$ and $X^{24}$ are independently selected from a Group II ligand.

In other non-limiting embodiments, the metallocene can have the formula:

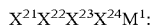

wherein:
$M^1$ is selected independently from Ti, Zr, or Hf;
$X^{21}$ and $X^{22}$ are Group I ligands not connected by a linking group; and
$X^{23}$ and $X^{24}$ are independently selected from a Group II ligand.

In yet another non-limiting embodiment, the metallocene can have the formula:

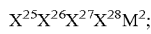

wherein
$M^2$ is Ti, Zr, Hf, or V;
$X^{25}$ is a Group I ligand;
$X^{26}$, $X^{27}$, and $X^{28}$ are selected independently from a substituted or an unsubstituted hydrocarbyl group having from 1 to 20 carbon atoms; and wherein any substituent on $X^{25}$, $X^{26}$, $X^{27}$, and $X^{28}$ can be independently a halide, a $C_1$ to $C_{20}$ hydrocarboxide group, an $C_1$ to $C_{20}$ aliphatic group, a $C_1$ to $C_{20}$ heterocyclic group, a $C_6$ to $C_{20}$ aromatic group, a $C_1$ to $C_{20}$ heteroaromatic group, an amido group, an $C_1$ to $C_{20}$ N-hydrocarbylamido group, a $C_1$ to $C_{20}$ N,N-dihydrocarbylamido group, a $C_1$ to $C_{20}$ hydrocarbylthiolate group, and a $C_3$ to $C_{30}$ trihydrocarbylsiloxy group.

In one aspect, and in any embodiment, the metallocene can include a linking group that connects a Group I ligand with another ligand (either another Group I ligand or a Group II ligand) in the metallocene. The linking group includes a bridge, comprising the smallest number of contiguous atoms required to traverse the connection between the Group I ligand and the other ligand it is connected to. For example, the linking group can comprise from 1 to 3 contiguous bridging atoms; alternatively, 1 or 2 contiguous bridging atoms; alternatively, 1 bridging atom; alternatively, 2 contiguous bridging atoms; alternatively, 3 bridging atoms. In an embodiment, each contiguous bridging atom can be C, O, S, N, P, Si, Ga, Sn, or Pb; alternatively, C, Si, Ge, or Sn; alternatively; C or Si; alternatively, C; or alternatively, Si. The linking group can be saturated, or the linking group can be unsaturated; alternatively, linking group can be saturated; or alternatively, linking group can be unsaturated.

Linking groups include, but are not limited to, a $C_1$-$C_{20}$ hydrocarbyl group, a $C_0$-$C_{20}$ nitrogen-bonded group, a $C_0$-$C_{20}$ phosphorus-bonded group, a $C_1$-$C_{20}$ organyl group, a $C_0$-$C_{30}$ silicon-bonded group, a $C_0$-$C_{20}$ germanium-bonded group, a $C_0$-$C_{20}$ tin-bonded group, or a $C_0$-$C_{20}$ lead-bonded group; alternatively, a $C_1$-$C_{20}$ hydrocarbyl group, or a $C_0$-$C_{30}$ silicon-bonded group; alternatively, a $C_1$-$C_{20}$ hydrocarbyl group; alternatively, a $C_0$-$C_{20}$ nitrogen-bonded group; alternatively, a $C_0$-$C_{20}$ phosphorus-bonded group; alternatively, a $C_1$-$C_{20}$ organyl group; alternatively, a $C_0$-$C_{30}$ silicon-bonded group; alternatively, a $C_0$-$C_{20}$ germanium-bonded group; alternatively, a $C_0$-$C_{20}$ tin-bonded group; or alternatively, a $C_0$-$C_{20}$ lead-bonded group.

Linking groups in any aspect or embodiment comprising linking groups, include those moieties having the formula >$CR^1R^2$, >$SiR^3R^4$, or —$CR^5R^6CR^7R^8$—, where $R^1$, $R^2$, $R^3$, $R^4$, $R^5$, $R^6$, $R^7$, and $R^8$ are selected independently from a hydrogen, a halide, a $C_1$-$C_{20}$ hydrocarbyl group, a $C_1$-$C_{20}$ oxygen-bonded group, a $C_1$-$C_{20}$ sulfur-bonded group, a $C_0$-$C_{20}$ nitrogen-bonded group, a $C_0$-$C_{20}$ phosphorus-bonded group, a $C_1$-$C_{20}$ organyl group, a $C_0$ to $C_{20}$ arsenic-bonded group, a $C_0$-$C_{30}$ silicon-bonded group, a $C_0$-$C_{20}$ germanium-bonded group, or a $C_0$-$C_{20}$ tin-bonded group; a $C_0$ to $C_{20}$ lead-bonded group, a $C_0$ to $C_{20}$ boron-bonded group, or a $C_0$ to $C_{20}$ aluminum-bonded group. In this aspect and in any embodiment, $R^1$, $R^2$, $R^3$, $R^4$, $R^5$, $R^6$, $R^7$, and $R^8$ can be, independently, saturated or unsaturated; alternatively, saturated; or alternatively, unsaturated. In some embodiments comprising linking groups, the linking group can have the formula >$CR^1R^2$, >$SiR^3R^4$ or —$CR^5R^6CR^7R^8$—, in which $R^1$, $R^2$, $R^3$, $R^4$, $R^5$, $R^6$, $R^7$, and $R^8$ are selected independently from a hydrogen, a halide, a saturated or unsaturated $C_1$-$C_{20}$ aliphatic group, or a $C_6$-$C_{20}$ aromatic group; alternatively, a saturated $C_1$-$C_{20}$ aliphatic group; alternatively, $R^1$, $R^2$, $R^3$, $R^4$, $R^5$, $R^6$, $R^7$, and $R^8$ can be selected independently from a hydrogen, a halide, a $C_1$-$C_{20}$ alkyl group, a $C_2$-$C_{20}$ alkenyl group, a $C_2$-$C_{20}$ alkynyl group, a $C_6$-$C_{20}$ aryl group, or a $C_6$-$C_{20}$ aromatic group; alternatively, a hydrogen, a $C_1$-$C_{20}$ alkyl group, a $C_2$-$C_{20}$ alkenyl group, or a $C_6$-$C_{20}$ aryl group; or alternatively, $R^1$, $R^2$, $R^3$, $R^4$, $R^5$, $R^6$, $R^7$, and $R^8$ are selected independently from a hydrogen, or saturated or unsaturated $C_1$-$C_{20}$ hydrocarbyl group. Hydrocarbyl, aliphatic, alkyl, alkenyl, alkynyl, aryl, and aromatic groups are described herein and can be utilized to describe $R^1$, $R^2$, $R^3$, $R^4$, $R^5$, $R^6$, $R^7$, and/or $R^8$ which can be utilized in the liking groups.

In yet another aspect and in any embodiment, in each occurrence of the Group I ligand in a metallocene can be a substituted or an unsubstituted $\eta^5$-cycloalkadienyl-ligand, a substituted or an unsubstituted $\eta^5$-alkadienyl-ligand, or a substituted or an unsubstituted $\eta^6$-boratabenzene-containing ligand; alternatively, a substituted or an unsubstituted cyclopentadienyl ligand, a substituted or an unsubstituted indenyl ligand, a substituted or an unsubstituted fluorenyl ligand, a substituted or an unsubstituted tetrahydroindenyl ligand, a substituted or an unsubstituted tetrahydrofluorenyl ligand, or a substituted or an unsubstituted octahydrofluorenyl ligand; or alternatively, a substituted or an unsubstituted cyclopentadienyl ligand, a substituted or an unsubstituted indenyl ligand, or a substituted or an unsubstituted fluorenyl ligand. Further, in any embodiment, in each occurrence of the Group I ligand in a metallocene a substituted or an unsubstituted cyclopentadienyl; alternatively, substituted or an unsubstituted indenyl; alternatively, substituted or an unsubstituted fluorenyl; alternatively, substituted or an unsubstituted tetrahydroindenyl; alternatively, substituted or an unsubstituted tetrahydrofluorenyl; or alternatively, a substituted or an unsubstituted octahydrofluorenyl. Alternatively, the metallocene can have two Group 1 ligands and in each occurrence of the Group I ligand can be independently two substituted or unsubstituted cyclopentadienyls, a substituted or an unsubstituted fluorenyl and a substituted or an unsubstituted cyclopentadienyl, a substituted or an unsubstituted fluorenyl and a substituted or an unsubstituted indenyl, two substituted or unsubstituted fluorenyls or two substituted or unsubstituted indenyls. Alternatively, in each occurrence of the Group I ligand, the Group I ligand can be selected independently from a substituted or an unsubstituted cyclopentadienyl, a substituted or an unsubstituted indenyl, or a substituted or an unsubstituted fluorenyl.

As disclosed herein, a linked Group I ligand can be further substituted with other, non-linking substituents or can be further unsubstituted. A non-linked Group I ligand can be substituted or can be unsubstituted. In this aspect, each non-linking substituent on a Group I ligand can be independently, but is not limited to, a halide, a $C_1$ to $C_{20}$ hydrocarbyl group, a $C_1$ to $C_{20}$ hydrocarboxy group, a $C_3$ to $C_{20}$ heterocyclic group, a $C_6$ to $C_{20}$ aromatic group, a $C_3$ to $C_{20}$ heteroaromatic group, a $C_1$ to $C_{20}$ hydrocarbylsilyl group, a $C_2$ to $C_{40}$ dihydrocarbylsilyl group, a $C_3$ to $C_{60}$ trihydrocarbylsilyl group, an aminyl group, a $C_1$ to $C_{20}$ N-hydrocarbyl aminyl group (sometimes referred to as a $C_1$ to $C_{20}$ N-hydrocarbylamido group), a $C_2$ to $C_{40}$ N,N-dihydrocarbyl aminyl group (sometimes referred to as a $C_2$ to $C_{40}$ N,N-dihydrocarbylamido group), a $C_1$ to $C_{20}$ hydrocarbylthiolate group, or a $C_3$ to $C_{60}$ trihydrocarbylsiloxy group; alternatively, a halide, a $C_1$ to $C_{20}$ hydrocarbyl group, or a $C_1$ to $C_{20}$ hydrocarboxy group; alternatively, a halide or a $C_1$ to $C_{20}$ hydrocarbyl group; alternatively, a halide or a $C_1$ to $C_{20}$ hydrocarboxy group; alternatively, a $C_1$ to $C_{20}$ hydrocarbyl group or a $C_1$ to $C_{20}$ hydrocarboxy group; alternatively, a halide; alternatively, a $C_1$ to $C_{20}$ hydrocarbyl group; or alternatively, a $C_1$ to $C_{20}$ hydrocarboxy group. In another aspect and any embodiment disclosed herein each non-linking substituent on a Group I ligand can be independently, but is not limited to, a halide, a $C_1$ to $C_{10}$ hydrocarbyl group, a $C_1$ to $C_{10}$ hydrocarboxy group, a $C_3$ to $C_{15}$ heterocyclic group, a $C_6$ to $C_{15}$ aromatic group, a $C_3$ to $C_{15}$ heteroaromatic group, a $C_1$ to $C_{10}$ hydrocarbylsilyl group, a $C_2$ to $C_{20}$ dihydrocarbylsilyl group, a $C_3$ to $C_{30}$ trihydrocarbylsilyl group, an aminyl group, a $C_1$ to $C_{10}$ N-hydrocarbyl aminyl group (sometimes referred to as a $C_1$ to $C_{10}$ N-hydrocarbylamido group), a $C_2$ to $C_{20}$ N,N-dihydrocarbyl aminyl group (sometimes referred to as a $C_2$ to $C_{20}$ N,N-dihydrocarbylamido group), a $C_1$ to $C_{10}$ hydrocarbylthiolate group, or a $C_3$ to $C_{30}$ trihydrocarbylsiloxy group; alternatively, a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group.

In yet another aspect and any embodiment disclosed herein, each non-linking substituent on a Group I ligand can be independently, but is not limited to, a halide, a $C_1$ to $C_5$ hydrocarbyl group, a $C_1$ to $C_5$ hydrocarboxy group, a $C_3$ to $C_{10}$ heterocyclic group, a $C_6$ to $C_{10}$ aromatic group, a $C_3$ to $C_{10}$ heteroaromatic group, a $C_1$ to $C_5$ hydrocarbylsilyl group, a $C_2$ to $C_{10}$ dihydrocarbylsilyl group, a $C_3$ to $C_{15}$ trihydrocarbylsilyl group, an aminyl group, a $C_1$ to $C_5$ N-hydrocarbyl aminyl group (sometimes referred to as a $C_1$ to $C_5$ N-hydrocarbylamido group), a $C_2$ to $C_{10}$ N,N-dihydrocarbyl aminyl group (sometimes referred to as a $C_2$ to $C_{10}$ N,N-dihydrocarbylamido group), a $C_1$ to $C_5$ hydrocarbylthiolate group, or a $C_3$ to $C_{15}$ trihydrocarbylsiloxy group; alternatively, a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; or alternatively, a $C_1$ to $C_5$ hydrocarboxy group.

In an embodiment, each halide substituent which may be utilized as non-linking substituent on a Group I ligand or as a halide utilized in a linking group can be independently a fluoride, a chloride, a bromide, or an iodide. In an embodiment, each halide substituent which may be utilized as non-linking substituent on a Group I ligand or as a halide utilized in a linking group can be independently a fluoride; alternatively, a chloride; alternatively, a bromide; or alternatively, an iodide.

In an embodiment, each hydrocarbyl substituent which may be utilized as non-linking substituent on a Group I ligand, a hydrocarbyl group utilized in a linking group, or as a hydrocarbyl group within a non-linking substituent on a Group I ligand (e.g. trihydrocarbylsilyl group, N,N-dihydrocarbyl aminyl group, or hydrocarbylthiolate group, among others), can be independently an alkyl group, an alkenyl group, a cycloalkyl group, an aryl group, or an aralkyl group; alternatively, an alkyl group or an alkenyl group; alternatively, an alkyl group; alternatively, an alkenyl group; alternatively, a cycloalkyl group; alternatively, an aryl group; or alternatively, an aralkyl group. Generally, the alkyl, alkenyl, cycloalkyl, aryl, and aralkyl substituent groups can have the same number of carbon atoms as the hydrocarbyl substituent group disclosed herein.

In an embodiment, each alkyl substituent which may be utilized as non-linking substituent on a Group I ligand, an alkyl group utilized in a linking group, or as a alkyl group within a non-linking substituent on a Group I ligand (e.g. trihydrocarbylsilyl group, N,N-dihydrocarbyl aminyl group, or hydrocarbylthiolate group, among others), can be independently a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, a neo-pentyl group, a n-hexyl group, a n-heptyl group, or a n-octyl group; alternatively, a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; alternatively, a neo-pentyl group; alternatively, an n-hexyl group; alternatively, an n-heptyl group; or alternatively, an n-octyl group.

In any embodiment disclosed herein, the Group I ligand, the Group II ligand, or both the Group I and Group II ligands can be substituted with a $C_2$ to $C_{20}$ alkenyl group; alternatively, a $C_3$ to $C_{15}$ alkenyl group; alternatively, a $C_4$ to $C_{10}$ alkenyl group; or alternatively, a $C_4$ to $C_8$ alkenyl group. Alternatively, in any embodiment disclosed herein, a substituent on a bridging atom of the linking group can be a $C_2$ to $C_{20}$ alkenyl group; alternatively, a $C_3$ to $C_{15}$ alkenyl group; alternatively, a $C_4$ to $C_{10}$ alkenyl group; or alternatively, a $C_4$ to $C_8$ alkenyl group. In any of these embodiments, and in one aspect the alkenyl groups can encompass those "ω-alkenyl" groups, having their carbon-carbon double bond in the omega (ω)-position of the alkenyl moiety, that is, between the two carbon atoms furthest removed from the ligand to which the alkenyl group is bonded. Examples of ω-alkenyl groups include, but are not limited to, groups having the formula —$CH_2(CH_2)_nCH=CH_2$, in which n can be an integer from 0 to 12; alternatively, n is an integer from 1 to 9; alternatively, n is an integer from 1 to 7; alternatively, n is an integer from 1 to 6; alternatively, n is an integer from 1 to 5; alternatively, n is an integer from 1 to 4; alternatively, n is an integer from 1 to 3; alternatively, n is an integer from 1 to 2. In a further aspect and in any embodiment, examples of ω-alkenyl groups include, but are not limited to, a group having the formula —$CH_2(CH_2)_mCH=CH_2$, in which m is 0; alternatively, m is 1, alternatively, m is 2, alternatively, m is 3, alternatively, m is 4, alternatively, m is 5, alternatively, m is 6, alternatively, m is 7, alternatively, m is 8, alternatively, m is 9, alternatively, m is 10, alternatively, m is 11, or alternatively, m is 12. In an embodiment, any alkenyl substituent which may be utilized as non-linking substituent on a Group I ligand, an alkenyl group utilized in a linking group, or as a alkenyl group within non-linking substituent on a Group I ligand (e.g. trihydrocarbylsilyl group, N,N-dihydrocarbyl aminyl group, or hydrocarbylthiolate group, among others), can be an ethenyl group, a propenyl group, a butenyl group, pentenyl group, a hexenyl group; a heptenyl group, or an octenyl group; alternatively, a propenyl group, a butenyl group, pentenyl group, a hexenyl group; alternatively, an ethenyl group; alternatively, a propenyl group; alternatively, a butenyl group; alternatively, pentenyl group; alternatively, a hexenyl group; alternatively, heptenyl group; or alternatively, an octenyl group.

In an embodiment, any cycloalkyl substituent which may be utilized as non-linking substituent on a Group I ligand, a cycloalkyl group utilized in a linking group, or as a cycloalkyl group within non-linking substituent on a Group I ligand (e.g. trihydrocarbylsilyl group, N,N-dihydrocarbyl aminyl group, or hydrocarbylthiolate group, among others), can be a cyclopropyl group, a cyclobutyl group, a cyclopentyl group, a cyclohexyl group, a cycloheptyl group, or a cyclooctyl group; alternatively, a cyclopentyl group or a cyclohexyl group; alternatively, a cyclopropyl group; alternatively, a cyclobutyl group; alternatively, a cyclopentyl group; alternatively, a cyclohexyl group; alternatively, a cycloheptyl group; or alternatively, a cyclooctyl group. In an embodiment, any aryl substituent which may be utilized as non-linking substituent on a Group I ligand, an aryl group utilized in a linking group, or as an aryl group within non-linking substituent on a Group I ligand (e.g. trihydrocarbylsilyl group, N,N-dihydrocarbyl aminyl group, or hydrocarbylthiolate group, among others), can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent which may be utilized as non-linking substituent on a Group I ligand, an aralkyl group utilized in a linking group, or as a aralkyl group within non-linking substituent on a Group I ligand (e.g. trihydrocarbylsilyl group, N,N-dihydrocarbyl aminyl group, or hydrocarbylthiolate group, among others), can be a benzyl group.

In an embodiment, any hydrocarboxy substituent(s) which may be utilized as non-linking substituent on a Group I ligand can be an alkoxy group, an aroxy group, or an aralkoxy group; alternatively, an alkoxy group; alternatively, an aroxy group; or alternatively, an aralkoxy group. Generally, the alkoxy, aroxy, and aralkoxy substituent groups can have the same number of carbon atoms as the hydrocarboxy substituent group disclosed herein. In an embodiment, any alkoxy substituent which may be utilized as non-linking substituent on a Group I ligand can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryl substituent which may be utilized as non-linking substituent on a Group I ligand can be a phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aroxy substituent which may be utilized as non-linking substituent on a Group I ligand can be a benzoxy group.

Throughout this disclosure, metallocenes are described as comprising at least one Group II ligand. In this aspect and in any embodiment, the Group II ligands include those sigma-bonded ligands and some pi-bonded ligands in the metallocene that are not the $\eta^5$-cycloalkadienyl-type ligands and are not the other pi-bonded $\eta^{x \geq 5}$ ligands typically associated with defining a metallocene compound. In any embodiment disclosed herein, examples and alternative embodiments of Group II ligands include, but are not limited to, a hydride, a halide, a $C_1$-$C_{30}$ $\eta^{x<5}$-organic group, a $C_1$-$C_{30}$ $\eta^{x<5}$-hydrocarbon group, a $C_1$-$C_{30}$ aliphatic group, a $C_6$-$C_{30}$ $\eta^{x<5}$-aromatic group, a $C_2$-$C_{30}$ $\eta^{x<5}$-heterocyclic group, a $C_2$-$C_{30}$ $\eta^{x<5}$-cyclohetero group, a $C_4$-$C_{30}$ $\eta^{x<5}$-heteroarene group, a $C_4$-$C_{30}$ $\eta^{x<5}$-arylhetero group, a $C_1$-$C_{30}$ $\eta^{x<5}$-organohetero group, a $C_5$-$C_{30}$ heteroaralkane group, a $C_5$-$C_{20}$ heteroaralkane group, a $C_5$-$C_{10}$ heteroaralkane, a $C_1$-$C_{30}$ oxygen group, a $C_1$-$C_{30}$ sulfur group, a $C_0$-$C_{30}$ nitrogen group, a $C_0$-$C_{30}$ phosphorus group, a $C_0$-$C_{30}$ arsenic group, a $C_0$-$C_{30}$ silicon group, a $C_0$-$C_{30}$ germanium group, a $C_0$-$C_{30}$ tin group, a $C_0$-$C_{30}$ lead group, a $C_0$-$C_{30}$ boron group, or a $C_0$-$C_{30}$ aluminum group; alternatively, a hydride, a halide, a $C_1$-$C_{20}$ $\eta^{x<5}$- organic group, a $C_1$-$C_{20}$ $\eta^{x<5}$-hydrocarbon group, a $C_1$-$C_{20}$ aliphatic group, a $C_6$-$C_{20}$ $\eta^{x<5}$-aromatic group, a $C_2$-$C_{20}$ $\eta^{x<5}$-heterocyclic group, a $C_2$-$C_{20}$ $\eta^{x<5}$-cyclohetero group, a $C_4$-$C_{20}$ $\eta^{x<5}$-heteroarene group, a $C_4$-$C_{20}$ $\eta^{x<5}$-arylhetero group, a $C_1$-$C_{20}$ $\eta^{x<5}$-organohetero group, a $C_5$-$C_{20}$ heteroaralkane group, a $C_1$-$C_{20}$ oxygen group, a $C_1$-$C_{20}$ sulfur group, a $C_0$-$C_{20}$ nitrogen group, a $C_0$-$C_{20}$ phosphorus group, a $C_0$-$C_{20}$ arsenic group, a $C_0$-$C_{20}$ silicon group, a $C_0$-$C_{20}$ germanium group, a $C_0$-$C_{20}$ tin group, a $C_0$-$C_{20}$ lead group, a $C_0$-$C_{20}$ boron group, or a $C_0$-$C_{20}$ aluminum group; alternatively, a hydride, a halide, a $C_1$-$C_{10}$ $\eta^{x<5}$-organic group, a $C_1$-$C_{10}$ $\eta^{x<5}$-hydrocarbon group, a $C_1$-$C_{10}$ aliphatic group, a $C_6$-$C_{10}$ $\eta^{x<5}$-aromatic group, a $C_2$-$C_{10}$ $\eta^{x<5}$-heterocyclic group, a $C_2$-$C_{10}$ $\eta^{x<5}$-cyclohetero group, a $C_4$-$C_{10}$ heteroarene group, a $C_4$-$C_{10}$ $\eta^{x<5}$-arylhetero group, a $C_1$-$C_{10}$ $\eta^{x<5}$-organohetero group, a $C_5$-$C_{10}$ heteroaralkane, a $C_1$-$C_{10}$ oxygen group, a $C_1$-$C_{10}$ sulfur group, a $C_0$-$C_{10}$ nitrogen group, a $C_0$-$C_{10}$ phosphorus group, a $C_0$-$C_{10}$ arsenic group, a $C_0$-$C_{10}$ silicon group, a $C_0$-$C_{10}$ germanium group, a $C_0$-$C_{10}$ tin group, a $C_0$-$C_5$ tin group, a $C_0$-$C_{10}$ lead group, a $C_0$-$C_{10}$ boron group, or a $C_0$-$C_{10}$ aluminum group; alternatively, a hydride, a halide, a fluoride, a $C_1$-$C_5$ $\eta^{x<5}$-organic group, a $C_1$-$C_5$ $\eta^{x<5}$-hydrocarbon group, a $C_1$-$C_5$ aliphatic group, a $C_6$-$C_{10}$ $\eta^{x<5}$-aromatic group, a $C_6$-$C_{10}$ $\eta^{x<5}$-arene group, a $C_2$-$C_5$ $\eta^{x<5}$-heterocyclic group, a $C_2$-$C_5$ $\eta^{x<5}$-cyclohetero group, a $C_4$-$C_5$ heteroarene group, a $C_4$-$C_5$ $\eta^{x<5}$-arylhetero group, a $C_1$-$C_5$ $\eta^{x<5}$-organohetero group, a $C_5$-$C_{10}$ heteroaralkane, a $C_1$-$C_5$ oxygen group, a $C_1$-$C_5$ sulfur group, a $C_0$-$C_5$ nitrogen group, a $C_0$-$C_5$ phosphorus group, a $C_0$-$C_5$ arsenic group, a $C_0$-$C_5$ silicon group, a $C_0$-$C_5$ germanium group, a $C_0$-$C_5$ tin group, a $C_0$-$C_5$ lead group, a $C_0$-$C_5$ boron group, or a $C_0$-$C_5$ aluminum group.

Alternatively and in any embodiment of this disclosure, in each occurrence the Group II ligand can independently be a halide, a hydride, a $C_1$-$C_{30}$ $\eta^{x<5}$-hydrocarbyl group, a $C_1$-$C_{30}$ oxygen-bonded group, a $C_1$-$C_{30}$ sulfur-bonded group, a $C_0$-$C_{30}$ nitrogen-bonded group, a $C_0$-$C_{30}$ phosphorus-bonded group, a $C_0$ to $C_{20}$ arsenic-bonded group, a $C_1$-$C_{30}$ $\eta^{x<5}$-organyl group, a $C_0$-$C_{30}$ silicon-bonded group, a $C_0$-$C_{30}$ germanium-bonded group, a $C_0$-$C_{30}$ tin-bonded group, a $C_0$ to $C_{30}$ lead-bonded group, a $C_0$ to $C_{30}$ boron-bonded group, a $C_0$ to $C_{30}$ aluminum-bonded group, or a $C_0$ to $C_{10}$ aluminum-bonded group; alternatively, a halide, a hydride, a $C_1$-$C_{20}$ $\eta^{x<5}$-hydrocarbyl group, a $C_1$-$C_{20}$ oxygen-bonded group, a $C_1$-$C_{20}$ sulfur-bonded group, a $C_0$-$C_{20}$ nitrogen-bonded group, a $C_0$-$C_{20}$ phosphorus-bonded group, a $C_0$ to $C_{20}$ arsenic-bonded group, a $C_1$-$C_{20}$ $\eta^{x<5}$-organyl group, a $C_0$-$C_{20}$ silicon-bonded group, a $C_0$-$C_{20}$ germanium-bonded group, a $C_0$-$C_{20}$ tin-bonded group, a $C_0$ to $C_{20}$ lead-bonded group, or a $C_0$ to $C_{20}$ aluminum-bonded group; alternatively, a halide, a hydride, a $C_1$-$C_{10}$ $\eta^{x<5}$-hydrocarbyl group, a $C_1$-$C_{10}$ oxygen-bonded group, a $C_1$-$C_{10}$ sulfur-bonded group, a $C_0$-$C_{10}$ nitrogen-bonded group, a $C_0$-$C_{10}$ phosphorus-bonded group, a $C_0$ to $C_{10}$ arsenic-bonded group, a $C_1$-$C_{10}$ $\eta^{x<5}$-organyl group, a $C_0$-$C_{10}$ silicon-bonded group, a $C_0$-$C_{10}$ germanium-bonded group, a $C_0$-$C_{10}$ tin-bonded group, a $C_0$ to $C_{10}$ lead-bonded group, $C_0$ to $C_{10}$ boron-bonded group, or a $C_0$ to $C_{10}$ aluminum-bonded group; or alternatively, a halide, a hydride, a $C_1$-$C_5$ $\eta^{x<5}$-hydrocarbyl group, a $C_1$-$C_{10}$ oxygen-bonded group, a $C_1$-$C_{10}$ sulfur-bonded group, a $C_0$-$C_{10}$ nitrogen-bonded group, a $C_0$-$C_{10}$ phosphorus-bonded group, a $C_0$ to $C_6$ arsenic-bonded group, a $C_1$-$C_5$ $\eta^{x<5}$-organyl group, a $C_0$-$C_{10}$ silicon-bonded group, a $C_0$-$C_{10}$ germanium-bonded group, a $C_0$-$C_{10}$ tin-bonded group, a $C_0$ to $C_{10}$ lead-bonded group, a $C_0$ to $C_{10}$ boron-bonded group, or a $C_0$ to $C_{10}$ aluminum-bonded group.

In a further aspect and in any embodiment disclosed herein, any Group II ligand in each occurrence can include, but are not limited to, a halide, a hydride, a $C_1$-$C_{20}$ $\eta^{x<5}$-hydrocarbyl group, a $C_1$-$C_{20}$ oxygen-bonded group, a $C_1$-$C_{20}$ sulfur-bonded group, a $C_0$-$C_{30}$ nitrogen-bonded group, a $C_0$-$C_{30}$ phosphorus-bonded group, a $C_1$-$C_{20}$ $\eta^{x<5}$-organyl group, a $C_0$-$C_{30}$ silicon-bonded group, a $C_1$-$C_{30}$ germanium-bonded group, or a $C_1$-$C_{30}$ tin-bonded group; alternatively, a halide, a hydride, a $C_1$-$C_{10}$ $\eta^{x<5}$-hydrocarbyl group, a $C_1$-$C_{10}$ oxygen-bonded group, a $C_1$-$C_{10}$ sulfur-bonded group, a $C_0$-$C_{20}$ nitrogen-bonded group, a $C_0$-$C_{20}$ phosphorus-bonded group, a $C_1$-$C_{10}$ $\eta^{x<5}$-organyl group, a $C_0$-$C_{30}$ silicon-bonded group, a $C_1$-$C_{20}$ germanium-bonded group, or a $C_1$-$C_{20}$ tin-bonded group; or alternatively, a halide, a hydride, a $C_1$-$C_5$ $\eta^{x<5}$-hydrocarbyl group, a $C_1$-$C_5$ oxygen-bonded group, a $C_1$-$C_5$ sulfur-bonded group, a $C_0$-$C_{10}$ nitrogen-bonded group, a $C_0$-$C_{10}$ phosphorus-bonded group, a $C_1$-$C_5$ $\eta^{x<5}$-organyl group, a $C_0$-$C_{10}$ silicon-bonded group, a $C_1$-$C_{10}$ germanium-bonded group, or a $C_1$-$C_{10}$ tin-bonded group.

Yet a further aspect provides that, in any embodiment disclosed, any Group II ligand in each occurrence can independently be a halide, a hydride, a $C_1$-$C_{20}$ $\eta^{x<5}$-hydrocarbyl group, a $C_1$-$C_{20}$ oxygen-bonded group, a $C_1$-$C_{20}$ sulfur-bonded group, a $C_0$-$C_{30}$ nitrogen-bonded group, a $C_1$-$C_{20}$ $\eta^{x<5}$-organyl group, or a $C_0$-$C_{30}$ silicon-bonded group; alternatively, a halide, a hydride, a $C_1$-$C_{10}$ $\eta^{x<5}$-hydrocarbyl group, a $C_1$-$C_{10}$ oxygen-bonded group, a $C_1$-$C_{10}$ sulfur-bonded group, a $C_0$-$C_{20}$ nitrogen-bonded group, a $C_0$-$C_{20}$ phosphorus-bonded group, a $C_1$-$C_{10}$ $\eta^{x<5}$-organyl group, or a $C_0$-$C_{20}$ silicon-bonded group; or alternatively, a halide, a hydride, a $C_1$-$C_5$ $\eta^{x<5}$-hydrocarbyl group, a $C_1$-$C_5$ oxygen-bonded group, a $C_1$-$C_5$ sulfur-bonded group, a $C_0$-$C_{10}$ phosphorus-bonded group, a $C_1$-$C_5$ $\eta^{x<5}$-organyl group, or a $C_0$-$C_{10}$ silicon-bonded group.

Alternatively, and any embodiment, in each occurrence the Group II ligand can independently be a halide, a hydride, a $C_1$ to $C_{20}$ hydrocarboxide group (also referred to as a hydrocarboxy group), a $C_1$ to $C_{20}$ heterocyclic group, a $C_6$ to $C_{20}$ $\eta^1$-aromatic group, a $C_1$ to $C_{20}$ $\eta^1$-heteroaromatic group, a $C_1$ to $C_{20}$ hydrocarbylsilyl group, a $C_1$ to $C_{20}$ dihydrocarbylsilyl group, a $C_1$ to $C_{20}$ trihydrocarbylsilyl group, an aminyl group, an $C_1$ to $C_{20}$ N-hydrocarbylaminyl group, a $C_1$ to $C_{20}$ N,N-dihydrocarbylaminyl group, a $C_1$ to $C_{20}$ hydrocarbylthiolate group, or a $C_3$ to $C_{30}$ trihydrocarbylsiloxy group. In a further alternative and in each occurrence, the Group II ligand can independently be a halide, a hydride, a $C_1$ to $C_{20}$ alkoxide, a $C_6$ to $C_{20}$ aryloxide, a $C_6$ to $C_{20}$ $\eta^1$-aromatic group, an amido group, a $C_1$ to $C_{20}$ N-alkylamido group, a $C_6$ to $C_{20}$ N-arylamido group, $C_1$ to $C_{20}$ N,N-dialkylamido group, a $C_7$ to $C_{20}$ N-alkyl-N-arylamido group, a $C_1$ to $C_{20}$ alkylthiolate, a $C_6$ to $C_{20}$ arylthiolate, a $C_3$ to $C_{20}$ trialkylsiloxy, or a $C_{18}$ to $C_{30}$ triarylsiloxy.

In one additional aspect, and in any embodiment, in each occurrence the Group II ligand can independently be a halide, a $C_1$ to $C_{20}$ hydrocarboxide (also referred to as a hydrocarboxy group), a $C_1$ to $C_{30}$ hydrocarbyl, or a $C_3$ to $C_{20}$ trihydrocarbylsiloxy; alternatively, a halide, a $C_1$ to $C_{10}$ hydrocarboxide, a $C_1$ to $C_{10}$ hydrocarbyl, or a $C_3$ to $C_{20}$ trihydrocarbylsiloxy; or alternatively, a halide, a $C_1$ to $C_5$ hydrocarboxide, a $C_1$ to $C_5$ hydrocarbyl, or a $C_3$ to $C_{15}$ trihydrocarbylsiloxy. In another aspect, and in any embodiment, in each occurrence the Group II ligand can independently be a halide, a $C_1$ to $C_{20}$ hydrocarboxide, or a $C_1$ to $C_{30}$ hydrocarbyl; alternatively, a halide, a $C_1$ to $C_{10}$ hydrocarboxide, or a $C_1$ to $C_{10}$ hydrocarbyl; or alternatively, a halide, a $C_1$ to $C_5$ hydrocarboxide, or a $C_1$ to $C_5$ hydrocarbyl. In another aspect, and in any embodiment, in each occurrence the Group II ligand can independently be a halide or a $C_1$ to $C_{20}$ hydrocarboxide; alternatively, a halide or a $C_1$ to $C_{10}$ hydrocarboxide; or alternatively, a halide or a $C_1$ to $C_5$ hydrocarbyl. In a further aspect, in each occurrence the Group II ligand can be a halide.

Halides have been disclosed herein as potential non-linking substituents on a Group I ligand or as a halide utilized in a linking group and these halide may be utilized, without limitation and in any aspect or embodiment, as a Group II ligand. Hydrocarbyl groups have been disclosed herein as potential non-linking substituent on a Group I ligand, a hydrocarbyl group utilized in a linking group, or as a hydrocarbyl group within a non-linking substituent on a Group I ligand and these hydrocarbyl groups can be utilized, without limitation and in any aspect or embodiment, as a Group II ligand. Hydrocarbyl groups have been disclosed herein as potential non-linking substituent on a Group I ligand and these hydrocarboxy groups can be utilized, without limitation and in any aspect or embodiment, as a Group II ligand.

Substituted aminyl groups which may be utilized in any embodiment calling for a substituted amide group can may be an N-hydrocarbyl aminyl group or an N,N-dihydrocarbyl aminyl group. Hydrocarbyl groups have been described herein and these hydrocarbyl groups can be utilized, without limitation, to further described the N-hydrocarbyl aminyl group or an N,N-dihydrocarbyl aminyl group which may be utilized in various aspects and embodiments described herein. In a non-limiting embodiment, N-hydrocarbyl aminyl groups which may be utilized in any embodiment calling for a N-hydrocarbyl aminyl group include, but are not limited to, N-methylaminyl group (—NHCH$_3$), a N-ethylaminyl group (—NHCH$_2$CH$_3$), a N-n-propylaminyl group (—NHCH$_2$CH$_2$CH$_3$), an N-iso-propylaminyl group (—NHCH(CH$_3$)$_2$), a N-n-butylaminyl group (—NHCH$_2$CH$_2$CH$_2$CH$_3$), a N-t-butylaminyl group (—NHC(CH$_3$)$_3$), a N-n-pentylaminyl group (—NHCH$_2$CH$_2$CH$_2$CH$_2$CH$_3$), a N-neo-pentylaminyl group (—NHCH$_2$C(CH$_3$)$_3$), a N-phenylaminyl group (—NHC$_6$H$_5$), a N-tolylaminyl group (—NHC$_6$H$_4$CH$_3$), or a N-xylylaminyl group (—NHC$_6$H$_3$(CH$_3$)$_2$); alternatively, a N-ethylaminyl group; alternatively, a N-propylaminyl group; or alternatively, a N-phenylaminyl group. A N,N-dihydrocarbyl aminyl group which may be utilized in any embodiment caring for a N,N-dihydrocarbylaminyl groups include, but are not limited to a N,N-dimethylaminyl group (—N(CH$_3$)$_2$), a N,N-diethylaminyl group (—N(CH$_2$CH$_3$)$_2$), a N,N-di-n-propylaminyl group (—N(CH$_2$CH$_2$CH$_3$)$_2$), a N,N-di-iso-propylaminyl group (—N(CH(CH$_3$)$_2$)$_2$), a N,N-di-n-butylaminyl group (—N(CH$_2$CH$_2$CH$_2$CH$_3$)$_2$), a N,N-di-t-butylaminyl group (—N(C(CH$_3$)$_3$)$_2$), a N,N-di-n-pentylaminyl group (—N(CH$_2$CH$_2$CH$_2$CH$_2$CH$_3$)$_2$), a N,N-di-neo-pentylaminyl group (—N(CH$_2$C(CH$_3$)$_3$)$_2$), a N,N-di-phenylaminyl group (—N(C$_6$H$_5$)$_2$), a N,N-di-tolylaminyl group (—N(C$_6$H$_4$CH$_3$)$_2$), or a N,N-di-xylylaminyl group (—N(C$_6$H$_3$(CH$_3$)$_2$)$_2$); alternatively, a N,N-di-ethylaminyl group; alternatively, a N,N-di-n-propylaminyl group; or alternatively, a N,N-di-phenylaminyl group. Halides which may be utilized in any embodiment caring for a halide substituent or group includes fluoride, chloride, bromide, or iodide; alternatively, fluoride; alternatively, chloride; or alternatively, bromide. In some embodiments, substituents or groups which may be utilized in an embodiment calling for a substituent or group can include a halogenated hydrocarbyl group. In an embodiment, the halogenated hydrocarbyl group can be a halogenated aromatic group or a halogenated alkyl group; alternatively, a halogenated aromatic group; or alternatively, a halogenated alkyl group. One popular halogenated aromatic group is pentafluorophenyl. One popular halogenated alky group is trifluoromethyl.

Examples of aromatic groups, in each instance, include, but are not limited to, phenyl, naphthyl, anthracenyl, and the like, including substituted derivatives thereof. In some embodiments, the aromatic group can be a substituted phenyl groups. The substituted phenyl group can be substituted at the 2 position, the 3 position, the 4 position, the 2 and 4 positions, the 2 and 6 positions, the 2 and 5 positions, the 3 and 5 positions, or the 2, 4, and 6 positions; alternatively, the 2 position, the 4 position, the 2 and 4 positions, the 2 and 6 positions, or the 2, 4, and 6 positions; alternatively, 2 position; alternatively, the 3 position; alternatively, the 4 position; alternatively, the 2 and 4 positions; alternatively, the 2 and 6 positions; alternatively, the 3 and 5 positions; or alternatively, the 2, 4, and 6 positions. Substituents which can be present included a halide, an alkyl group, an alkoxy group, an aminyl group, an N-hydrocarbylaminyl, and/or a N,N-dihydrocarbylaminyl group; alternatively, a halide, an alkyl group, or an alkoxy group; alternatively, a halide or an alkyl group; alternatively, a halide or an alkoxy group; alternatively, a halide; alternatively, an alkyl group; or alternatively, an alkoxy group. Halides, alkyl groups, and alkoxy group have been independently described herein and can be utilized, without limitation as each independent substituent. Some non-limiting embodiments, substituted aromatic groups include, but are not limited to, tolyl (2-, 3-, 4-, or mixtures thereof), xylyl (2,3-, 2,4-, 2,5-, 3,4-, 3,5-, 2,6-, or mixtures thereof), mesityl, pentafluorophenyl, $C_6H_4OMe$ (2-, 3-, 4-, or mixtures thereof), $C_6H_4NH_2$ (2-, 3-, 4-, or mixtures thereof), $C_6H_4NMe_2$ (2-, 3-, 4-, or mixtures thereof), $C_6H_4CF_3$ (2-, 3-, 4-, or mixtures thereof), $C_6H_4F$, $C_6H_4Cl$ (2-, 3-, 4-, or mixtures thereof), $C_6H_3(OMe)_2$ (2,3-, 2,4-, 2,5-, 3,4-, 3,5-, 2,6-, or mixtures thereof), $C_6H_3(CF_3)_2$ (2,3-, 2,4-, 2,5-, 3,4-, 3,5-, 2,6-, or mixtures thereof), and the like, including any heteroatom substituted analogs thereof as described in the definitions section. Other substituted aromatic groups, and combinations of substituted aromatic groups, can be envisioned utilizing the present disclosure.

Examples of heterocyclic compounds from which heteroatom groups can be derived include, but are not limited to, aziridine, azirine, oxirane (ethylene oxide), oxirene, thiirane (ethylene sulfide), dioxirane, azetidine, oxetane, thietane, dioxetane, dithietane, tetrahydropyrrole, pyrrole, tetrahydrofuran, furan, tetrahydrothiophene, thiophene, imidazolidine, pyrazole, imidazole, oxazolidine, oxazole, isoxazole, thiazolidine, thiazole, isothiazole, dioxolane, dithiolane, triazoles, dithiazole, tetrazole, piperidine, pyridine, tetrahydropyran, pyran, thiane, thiine, piperazine, diazines, oxazines, thiazines, dithiane, dioxane, dioxin, triazine, trioxane, tetrazine, azepine, thiepin, diazepine, morpholine, quinoline, 1,2-thiazole, bicyclo[3.3.1]tetrasiloxane, and their substituted analogs. Accordingly and as applicable to the particular heterocyclic compound, heterocyclyl groups, heterocyclylene groups, heterocyclic groups, cycloheteryl groups, cycloheterylene groups, cyclohetero groups, heteroaryl groups, heteroarylene groups, heteroarene groups, arylheteryl groups, arylheterylene groups, arylhetero groups, organoheteryl groups, organoheterylene groups, or organohetero groups can be derived from these and similar heterocyclic compounds and their substituted analogs. Additional description is provided in the definitions section.

In a further aspect, and in any embodiment disclosed herein in which ligands are selected to impart optical activity to the metallocene, the metallocene can be racemic. Alternatively, and in any embodiment in which ligands are selected to impart optical activity to the metallocene, the metallocene can be non-racemic. Further, and in any embodiment in which ligands are selected to impart optical activity to the metallocene, the metallocene can be substantially optically pure (having an enantiomeric excess of greater than or equal to 99.5%), or not optically pure. Thus, any enantiomer, diastereomer, epimer, and the like of the metallocene used in the methods described herein are encompassed by this disclosure.

In another aspect and in any embodiment disclosed herein, the metallocene can have the formula $(\eta^5$-cycloalkadienyl)$M^3R^9{}_nX^9{}_{3-n}$; or alternatively, have the formula $(\eta^5$-cycloalkadienyl)$_2M^3X^9{}_2$. In an embodiment, $M^3$ can be any metallocene metal described herein each $\eta^5$-cycloalkadienyl ligand can be independently any $\eta^5$-cycloalkadienyl ligand described herein, each $R^9$ can be independently any hydrocarbyl group described herein, each $X^9$ can be independently any halide, hydrocarbyl group, hydrocarboxy group described herein, and can be an integer from 1 to 3. In some non-limiting embodiments, $M^3$ can be Ti, Zr, or Hf, each $\eta^5$-cycloalkadienyl ligand can be a substituted or an unsubstituted cyclopentadienyl ligand, a substituted or an unsubstituted indenyl ligand, or a substituted or an unsubstituted fluorenyl ligand, each $R^9$ can be independently a substituted or an unsubstituted $C_1$-$C_{20}$ alkyl group, $C_1$-$C_{20}$ cycloalkyl group, $C_6$-$C_{20}$ aryl group, or $C_7$-$C_{20}$ aralkyl group, each $X^9$ can be independently a halide, a substituted or an unsubstituted $C_1$-$C_{20}$ alkyl group, a substituted or an unsubstituted $C_1$-$C_{20}$ cycloalkyl group, a substituted or an unsubstituted $C_6$-$C_{20}$ aryl group, a substituted or an unsubstituted $C_7$-$C_{20}$ aralkyl group, a substituted or an unsubstituted $C_1$-$C_{20}$ alkoxide group, or a substituted or an unsubstituted $C_6$-$C_{20}$ aryloxide group, and n can be an integer from 1 to 3. When the metallocene has the formula $(\eta^5$-cycloalkadienyl)$_2M^3X^9{}_2$ the two $(\eta^5$-cycloalkadienyl) ligand can be linked by any linking group described herein. When the metallocene having the formula $(\eta^5$-cycloalkadienyl)$M^3R^9{}_nX^9{}_{3-n}$ or the formula $(\eta^5$-cycloalkadienyl)$_2M^3X^9{}_2$, any non-linking substituent on the $\eta^5$-cycloalkadienyl, $R^9$, and/or $X^9$ may independently be any substituent group disclosed herein. In some embodiments, when the metallocene having the formula $(\eta^5$-cycloalkadienyl)$M^3R^9{}_nX^9{}_{3-n}$ or the formula $(\eta^5$-cycloalkadienyl)$_2M^3X^9{}_2$, any non-linking substituent on the $\eta^5$-cycloalkadienyl, $R^9$, and/or $X^9$ may independently be a halide, a $C_1$ to $C_{20}$ alkoxide group, a $C_6$ to $C_{20}$ aryloxide group, a $C_6$ to $C_{20}$ aromatic group, an amido group, a $C_1$ to $C_{20}$ N-alkylamido group, a $C_6$ to $C_{20}$ N-arylamido group, $C_1$ to $C_{40}$ N,N-dialkylamido group, a $C_7$ to $C_{40}$ N-alkyl-N-arylamido group, a $C_1$ to $C_{20}$ alkylthiolate group, a $C_6$ to $C_{20}$ arylthiolate group, a $C_3$ to $C_{20}$ trialkylsiloxy group, or a $C_{18}$ to $C_{45}$ triarylsiloxy group.

A wide range of metallocenes are useful in the catalyst systems disclosed herein and/or the practice of the methods disclosed herein. In an aspect and in any embodiment disclosed herein, the metallocene can have the formula:

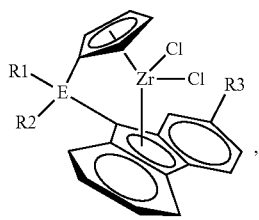

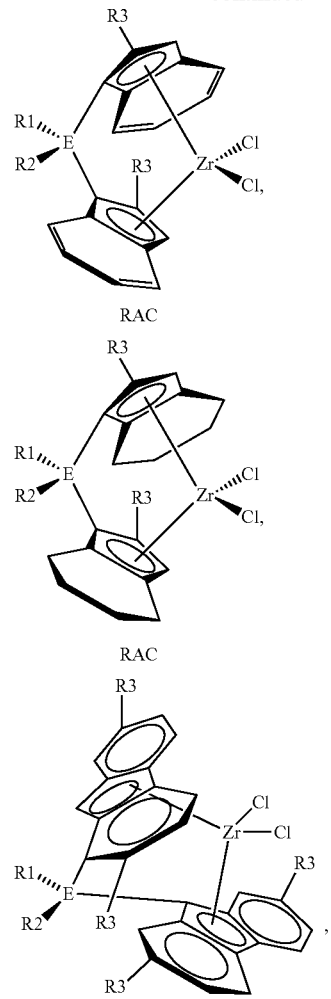

or any combination thereof. In an aspect and in any embodiment disclosed herein, the metallocene have the formula:

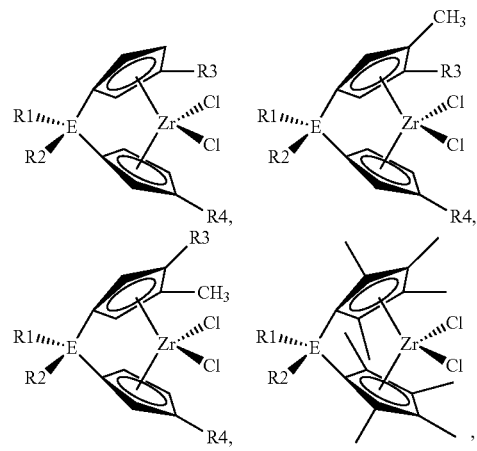

or any combination thereof. In these aspects, E can be any bridging atom disclosed herein, and R1, R2, and R3, in each occurrence can be independently any hydrocarbyl group disclosed herein. In some non-limiting embodiments, E can be C, Si, Ge, or Sn, and in each occurrence, R1, R2, and R3, can be independently H or any $C_1$-$C_{20}$ hydrocarbyl group described herein.

In another non-limiting aspect and in any embodiment disclosed herein, the metallocene can have the formula:

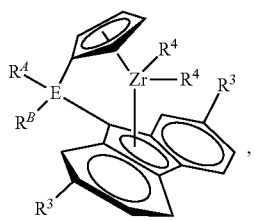

In this aspect, E can be any bridging atom disclosed herein, $R^A$ can be H or any hydrocarbyl group disclosed herein, $R^B$ can be any alkenyl group disclosed herein, $R^3$ can be H or any hydrocarbyl group disclosed herein, and $R^4$ can be H or any hydrocarbyl group disclosed herein. In some non-limiting embodiments, E can be C, Si, Ge, or Sn, $R^A$ can be H or a $C_1$-$C_{20}$ hydrocarbyl group, $R^B$ can be a $C_3$-$C_{12}$ alkenyl group, $R^3$ can be H or a $C_1$-$C_{15}$ hydrocarbyl group, and $R^4$ can be H or a $C_1$-$C_{20}$ hydrocarbyl group.

In yet another aspect and in any embodiment disclosed herein, the metallocene can comprise, consist essentially of, or consist of, singly or in any combination:

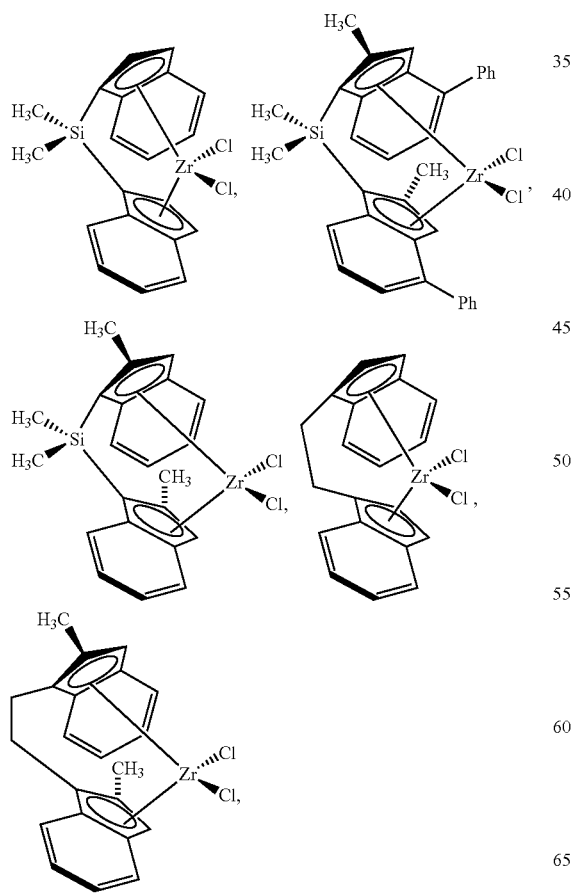

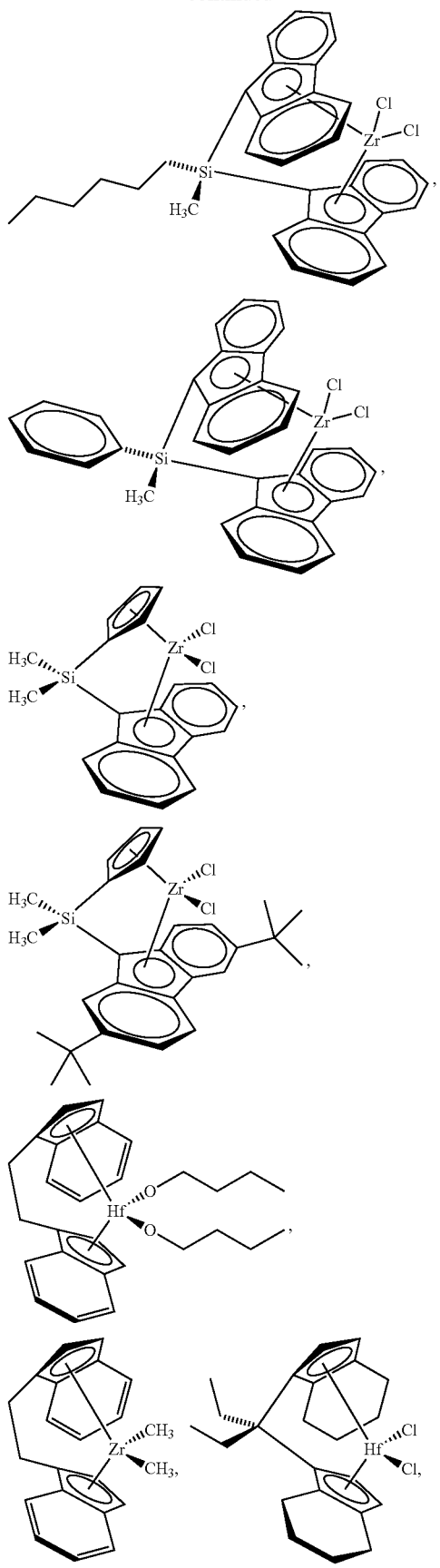

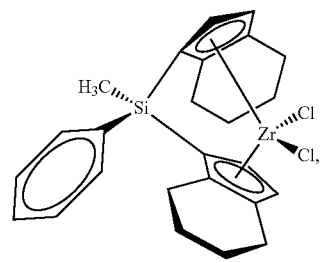
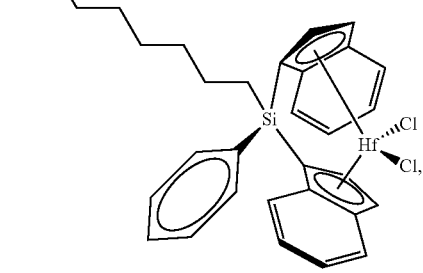
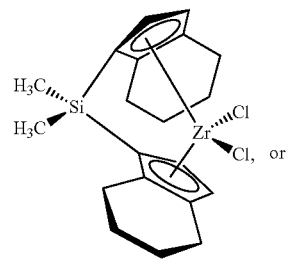
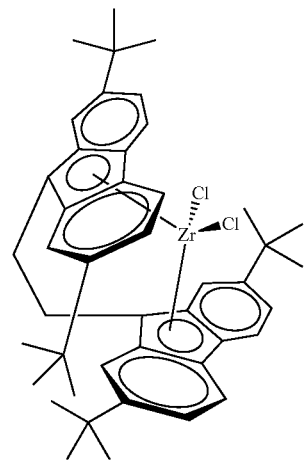
Still a further aspect and in any embodiment disclosed herein, the metallocene can comprise, consist essentially of, or consist of, singly or in any combination:
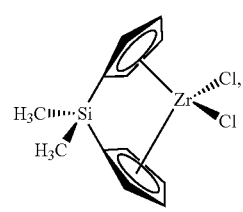
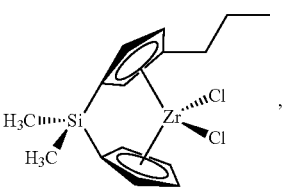
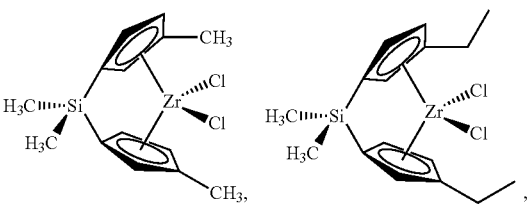
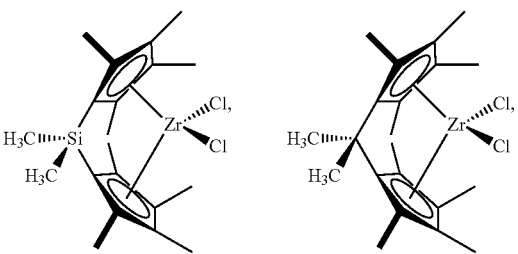
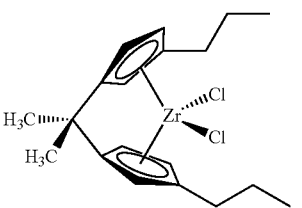
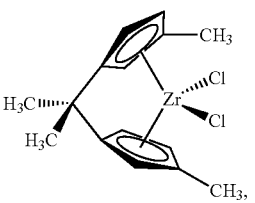
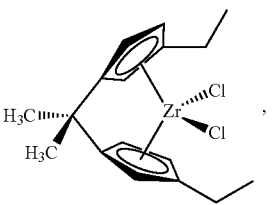
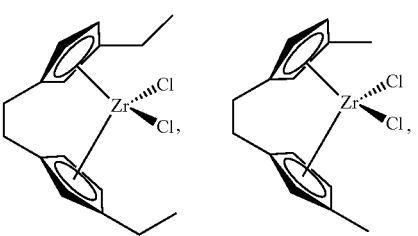

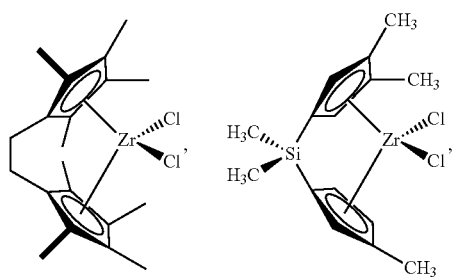
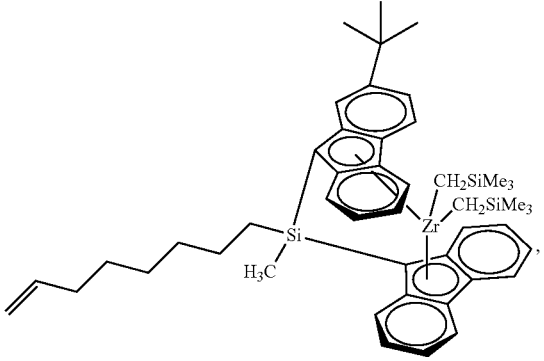
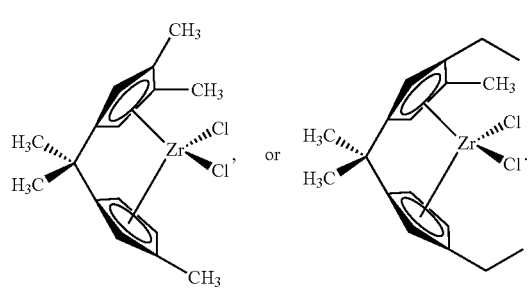
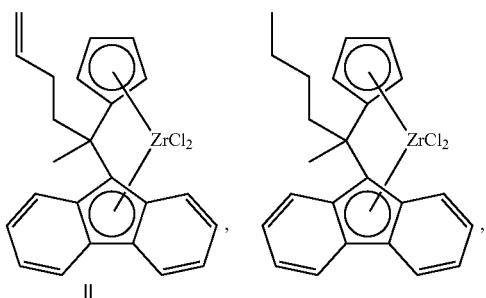
An additional aspect and in any embodiment of this disclosure, the metallocene can comprise, consist essentially of, or consist of, singly or in any combination:
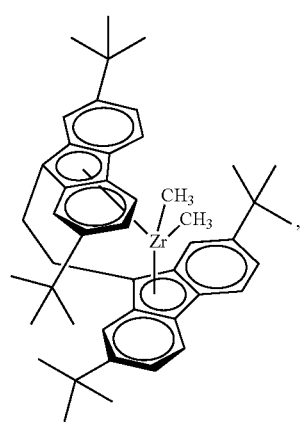
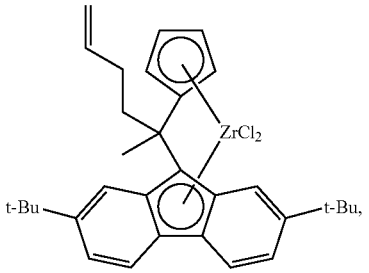
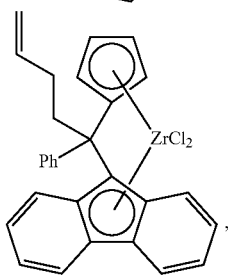
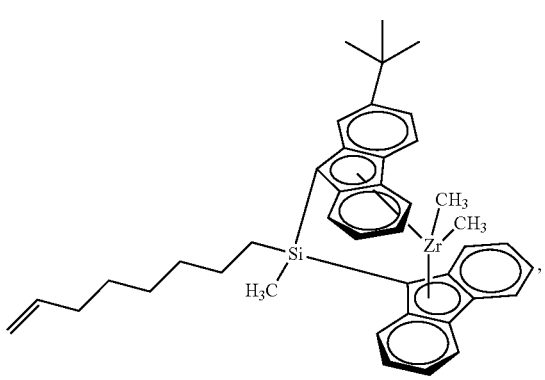
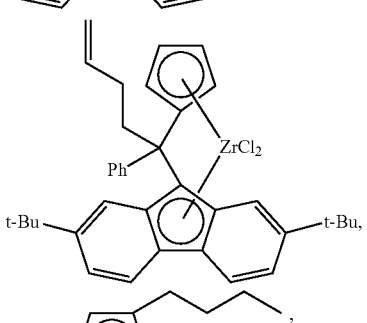

-continued
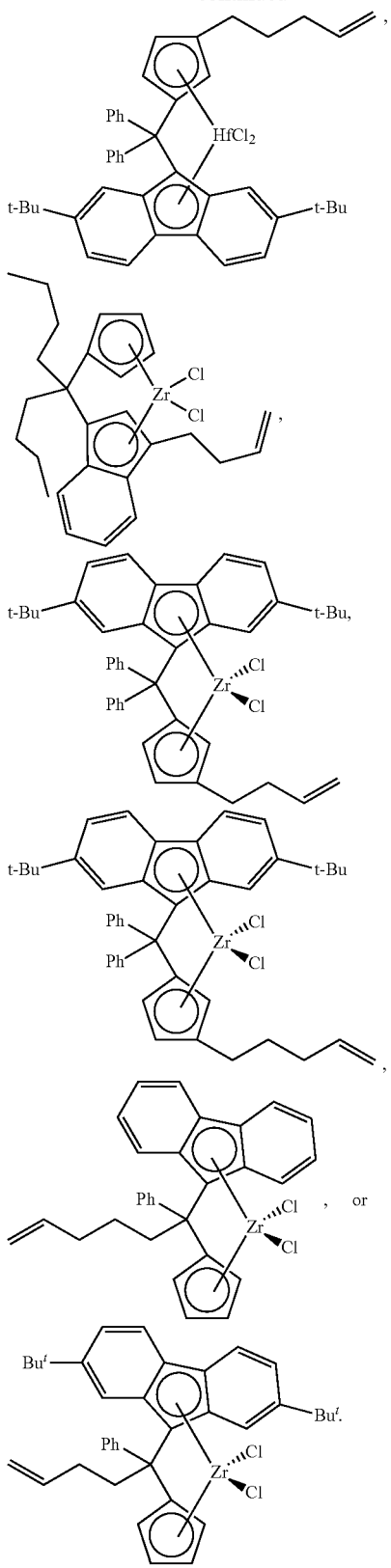
Another aspect an any embodiment disclosed herein, the metallocene can comprise, consist essentially of, or consist of, singly or in any combination:
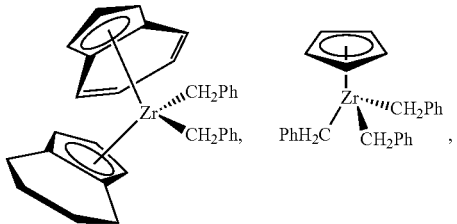
RAC
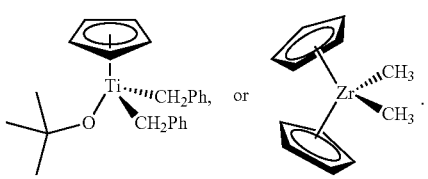
According to another aspect and in any embodiment disclosed herein, the metallocene can comprise, consist essentially of, or consist of:
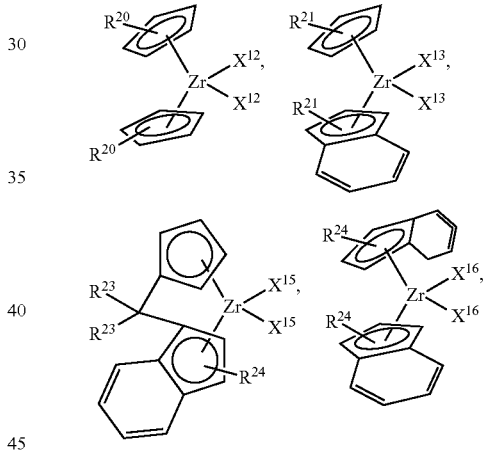
or combinations thereof; alternatively,
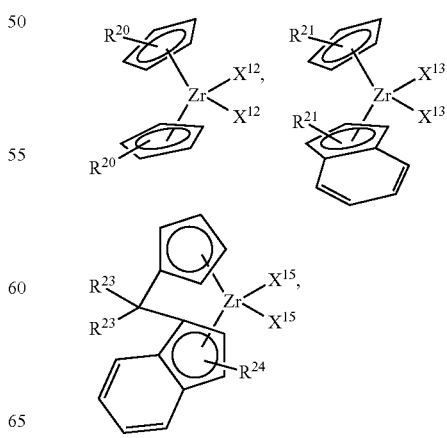

or combinations thereof; alternatively,
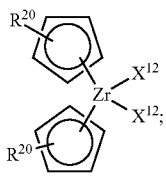
alternatively,
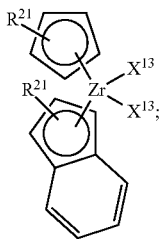
alternatively,
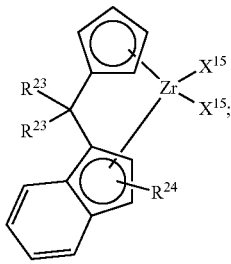
or alternatively,
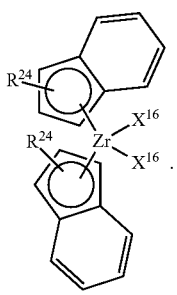
According to yet another aspect and in any embodiment disclosed herein, the metallocene can comprise, consist essentially of, or consist of:
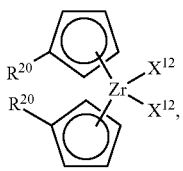 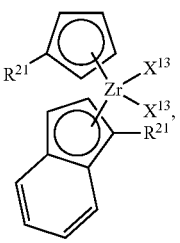
-continued
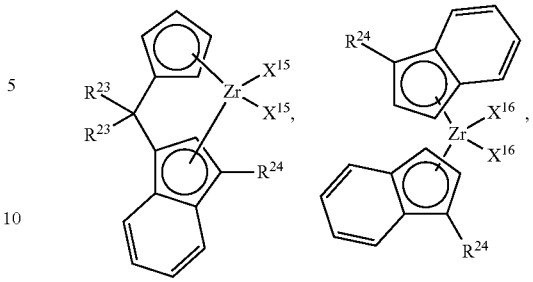
or any combinations thereof; alternatively,
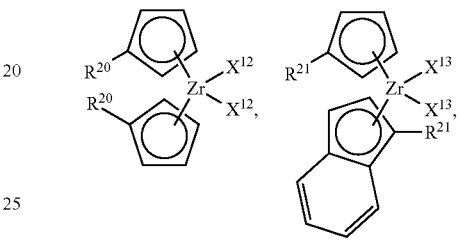
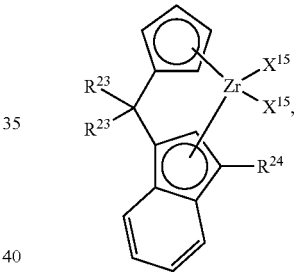
or any combination thereof; alternatively,
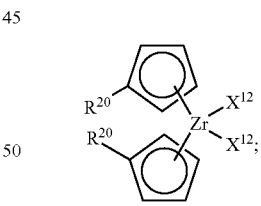
alternatively,
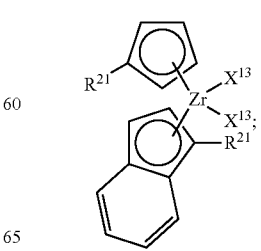

alternatively,

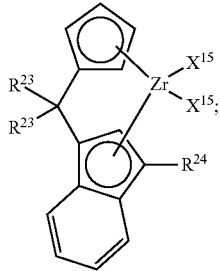

or alternatively,

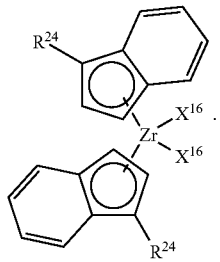

In these aspects, each $R^{20}$, $R^{21}$, $R^{23}$, and $R^{24}$ can be independently hydrogen or any hydrocarbyl group disclosed herein, and each $X^{12}$, $X^{13}$, $X^{15}$, and $X^{16}$ can be independently any halide described herein. In some embodiments, each $R^{20}$, $R^{21}$, $R^{23}$, and $R^{24}$ can be independently a hydrogen, a $C_1$ to $C_{20}$ alkyl group, or a $C_1$ to $C_{20}$ alkenyl group, and each $X^{12}$, $X^{13}$, $X^{15}$, $X^{16}$ can be independently F, Cl, Br, or I. In other embodiments, each $R^{20}$, $R^{21}$, and $R^{23}$ can be independently a hydrogen, a $C_1$ to $C_{10}$ alkyl group, or a $C_1$ to $C_{10}$ alkenyl group, and each $X^{12}$, $X^{13}$, and $X^{15}$ can independently be Cl or Br.

According to yet a further aspect and any embodiment disclosed herein, the metallocene can comprise, consist essentially of, or consist of:

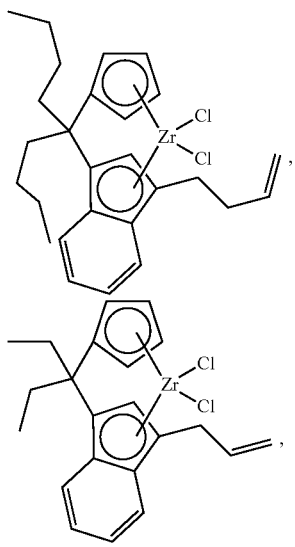

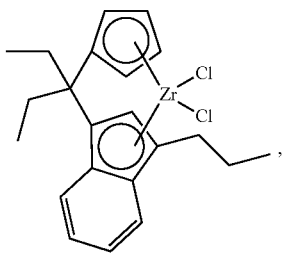

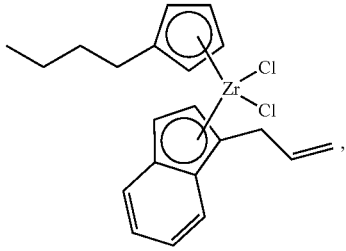

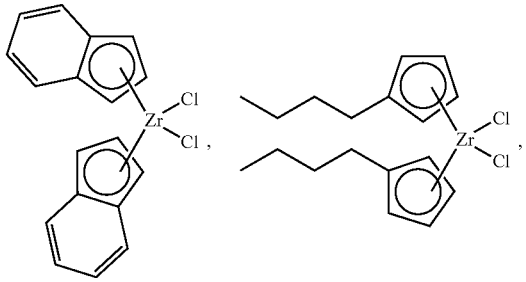

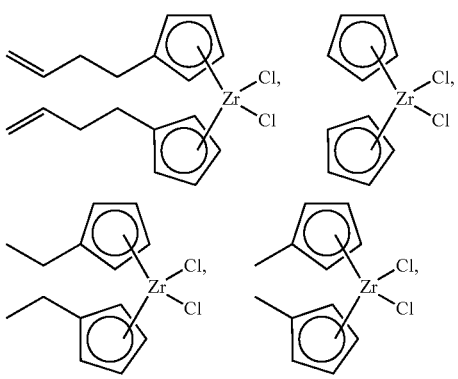

or any combination thereof; alternatively,

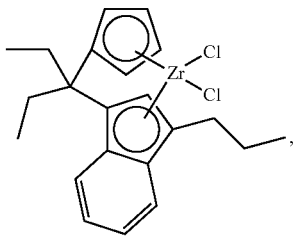

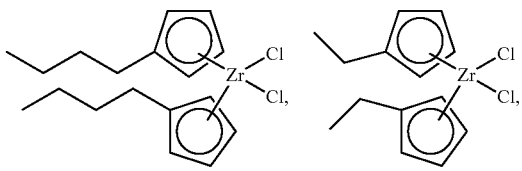

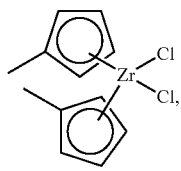
or any combination thereof; alternatively,
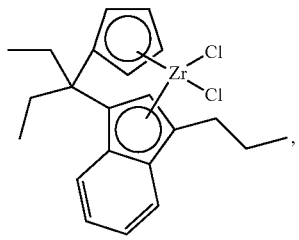
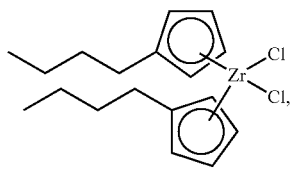 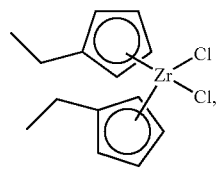
or any combination thereof; alternatively,
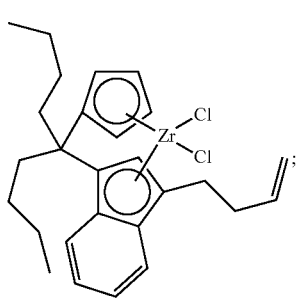
alternatively,
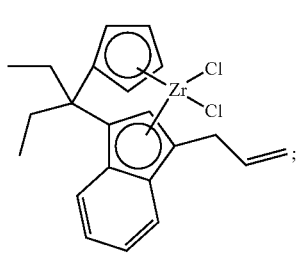
alternatively,
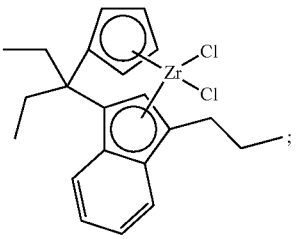
alternatively,
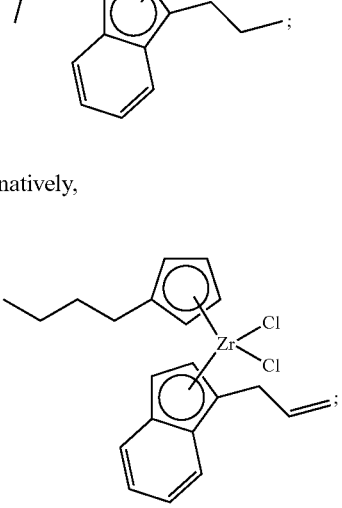
alternatively,
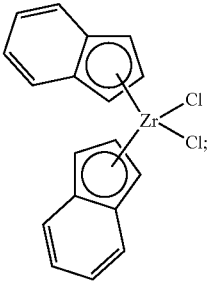
alternatively,
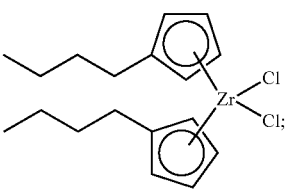
alternatively,
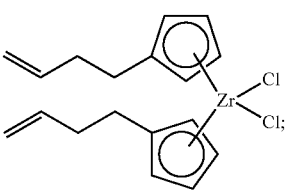

alternatively,

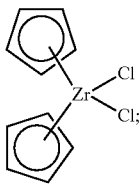

or alternatively,

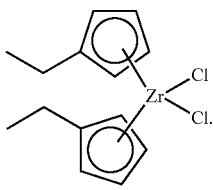

In another aspect and in any embodiment disclosed herein, the metallocene can comprise, consist essentially of, or consist of:

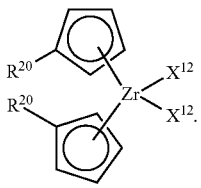

In an embodiment, each $R^{20}$ can be independently a hydrogen, a $C_1$ to $C_{10}$ alkyl group, or a $C_1$ to $C_{10}$ alkenyl group, and each $X^{12}$ can be independently Cl or Br. In other embodiments, each $R^{20}$ can be independently a $C_1$ to $C_{10}$ alkyl group and each $X^{12}$ can be independently Cl or Br. In a non-limiting embodiment, the metallocene can comprise, consist essentially of, or consists of:

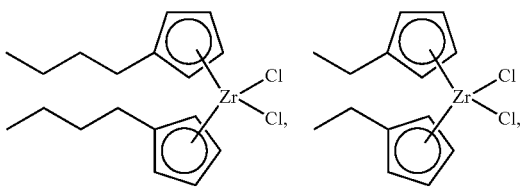

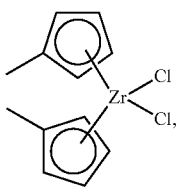

or any combination thereof; alternatively,

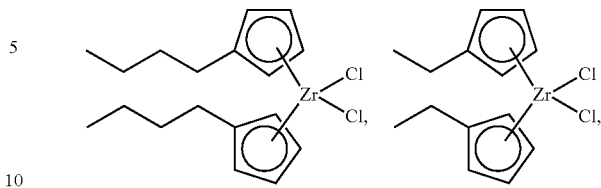

or any combination thereof.

Still a further aspect and any embodiment disclosed herein, the metallocene can comprise, consist essentially of, or consists of:

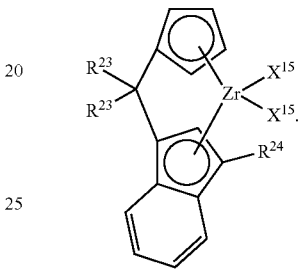

In some non-limiting embodiments, each $R^{23}$ and $R^{24}$ can be independently hydrogen, a $C_1$ to $C_{10}$ alkyl group, or a $C_1$ to $C_{10}$ alkenyl group, and each $X^{15}$ can be independently Cl or Br. In other non-limiting embodiments, each $R^{23}$ and $R^{24}$ can be independently a $C_1$ to $C_{10}$ alkyl group or a $C_1$ to $C_{10}$ alkenyl group, and each $X^{15}$ can be independently Cl or Br. In yet another non-limiting embodiment, the metallocene can comprise, consist essentially of, or consist of:

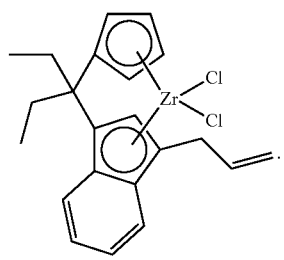

Still a further aspect and any embodiment disclosed herein, the metallocene can comprise, consist essentially of, or consists of:

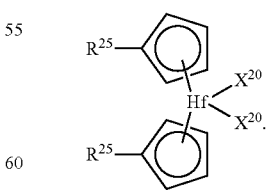

In some non-limiting embodiments, each $R^{25}$ can be independently hydrogen, a $C_1$ to $C_{10}$ alkyl group, or a $C_1$ to $C_{10}$ alkenyl group, and each $X^{20}$ can be independently Cl or Br. In other non-limiting embodiments, each $R^{25}$ can be independently a $C_1$ to $C_{10}$ alkyl group or a $C_1$ to $C_{10}$ alkenyl group, and each $X^{20}$ can be independently Cl or Br. In yet other non-limiting embodiments, each $R^{25}$ can be independently a $C_1$ to $C_{10}$ alkyl group, and each $X^{20}$ can be independently Cl or Br. In yet another non-limiting embodiment, the metallocene can comprise, consist essentially of, or consist of:

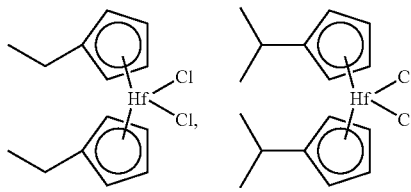

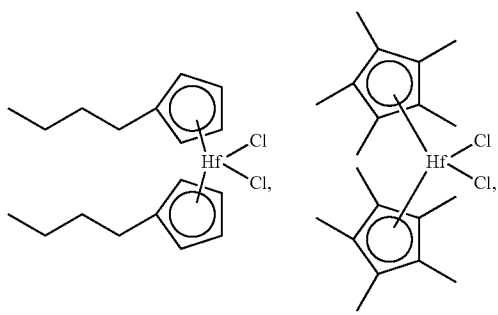

or combinations thereof; alternatively,

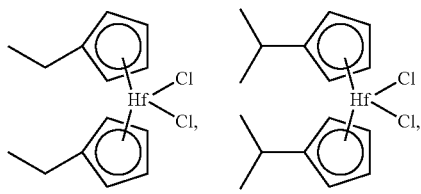

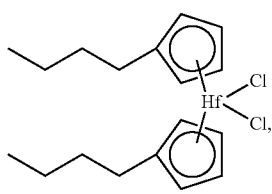

or combinations thereof; alternatively,

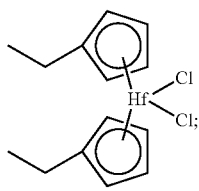

alternatively,

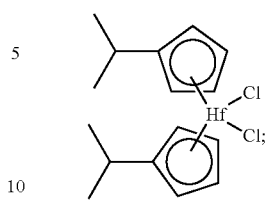

alternatively,

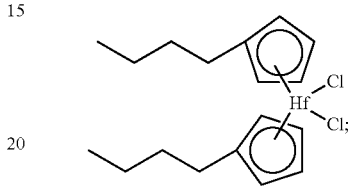

or alternatively,

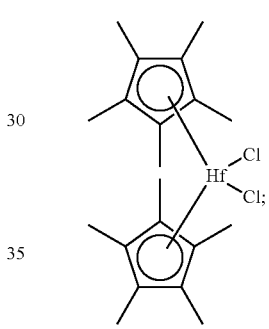

In other aspect and in any embodiment disclosed herein, the metallocene can comprise, consist essentially of, or consist of, singly or in any combination thereof:
bis(cyclopentadienyl)hafnium dichloride,
bis(cyclopentadienyl)zirconium dichloride,
1,2-ethanediylbis($\eta^5$-1-indenyl)di-n-butoxyhafnium,
1,2-ethanediylbis($\eta^5$-1-indenyl)dimethylzirconium,
3,3-pentanediylbis($\eta^5$-4,5,6,7-tetrahydro-1-indenyl) hafnium dichloride,
methylphenylsilylbis($\eta^5$-4,5,6,7-tetrahydro-1-indenyl)zirconium dichloride,
bis(n-butylcyclopentadienyl)di-t-butylamido hafnium,
bis(n-butylcyclopentadienyl)zirconium dichloride,
bis(ethylcyclopentadienyl)zirconium dichloride,
bis(propylcyclopentadienyl)zirconium dichloride,
dimethylsilylbis(1-indenyl)zirconium dichloride,
nonyl(phenyl)silylbis(1-indenyl)hafnium dichloride,
dimethylsilylbis($\eta^5$-4,5,6,7-tetrahydro-1-indenyl)zirconium dichloride,
dimethylsilylbis(2-methyl-1-indenyl)zirconium dichloride,
1,2-ethanediylbis(9-fluorenyl)zirconium dichloride,
indenyl diethoxy titanium(IV) chloride,
(isopropylamidodimethylsilyl)cyclopentadienyltitanium dichloride,
bis(pentamethylcyclopentadienyl)zirconium dichloride,
bis(indenyl)zirconium dichloride,
methyloctylsilyl bis(9-fluorenyl)zirconium dichloride,
bis-[1-(N,N-diisopropylamino)boratabenzene]hydridozirconium trifluoromethylsulfonate, bis(cyclopentadienyl)hafnium dimethyl,
bis(cyclopentadienyl)zirconium dibenzyl,
1,2-ethanediylbis($\eta^5$-1-indenyl)dimethylhafnium,
1,2-ethanediylbis($\eta^5$-1-indenyl)dimethylzirconium,
3,3-pentanediylbis($\eta^5$-4,5,6,7-tetrahydro-1-indenyl) hafnium dimethyl,
methylphenylsilylbis($\eta^5$-4,5,6,7-tetrahydro-1-indenyl)zirconium dimethyl,
bis(1-n-butyl-3-methyl-cyclopentadienyl)zirconium dimethyl,
bis(n-butylcyclopentadienyl)zirconium dimethyl,
dimethylsilylbis(1-indenyl)zirconium bis(trimethylsilylmethyl),
octyl(phenyl)silylbis(1-indenyl)hafnium dimethyl,
dimethylsilylbis($\eta^5$-4,5,6,7-tetrahydro-1-indenyl)zirconium dimethyl,
dimethylsilylbis(2-methyl-1-indenyl)zirconium dibenzyl,
1,2-ethanediylbis(9-fluorenyl)zirconium dimethyl,
(indenyl)trisbenzyl titanium(IV),
(isopropylamidodimethylsilyl)cyclopentadienyltitanium dibenzyl,
bis(pentamethylcyclopentadienyl)zirconium dimethyl,
bis(indenyl)zirconium dimethyl,
methyl(octyl)silylbis(9-fluorenyl)zirconium dimethyl,
bis(2,7-di-tert-butylfluorenyl)-ethan-1,2-diyl)zirconium(IV) dimethyl,
2-($\eta^5$-cyclopentadienyl)-2-($\eta^5$-fluoren-9-yl)hex-5-ene zirconium(IV)dichloride,
2-($\eta^5$-cyclopentadienyl)-2-($\eta^5$-2,7-di-tert-butylfluoren-9-yl)hex-5-ene zirconium(IV)dichloride,
2-($\eta^5$-cyclopentadienyl)-2-($\eta^5$-fluoren-9-yl)hept-6-ene zirconium(IV)dichloride,
2-($\eta^5$-cyclopentadienyl)-2-($\eta^5$-2,7-di-tert-butylfluoren-9-yl)hept-6-ene zirconium(IV)dichloride,
1-($\eta^5$-cyclopentadienyl)-1-($\eta^5$-fluoren-9-yl)-1-phenylpent-4-ene zirconium(IV)dichloride,
1-($\eta^5$-cyclopentadienyl)-1-($\eta^5$-2,7-di-tert-butyl fluoren-9-yl)-1-phenylpent-4-ene zirconium(IV)dichloride,
1-($\eta^5$-cyclopentadienyl)-1-($\eta^5$-fluoren-9-yl)-1-phenylhex-5-ene zirconium(IV)dichloride, or
1-($\eta^5$-cyclopentadienyl)-1-($\eta^5$-2,7-di-tert-butylfluoren-9-yl)-1-phenylhex-5-ene zirconium(IV)dichloride.

In another aspect and in any embodiment disclosed herein, the metallocene can comprise, consist essentially of, consist of, singly or in any combination, rac-$C_2H_4(\eta^5$-indenyl$)_2ZrCl_2$, rac-Me$_2$Si($\eta^5$-indenyl$)_2ZrCl_2$, Me(octyl)Si ($\eta^5$-fluorenyl$)_2ZrCl_2$, rac-Me$_2$Si($\eta^5$-2-Me-4-Ph-indenyl$)_2ZrCl_2$, rac-$C_2H_4(\eta^5$-2-Me-indenyl$)_2ZrCl_2$, Me(Ph)Si($\eta^5$-fluorenyl$)_2ZrCl_2$, rac-Me$_2$Si($\eta^5$-3-n-Pr-cyclopentadienyl$)_2ZrCl_2$, Me$_2$Si($\eta^5$-Me$_4$-cyclopentadienyl$)_2ZrCl_2$, or Me$_2$Si($\eta^5$-cyclopentadienyl$)_2ZrCl_2$.

In a further aspect and in any embodiment disclosed herein, the metallocene can comprise two $\eta^5$-cyclopentadienyl-type ligands that are connected by linking group consisting of one, two, or three bridging atoms. In a another aspect and in any embodiment disclosed herein, the metallocene can comprise one $\eta^5$-cyclopentadienyl-type ligand that is connected by a bridge consisting of one, two, or three bridging atoms to another ligand in the metallocene that is not an $\eta^5$-cyclopentadienyl-type ligand. Each of these bridges can be further substituted if desired. The complete substituted bridging group or bridging atoms are described along with their substituents, other than the cyclopentadienyl-type ligand substituents, as the "linking group." By way of example of this terminology, possible linking groups include —CH$_2$CH$_2$— or —CH(CH$_3$)CH(CH$_3$)—, both of which comprise a C$_2$ bridge. Thus, the —CH$_2$CH$_2$-linking group is generally described as unsubstituted linking group, while linking groups such as —CH(CH$_3$)CH(CH$_3$)— are generally described as a substituted linking group.

Chemically-Treated Solid Oxide

One aspect of this disclosure provides for an oligomerization method comprising (or a method of producing a PAO comprising a step of) contacting an alpha olefin monomer and a catalyst system comprising a metallocene. In an embodiment the catalyst system can further comprise an activator. In one aspect, this disclosure encompasses a catalyst system comprising at least one metallocene and at least one activator. One exemplary activator that may be utilized is a chemically-treated solid oxide. The term "chemically-treated solid oxide" is used interchangeably with similar terms such as, "solid oxide treated with an electron-withdrawing anion," "treated solid oxide," or "solid super acid," which is also termed "SSA." While not intending to be bound by theory, it is thought that the chemically-treated solid oxide can serve as an acidic activator-support. In one aspect and in any embodiment, the chemically-treated solid oxide can be used in combination with an organoaluminum compound or similar activating agent or alkylating agent. In one aspect and in any embodiment, the chemically-treated solid oxide can be used in combination with an organoaluminum compound. In another aspect and in any embodiment, the metallocene can be "pre-activated" by, being alkylated prior to its use in the catalyst system. In an aspect and in any embodiments, the chemically-treated solid oxide can be used as the only activator. In yet another aspect and in any embodiment, the metallocene is "pre-activated" and the chemically-treated solid oxide can be used in conjunction with another activator; or alternatively, multiple other activators.

In one aspect and any embodiment of this disclosure, the catalyst system can comprise at least one chemically-treated solid oxide comprising at least one solid oxide treated with at least one electron-withdrawing anion, wherein the solid oxide can comprise any oxide that is characterized by a high surface area, and the electron-withdrawing anion can comprise any anion that increases the acidity of the solid oxide as compared to the solid oxide that is not treated with at least one electron-withdrawing anion.

In another aspect and in any embodiment of this disclosure, the catalyst system can comprise a chemically-treated solid oxide comprising a solid oxide treated with an electron-withdrawing anion, wherein:
the solid oxide is selected from silica, alumina, silica-alumina, aluminum phosphate, heteropolytungstates, titania, zirconia, magnesia, boria, zinc oxide, mixed oxides thereof, or mixtures thereof; and
the electron-withdrawing anion is selected from fluoride, chloride, bromide, phosphate, triflate, bisulfate, sulfate, fluorophosphate, fluorosulfate, or any combination thereof.

In another aspect and in any embodiment of this disclosure, the catalyst system can comprise a chemically-treated solid oxide comprising a solid oxide treated with an electron-withdrawing anion, wherein:
the solid oxide is selected from silica, alumina, silica-alumina, titania, zirconia, mixed oxides thereof, or mixtures thereof; and
the electron-withdrawing anion is selected from fluoride, chloride, bisulfate, sulfate, or any combination thereof.

In another aspect and in any embodiment of this disclosure, the chemically-treated solid oxide can be fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, or any combination thereof; alternatively, fluorided alumina, chlorided alumina, sulfated alumina, fluorided silica-alumina, chlorided silica-alumina, sulfated silica-alumina, fluorided silica-zirconia, sulfated silica-zirconia, or any combination thereof; alternatively, fluorided alumina; alternatively, chlorided alumina; alternatively, bromided alumina; alternatively, sulfated alumina; alternatively, fluorided silica-alumina; alternatively, chlorided silica-alumina; alternatively, bromided silica-alumina; alternatively, sulfated silica-alumina; alternatively, fluorided silica-zirconia; alternatively, chlorided silica-zirconia; alternatively, bromided silica-zirconia; or alternatively, sulfated silica-zirconia. Further, and in yet another aspect, the chemically-treated solid oxide can further comprise a metal or metal ion selected from zinc, nickel, vanadium, silver, copper, gallium, tin, tungsten, molybdenum, or any combination thereof; alternatively, zinc, nickel, vanadium, tin, or any combination thereof; alternatively, zinc; alternatively, nickel; alternatively, vanadium; alternatively, silver; alternatively, copper; alternatively, gallium; alternatively, tin; alternatively, tungsten; or alternatively, molybdenum.

In yet a further aspect and in any embodiment of this disclosure, the chemically-treated solid oxide can comprise the contact product of at least one solid oxide compound and at least one electron-withdrawing anion source. The solid oxide compound and electron-withdrawing anion source are described independently herein and can be utilized in any combination to further describe the chemically-treated solid oxide comprising the contact product of at least one solid oxide compound and at least one electron-withdrawing anion source. That is, the chemically-treated solid oxide is provided upon contacting or treating the solid oxide with the electron-withdrawing anion source. The solid oxide compound and electron-withdrawing anion source are described independently herein and can be utilized in any combination to further describe the chemically-treated solid oxide comprising the contact product of at least one solid oxide compound and at least one electron-withdrawing anion source. In one aspect, the solid oxide compound can comprise, consist essentially of, or consist of, an inorganic oxide. It is not required that the solid oxide compound be calcined prior to contacting the electron-withdrawing anion source. The contact product can be calcined either during or after the solid oxide compound is contacted with the electron-withdrawing anion source. In this aspect, the solid oxide compound can be calcined or uncalcined; alternatively, calcined; or alternatively, uncalcined. In another aspect, the activator-support can comprise the contact product of at least one calcined solid oxide compound and at least one electron-withdrawing anion source.

While not intending to be bound by theory, the chemically-treated solid oxide, also termed the activator-support, exhibits enhanced acidity as compared to the corresponding untreated solid oxide compound. The chemically-treated solid oxide can also function as a catalyst activator as compared to the corresponding untreated solid oxide. While the chemically-treated solid oxide can activate the metallocene in the absence of additional activators, additional activators can be utilized in the catalyst system. By way of example, it may be useful to include an organoaluminum compound in the catalyst system along with the metallocene and chemically-treated solid oxide. The activation function of the activator-support is evident in the enhanced activity of catalyst system as a whole, as compared to a catalyst system containing the corresponding untreated solid oxide.

In one aspect, the chemically-treated solid oxide of this disclosure can comprise, consist essentially of, or consist of, a solid inorganic oxide material, a mixed oxide material, or a combination of inorganic oxide materials, that is chemically-treated with an electron-withdrawing component, and optionally treated with a metal; alternatively, a solid inorganic oxide material that is chemically-treated with an electron-withdrawing component and optionally treated with a metal; alternatively, a mixed oxide material that is chemically-treated with an electron-withdrawing component and optionally treated with a metal; or alternatively, a combination of inorganic oxide materials, that is chemically-treated with an electron-withdrawing component, and optionally treated with a metal. Thus, the solid oxide of this disclosure encompasses oxide materials (e.g. alumina), "mixed oxide" compounds (e.g. silica-alumina), and combinations and mixtures thereof. The mixed oxide compounds (e.g. silica-alumina) can be single or multiple chemical phases with more than one metal combined with oxygen to form a solid oxide compound, and are encompassed by this disclosure. The solid inorganic oxide material, mixed oxide material, combination of inorganic oxide materials, electron-withdrawing component, and optional metal are independently described herein and can be utilized in any combination to further described the chemically-treated solid oxide.

In one aspect of this disclosure and in any embodiment, the chemically-treated solid oxide further can comprise a metal or metal ion. In an embodiment, the metal or metal of the metal ion can comprise, consist essentially of, or consist of, zinc, nickel, vanadium, titanium, silver, copper, gallium, tin, tungsten, molybdenum, or any combination thereof; alternatively, zinc, nickel, vanadium, titanium, or tin, or any combination thereof; alternatively, zinc, nickel, vanadium, tin, or any combination thereof. In some embodiments, the metal or metal of the metal ion can comprise, consist essentially of, or consist of, zinc; alternatively, nickel; alternatively, vanadium; alternatively, titanium; alternatively, silver; alternatively, copper; alternatively, gallium; alternatively, tin; alternatively, tungsten; or alternatively, molybdenum.

In an aspect and any embodiment, the chemically-treated solid oxides that further comprise a metal or metal ion include, but are not limited to, zinc-impregnated chlorided alumina, titanium-impregnated fluorided alumina, zinc-impregnated fluorided alumina, zinc-impregnated chlorided silica-alumina, zinc-impregnated fluorided silica-alumina, zinc-impregnated sulfated alumina, chlorided zinc aluminate, fluorided zinc aluminate, sulfated zinc aluminate, or any combination thereof; alternatively, the chemically-treated solid oxide can be fluorided alumina, chlorided alumina, sulfated alumina, fluorided silica-alumina, chlorided silica-alumina, sulfated silica-alumina, fluorided silica-zirconia, sulfated silica-zirconia, or any combination thereof. In some embodiments, the chemically-treated solid oxides that further comprise a metal or metal ion can comprise, consist essentially of, or consist of, zinc-impregnated chlorided alumina; alternatively, titanium-impregnated fluorided alumina; alternatively, zinc-impregnated fluorided alumina; alternatively, zinc-impregnated chlorided silica-alumina; alternatively, zinc-impregnated fluorided silica-alumina; alternatively, zinc-impregnated sulfated alumina; alternatively, chlorided zinc aluminate; alternatively, fluorided zinc aluminate; alternatively, or sulfated zinc aluminate.

In another aspect and any embodiment, the chemically-treated solid oxide of this disclosure can comprise a solid oxide of relatively high porosity, which exhibits Lewis acidic or Brønsted acidic behavior. The solid oxide can be chemically-treated with an electron-withdrawing component, typically an electron-withdrawing anion, to form an activator-support. While not intending to be bound by the following statement, it is believed that treatment of the inorganic oxide with an electron-withdrawing component augments or enhances the acidity of the oxide. Thus in one aspect, the activator-support exhibits Lewis or Brønsted acidity which is typically greater than the Lewis or Brønsted acid strength than the untreated solid oxide, or the activator-support has a greater number of acid sites than the untreated solid oxide, or both. One method to quantify the acidity of the chemically-treated and untreated solid oxide materials is by comparing the oligomerization activities of the treated and untreated oxides under acid catalyzed reactions.

In one aspect an in any embodiment, the chemically-treated solid oxide can comprise, consist essentially of, or consist of, a solid inorganic oxide comprising oxygen and at least one element selected from Group 2, 3, 4, 5, 6, 7, 8, 9, 10, 11, 12, 13, 14, or 15 of the periodic table, or comprising oxygen and at least one element selected from the lanthanide or actinide elements; alternatively, the chemically-treated solid oxide can comprise a solid inorganic oxide comprising oxygen and at least one element selected from Group 4, 5, 6, 12, 13, or 14 of the periodic table, or comprising oxygen and at least one element selected from the lanthanide elements. (See: $Hawley's$ $Condensed$ $Chemical$ $Dictionary$, $11^{th}$ Ed., John Wiley & Sons; 1995; Cotton, F. A.; Wilkinson, G.; Murillo; C. A.; and Bochmann; M. $Advanced$ $Inorganic$ $Chemistry$, $6^{th}$ Ed., Wiley-Interscience, 1999.) In some embodiments, the inorganic oxide can comprise oxygen and at least one element selected from Al, B, Be, Bi, Cd, Co, Cr, Cu, Fe, Ga, La, Mn, Mo, Ni, Sb, Si, Sn, Sr, Th, Ti, V, W, P, Y, Zn or Zr; alternatively, the inorganic oxide can comprise oxygen and at least one element selected from Al, B, Si, Ti, P, Zn or Zr.

In an embodiment, the solid oxide utilized in the chemically-treated solid oxide can include, but is not limited to, $Al_2O_3$, $B_2O_3$, $BeO$, $Bi_2O_3$, $CdO$, $Co_3O_4$, $Cr_2O_3$, $CuO$, $Fe_2O_3$, $Ga_2O_3$, $La_2O_3$, $Mn_2O_3$, $MoO_3$, $NiO$, $P_2O_5$, $Sb_2O_5$, $SiO_2$, $SnO_2$, $SrO$, $ThO_2$, $TiO_2$, $V_2O_5$, $WO_3$, $Y_2O_3$, $ZnO$, $ZrO_2$, mixed oxides thereof, and combinations thereof; alternatively, $Al_2O_3$, $B_2O_3$, $SiO_2$, $SnO_2$, $TiO_2$, $V_2O_5$, $WO_3$, $Y_2O_3$, $ZnO$, $ZrO_2$, including mixed oxides thereof, and combinations thereof; alternatively, $Al_2O_3$, $SiO_2$, $TiO_2$, $ZrO_2$, and the like, including mixed oxides thereof, and combinations thereof. In some embodiments, the solid oxide utilized in the chemically-treated solid oxide can comprise, consist essentially of, or consist of, $Al_2O_3$; alternatively, $B_2O_3$; alternatively, $BeO$; alternatively, $Bi_2O_3$; alternatively, $CdO$; alternatively, $Co_3O_4$; alternatively, $Cr_2O_3$; alternatively, $CuO$; alternatively, $Fe_2O_3$; alternatively, $Ga_2O_3$; alternatively, $La_2O_3$; alternatively, $Mn_2O_3$; alternatively, $MoO_3$; alternatively, $NiO$; alternatively, $P_2O_5$; alternatively, $Sb_2O_5$; alternatively, $SiO_2$; alternatively, $SnO_2$; alternatively, $SrO$; alternatively, $ThO_2$; alternatively, $TiO_2$; alternatively, $V_2O_5$; alternatively, $WO_3$; alternatively, $Y_2O_3$; alternatively, $ZnO$; or alternatively, $ZrO_2$. In an embodiment, the mixed oxides that can be used in the activator-support of the present disclosure include, but are not limited to, silica-alumina, silica-titania, silica-zirconia, zeolites, clay minerals, alumina-titania, alumina-zirconia, and zinc-aluminate; alternatively, silica-alumina, silica-titania, silica-zirconia, alumina-titania, alumina-zirconia, and zinc-aluminate; alternatively, silica-alumina, silica-titania, silica-zirconia, and alumina-titania. In some embodiments, the mixed oxides that can be used in the activator-support of the present disclosure can comprise, consist essentially of, or consist of, silica-alumina; alternatively, silica-titania; alternatively, silica-zirconia; alternatively, zeolites; alternatively, clay minerals; alternatively, alumina-titania; alternatively, alumina-zirconia; alternatively, and zinc-aluminate. In some embodiments, aluminosilicates such as clay minerals, calcium aluminosilicate, or sodium aluminosilicate are useful oxides that can be used in the activator-support of the present disclosure.

In one aspect and any embodiment of this disclosure, the solid oxide material is chemically-treated by contacting it with at least one electron-withdrawing component (e.g. an electron-withdrawing anion source). Further, the solid oxide material can be chemically-treated with a metal ion if desired, then calcined to form a metal-containing or metal-impregnated chemically-treated solid oxide. Alternatively, a solid oxide material and an electron-withdrawing anion source can be contacted and calcined simultaneously. The method by which the oxide is contacted with an electron-withdrawing component (e.g. a salt or an acid of an electron-withdrawing anion), includes, but is not limited to, gelling, co-gelling, impregnation of one compound onto another, and the like. Typically, following any contacting method, the contacted mixture of oxide compound, electron-withdrawing anion, and the metal ion, if present, can be calcined.

The electron-withdrawing component used to treat the oxide can be any component that increases the Lewis or Brønsted acidity of the solid oxide upon treatment. In one aspect, the electron-withdrawing component can be an electron-withdrawing anion derived from a salt, an acid, or other compound (e.g. a volatile organic compound) that can serve as a source or precursor for that anion. In an aspect, electron-withdrawing anions include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, trifluoroacetate, triflate, and combinations thereof; alternatively, sulfate, bisulfate, fluoride, chloride, fluorosulfate, fluoroborate, phosphate, fluorophosphate, trifluoroacetate, triflate, fluorozirconate, fluorotitanate, and combinations thereof; alternatively, fluoride, chloride, bisulfate, sulfate, combinations thereof; alternatively, sulfate, bisulfate, and combinations thereof; alternatively, fluoride, chloride, bromide, iodide, and combinations thereof; alternatively, fluorosulfate, fluoroborate, trifluoroacetate, triflate, fluorozirconate, fluorotitanate, trifluoroacetate, triflate, and combinations thereof; alternatively, fluoride, chloride, combinations thereof; or alternatively, bisulfate, sulfate, combinations thereof. In some embodiments, the electron-withdrawing anion can comprise, consist essentially of, or consist of, sulfate; alternatively, bisulfate; alternatively, fluoride; alternatively, chloride; alternatively, bromide; alternatively, iodide; alternatively, fluorosulfate; alternatively, fluoroborate; alternatively, phosphate; alternatively, fluorophosphate; alternatively, trifluoroacetate; alternatively, triflate; alternatively, fluorozirconate; alternatively, fluorotitanate; alternatively, trifluoroacetate; or alternatively, triflate. In addition, other ionic or non-ionic compounds that serve as sources for these electron-withdrawing anions can also be employed in the present disclosure.

When the electron-withdrawing component comprises a salt of an electron-withdrawing anion, the counterion or cation of that salt can be any cation that allows the salt to revert or decompose back to the acid during calcining. Factors that dictate the suitability of the particular salt to serve as a source for the electron-withdrawing anion include, but are not limited to, the solubility of the salt in the desired solvent, the lack of adverse reactivity of the cation, ion-pairing effects between the cation and anion, hygroscopic properties imparted to the salt by the cation and thermal stability of the anion. In an aspect, suitable cations in the salt of the electron-withdrawing anion include, but are not limited to, ammonium, trialkyl ammonium, tetraalkyl ammonium, tetraalkyl phosphonium, H$^+$, and [H(OEt$_2$)$_2$]$^+$; alternatively, ammonium; alternatively, trialkyl ammonium; alternatively, tetraalkyl ammonium; alternatively, tetraalkyl phosphonium; alternatively, H$^+$; or alternatively, [H(OEt$_2$)$_2$]$^+$.

Further, combinations of one or more different electron withdrawing anions, in varying proportions, can be used to tailor the specific acidity of the activator-support to the desired level. Combinations of electron withdrawing components can be contacted with the oxide material simultaneously or individually, and any order that affords the desired chemically-treated solid oxide acidity. For example, one aspect of this disclosure is employing two or more electron-withdrawing anion source compounds in two or more separate contacting steps. In an non-limiting aspect of such a process by which an chemically-treated solid oxide is prepared can be as follows: a selected solid oxide compound, or combination of oxide compounds, is contacted with a first electron-withdrawing anion source compound to form a first mixture, this first mixture is then calcined, the calcined first mixture is then contacted with a second electron-withdrawing anion source compound to form a second mixture, followed by calcining said second mixture to form a treated solid oxide compound. In such a process, the first and second electron-withdrawing anion source compounds are typically different compounds, although they can be the same compound.

In one aspect of the disclosure, the solid oxide activator-support (chemically-treated solid oxide) can be produced by a process comprising:
1) contacting a solid oxide compound with at least one electron-withdrawing anion source compound to form a first mixture; and
2) calcining the first mixture to form the solid oxide activator-support.

In another aspect of this disclosure, the solid oxide activator-support (chemically-treated solid oxide) can be produced by a process comprising:
1) contacting at least one solid oxide compound with a first electron-withdrawing anion source compound to form a first mixture;
2) calcining the first mixture to produce a calcined first mixture;
3) contacting the calcined first mixture with a second electron-withdrawing anion source compound to form a second mixture; and
4) calcining the second mixture to form the solid oxide activator-support.

The solid oxide activator-support may be sometimes referred to simply as a treated solid oxide compound.

In another aspect of this disclosure, the chemically-treated solid oxide can be produced or formed by contacting at least one solid oxide with at least one electron-withdrawing anion source compound, wherein the at least one solid oxide compound is calcined before, during, or after contacting the electron-withdrawing anion source, and wherein there is a substantial absence of aluminoxanes and organoborates. In an embodiment, the chemically-treated solid oxide can be produced or formed by contacting at least one solid oxide with at least one electron-withdrawing anion source compound, wherein the at least one solid oxide compound is calcined before contacting the electron-withdrawing anion source, and wherein there is a substantial absence of aluminoxanes and organoborates; alternatively, by contacting at least one solid oxide with at least one electron-withdrawing anion source compound, wherein the at least one solid oxide compound is calcined during contacting the electron-withdrawing anion source, and wherein there is a substantial absence of aluminoxanes and organoborates; or alternatively, by contacting at least one solid oxide with at least one electron-withdrawing anion source compound, wherein the at least one solid oxide compound is calcined after contacting the electron-withdrawing anion source, and wherein there is a substantial absence of aluminoxanes and organoborates.

In one aspect of this disclosure, once the solid oxide has been treated and dried, it can be subsequently calcined. Calcining of the treated solid oxide is generally conducted in an ambient atmosphere; alternatively, in a dry ambient atmosphere. The solid oxide can be calcined at a temperature from 200° C. to 900° C.; alternatively, from 300° C. to 800° C.; alternatively, from 400° C. to 700° C.; or alternatively, from 350° C. to 550° C. The period of time at which the solid oxide is maintained at the calcining temperature can be 1 minute to 100 hours; alternatively, from 1 hour to 50 hours; alternatively, from 3 hours to 20 hours; or alternatively, from 1 to 10 hours.

Further, any type of suitable atmosphere can be used during calcining. Generally, calcining is conducted in an oxidizing atmosphere, such as air. Alternatively, an inert atmosphere, such as nitrogen or argon, or a reducing atmosphere such as hydrogen or carbon monoxide, can be used. In an embodiment, the atmosphere utilized for calcining can comprise, or consist essentially of air, nitrogen, argon, hydrogen, or carbon monoxide, or any combination thereof; alternatively, nitrogen, argon, hydrogen, carbon monoxide, or any combination thereof; alternatively, air; alternatively, nitrogen; alternatively, argon; alternatively, hydrogen; or alternatively, carbon monoxide.

In another aspect and any embodiment of the disclosure, the solid oxide component used to prepare the chemically-treated solid oxide can have a pore volume greater than 0.1 cc/g. In another aspect, the solid oxide component can have a pore volume greater than 0.5 cc/g; alternatively, greater than 1.0 cc/g. In still another aspect, the solid oxide component can have a surface area from 100 to 1000 m$^2$/g. In another aspect, solid oxide component can have a surface area from 200 to 800 m$^2$/g; alternatively, from 250 to 600 m$^2$/g.

The solid oxide material can be treated with a source of halide ion, sulfate ion, or a combination thereof, and optionally treated with a metal ion, then calcined to provide the chemically-treated solid oxide in the form of a particulate solid. In one aspect, the solid oxide material is treated with a source of sulfate (termed a sulfating agent), a source of phosphate (termed a phosphating agent), a source of iodide ion (termed a iodiding agent), a source of bromide ion (termed a bromiding agent), a source of chloride ion (termed a chloriding agent), a source of fluoride ion (termed a fluoriding agent), or any combination thereof, and calcined to provide the solid oxide activator. In another aspect, useful acidic activator-supports can comprise, consist essentially of, or consist of, iodided alumina, bromided alumina, chlorided alumina, fluorided alumina, sulfated alumina, phosphated alumina, iodided silica-alumina, bromided silica-alumina, chlorided silica-alumina, fluorided silica-alumina, sulfated silica-alumina, phosphated silica-alumina, iodided silica-zirconia, bromided silica-zirconia, chlorided silica-zirconia, fluorided silica-zirconia, sulfated silica-zirconia, phosphated silica-zirconia, a pillared clay (e.g. a pillared montmorillonite) treated with iodide, bromide, chloride, fluoride, sulfate, or phosphate, an aluminophosphate (e.g. a molecular sieve) treated with iodide, bromide, chloride, fluoride, sulfate, or phosphate, or any combination of these acidic activator-supports. Further, any of the activator-supports can optionally be treated with a metal ion, as provided herein.

Alternatively, useful acidic activator-supports can comprise, consist essentially of, or consist of, chlorided alumina, fluorided alumina, sulfated alumina, phosphated alumina, chlorided silica-alumina, fluorided silica-alumina, sulfated silica-alumina, chlorided silica-zirconia, fluorided silica-zirconia, sulfated silica-zirconia, an aluminophosphate treated with sulfate, fluoride, or chloride, or any combination of these acidic activator-supports. Moreover, the solid oxide can be treated with more than one electron-withdrawing anion, for example, the acidic activator-support can be or can comprise, consist essentially of, or consist of, an aluminophosphate or aluminosilicate treated with sulfate and fluoride, silica-alumina treated with fluoride and chloride; or alumina treated with phosphate and fluoride.

Alternatively and in another aspect, useful acidic activator-supports can comprise, consist essentially of, or consist of, fluorided alumina, sulfated alumina, fluorided silica-alumina, sulfated silica-alumina, fluorided silica-zirconia, sulfated silica-zirconia, or phosphated alumina, or any combination of these acidic activator-supports. In yet another aspect, useful acidic activator-supports can comprise, consist essentially of, or consist of, iodided alumina; alternatively, bromided alumina; alternatively, chlorided alumina; alternatively, fluorided alumina; alternatively, sulfated alumina; alternatively, phosphated alumina; alternatively, iodided silica-alumina; alternatively, bromided silica-alumina; alternatively, chlorided silica-alumina; alternatively, fluorided silica-alumina; alternatively, sulfated silica-alumina; alternatively, phosphated silica-alumina; alternatively, iodided silica-zirconia; alternatively, bromided silica-zirconia; alternatively, chlorided silica-zirconia; alternatively, fluorided silica-zirconia; alternatively, sulfated silica-zirconia; alternatively, phosphated silica-zirconia; alternatively, a pillared clay (e.g. a pillared montmorillonite); alternatively, an iodided pillared clay; alternatively, a bromided pillared clay; alternatively, a chlorided pillared clay; alternatively, a fluorided pillared clay; alternatively, a sulfated pillared clay; alternatively, a phosphated pillared clay; alternatively, an iodided aluminophosphate; alternatively, a bromided aluminophosphate; alternatively, a chlorided aluminophosphate; alternatively, a fluorided aluminophosphate; alternatively, a sulfated aluminophosphate; alternatively, a phosphated aluminophosphate; or any combination of these acidic activator-supports. Again, any of the activator-supports disclosed herein can optionally be treated with a metal ion.

In one aspect of this disclosure, the chemically-treated solid oxide can comprise, consist essentially of, or consist of, a fluorided solid oxide in the form of a particulate solid, where a source of fluoride ion is added to the solid oxide by treatment with a fluoriding agent. In still another aspect, fluoride ion can be added to the solid oxide by forming a slurry of the solid oxide in a suitable solvent. In an embodiment, the solvent can be alcohol, water, or a combination thereof; alternatively, alcohol; or alternatively, water. In an embodiment suitable alcohols can have from one to three carbon alcohols because of their volatility and low surface tension. In another aspect of the present disclosure, the solid oxide can be treated with a fluoriding agent during the calcining step. Any fluoriding agent capable of serving as a source of fluoride and thoroughly contacting the solid oxide during the calcining step can be used. In an non-limiting embodiment, fluoriding agents that can be used in this disclosure include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4)_2SiF_6$), ammonium hexafluorophosphate ($NH_4PF_6$), and combinations thereof; alternatively, hydrofluoric acid (HF), ammonium fluoride ($NH_4F$), ammonium bifluoride ($NH_4HF_2$), ammonium tetrafluoroborate ($NH_4BF_4$), and combinations thereof. In other non-limiting embodiments, the fluoriding agents can comprise, consist essentially of, or consist of hydrofluoric acid (HF); alternatively, ammonium fluoride ($NH_4F$); alternatively, ammonium bifluoride ($NH_4HF_2$); alternatively, ammonium tetrafluoroborate ($NH_4BF_4$); alternatively, ammonium silicofluoride (hexafluorosilicate) (($NH_4)_2SiF_6$); or alternatively, ammonium hexafluorophosphate ($NH_4PF_6$). For example, ammonium bifluoride $NH_4HF_2$ can be used as the fluoriding agent, due to its ease of use and ready availability.

In another aspect of the present disclosure, the solid oxide can be treated with a fluoriding agent during the calcining step. Any fluoriding agent capable of thoroughly contacting the solid oxide during the calcining step can be used. For example, in addition to those fluoriding agents described previously, volatile organic fluoriding agents can be used. Volatile organic fluoriding agents useful in this aspect of the disclosure include, but are not limited to, freons, perfluorohexane, perfluorobenzene, fluoromethane, trifluoroethanol, and combinations thereof. In some embodiments, the volatile fluoriding agent can comprise, consist essentially of, or consist of, a freon; alternatively, perfluorohexane; alternatively, perfluorobenzene; alternatively, fluoromethane; or alternatively, trifluoroethanol. Gaseous hydrogen fluoride or fluorine itself can also be used with the solid oxide is fluorided during calcining. One convenient method of contacting the solid oxide with the fluoriding agent is to vaporize a fluoriding agent into a gas stream used to fluidize the solid oxide during calcination.

Similarly, in another aspect of this disclosure, the chemically-treated solid oxide can comprise, consist essentially of, or consist of, a chlorided solid oxide in the form of a particulate solid, where a source of chloride ion is added to the solid oxide by treatment with a chloriding agent. The chloride ion can be added to the solid oxide by forming a slurry of the solid oxide in a suitable solvent. In an embodiment, the solvent can be alcohol, water, or a combination thereof; alternatively, alcohol; or alternatively, water. In an embodiment suitable alcohols can have from one to three carbon alcohols because of their volatility and low surface tension. In another aspect of the present disclosure, the solid oxide can be treated with a chloriding agent during the calcining step. Any chloriding agent capable of serving as a source of chloride and thoroughly contacting the solid oxide during the calcining step can be used. In a non-limiting embodiment, volatile organic chloriding agents can be used. In some embodiments, the volatile organic chloriding agents include, but are not limited to, chloride containing freons, perchlorobenzene, chloromethane, dichloromethane, trichloroethane, tetrachloroethylene, chloroform, carbon tetrachloride, trichloroethanol, or any combination thereof. In some embodiments, the volatile organic chloriding agents can comprise, consist essentially of, or consist of, chloride containing freons; alternatively, perchlorobenzene; alternatively, chloromethane; alternatively, dichloromethane; alternatively, chloroform; alternatively, carbon tetrachloride; or alternatively, trichloroethanol. Gaseous hydrogen chloride or chlorine itself can also be used with the solid oxide during calcining. One convenient method of contacting the oxide with the chloriding agent is to vaporize a chloriding agent into a gas stream used to fluidize the solid oxide during calcination.

In still another aspect, the chemically-treated solid oxide can comprise, consist essentially of, or consist of, a bromided solid oxide in the form of a particulate solid, where a source of bromide ion is added to the solid oxide by treatment with a bromiding agent. The bromide ion can be added to the solid oxide by forming a slurry of the solid oxide in a suitable solvent. In an embodiment, the bromiding solvent can be alcohol, water, or a combination thereof; alternatively, alcohol; or alternatively, water. In an embodiment suitable alcohols can have from one to three carbon alcohols because of their volatility and low surface tension. In another aspect of the present disclosure, the solid oxide can be treated with a bromiding agent during the calcining step. Any bromiding agent capable of serving as a source of bromide and thoroughly contacting the solid oxide during the calcining step can be used. In a non-limiting embodiment, volatile organic bromiding agents can be used. In some embodiments, the volatile organic chloriding agents include, but are not limited to, bromide containing freons, bromomethane, dibromomethane, tribromoethane, tetrabromoethylene, bromoform, carbon tetrabromide, tribromoethanol, or any combination thereof. In some embodiments, the volatile organic chloriding agents can comprise, consist essentially of, or consist of, bromide containing freons; alternatively, bromomethane; alternatively, dibromomethane; alternatively, bromoform; alternatively, carbon tetrabromide; or alternatively, tribromoethanol. Gaseous hydrogen bromide or bromine itself can also be used with the solid oxide during calcining. One convenient method of contacting the oxide with the bromiding agent is to vaporize a bromiding agent into a gas stream used to fluidize the solid oxide during calcination.

In one aspect, the amount of fluoride ion, chloride ion, or bromide ion present before calcining the solid oxide is generally from 2 to 50% by weight, where the weight percents are based on the weight of the solid oxide, before calcining. In another aspect, the amount of fluoride or chloride ion present before calcining the solid oxide is from 3 to 25% by weight; alternatively, from 4 to 20% by weight. Once impregnated with halide, the halided solid oxide can be dried by any method known in the art including, but not limited to, suction filtration followed by evaporation, drying under vacuum, spray drying, and the like. In an embodiment, the calcining step can be initiated without drying the impregnated solid oxide.

In an aspect, silica-alumina, or a combination thereof can be utilized as the solid oxide material. The silica-alumina used to prepare the treated silica-alumina can have a pore volume greater than 0.5 cc/g. In one aspect, the pore volume can be greater than 0.8 cc/g; alternatively, greater than 1 cc/g. Further, the silica-alumina can have a surface area greater than 100 m$^2$/g. In one aspect, the surface area is greater than 250 m$^2$/g; alternatively, greater than 350 m$^2$/g. Generally, the silica-alumina has an alumina content from 5 to 95%. In one aspect, the alumina content of the silica-alumina can be from 5 to 50%; alternatively, from 8% to 30% alumina by weight. In yet other aspects, the solid oxide component can comprise alumina without silica, or silica without alumina.

In another aspect, the chemically-treated solid oxide can comprise, consist essentially of, or consist of, a sulfated solid oxide in the form of a particulate solid, where a source of sulfate ion is added to the solid oxide by treatment with a sulfating agent. The sulfated solid oxide can comprise sulfate and a solid oxide component any solid oxide component described (e.g. alumina or silica-alumina), in the form of a particulate solid. The sulfated solid oxide can be further treated with a metal ion if desired such that the calcined sulfated solid oxide can comprise a metal. In one aspect, the sulfated solid oxide can comprise sulfate and alumina; alternatively, the sulfated solid oxide can comprise sulfate and silica-alumina. In one aspect of this disclosure, the sulfated alumina is formed by a process wherein the alumina or silica alumina is treated with a sulfate source. Any sulfate source capable of thoroughly contacting the solid oxide can be utilized. In an embodiment, the sulfate source may include, but is not limited to, sulfuric acid or a sulfate containing salt (e.g. ammonium sulfate). In one aspect, this process can be performed by forming a slurry of the solid oxide in a suitable solvent. In an embodiment, the solvent can be alcohol, water, or a combination thereof; alternatively, alcohol; or alternatively, water. In an embodiment suitable alcohols can have from one to three carbon alcohols because of their volatility and low surface tension.

In one aspect and any embodiment of the disclosure, the amount of sulfate ion present before calcining is generally from 0.5 parts by weight to 100 parts by weight sulfate ion to 100 parts by weight solid oxide. In another aspect, the amount of sulfate ion present before calcining is generally from 1 part by weight to 50 parts by weight sulfate ion to 100 parts by weight solid oxide; alternatively, from 5 parts by weight to 30 parts by weight sulfate ion to 100 parts by weight solid oxide. Once impregnated with sulfate, the sulfated solid oxide can be dried by any method known in the art including, but not limited to, suction filtration followed by evaporation, drying under vacuum, spray drying, and the like. In an embodiment, the calcining step can be initiated without drying the impregnated solid oxide.

In still another aspect, the chemically-treated solid oxide can comprise, consist essentially of, or consist of, a phosphated solid oxide in the form of a particulate solid, where a source of phosphate ion is added to the solid oxide by treatment with a phosphating agent. The phosphated solid oxide can comprise phosphate and any solid oxide component described (e.g. alumina or silica-alumina), in the form of a particulate solid. The phosphated solid oxide can be further treated with a metal ion if desired such that the calcined phosphated solid oxide can comprise a metal. In one aspect, the phosphated solid oxide can comprise phosphate and alumina; alternatively phosphate and silica-alumina. In one aspect of this disclosure, the phosphated alumina is formed by a process wherein the alumina or silica-alumina is treated with a phosphate source. Any phosphate source capable of thoroughly contacting the solid oxide can be utilized. In an embodiment, the phosphate source can include, but is not limited to, phosphoric acid, phosphorous acid, or a phosphate containing salt (e.g. ammonium phosphate). In one aspect, this process can be performed by forming a slurry of the solid oxide in a suitable solvent. In an embodiment, the solvent can be alcohol, water, or combination thereof; alternatively, alcohol; or alternatively, water. In an embodiment suitable alcohols can have from one to three carbon alcohols because of their volatility and low surface tension.

In one aspect and any embodiment of the disclosure, the amount of phosphate ion present before calcining is generally from 0.5 parts by weight to 100 parts by weight phosphate ion to 100 parts by weight solid oxide. In another aspect, the amount of phosphate ion present before calcining is generally from 1 part by weight to 50 parts by weight phosphate ion to 100 parts by weight solid oxide; alternatively, from 5 parts by weight to 30 parts by weight phosphate ion to 100 parts by weight solid oxide. Once impregnated with sulfate, the phosphate solid oxide can be dried by any method known in the art including, but not limited to, suction filtration followed by evaporation, drying under vacuum, spray drying, and the like. In an embodiment, the calcining step can be initiated without drying the impregnated solid oxide.

In addition to being treated with an electron-withdrawing component (for example, halide or sulfate ion), the solid inorganic oxide of this disclosure can be optionally treated with a metal source. In an embodiment, the metal source can be a metal salt or a metal-containing compound. In one aspect of the disclosure, the metal salt of metal containing compound can be added to or impregnated onto the solid oxide in solution form and converted into the supported metal upon calcining. Accordingly, the metal impregnated onto the solid inorganic oxide can comprise, consist essentially of, or consist of, zinc, titanium, nickel, vanadium, silver, copper, gallium, tin, tungsten, molybdenum, or a combination thereof; alternatively, zinc, titanium, nickel, vanadium, silver, copper, tin, or any combination thereof; alternatively, zinc, nickel, vanadium, tin, or any combination thereof. In an embodiment, the metal impregnated onto the solid inorganic oxide can comprise, consist essentially of, or consist of, zinc; alternatively, titanium; alternatively, nickel; alternatively, vanadium; alternatively, silver; alternatively, copper; alternatively, gallium; alternatively, tin; alternatively, tungsten; or alternatively, molybdenum. In some embodiments, zinc can be used to impregnate the solid oxide because it provides good catalyst activity and low cost. The solid oxide can be treated with metal salts or metal-containing compounds before, after, or at the same time that the solid oxide is treated with the electron-withdrawing anion; alternatively, before the solid oxide is treated with the electron-withdrawing anion; alternatively, after the solid oxide is treated with the electron-withdrawing anion; or alternatively, at the same time that the solid oxide is treated with the electron-withdrawing anion.

Further, any method of impregnating the solid oxide material with a metal can be used. The method by which the solid oxide is contacted with a metal source (e.g. a metal salt or metal-containing compound), includes, but is not limited to, gelling, co-gelling, and impregnation of one compound onto another. Following any contacting method, the contacted mixture of solid oxide, electron-withdrawing anion, and the metal ion is typically calcined. Alternatively, a solid oxide, an electron-withdrawing anion source, and the metal salt or metal-containing compound are contacted and calcined simultaneously.

In an aspect, the metallocene or combination of metallocenes can be precontacted with an alpha olefin monomer and/or an organoaluminum compound for a first period of time prior to contacting this mixture with the chemically-treated solid oxide. Once the precontacted mixture of the metallocene, alpha olefin monomer, and/or organoaluminum compound is contacted with the chemically-treated solid oxide, the composition further comprising the chemically-treated solid oxide is termed the "postcontacted" mixture. The postcontacted mixture can be allowed to remain in further contact for a second period of time prior to being charged into the reactor in which the oligomerization process will be carried out.

Various chemically-treated solid oxides and various processes to prepare chemically-treated solid oxides that can be employed in this disclosure have been reported. The following U.S. patents and published U.S. patent application provide such disclosure, and each of these patents and publications is incorporated by reference herein in its entirety: U.S. Pat. Nos. 6,107,230, 6,165,929, 6,294,494, 6,300,271, 6,316,553, 6,355,594, 6,376,415, 6,391,816, 6,395,666, 6,524,987, 6,548,441, 6,750,302, 6,831,141, 6,936,667, 6,992,032, 7,601,665, 7,026,494, 7,148,298, 7,470,758, 7,517,939, 7,576,163, 7,294,599, 7,629,284, 7,501,372, 7,041,617, 7,226,886, 7,199,073, 7,312,283, 7,619,047, and 2010/0076167, among other patents.

Organoaluminum Compounds

One aspect of this disclosure provides for an oligomerization method comprising (or a method of producing a PAO comprising a step of) contacting an alpha olefin monomer and a catalyst system comprising a metallocene. In an embodiment, the catalyst system can further comprise an activator. In any embodiment provided here, the activator can comprise a solid oxide chemically-treated with an electron withdrawing anion. In a further aspect of any embodiment provided here, the catalyst system can comprise, either in combination with the chemically-treated solid oxide and/or any other activator(s) or alone, at least one organoaluminum compound. In some embodiments, the catalyst system can, comprise, consist essentially of, or consist of a metallocene, a first activator comprising a chemically-treated solid oxide, and a second activator comprising an organoaluminum compound. In an aspect, organoaluminum compounds that can be used in the catalyst system of this disclosure include but are not limited to compounds having the formula:

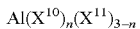

In an embodiment, each $X^{10}$ can be independently a $C_1$ to $C_{20}$ hydrocarbyl group; alternatively, a $C_1$ to $C_{10}$ hydrocarbyl group; alternately, a $C_6$ to $C_{20}$ aryl group; alternatively, a $C_6$ to $C_{10}$ aryl group; alternatively, a $C_1$ to $C_{20}$ alkyl group; alternatively, a $C_1$ to $C_{10}$ alkyl group; or alternatively, a $C_1$ to $C_5$ alkyl group. In an embodiment, each $X^{11}$ can be independently a halide, a hydride, or a $C_1$ to $C_{20}$ hydrocarboxide group (also referred to as a hydrocarboxy group); alternatively, a halide, a hydride, or a $C_1$ to $C_{10}$ hydrocarboxide group; alternatively, a halide, a hydride, or a $C_6$ to $C_{20}$ aryloxide group (also referred to as an aroxide or aroxy group); alternatively, a halide, a hydride, or a $C_6$ to $C_{10}$ aryloxide group; alternatively, a halide, a hydride, or a $C_1$ to $C_{20}$ alkoxide group (also referred to as an alkoxy group); alternatively, a halide, a hydride, or a $C_1$ to $C_{10}$ alkoxide group; alternatively, a halide, a hydride, or, or a $C_1$ to $C_5$ alkoxide group; alternatively, a halide; alternatively, a hydride; alternatively, a $C_1$ to $C_{20}$ hydrocarboxide group; alternatively, a $C_1$ to $C_{10}$ hydrocarboxide group; alternatively, a $C_6$ to $C_{20}$ aryloxide group; alternatively, a $C_6$ to $C_{10}$ aryloxide group; alternatively, a $C_1$ to $C_{20}$ alkoxide group; alternatively, a $C_1$ to $C_{10}$ alkoxide group; alternatively, a $C_1$ to $C_5$ alkoxide group. In an embodiment, n can be a number (whole or otherwise) from 1 to 3, inclusive; alternatively, about 1.5, alternatively, or alternatively, 3.

In an embodiment, each alkyl group(s) of the organoaluminum compound having the formula $Al(X^{10})_n(X^{11})_{3-n}$ can be independently a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some embodiments, each alkyl group(s) of the organoaluminum compound having the formula $Al(X^{10})_n(X^{11})_{3-n}$ can be independently a methyl group, an ethyl group, an n-propyl group, an n-butyl group, an iso-butyl group, a n-hexyl group, or an n-octyl group; alternatively, a methyl group, an ethyl group, a n-butyl group, or an iso-butyl group; alternatively, a methyl group; alternatively, an ethyl group; alternatively, an n-propyl group; alternatively, an n-butyl group; alternatively, an iso-butyl group; alternatively, a n-hexyl group; or alternatively, an n-octyl group. In an embodiment, each aryl group of the organoaluminum compound having the formula $Al(X^{10})_n(X^{11})_{3-n}$ can be independently a phenyl group or a substituted phenyl group; alternatively, a phenyl group; or alternatively, a substituted phenyl group.

In an embodiment, each halide of the organoaluminum compound having the formula $Al(X^{10})_n(X^{11})_{3-n}$ can be independently a fluoride, chloride, bromide, or iodide. In some embodiments, each halide of the organoaluminum compound having the formula $Al(X^{10})_n(X^{11})_{3-n}$ can be independently a fluoride; alternatively, chloride; alternatively, bromide; or alternatively, iodide.

In an embodiment, each alkoxide of the organoaluminum compound having the formula $Al(X^{10})_n(X^{11})_{3-n}$ can be independently a methoxy group, an ethoxy group, a propoxy group, a butoxy group, a pentoxy group, a hexoxy group, a heptoxy group, or an octoxy group; alternatively, a methoxy group, a ethoxy group, a butoxy group, a hexoxy group, or an octoxy group. In some embodiments, the alkoxy group can be independently a methoxy group, an ethoxy group, an n-propoxy group, an n-butoxy group, an iso-butoxy group, a n-hexoxy group, or an n-octoxy group; alternatively, a methoxy group, an ethoxy group, a n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, a n-hexoxy group; or alternatively, an n-octoxy group. In an embodiment, each aryloxide of the organoaluminum compound having the formula $Al(X^{10})_n(X^{11})_{3-n}$ can be independently a be a phenoxide or a substituted phenoxide; alternatively, a phenoxide; or alternatively, a substituted phenoxide.

In an embodiment, the organoaluminum compound that can utilized in any aspect or embodiment of this disclosure can comprise, consist essentially of, or consist of, a trialkylaluminum, a dialkylaluminium halide, an alkylaluminum dihalide, a dialkylaluminum alkoxide, an alkylaluminum dialkoxide, a dialkylaluminum hydride, a alkylaluminum dihydride, and combinations thereof. In other embodiments, the organoaluminum compound that can utilized in any aspect or embodiment of this disclosure can comprise, consist essentially of, or consist of, a trialkylaluminum, a dialkylaluminium halide, an alkylaluminum dihalide, and combinations thereof; alternatively, a trialkylaluminum; alternatively, a dialkylaluminium halide; alternatively, an alkylaluminum dihalide; alternatively, a dialkylaluminum alkoxide; alternatively, an alkylaluminum dialkoxide; alternatively, a dialkylaluminum hydride; or alternatively, an alkylaluminum dihydride. In yet other embodiments, the organoaluminum compound that that can utilized in any aspect or embodiment of this disclosure can comprise, consist essentially of, or consist of, a trialkylaluminum, an alkylaluminum halide, or a combination thereof; alternatively, a trialkylaluminum; or alternatively, an alkylaluminum halide.

In a non-limiting embodiment, useful trialkylaluminum compounds can include trimethylaluminum, triethylaluminum, tripropylaluminum, tributylaluminum, trihexylaluminum, trioctylaluminum, or mixtures thereof. In some non-limiting embodiments, useful trialkylaluminum compounds can include trimethylaluminum, triethylaluminum, tripropylaluminum, tri-n-butylaluminum, tri-isobutylaluminum, tri-hexylaluminum, tri-n-octylaluminum, or mixtures thereof; alternatively, triethylaluminum, tri-n-butylaluminum, tri-isobutylaluminum, tri-n-hexylaluminum, tri-n-octylaluminum, or mixtures thereof; alternatively, triethylaluminum, tri-n-butylaluminum, tri-n-hexylaluminum, tri-n-octylaluminum, or mixtures thereof. In other non-limiting embodiments, useful trialkylaluminum compounds can be trimethylaluminum; alternatively, triethylaluminum; alternatively, tripropylaluminum; alternatively, tri-n-butylaluminum; alternatively, tri-isobutylaluminum; alternatively, tri-n-hexylaluminum; or alternatively, tri-n-octylaluminum.

In a non-limiting embodiment, useful alkylaluminum halides can include diethylaluminum chloride, diethylaluminum bromide, ethylaluminum dichloride, ethylaluminum sesquichloride, and mixtures thereof. In some non-limiting embodiments, useful alkylaluminum halides can include diethylaluminum chloride, ethylaluminum dichloride, ethylaluminum sesquichloride, and mixtures thereof. In other non-limiting embodiments, useful alkylaluminum halides can be diethylaluminum chloride; alternatively, diethylaluminum bromide; alternatively, ethylaluminum dichloride; or alternatively, ethylaluminum sesquichloride.

In one aspect, the present disclosure provides for precontacting the metallocene with at least one organoaluminum compound and an olefin monomer to form a precontacted mixture, prior to contact this precontacted mixture with the solid oxide activator-support to form the active catalyst. When the catalyst system is prepared in this manner, typically, though not necessarily, a portion of the organoaluminum compound can be added to the precontacted mixture and another portion of the organoaluminum compound can be added to the postcontacted mixture prepared when the precontacted mixture can be contacted with the solid oxide activator. However, all the organoaluminum compound can be used to prepare the catalyst system in either the precontacting or postcontacting step. Alternatively, all the catalyst system components can be contacted in a single step.

Further, more than one organoaluminum compounds can be used, in either the precontacting or the postcontacting step. When an organoaluminum compound is added in multiple steps, the amounts of organoaluminum compound disclosed herein include the total amount of organoaluminum compound used in both the precontacted and postcontacted mixtures, and any additional organoaluminum compound added to the oligomerization reactor. Therefore, total amounts of organoaluminum compounds are disclosed, regardless of whether a single organoaluminum compound is used, or more than one organoaluminum compound. In another aspect, triethylaluminum (TEA) or triisobutylaluminum are typical organoaluminum compounds used in this disclosure. In some embodiments, the organoaluminum compound can be triethylaluminum; or alternatively, triisobutylaluminum.

In one aspect and in any embodiment disclosed herein wherein the catalyst system utilizes an organoaluminum compound, the molar ratio aluminum of the organoaluminum compound to the metal of the metallocene (Al:metal of the metallocene) can be greater than 0.1:1; alternatively, greater than 1:1; or alternatively, greater than 10:1; or alternatively, greater than 50:1. In some embodiments wherein the catalyst system utilizes an organoaluminum compound, the molar ratio aluminum of the organoaluminum compound to the metal of the metallocene (Al:metal of the metallocene) can range from 0.1:1 to 100,000:1; alternatively, range from 1:1 to 10,000:1; alternatively, range from 10:1 to 1,000:1; or alternatively, range from 50:1 to 500:1. When the metallocene contains a specific metal (e.g. Zr) the molar ratio can be stated as an Al:specific metal molar ratio (e.g. Al:Zr molar ratio).

In another aspect and in any embodiment disclosed herein wherein the catalyst system utilizes an organoaluminum compound, the molar ratio of the aluminum-carbon bonds of the organoaluminum compound to the metal of the metallocene (Al—C bonds:metal of the metallocene) can be greater than 0.1:1; alternatively, greater than 1:1; or alternatively, greater than 10:1; or alternatively, greater than 50:1. In some embodiments wherein the catalyst system utilizes an organoaluminum compound, the molar ratio of the aluminum-carbon bonds or the organoaluminum compound to the metal of the metallocene (Al—C bonds:metal of the metallocene) can range from 0.1:1 to 100,000:1; alternatively, range from 1:1 to 10,000:1; alternatively, range from 10:1 to 1,000:1; or alternatively, range from 50:1 to 500:1. When the metallocene contains a specific metal (e.g. Zr) the ratio can be stated as an Al—C bonds:specific metal ratio (e.g. Al—C bonds:Zr molar ratio).

Aluminoxanes

In one aspect, this disclosure encompasses a catalyst system comprising at least one metallocene and at least one activator. The disclosure further encompasses a method for an oligomerization method comprising (or a method of producing a PAO comprising a step of) contacting an alpha olefin monomer and a catalyst system comprising a metallocene. In an embodiment, the catalyst system can further comprise an activator. Aluminoxanes are referred to alternatively as poly(hydrocarbyl aluminum oxides), organoaluminoxanes, or alumoxanes. In a further aspect of any embodiment provided here, the catalyst system can comprise, either in combination with the chemically-treated solid oxide and/or any other activator(s) or alone, at least one aluminoxane compound. Aluminoxanes are described herein and may be utilized without limitation in combination with the chemically-treated solid oxide; or alternatively, with a chemically-treated solid oxide and another activator. In some embodiments, the catalyst system can comprise, consist essentially of, or consist of a metallocene, a first activator comprising a chemically-treated solid oxide, and a second activator comprising an aluminoxane.

Alumoxane compounds that can be used in the catalyst system of this disclosure include, but are not limited to, oligomeric compounds. The oligomeric aluminoxane compounds can comprise linear structures, cyclic, or cage structures, or mixtures of all three. Oligomeric aluminoxanes, whether oligomeric or polymeric compounds, have the repeating unit formula:

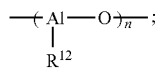

wherein
$R^{12}$ is a linear or branched alkyl group. Linear aluminoxanes having the formula:

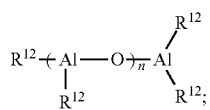

wherein
$R^{12}$ is a linear or branched alkyl group are also encompassed by this disclosure. Alkyl groups for organoaluminum compounds formula $Al(X^{10})_n(X^{11})_{3-n}$ have been independently described herein and these alkyl groups can be utilized, without limitation, to further describe the aluminoxanes having Formula I. Generally, n of the alumoxanes can be, or can have an average, greater than 1; or alternatively, greater than 2. In an embodiment, n can range, or have an average with the range, from 2 to 15; or alternatively, from 3 to 10.

Further, aluminoxanes can also have cage structures of the formula $R^t_{5m+\alpha}R^b_{m-\alpha}Al_{4m}O_{3m}$, wherein m is 3 or 4 and $\alpha$ is $=n_{Al(3)}-n_{O(2)}+n_{O(4)}$; wherein $n_{Al(3)}$ is the number of three coordinate aluminum atoms, $n_{O(2)}$ is the number of two coordinate oxygen atoms, $n_{O(4)}$ is the number of 4 coordinate oxygen atoms, $R^t$ represents a terminal alkyl group, and $R^b$ represents a bridging alkyl group; wherein R is a linear or branched alkyl having from 1 to 10 carbon atoms. Alkyl groups for organoaluminum compounds formula $Al(X^{10})_n(X^{11})_{3-n}$ have been independently described herein and these alkyl groups can be utilized, without limitation, to further describe the aluminoxanes having the cage structure of the formula $R^t_{5m+\alpha}R^b_{m-\alpha}Al_{4m}O_{3m}$.

In a non-limiting embodiment, useful aluminoxanes can include methylaluminoxane (MAO), ethylaluminoxane, modified methylaluminoxane (MMAO), n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof; In some non-limiting embodiments, useful aluminoxanes can include methylaluminoxane (MAO), modified methylaluminoxane (MMAO), isobutyl aluminoxane, t-butyl aluminoxane, or mixtures thereof. In other non-limiting embodiments, useful aluminoxanes can be methylaluminoxane (MAO); alternatively, ethylaluminoxane; alternatively, modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butyl aluminoxane; alternatively, 1-pentylaluminoxane; alternatively, 2-pentylaluminoxane; alternatively, 3-pentylaluminoxane; alternatively, iso-pentylaluminoxane; or alternatively, neopentylaluminoxane.

While organoaluminoxanes with different types of "R" groups such as $R^{12}$ are encompassed by the present disclosure, methyl aluminoxane (MAO), ethyl aluminoxane, or isobutyl aluminoxane can also be utilized as aluminoxane activators used in the catalyst systems of this disclosure. These aluminoxanes are prepared from trimethylaluminum, triethylaluminum, or triisobutylaluminum, respectively, and are sometimes referred to as poly(methyl aluminum oxide), poly(ethyl aluminum oxide), and poly(isobutyl aluminum oxide), respectively. It is also within the scope of the disclosure to use an aluminoxane in combination with a trialkylaluminum, such as disclosed in U.S. Pat. No. 4,794,096, which is herein incorporated by reference in its entirety.

The present disclosure contemplates many values of n in the aluminoxane formulas $(\text{—}Al(R^{12})O\text{—})_n$ and $R^{12}(\text{—}Al(R^{12})O\text{—})_nAl(R^{12})_2$, and preferably n is at least about 3. However, depending upon how the organoaluminoxane is prepared, stored, and used, the value of n can be variable within a single sample of aluminoxane, and such a combination of organoaluminoxanes are comprised in the methods and compositions of the present disclosure.

In preparing the catalyst system that includes an aluminoxane, the molar ratio of the aluminum in the aluminoxane to the metal of the metallocene (Al:metal of the metallocene) in catalyst system can be greater than 0.1:1; alternatively, greater than 1:1; or alternatively, greater than 10:1; or alternatively, greater than 50:1. In an embodiment, the molar ratio of the aluminum in the aluminoxane to the metal of the metallocene (Al:metal of the metallocene) in catalyst system can range from 0.1:1 to 100,000:1; alternatively, range from 1:1 to 10,000:1; alternatively, range from 10:1 to 1,000:1; or alternatively, range from 50:1 to 500:1. When the metallocene contains a specific metal (e.g. Zr) the ratio can be stated as an Al:specific metal ratio (e.g Al:Zr molar ratio). In an aspect, the amount of aluminoxane added to an oligomerization zone can be in an amount within a range from 0.01 mg/L to 1000 mg/L; alternatively, from 0.1 mg/L to 100 mg/L; or alternatively, or from 1 mg/L to 50 mg/L.

Organoaluminoxanes can be prepared by various procedures which are well known in the art. Examples of organoaluminoxane preparations are disclosed in U.S. Pat. Nos. 3,242,099 and 4,808,561, each of which is incorporated by reference herein, in its entirety. One example of how an aluminoxane can be prepared is as follows. Water which is dissolved in an inert organic solvent can be reacted with an aluminum alkyl compound such as $AlR_3$ to form the desired organoaluminoxane compound. While not intending to be bound by this statement, it is believed that this synthetic method can afford a mixture of both linear and cyclic $(R-Al-O)_n$ aluminoxane species, both of which are encompassed by this disclosure. Alternatively, organoaluminoxanes can be prepared by reacting an aluminum alkyl compound such as $AlR_3$ with a hydrated salt, such as hydrated copper sulfate, in an inert organic solvent.

The other catalyst components can be contacted with the aluminoxane in a solvent which is substantially inert to the reactants, intermediates, and products of the activation step can be used. The catalyst system formed in this manner can be collected by methods known to those of skill in the art, including but not limited to filtration, or the catalyst system can be introduced into the oligomerization reactor without being isolated.

Organozinc Compounds

As disclosed, one aspect of this disclosure provides for an oligomerization method comprising (or a method of producing a PAO comprising a step of) contacting an alpha olefin monomer and a catalyst system comprising a metallocene. In an embodiment the catalyst system can further comprise an activator. In any embodiment provided here, the catalyst system can further comprise activator can comprise a solid oxide chemically-treated with an electron withdrawing anion. In a further aspect of any embodiment provided here, the catalyst system can comprise, either in combination with the chemically-treated solid oxide and/or any other activator(s) or alone, at least one organozinc compound. In some embodiments, the catalyst system can, comprise, consist essentially of, or consist of a metallocene, a first activator comprising a chemically-treated solid oxide, and a second activator comprising an organozinc compound. In an aspect, the organozinc compounds that can be used in the catalyst system of this disclosure include but are not limited to compounds having the formula:

$$Zn(X^{12})_p(X^{13})_{2-p}.$$

In an embodiment, each $X^{12}$ can be independently a $C_1$ to $C_{20}$ hydrocarbyl group; alternatively, a $C_1$ to $C_{10}$ hydrocarbyl group; alternately, a $C_6$ to $C_{20}$ aryl group; alternatively, a $C_6$ to $C_{10}$ aryl group; alternatively, a $C_1$ to $C_{20}$ alkyl group; alternatively, a $C_1$ to $C_{10}$ alkyl group; or alternatively, a $C_1$ to $C_5$ alkyl group. In an embodiment, each $X^{13}$ can be independently a halide, a hydride, or a $C_1$ to $C_{20}$ hydrocarboxide group; alternatively, a halide, a hydride, or a $C_1$ to $C_{10}$ hydrocarboxide group; alternatively, a halide, a hydride, or a $C_6$ to $C_{20}$ aryloxide group; alternatively, a halide, a hydride, or a $C_6$ to $C_{10}$ aryloxide group; alternatively, a halide, a hydride, or a $C_1$ to $C_{20}$ alkoxide group; alternatively, a halide, a hydride, or a $C_1$ to $C_{10}$ alkoxide group; alternatively, a halide, a hydride, or, or a $C_1$ to $C_5$ alkoxide group; alternatively, a halide; alternatively, a hydride; alternatively, a $C_1$ to $C_{20}$ hydrocarboxide group; alternatively, a $C_1$ to $C_{10}$ hydrocarboxide group; alternatively, a $C_6$ to $C_{20}$ aryloxide group; alternatively, a $C_6$ to $C_{10}$ aryloxide group; alternatively, a $C_1$ to $C_{20}$ alkoxide group; alternatively, a $C_1$ to $C_{10}$ alkoxide group; alternatively, a $C_1$ to $C_5$ alkoxide group. In an embodiment, p can be a number (whole or otherwise) from 1 to 2, inclusive; alternatively, 1; or alternatively, 2. Alkyl groups, aryl groups, alkoxide groups, aryloxide groups, and halides have been independently described herein potential group for $X^{10}$ and $X^{11}$ of the organoaluminum compound having the formula $Al(X^{10})_n(X^{11})_{3-n}$ and these alkyl groups, aryl groups, alkoxide groups, aryloxide groups, and halides can be utilized without limitation to describe the organozinc compounds having the formula $Zn(X^{12})_p(X^{13})_{2-p}$ that can be used in the aspects and embodiments described in this disclosure.

In another aspect an in any embodiment of this disclosure, useful organozinc compounds can comprise, consist essentially of, or consist of, dimethylzinc, diethylzinc, dipropylzinc, dibutylzinc, dineopentylzinc, di(trimethylsilylmethyl)zinc, any combinations thereof; alternatively, dimethylzinc; alternatively, diethylzinc; alternatively, dipropylzinc; alternatively, dibutylzinc; alternatively, dineopentylzinc; or alternatively, di(trimethylsilylmethyl)zinc.

In one aspect and in any embodiment disclosed herein wherein the catalyst system utilizes an organozinc compound, the molar ratio of the organozinc compound to the metal of the metallocene (Zn:metal of the metallocene) can be greater than 0.1:1; alternatively, greater than 1:1; or alternatively, greater than 10:1; or alternatively, greater than 50:1. In some embodiments wherein the catalyst system utilizes an organozinc compound, the molar ratio of the organozinc compound to the metal of the metallocene (Zn:metal of the metallocene) can range from 0.1:1 to 100,000:1; alternatively, range from 1:1 to 10,000:1; alternatively, range from 10:1 to 1,000:1; or alternatively, range from 50:1 to 500:1. When the metallocene contains a specific metal (e.g. Zr) the ratio may be stated as a Zn:specific metal ratio (e.g. Zn:Zr molar ratio).

Organomagnesium Compounds

A further aspect of this disclosure provides for an oligomerization method comprising (or a method of producing a PAO comprising a step of) contacting an alpha olefin monomer and a catalyst system comprising a metallocene. In an embodiment, the catalyst system can further comprise an activator. In any embodiment provided here, the activator can comprise a solid oxide chemically-treated with an electron withdrawing anion. In a further aspect of any embodiment provided here, the catalyst system can comprise, either in combination with the chemically-treated solid oxide and/or any other activator(s) or alone, at least one organomagnesium compound. In some embodiments, the catalyst system can comprise, consist essentially of, or consist of a metallocene, a first activator comprising a chemically-treated solid oxide, and a second activator comprising an organomagnesium compound. In an aspect, the organomagnesium compounds that can be used in the catalyst system of this disclosure include but are not limited to compounds having the formula.

$$Mg(X^{17})_q(X^{18})_{2-q}.$$

In an embodiment, each $X^{17}$ can be independently a $C_1$ to $C_{20}$ hydrocarbyl group; alternatively, a $C_1$ to $C_{10}$ hydrocarbyl group; alternatively, a $C_6$ to $C_{20}$ aryl group; alternatively, a $C_6$ to $C_{10}$ aryl group; alternatively, a $C_1$ to $C_{20}$ alkyl group; alternatively, a $C_1$ to $C_{10}$ alkyl group; or alternatively, a $C_1$ to $C_5$ alkyl group. In an embodiment, each $X^{18}$ can be independently a halide, a hydride, or a $C_1$ to $C_{20}$ hydrocarboxide group; alternatively, a halide, a hydride, or a $C_1$ to $C_{10}$ hydrocarboxide group; alternatively, a halide, a hydride, or a $C_6$ to $C_{20}$ aryloxide group; alternatively, a halide, a hydride, or a $C_6$ to $C_{10}$ aryloxide group; alternatively, a halide, a hydride, or a $C_1$ to $C_{20}$ alkoxide group; alternatively, a halide, a hydride, or a $C_1$ to $C_{10}$ alkoxide group; alternatively, a halide, a hydride, or, or a $C_1$ to $C_5$ alkoxide group; alternatively, a halide; alternatively, a hydride; alternatively, a $C_1$ to $C_{20}$ hydrocarboxide group; alternatively, a $C_1$ to $C_{10}$ hydrocarboxide group; alternatively, a $C_6$ to $C_{20}$ aryloxide group; alternatively, a $C_6$ to $C_{10}$ aryloxide group; alternatively, a $C_1$ to $C_{20}$ alkoxide group;

alternatively, a $C_1$ to $C_{10}$ alkoxide group; alternatively, a $C_1$ to $C_5$ alkoxide group. In an embodiment, q can be a number (whole or otherwise) from 1 to 2, inclusive; alternatively, 1; or alternatively, 2. Alkyl groups, aryl groups, alkoxide groups, aryloxide groups, and halides have been independently described herein as potential group for $X^{10}$ and $X^{11}$ of the organoaluminum compound having the formula $Al(X^{10})_n(X^{11})_{3-n}$ and these alkyl groups, aryl groups, alkoxide groups, aryloxide groups, and halides can be utilized without limitation to describe the organomagnesium compounds having the formula $Mg(X^{17})_q(X^{18})_{2-q}$ that can be used in the aspects and embodiments described in this disclosure. As an example, the organomagnesium compound can include or can be selected from dihydrocarbyl magnesium compounds, Grignard reagents, and similar compounds such as alkoxymagnesium alkyl compounds.

In another aspect an in any embodiment of this disclosure, useful organomagnesium compounds can comprise, consist essentially of, or consist of, dimethylmagnesium, diethylmagnesium, dipropylmagnesium, dibutylmagnesium, dineopentylmagnesium, di(trimethylsilylmethyl)magnesium, methylmagnesium chloride, ethylmagnesium chloride, propylmagnesium chloride, butylmagnesium chloride, neopentylmagnesium chloride, trimethylsilylmethylmagnesium chloride, methylmagnesium bromide, ethylmagnesium bromide, propylmagnesium bromide, butylmagnesium bromide, neopentylmagnesium bromide, trimethylsilylmethylmagnesium bromide, methylmagnesium iodide, ethylmagnesium iodide, propylmagnesium iodide, butylmagnesium iodide, neopentylmagnesium iodide, trimethylsilylmethylmagnesium iodide, methylmagnesium ethoxide, ethylmagnesium ethoxide, propylmagnesium ethoxide, butylmagnesium ethoxide, neopentylmagnesium ethoxide, trimethylsilylmethylmagnesium ethoxide, methylmagnesium propoxide, ethylmagnesium propoxide, propylmagnesium propoxide, butylmagnesium propoxide, neopentylmagnesium propoxide, trimethylsilylmethylmagnesium propoxide, methylmagnesium phenoxide, ethylmagnesium phenoxide, propylmagnesium phenoxide, butylmagnesium phenoxide, neopentylmagnesium phenoxide, trimethylsilylmethylmagnesium phenoxide, any combinations thereof; alternatively, dimethylmagnesium; alternatively, diethylmagnesium; alternatively, dipropylmagnesium; alternatively, dibutylmagnesium; alternatively, dineopentylmagnesium; alternatively, di(trimethylsilylmethyl)magnesium; alternatively, methylmagnesium chloride; alternatively, ethylmagnesium chloride; alternatively, propylmagnesium chloride; alternatively, butylmagnesium chloride; alternatively, neopentylmagnesium chloride; alternatively, trimethylsilylmethylmagnesium chloride; alternatively, methylmagnesium bromide; alternatively, ethylmagnesium bromide; alternatively, propylmagnesium bromide; alternatively, butylmagnesium bromide; alternatively, neopentylmagnesium bromide; alternatively, trimethylsilylmethylmagnesium bromide; alternatively, methylmagnesium iodide; alternatively, ethylmagnesium iodide; alternatively, propylmagnesium iodide; alternatively, butylmagnesium iodide; alternatively, neopentylmagnesium iodide; alternatively, trimethylsilylmethylmagnesium iodide; alternatively, methylmagnesium ethoxide; alternatively, ethylmagnesium ethoxide; alternatively, propylmagnesium ethoxide; alternatively, butylmagnesium ethoxide; alternatively, neopentylmagnesium ethoxide; alternatively, trimethylsilylmethylmagnesium ethoxide; alternatively, methylmagnesium propoxide; alternatively, ethylmagnesium propoxide; alternatively, propylmagnesium prop oxide; alternatively, butylmagnesium propoxide; alternatively, neopentylmagnesium propoxide; alternatively, trimethylsilylmethylmagnesium propoxide; alternatively, methylmagnesium phenoxide; alternatively, ethylmagnesium phenoxide; alternatively, propylmagnesium phenoxide; alternatively, butylmagnesium phenoxide; alternatively, neopentylmagnesium phenoxide; or alternatively, trimethylsilylmethylmagnesium phenoxide.

In one aspect and in any embodiment disclosed herein wherein the catalyst system utilizes an organomagnesium compound, the molar ratio of the organomagnesium compound to the metal of the metallocene (Mg:metal of the metallocene) can be greater than 0.1:1; alternatively, greater than 1:1; or alternatively, greater than 10:1; or alternatively, greater than 50:1. In some embodiments wherein the catalyst system utilizes an organomagnesium compound, the molar ratio of the organomagnesium compound to the metal of the metallocene (Mg:metal of the metallocene) can range from 0.1:1 to 100,000:1; alternatively, range from 1:1 to 10,000:1; alternatively, range from 10:1 to 1,000:1; or alternatively, range from 50:1 to 500:1. When the metallocene contains a specific metal (e.g. Zr) the ratio can be stated as a Mg:specific metal ratio (e.g Mg:Zr molar ratio).

Organolithium Compounds

A further aspect of this disclosure provides for an oligomerization method comprising (or a method of producing a PAO comprising a step of) contacting an alpha olefin monomer and a catalyst system comprising a metallocene. In an embodiment, the catalyst system can further comprise an activator. In any embodiment provided here, the activator can comprise a solid oxide chemically-treated with an electron withdrawing anion. In a further aspect of any embodiment provided here, the catalyst system can comprise, either in combination with the chemically-treated solid oxide and/or any other activator(s) or alone, at least one organolithium compound. In some embodiments, the catalyst system can comprise, consist essentially of, or consist of a metallocene, a first activator comprising a chemically-treated solid oxide, and a second activator comprising an organolithium compound. In an aspect, the organolithium compounds that can be used in the catalyst system of this disclosure include but are not limited to compounds having the formula:

$$Li(X^{19}).$$

In an embodiment, $X^{19}$ can be a $C_1$ to $C_{20}$ hydrocarbyl group or hydride; alternatively, a $C_1$ to $C_{10}$ hydrocarbyl group; alternatively, a $C_6$ to $C_{20}$ aryl group; alternatively, a $C_6$ to $C_{10}$ aryl group; alternatively, a $C_1$ to $C_{20}$ alkyl group; alternatively, a $C_1$ to $C_{10}$ alkyl group; alternatively, a $C_1$ to $C_5$ alkyl group; or alternatively, hydride. Alkyl groups and aryl groups have been independently described herein as potential group for $X^{10}$ and $X^{11}$ of the organoaluminum compound having the formula $Al(X^{10})_n(X^{11})_{3-n}$ and these alkyl groups and aryl groups can be utilized without limitation to describe the organolithium compounds having the formula $Li(X^{19})$ that can be used in the aspects and embodiments described in this disclosure.

In another aspect an in any embodiment of this disclosure, useful organolithium compound can comprise, consist essentially of, or consist of, methyllithium, ethyllithium, propyllithium, n-butyllithium, sec-butyllithium, t-butyllithium, neopentyllithium, trimethylsilylmethyllithium, phenyllithium, tolyllithium, xylyllithium, benzyllithium, (dimethylphenyl)methyllithium, allyllithium, or combinations thereof. In an embodiment, the organolithium compound can comprise, consist essentially of, or consist of, methyllithium, ethyllithium, propyllithium, n-butyllithium, sec-butyllithium, t-butyllithium, or any combination thereof; alternatively, phenyllithium, tolyllithium, xylyllithium, or any combination thereof. In some embodiments, the organolithium compound can comprise, consist essentially of, or consist of, methyllithium; alternatively, ethyllithium; alternatively, propyllithium; alternatively, n-butyllithium; alternatively, sec-butyllithium; alternatively, t-butyllithium; alternatively, neo-pentyllithium; alternatively, trimethylsilylmethyllithium; alternatively, phenyllithium; alternatively, tolyllithium; alternatively, xylyllithium; alternatively, benzyllithium; alternatively, (dimethylphenyl)methyllithium; or alternatively, allyllithium.

In one aspect and in any embodiment disclosed herein wherein the catalyst system utilizes an organolithium compound, the molar ratio of the organolithium compound to the metal of the metallocene (Li:metal of the metallocene) can be greater than 0.1:1; alternatively, greater than 1:1; or alternatively, greater than 10:1; or alternatively, greater than 50:1. In some embodiments wherein the catalyst system utilizes an organolithium compound, the molar ratio of the organolithium compound to the metal of the metallocene (Li:metal of the metallocene) can range from 0.1:1 to 100,000:1; alternatively, range from 1:1 to 10,000:1; alternatively, range from 10:1 to 1,000:1; or alternatively, range from 50:1 to 500:1. When the metallocene contains a specific metal (e.g. Zr) the ratio can be stated as a Li:specific metal ratio (e.g Li:Zr molar ratio).1

Organoboron Compounds

Still a further aspect of this disclosure provides for an oligomerization method comprising (or a method of producing a PAO comprising a step of) contacting an alpha olefin monomer and a catalyst system comprising a metallocene. In an embodiment the catalyst system can further comprise an activator. In any embodiment provided here, the activator can comprise a solid oxide chemically-treated with an electron withdrawing anion. In a further aspect of any embodiment provided here, the catalyst system can comprise, either in combination with the chemically-treated solid oxide and/or any other activator(s) or alone, at least one organoboron compound. In some embodiments, the catalyst system can comprise, consist essentially of, or consist of a metallocene, a first activator comprising a chemically-treated solid oxide, and a second activator comprising an organoboron compound.

In an aspect, organoboron compounds that can be used in the catalyst system of this disclosure are varied. In one aspect, the organoboron compound can comprise neutral boron compounds, borate salts, or combinations thereof; alternatively, neutral organoboron compound; or alternatively, borate salts. In an aspect, the organoboron compounds of this disclosure can comprise a fluoroorganoboron compound, a fluoroorganoborate compound, or a combination thereof; alternatively, a fluoroorganoboron compound; or alternatively, a fluoroorganoborate compound. Any fluoroorganoboron or fluoroorganoborate compound known in the art can be utilized. The term fluoroorganoboron compound has its usual meaning to refer to neutral compounds of the form $BY_3$. The term fluoroorganoborate compound also has its usual meaning to refer to the monoanionic salts of a fluoroorganoboron compound of the form $[cation]^+[BY_4]^-$, where Y represents a fluorinated organic group. For convenience, fluoroorganoboron and fluoroorganoborate compounds are typically referred to collectively by organoboron compounds, or by either name as the context requires.

In an embodiment, the fluoroorganoborate compounds that can be used as activators in the present disclosure include, but are not limited to, fluorinated aryl borates such as, N,N-dimethylanilinium tetrakis(pentafluorophenyl)borate, triphenylcarbenium tetrakis(pentafluorophenyl)borate, lithium tetrakis-(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, and mixtures thereof; alternatively, N,N-dimethylanilinium tetrakis(pentafluorophenyl)borate; alternatively, triphenylcarbenium tetrakis(pentafluorophenyl)borate; alternatively, lithium tetrakis(pentafluorophenyl)borate; alternatively, N,N-dimethylanilinium tetrakis[3,5-bis(trifluoromethyl) phenyl]borate; or alternatively, triphenylcarbenium tetrakis [3,5-bis(trifluoromethyl)phenyl]borate. Examples of fluoroorganoboron compounds that can be used as activators in the present disclosure include, but are not limited to, tris(pentafluorophenyl)boron, tris[3,5-bis(trifluoromethyl)phenyl] boron, and mixtures thereof.

Although not intending to be bound by the following theory, these fluoroorganoborate and fluoroorganoboron compounds, and related compounds, are thought to form "weakly-coordinating" anions when combined with organo-metal compounds, as disclosed in U.S. Pat. No. 5,919,983, which is incorporated herein by reference in its entirety.

Generally, any amount of organoboron compound can be utilized in this disclosure. In one aspect and in any embodiment disclosed herein, the molar ratio of the organoboron compound to the metallocene can be from 0.001:1 to 100, 000:1. Alternatively and in any embodiment, the molar ratio of the organoboron compound to the metallocene can be from 0.01:1 to 10,000:1; alternatively, from 0.1:1 to 100:1; alternatively, from 0.5:1 to 10:1; or alternatively, from 0.2:1 to 5:1. Typically, the amount of the fluoroorganoboron or fluoroorganoborate compound used as an activator for the metallocenes can be in a range of from 0.5 mole to 10 moles of organoboron compound per total mole of metallocene compounds employed. In one aspect, the amount of fluoroorganoboron or fluoroorganoborate compound used as an activator for the metallocene is in a range of 0.8 mole to 5 moles of organoboron compound per total moles of metallocene compound.

Ionizing Ionic Compounds

In a further aspect of this disclosure for an oligomerization method comprising (or a method of producing a PAO comprising a step of) contacting an alpha olefin monomer and a catalyst system comprising a metallocene. In an embodiment, the catalyst system can further comprise an activator. In any embodiment provided here, the activator can comprise a solid oxide chemically-treated with an electron withdrawing anion. In a further aspect of any embodiment provided here, the catalyst system can comprise, either in combination with the chemically-treated solid oxide and/or any other activator(s) or alone, at least one ionizing ionic compound. In some embodiments, the catalyst system can comprise, consist essentially of, or consist of a metallocene, a first activator comprising a chemically-treated solid oxide, and a second activator comprising an ionizing ionic compound. Examples of ionizing ionic compound are disclosed in U.S. Pat. Nos. 5,576,259 and 5,807,938, each of which is incorporated herein by reference, in its entirety.

An ionizing ionic compound is an ionic compound which can function to enhance the activity of the catalyst system. While not bound by theory, it is believed that the ionizing ionic compound can be capable of reacting with the metallocene compound and converting it into a cationic metallocene compound or a metallocene compound that can be an incipient cation. Again, while not intending to be bound by theory, it is believed that the ionizing ionic compound can function as an ionizing compound by at least partially extracting an anionic ligand, possibly a Group II (non-$\eta^5$-alkadienyl) ligand from the metallocenes. However, the ionizing ionic compound is an activator regardless of whether it is ionizes the metallocenes, abstracts a Group II ligand in a fashion as to form an ion pair, weakens the metal-Group II ligand bond in the metallocene, simply coordinates to a Group II ligand, or any other mechanisms by which activation may occur.

Further, it is not necessary that the ionizing ionic compound activate the metallocenes only. The activation function of the ionizing ionic compound may be evident in the enhanced activity of the catalyst system as a whole, as compared to a catalyst system that does not comprise any ionizing ionic compound. It is also not necessary that the ionizing ionic compound activate different metallocenes to the same extent.

In one aspect and in any embodiment disclosed herein, the ionizing ionic compound can have the formula:

$$[Q]^+[M^4Z_4]^-.$$

In an embodiment, Q is can be $[NR^AR^BR^CR^D]^+$, $[CR^ER^FR^G]^+$, $[C_7H_7]^+$, $Li^+$, $Na^+$, or $K^+$; alternatively, $[NR^AR^BR^CR^D]^+$; alternatively, $[CR^ER^FR^G]^+$; alternatively, $[C_7H_7]^+$; alternatively, $Li^+$, $Na^+$, or $K^+$; alternatively, $Li^+$; alternatively, $Na^+$; or alternatively, $K^+$. In an embodiment, $R^A$, $R^B$, and $R^C$ can each independently be a hydrogen, and a $C_1$ to $C_{20}$ hydrocarbyl group; alternatively, hydrogen and a $C_1$ to $C_{10}$ hydrocarbyl group; alternatively, hydrogen and a $C_1$ to $C_5$ hydrocarbyl group; alternatively, hydrogen and a $C_6$ to $C_{20}$ aryl group; alternatively, hydrogen and a $C_6$ to $C_{15}$ aryl group; alternatively, hydrogen and a $C_6$ to $C_{10}$ aryl group; alternatively, hydrogen and a $C_1$ to $C_{20}$ alkyl group; alternatively, hydrogen and a $C_1$ to $C_{10}$ alkyl group; or alternatively, hydrogen and a $C_1$ to $C_5$ alkyl group; alternatively, hydrogen; alternatively, a $C_1$ to $C_{20}$ hydrocarbyl group; alternatively, a $C_1$ to $C_{10}$ hydrocarbyl group; alternatively, a $C_1$ to $C_5$ hydrocarbyl group; alternatively, a $C_6$ to $C_{20}$ aryl group; alternatively, a $C_6$ to $C_{15}$ aryl group; alternatively, $C_6$ to $C_{10}$ aryl group; alternatively, a $C_1$ to $C_{20}$ alkyl group; alternatively, a $C_1$ to $C_{10}$ alkyl group; or alternatively, a $C_1$ to $C_5$ alkyl group. In an embodiment, $R^D$ is selected from hydrogen, a halide, and a $C_1$ to $C_{20}$ hydrocarbyl group; alternatively, hydrogen, a halide, and a $C_1$ to $C_{10}$ hydrocarbyl group; alternatively, hydrogen, a halide, and a $C_1$ to $C_5$ hydrocarbyl group; alternatively, hydrogen, a halide, and a $C_6$ to $C_{20}$ aryl group; alternatively, hydrogen, a halide, and a $C_6$ to $C_{15}$ aryl group; alternatively, hydrogen, a halide, and a $C_6$ to $C_{10}$ aryl group; alternatively, hydrogen, a halide, and a $C_1$ to $C_{20}$ alkyl group; alternatively, hydrogen, a halide, and a $C_1$ to $C_{10}$ alkyl group; or alternatively, hydrogen, a halide, and a $C_1$ to $C_5$ alkyl; alternatively, hydrogen; alternatively, a halide; alternatively, and a $C_1$ to $C_{20}$ hydrocarbyl group; alternatively, a $C_1$ to $C_{10}$ hydrocarbyl group; alternatively, a $C_1$ to $C_5$ hydrocarbyl group; alternatively, a $C_6$ to $C_{20}$ aryl group; alternatively, a $C_6$ to $C_{15}$ aryl group; alternatively, a $C_6$ to $C_{10}$ aryl group; alternatively, a $C_1$ to $C_{20}$ alkyl group; alternatively, a $C_1$ to $C_{10}$ alkyl group; or alternatively, a $C_1$ to $C_5$ alkyl group. In an embodiment, $R^E$, $R^F$, and $R^G$ are each selected independently from hydrogen, a halide, and a $C_1$ to $C_{20}$ hydrocarbyl group; alternatively, hydrogen, a halide, and a $C_1$ to $C_{10}$ hydrocarbyl group; alternatively, hydrogen, a halide, and a $C_1$ to $C_5$ hydrocarbyl group; alternatively, hydrogen, a halide, and a $C_6$ to $C_{20}$ aryl group; alternatively, hydrogen, a halide, and a $C_6$ to $C_{15}$ aryl group; or alternatively, hydrogen, a halide, and a $C_6$ to $C_{10}$ aryl group; alternatively, hydrogen; alternatively, a halide; alternatively, a $C_1$ to $C_{20}$ hydrocarbyl group; alternatively, a $C_1$ to $C_{10}$ hydrocarbyl group; alternatively, a $C_1$ to $C_5$ hydrocarbyl group; alternatively, a $C_6$ to $C_{20}$ aryl group; alternatively, a $C_6$ to $C_{15}$ aryl group; or alternatively, a $C_6$ to $C_{10}$ aryl group. Alkyl groups, aryl groups, and halides have been independently described herein potential group for $X^{10}$ and $X^{11}$ of the organoaluminum compound having the formula $Al(X^{10})_n(X^{11})_{3-n}$ and these alkyl groups, aryl groups, and halides can be utilized without limitation to describe the ionizing ionic compound having the formula $[NR^AR^BR^CR^D]^+$ or $[CR^ER^FR^G]^+$ that can be used in the aspects and embodiments described in this disclosure.

In some embodiments, Q can be a trialkyl ammonium or a dialkylarylammonium (e g dimethyl anilinium); alternatively, triphenylcarbenium or substituted triphenylcarbenium; alternatively, tropylium or a substituted tropylium; alternatively, a trialkylammonium; alternatively, a dialkylarylammonium (e.g. dimethyl anilinium) alternatively, a triphenylcarbenium; or alternatively, tropylium. In other embodiments, Q can be tri(n-butyl)ammonium, N,N-dimethylanilinium, triphenylcarbenium, tropylium, lithium, sodium, and potassium; alternatively, tri(n-butyl)ammonium and N,N-dimethylanilinium; alternatively, triphenylcarbenium, tropylium; or alternatively, lithium, sodium and potassium. In an embodiment, $M^4$ can be B or Al; alternatively, B; or alternatively, Al. In an embodiment, Z can be halide or

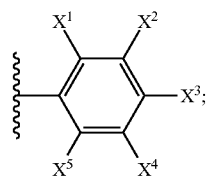

alternatively, halide; or alternatively,

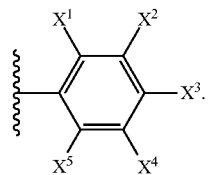

In an embodiment, $X^1$, $X^2$, $X^3$, $X^4$, and $X^5$ can be independently hydrogen, a halide, a $C_1$ to $C_{20}$ hydrocarbyl group, or a $C_1$ to $C_{20}$ hydrocarboxide group (also referred to herein as a hydrocarboxy group); alternatively, hydrogen, a halide, a $C_1$ to $C_{10}$ hydrocarbyl group, or a $C_1$ to $C_{10}$ hydrocarboxide group; alternatively, hydrogen, a halide, a $C_6$ to $C_{20}$ aryl group, or a $C_6$ to $C_{20}$ aryloxide group; alternatively, hydrogen, a halide, a $C_6$ to $C_{10}$ aryl group, or a $C_6$ to $C_{10}$ aryloxide group; alternatively, hydrogen, a halide, a $C_1$ to $C_{20}$ alkyl group, or a $C_1$ to $C_{20}$ alkoxide group (also referred to herein as an alkoxy group); alternatively, hydrogen, a halide, a $C_1$ to $C_{10}$ alkyl group, or a $C_1$ to $C_{10}$ alkoxide group; or alternatively, hydrogen, a halide, a $C_1$ to $C_5$ alkyl group, or a $C_1$ to $C_5$ alkoxide group. Alkyl groups, aryl groups, alkoxide groups, aryloxide groups, and halides have been independently described herein potential group for $X^{10}$ and $X^{11}$ of the organoaluminum compound having the formula $Al(X^{10})_n(X^{11})_{3-n}$ and these alkyl groups, aryl groups, alkoxide groups, aryloxide groups, and halides can be utilized without limitation as $X^1$, $X^2$, $X^3$, $X^4$, and $X^5$. In some embodiments,

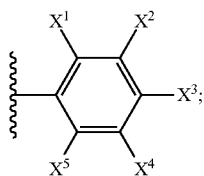

can be phenyl, p-tolyl, m-tolyl, 2,4-dimethylphenyl, 3,5-dimethylphenyl, pentafluorophenyl, and 3,5-bis(trifluoromethyl)phenyl; alternatively, phenyl; alternatively, p-tolyl; alternatively, m-tolyl; alternatively, 2,4-dimethylphenyl; alternatively, 3,5-dimethylphenyl; alternatively, pentafluorophenyl; or alternatively, 3,5-bis(trifluoromethyl)phenyl.

Examples of ionizing ionic compounds include, but are not limited to, the following compounds: tri(n-butyl)ammonium tetrakis(p-tolyl)borate, tri(n-butyl)ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethylphenyl)borate, N,N-dimethylanilinium tetrakis[3,5-bis(trifluoromethyl)phenyl]borate, or N,N-dimethylanilinium tetrakis(pentafluorophenyl)borate; alternatively, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoromethyl)phenyl]borate, or triphenylcarbenium tetrakis(pentafluorophenyl)borate; alternatively, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, or tropylium tetrakis(pentafluorophenyl)borate; alternatively, lithium tetrakis(pentafluorophenyl)borate, lithium tetrakis(phenyl)borate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, or lithium tetrafluoroborate; alternatively, sodium tetrakis(pentafluorophenyl)borate, sodium tetrakis(phenyl) borate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, or sodium tetrafluoroborate; alternatively, potassium tetrakis-(pentafluorophenyl)borate, potassium tetrakis(phenyl)borate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, or potassium tetrafluoroborate; alternatively, tri(n-butyl)ammonium tetrakis(p-tolyl)aluminate, tri(n-butyl)ammonium tetrakis(m-tolyl)aluminate, tri(n-butyl)ammonium tetrakis(2,4-dimethylphenyl)aluminate, tri(n-butyl)ammonium tetrakis(3,5-dimethylphenyl)aluminate, tri(n-butyl)ammonium tetrakis(pentafluorophenyl)aluminate, N,N-dimethylanilinium tetrakis(p-tolyl)-aluminate, N,N-dimethylanilinium tetrakis(m-tolyl)aluminate, N,N-dimethylanilinium tetrakis(2,4-dimethylphenyl)aluminate, N,N-dimethylanilinium tetrakis(3,5-dimethylphenyl)aluminate, or N,N-dimethylanilinium tetrakis (pentafluorophenyl)aluminate; alternatively, triphenylcarbenium tetrakis(p-tolyl)aluminate, triphenylcarbenium tetrakis(m-tolyl)aluminate, triphenylcarbenium tetrakis(2,4-dimethylphenyl)aluminate, triphenylcarbenium tetrakis(3,5-dimethylphenyl)aluminate, or triphenylcarbenium tetrakis(pentafluorophenyl)aluminate; alternatively, tropylium tetrakis(p-tolyl)aluminate, tropylium tetrakis(m-tolyl)aluminate, tropylium tetrakis(2,4-dimethylphenyl)aluminate, tropylium tetrakis(3,5-dimethylphenyl)aluminate, or tropylium tetrakis(pentafluorophenyl)aluminate; alternatively, lithium tetrakis(pentafluorophenyl)aluminate, lithium tetrakis(phenyl)aluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, or lithium tetrafluoroaluminate; alternatively, sodium tetrakis(pentafluorophenyl)aluminate, sodium tetrakis(phenyl)aluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl)aluminate, or sodium tetrafluoroaluminate; or alternatively, potassium tetrakis(pentafluorophenyl)aluminate, potassium tetrakis-(phenyl)aluminate, potassium tetrakis(p-tolyl)aluminate, potassium tetrakis(m-tolyl)aluminate, potassium tetrakis(2,4-dimethylphenyl)aluminate, potassium tetrakis (3,5-dimethylphenyl)aluminate, potassium tetrafluoroaluminate. In some embodiments, the ionizing ionic compound can be tri (n-butyl)ammonium tetrakis(3,5-dimethylphenyl)borate, tri (n-butyl)ammonium tetrakis[3,5-bis(trifluoromethyl)phenyl]borate, tri(n-butyl)ammonium tetrakis (pentafluorophenyl)borate, N,N-dimethylanilinium tetrakis (p-tolyl)borate, N,N-dimethylanilinium tetrakis(m-tolyl) borate, N,N-dimethylanilinium tetrakis[3,5-bis(trifluoromethyl)phenyl]borate, N,N-dimethylanilinium tetrakis (pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoromethyl)phenyl] borate, lithium tetrakis(p-tolyl)aluminate, lithium tetrakis(m-tolyl)aluminate, lithium tetrakis(2,4-dimethylphenyl)aluminate, or lithium tetrakis(3,5-dimethylphenyl)aluminate.

Alternatively and in some embodiments, the ionizing ionic compound can be tri(n-butyl)-ammonium tetrakis[3,5-bis(trifluoromethyl)phenyl]borate, tri(n-butyl)ammonium tetrakis(pentafluorophenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis[3,5-bis(trifluoro-methyl)phenyl]borate, lithium tetrakis(p-tolyl)aluminate, or lithium tetrakis(m-tolyl)aluminate; alternatively, tri(n-butyl)ammonium tetrakis[3,5-bis(trifluoromethyl)phenyl]borate; alternatively, tri(n-butyl)ammonium tetrakis(pentafluorophenyl)borate; alternatively, N,N-dimethylanilinium tetrakis[3,5-bis(trifluoromethyl)phenyl]borate; alternatively, N,N-dimethylanilinium tetrakis(pentafluorophenyl)borate; alternatively, triphenylcarbenium tetrakis[3,5-bis(trifluoromethyl)phenyl]borate; alternatively, lithium tetrakis(p-tolyl)aluminate; or alternatively, lithium tetrakis(m-tolyl)aluminate. In other embodiments, the ionizing compound can be a combination of any ionizing compound recited herein. However, the ionizing ionic compound is not limited thereto in the present disclosure.

In one aspect and in any embodiment disclosed herein, the molar ratio of the ionizing ionic compound to the metallocene can be from 0.001:1 to 100,000:1. Alternatively and in any aspect or embodiment, the molar ratio of the ionizing ionic compound to the metallocene can be from 0.01:1 to 10,000:1; alternatively, from 0.1:1 to 100:1; alternatively, from 0.5:1 to 10:1; or alternatively, from 0.2:1 to 5:1.

Preparation of the Catalyst System

In one aspect and an embodiment of this disclosure, the catalyst system can comprise a metallocene and at least one chemically-treated solid oxide; alternatively, the catalyst system can comprise, consist essentially of, or consist of, a metallocene and at least one aluminoxane. In an embodiment, the catalyst system, can comprise consist essentially of, or consist of, a metallocene, a first activator, and a second activator. Activators are provided herein and can be utilized without limitation as any activators of a catalyst system described herein. In an aspect and in any embodiment disclosed herein, the catalyst system can comprise, consist essentially of, consist of, a metallocene, a first activator comprising (or consisting essentially of, or consisting of) at least one chemically-treated solid oxide, and a second activator comprising (or consisting essentially of, or consisting of) an organoaluminum compound. Other activators such as at least one organoaluminum compound can also be used in the catalyst system. In another aspect, this disclosure encompasses methods of making the catalyst system. Generally, the catalyst system can be obtained with the catalyst system components being contacted in any sequence or order.

In another aspect an any embodiment of this disclosure, the metallocene compound can optionally be precontacted with an olefinic monomer, not necessarily the alpha olefin monomer to be oligomerized, and an organoaluminum compound for a first period of time prior to contacting this precontacted mixture with the chemically treated solid oxide. In one aspect, the first period of time for contact, the precontact time, between the metallocene compound or compounds, the olefinic monomer, and the organoaluminum compound typically range from time 0.1 hour to 24 hours; alternatively, from 0.1 to 1 hour; or alternatively, from 10 minutes to 30 minutes.

In yet another aspect of this disclosure, once the precontacted mixture of the first, second, or both metallocene compounds, olefin monomer, and organoaluminum compound can be contacted with the chemically treated solid oxide. The composition further comprising the chemically treated solid oxide is termed the postcontacted mixture. Typically, the postcontacted mixture can optionally be allowed to remain in contact for a second period of time, the postcontact time, prior to being initiating the oligomerization process. In one aspect, postcontact times between the precontacted mixture and the chemically treated solid oxide can range from 0.1 hour to 24 hours. In another aspect, the postcontact time can be from 0.1 hour to 1 hour.

In one aspect, the precontacting, the postcontacting step, or both can increase the productivity of the oligomerization as compared to the same catalyst system that is prepared without precontacting or postcontacting. However, neither a precontacting step nor a postcontacting step is required for this disclosure.

When an organoaluminum compound is utilized in combination with a chemically treated solid oxide, the postcontacted mixture can be heated at a temperature and for a duration sufficient to allow adsorption, impregnation, or interaction of precontacted mixture and the chemically treated solid oxide, such that a portion of the components of the precontacted mixture is immobilized, adsorbed, or deposited thereon. For example, the postcontacted mixture can be heated from between 0° F. to 150° F.; or alternatively, between 40° F. to 95° F.

When an organoaluminum compound is used as an activator (first, second, or other), the molar ratio of aluminum of the organoaluminum activator to metal of the metallocene can be a specified molar ratio (sometimes stated as Al:metal of the metallocene. In one aspect, the molar ratio aluminum in the organoaluminum compound to the total moles of metal in the metallocene compounds, that is, the total moles metal of all metallocene compounds combined if more than one metallocene is employed, can be greater than 0.1:1; alternatively, greater than 1:1; or alternatively, greater than 10:1; or alternatively, greater than 50:1. In some embodiments, the molar ratio aluminum in the organoaluminum compound to the total moles of metal in the metallocene compounds can range from 0.1:1 to 100,000:1; alternatively, range from 1:1 to 10,000:1; alternatively, range from 10:1 to 1,000:1; or alternatively, range from 50:1 to 500:1. When the metallocene contains a specific metal (e.g. Zr) the molar ratio can be stated as molar ratio of aluminum of the organoaluminum activator to specific metal ratio (e.g. Al:Zr molar ratio when zirconium metallocenes are utilized). These molar ratios reflect the ratio of moles of aluminum of the organoaluminum activator to the total moles of metal in the metallocene compound(s) in both the precontacted mixture and the postcontacted mixture combined.

When a precontacting step is used, generally, the molar ratio of olefin monomer to total moles of metallocene combined in the precontacted mixture can be from 1:10 to 100,000:1; or alternatively, from 10:1 to 1,000:1.

In another aspect of this disclosure, when an organoaluminum compound is utilized in combination with a chemically treated solid oxide, the weight ratio of the chemically treated solid oxide to the organoaluminum compound can range from 1:5 to 1,000:1. In another aspect, the weight ratio of the chemically treated solid oxide to the organoaluminum compound can be from 1:3 to 100:1, and in yet another aspect, from 1:1 to 50:1.

In a further aspect of this disclosure, the weight ratio of the chemically treated solid oxide to the total metallocene compounds employed can be less than 1,000,000:1; alternatively, less than 100,000:1; alternatively, less than 10,000:1; or alternatively, less than 5,000:1. In some embodiments, the weight ratio of the chemically treated solid oxide to the total metallocene compounds employed can range from 1:1 to 100,000:1; alternatively, range from 10:1 to 10,000:1; alternatively, range from 50:1 to 5,000:1; or alternatively, range from 100:1 to 1,000:1.

One aspect of this disclosure can be that when utilizing a chemically treated solid oxide, an aluminoxane is not required to form the catalyst system disclosed herein, a feature that allows lower oligomer production costs. Thus, in one aspect, an oligomerization method comprising (or a method of producing a PAO comprising a step of) contacting an alpha olefin monomer and a catalyst system, can utilize a catalyst system that is substantially devoid of added alumoxane. In an aspect and in any embodiment of the present disclosure the catalyst system can utilize a trialkylaluminum compound a chemically treated solid oxide in the substantial absence of an added aluminoxane.

Additionally, when utilizing a chemically treated solid oxide, it may not be necessary to include an expensive borate compounds or $MgCl_2$ in the catalyst system. However, aluminoxanes, organoboron compounds, ionizing ionic compounds, organozinc compounds, $MgCl_2$, or any combination thereof can be used in the catalyst system if desired. Further, in one aspect, activators such as aluminoxanes, organoboron compounds, ionizing ionic compounds, organozinc compounds, or any combination thereof can be used as activators with the metallocene, either in the presence or in the absence of the chemically treated solid oxide; or alternatively, either in the presence or in the absence of the organoaluminum compounds.

In one aspect, the activity of the catalyst system described herein can be greater than or equal to (≥) 10 grams olefin oligomers/gram metallocene; alternatively, greater than or equal to 100 grams olefin oligomer/gram of metallocene; alternatively, greater than or equal to 1,000 grams olefin oligomer/gram of metallocene; alternatively, greater than or equal to 5,000 grams olefin oligomer/gram of metallocene; alternatively, greater than or equal to 10,000 grams olefin oligomer/gram of metallocene; alternatively, greater than or equal to 25,000 grams olefin oligomer/gram of metallocene; alternatively, greater than or equal to 50,000 grams olefin oligomer/gram of metallocene; alternatively, greater than or equal to 75,000 grams olefin oligomer/gram of metallocene; or alternatively, greater than or equal to 100,000 grams olefin oligomer/gram of metallocene. In an embodiment, the activity of the catalyst system described herein can range 1,000 grams olefin oligomer/gram of metallocene to 1,000,000,000 grams olefin oligomer/gram of metallocene alternatively, range from 5,000 grams olefin oligomer/gram of metallocene to 750,000,000 grams olefin oligomer/gram of metallocene; alternatively, range from 10,000 grams olefin oligomer/gram of metallocene to 500,000,000 grams olefin oligomer/gram of metallocene; alternatively, range from 25,000 grams olefin oligomer/gram of metallocene to 250,000,000 grams olefin oligomer/gram of metallocene; alternatively, range from 50,000 grams olefin oligomer/gram of metallocene to 100,000,000 grams olefin oligomer/gram of metallocene; alternatively, range from 75,000 grams olefin oligomer/gram of metallocene to 50,000,000 grams olefin oligomer/gram of metallocene; or alternatively, range from 100,000 grams olefin oligomer/gram of metallocene to 10,000,000 grams olefin oligomer/gram of metallocene.

In one aspect, the catalyst activity of the catalyst of this disclosure typically can be greater than or equal to (≥) 0.1 grams olefin oligomers per gram of chemically treated solid oxide per hour (abbreviated g oligomer/g CTSO·hr). Catalyst activity is measured under the olefin oligomerization conditions employed. Any reactor used in these measurements should have substantially no indication of any wall scale, coating or other forms of fouling upon making these measurements. In another aspect, the catalyst of this disclosure can be characterized by an activity of greater than or equal to 0.5 g oligomer/g CTSO·hr; alternatively, greater than or equal to 0.7 g oligomer/g CTSO·hr; alternatively, greater than or equal to 1 g oligomer/g CTSO·hr; alternatively, greater than or equal to 1.5 g oligomer/g CTSO·hr; alternatively, greater than or equal to 2 g oligomer/g CTSO·hr; alternatively, greater than or equal to 2.5 g oligomer/g CTSO·hr; alternatively, greater than or equal to 5 g oligomer/g CTSO·hr; alternatively, greater than or equal to 10 g oligomer/g CTSO·hr; alternatively, greater than or equal to 20 g oligomer/g CTSO·hr; alternatively, greater than or equal to 50 g oligomer/g CTSO·hr; alternatively, greater than or equal to 100 g oligomer/g CTSO·hr; alternatively, greater than or equal to 200 g oligomer/g CTSO·hr; alternatively, greater than or equal to 500 g oligomer/g CTSO·hr; or alternatively, greater than or equal to 1000 g oligomer/g CTSO·hr; when measured under the stated conditions. In another aspect, the catalyst systems of this disclosure can be characterized by an activity from 0.1 g oligomer/g CTSO·hr to 5000 g oligomer/g CTSO·hr; alternatively, from 0.25 g oligomer/g CTSO·hr to 2,500 g oligomer/g CTSO·hr; alternatively, from 0.5 g oligomer/g CTSO·hr to 1,000 g oligomer/g CTSO·hr; alternatively, from 0.75 g oligomer/g CTSO·hr to 750 g oligomer/g CTSO·hr; alternatively, from 1 g oligomer/g CTSO·hr to 500 g oligomer/g CTSO·hr; or alternatively, from 5 g oligomer/g CTSO·hr to 250 g oligomer/g CTSO·hr; when measured under the stated conditions.

The Oligomerization Process

Olefin oligomerization according to this disclosure can be carried out in any manner known in the art suitable for the specific alpha olefin monomer(s) employed in the oligomerization process. For example, oligomerization processes can include, but are not limited to slurry oligomerizations, solution oligomerizations, and the like, including multi-reactor combinations thereof. For example, a stirred reactor can be utilized for a batch process, or the reaction can be carried out continuously in a loop reactor or in a continuous stirred reactor. Slurry oligomerization processes (also known as the particle form process) are well known in the art and are disclosed, for example in U.S. Pat. No. 3,248,179, which is incorporated by reference herein, in its entirety. Other oligomerization methods of the present disclosure for slurry processes are those employing a loop reactor of the type disclosed in U.S. Pat. No. 3,248,179, and those utilized in a plurality of stirred reactors either in series, parallel, or combinations thereof, wherein the reaction conditions are different in the different reactors, which is also incorporated by reference herein, in its entirety.

In one aspect, the alpha olefin oligomerization process according to this disclosure involves contacting at least one alpha olefin monomer with a catalyst system to form an oligomer product. The oligomerization reactor effluent that is contained in the reactor following the oligomerization process, which contains the oligomer product and typically some residual monomer (along with other components—e.g. catalyst system or catalyst system components), can be subjected to a separation process to remove some of the more volatile components from the oligomerization reactor effluent, to provide a heavy oligomer product. The heavy oligomer product can then be subjected to hydrogenation to form a polyalphaolefin (PAO). In some non-limiting embodiments, the reactor effluent can be treated with an agent to deactivate the system (a deactivation agent) before performing the separation. In a non-limiting embodiment, the deactivation agent can comprise, consist essentially of, or consist of, water, an alcohol, or any combination thereof; alternatively, water; or alternatively, an alcohol.

Some suitable and/or desirable oligomerization conditions, catalyst components, order of contacting, monomers are provided here, and some characterization features of the oligomer product, the heavy oligomer product, and the PAO are further described. These examples are not intended to be limiting, but rather illustrative of how selections of the possible catalyst components and reaction conditions can be made, and how the properties of the resulting products can be characterized.

In an aspect, the present disclosure relates to an oligomerization method comprising: a) contacting an alpha olefin monomer and catalyst system, the catalyst system comprising a metallocene, and b) forming an oligomer product under oligomerization conditions. In another aspect, the present disclosure relates to an oligomerization method comprising: a) contacting an alpha olefin monomer and catalyst system, the catalyst system comprising a metallocene, b) forming an oligomer product under oligomerization conditions, and c) separating an oligomerization reactor effluent comprising the oligomer product to provide a heavy oligomer product. In a further aspect, the present disclosure relates to an oligomerization method comprising: a) contacting an alpha olefin monomer and catalyst system, the catalyst system comprising a metallocene, b) forming an oligomer product under oligomerization conditions, c) separating an oligomerization reactor effluent comprising the oligomer product to provide a heavy oligomer product and d) hydrogenating the heavy oligomer product to provide a polyalphaolefin. In yet another aspect, the present disclosure relates to method of producing an polyalphaolefin comprising: a) contacting an alpha olefin monomer and catalyst system, the catalyst system comprising a metallocene, b) forming an oligomer product under oligomerization conditions, c) separating an oligomerization reactor effluent comprising the oligomer product to provide a heavy oligomer product, and d) hydrogenating the heavy oligomer product to provide a polyalphaolefin. Generally, the alpha olefin monomer, the catalyst system, the components of the catalyst system (e.g. metallocene, activators, and other components), solvents (if utilized), the oligomer product, the oligomerization conditions, the reactor effluent, the heavy oligomer product, the hydrogenation conditions, and/or the polyalphaolefin are independent elements of the oligomerization methods and/or the method of producing a polyalphaolefin described in this disclosure. These features are independently described herein and the oligomerization method(s) and/or the method(s) of producing a polyalphaolefin can be described using any combination of the alpha olefin monomer described herein, the catalyst system described herein, the components of the catalyst system (e.g. metallocene, activators, and other components) described herein, solvents (if utilized), the oligomer product described herein, the oligomerization conditions described herein, the reactor effluent described herein, the heavy oligomer product described herein, the hydrogenation conditions described herein, and/or the polyalphaolefin described herein. In an embodiment, the oligomer product can be recovered. In some embodiments, the heavy oligomer product can be recovered. In other embodiments, the hydrogenated heavy oligomer product can be recovered. In yet other embodiments, the polyalphaolefin can be recovered.

In a non-limiting embodiment, the alpha olefin monomer utilized in the oligomerization method(s) or method(s) of producing a polyalphaolefin can comprise, consist essentially of, a $C_6$ to $C_{16}$ normal alpha olefin; alternatively, comprise or consist essentially of, a $C_6$ normal alpha olefin, a $C_8$ normal alpha olefin, a $C_{10}$ normal alpha olefin, a $C_{12}$ normal alpha olefin, a $C_{14}$ normal alpha olefin, or any combination thereof; or alternatively, a $C_8$ normal alpha olefin, a $C_{10}$ normal alpha olefin, a $C_{12}$ normal alpha olefin, or any combination thereof. In some non-limiting embodiments, the alpha olefin monomer utilized in the oligomerization method(s) or method(s) of producing a polyalphaolefin can comprise, or consist essentially of, a $C_6$ normal alpha olefin; alternatively, a $C_8$ normal alpha olefin; alternatively, a $C_{10}$ normal alpha olefin; alternatively, a $C_{12}$ normal alpha olefin; alternatively, a $C_{14}$ normal alpha olefin. Other alpha olefin monomers are disclosed herein and may be utilized, without limitation, within the methods described.

In a non-limiting embodiment, the catalyst system utilized in the oligomerization method(s) or method(s) of producing a polyalphaolefin can comprise, consist essentially of, or consist of, a metallocene and an activator; alternatively, a metallocene, a first activator, and a second activator. Generally, the metallocene and the activators are independent elements of the catalyst system. These catalyst system features are independently described herein and can be utilized in any combination to describe the catalyst system. These independent combinations, in turn, can be utilized in any olefin oligomerization method(s) described herein and/or method(s) of producing a polyalphaolefin described herein. According to a further aspect, the catalyst system can comprise, consist essentially of, or consist of, a metallocene, a first activator comprising a chemically-treated solid oxide, and a second activator. In another aspect, the catalyst system utilized in the oligomerization method(s) or method(s) of producing a polyalphaolefin can comprise, consist essentially of, or consist of, a metallocene, a first activator comprising a chemically-treated solid oxide, and a second activator comprising an organoaluminum compound. Other catalyst systems, and/or catalyst system components, are disclosed herein and can be utilized, without limitation, within the methods described.

In a non-limiting embodiment, the chemically-treated solid oxide first activator which may be utilized in the catalyst system utilized in the oligomerization method(s) or method(s) of producing a polyalphaolefin can comprise, consist essentially of, or consist of, fluorided alumina, chlorided alumina, sulfated alumina, fluorided silica-alumina, or any combination thereof. In a non-limiting embodiment, the chemically-treated solid oxide first activator which may be utilized in the catalyst system utilized in the oligomerization method(s) or method(s) of producing a polyalphaolefin can comprise, consist essentially of, or consist of, fluorided alumina, chlorided alumina, sulfated alumina, fluorided silica-alumina, and any combination thereof; alternatively, fluorided alumina; alternatively, chlorided alumina; alternatively, sulfated alumina; alternatively, fluorided silica-alumina. Other chemically-treated solid oxides are disclosed herein and can be utilized, without limitation, within the methods described.

In a non-limiting embodiment, the organoaluminum compound second activator which may be utilized in the catalyst system utilized in the oligomerization method(s) or method(s) of producing a polyalphaolefin can comprise, consist essentially of, or consist of an organoaluminum compound having the formula $Al(X^{10})_n(X^{11})_{3-n}$; or alternatively, comprise, consist essentially of, or consist of an alumoxane. In some non-limiting embodiments, each $X^{10}$ of the organoaluminum compound having the formula $Al(X^{10})_n(X^{11})_{3-n}$ can be independently a $C_1$ to $C_{20}$ hydrocarbyl. In other non-limiting embodiments, each $X^{11}$ of the organoaluminum compound having the formula $Al(X^{10})_n(X^{11})_{3-n}$ can be independently a halide, a hydride, or a $C_1$ to $C_{20}$ hydrocarboxide. In some non-limiting embodiments, n of the organoaluminum compound having the formula $Al(X^{10})_n(X^{11})_{3-n}$ can be a number from 1 to 3. In other non-limiting embodiments, the organoaluminum compound second activator which can be utilized in the catalyst system utilized in the oligomerization method(s) or method(s) of producing a polyalphaolefin comprise, consist essentially of, or consist of a trialkylaluminum; alternatively, triisobutylaluminum. Other organoaluminum compounds are disclosed herein and can be utilized, without limitation, within the methods described.

In a non-limiting embodiment, the metallocene which may be utilized in the catalyst system utilized in the oligomerization method(s) or method(s) of producing a polyalphaolefin can comprise, consist essentially of, or consist of, a metallocene having a formula

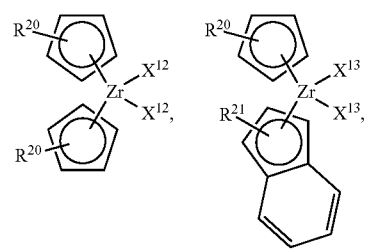

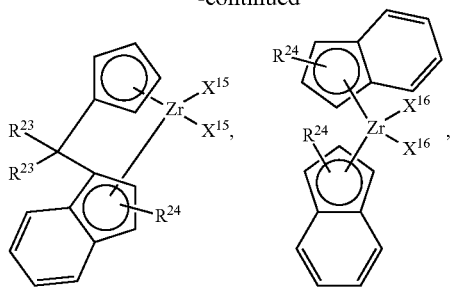

or combinations thereof; alternatively,

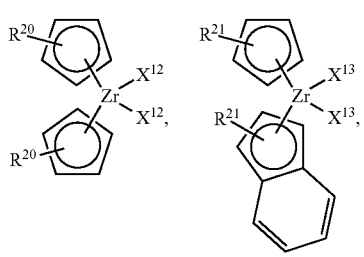

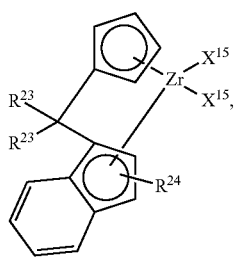

or combinations thereof; alternatively,

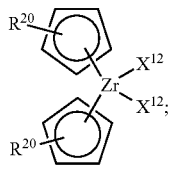

alternatively,

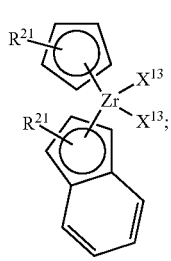

alternatively,

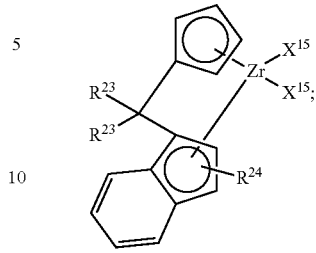

or alternatively,

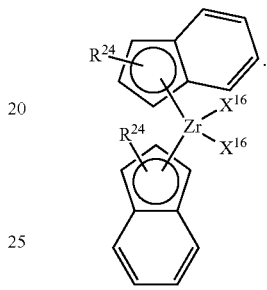

In another non-limiting embodiment, the metallocene which may be utilized in the catalyst system utilized in the oligomerization method(s) or method(s) of producing a polyalphaolefin can comprise, consist essentially of, or consist of, a metallocene having a formula

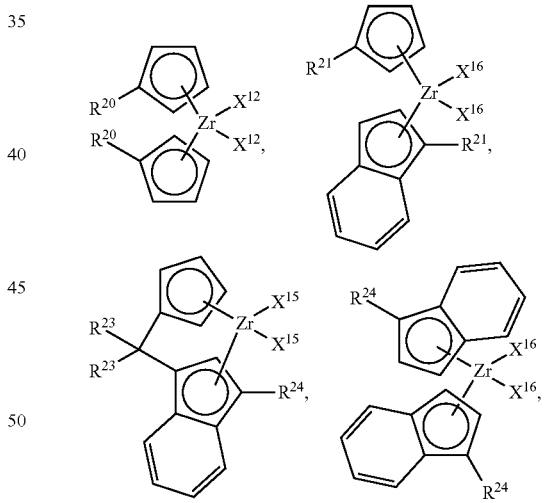

or any combination there of; alternatively,

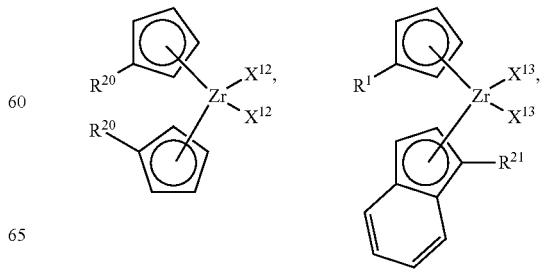

-continued

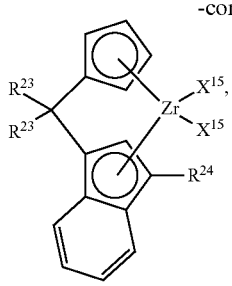

or any combination thereof; alternatively,

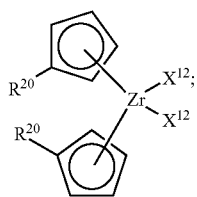

alternatively,

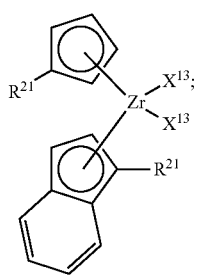

alternatively,

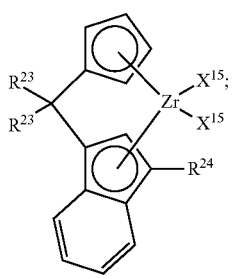

or alternatively,

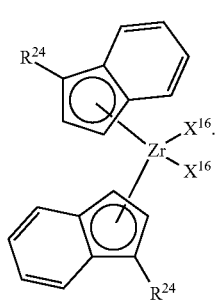

In some non-limiting embodiments, each $R^{20}$, $R^{21}$, $R^{23}$, and $R^{24}$ can be independently hydrogen, a $C_1$ to $C_{20}$ alkyl group, or a $C_1$ to $C_{20}$ alkenyl group; alternatively, a hydrogen; alternatively, a $C_1$ to $C_{20}$ alkyl group; or alternatively, a $C_1$ to $C_{20}$ alkenyl group. In some non-limiting embodiments, each $X^{12}$, $X^{13}$, $X^{15}$, and $X^{16}$ can be independently F, Cl, Br, or I; alternatively, Cl or Br; alternatively, F; alternatively, Cl; alternatively, or alternatively, I. In some non-limiting embodiments, the metallocene which may be utilized in the catalyst system utilized in the oligomerization method(s) or method(s) of producing a polyalphaolefin can comprise, consist essentially of, or consist of, a metallocene having a formula

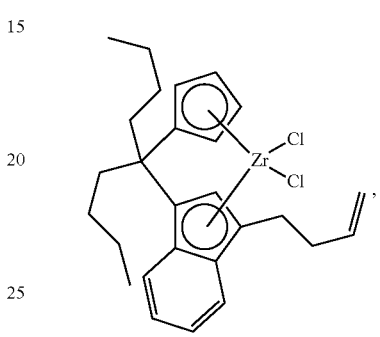

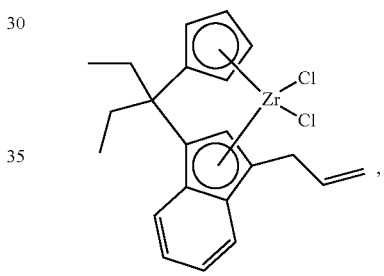

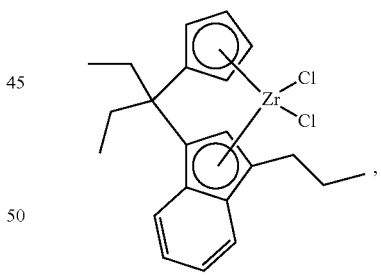

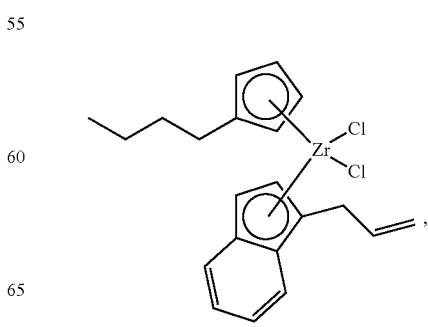

-continued
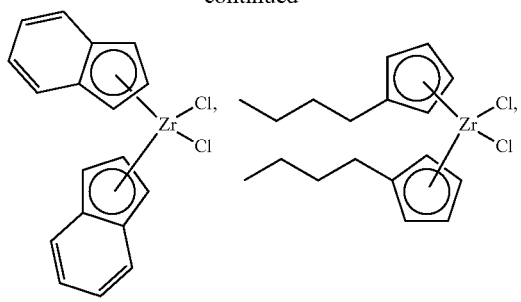
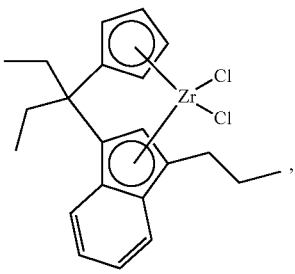
or any combination thereof; alternatively,
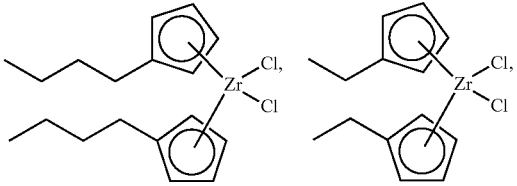
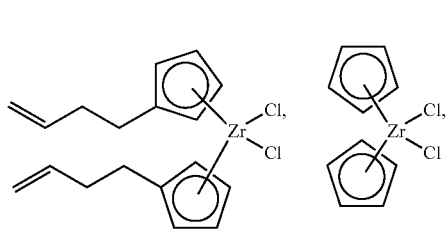
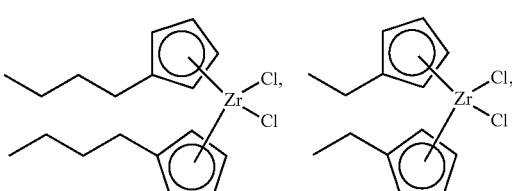
or any combination thereof; alternatively,
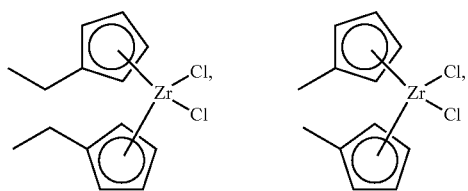
or any combination thereof; alternatively,
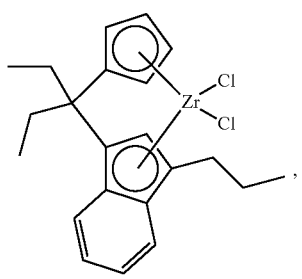
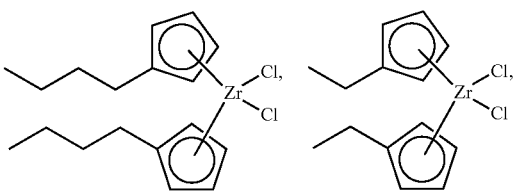
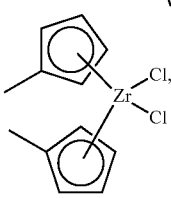
or any combination thereof; alternatively,
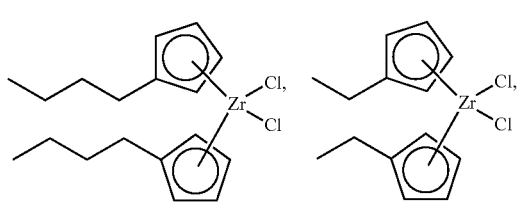
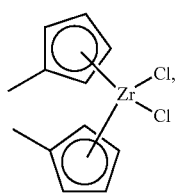
or any combination thereof; alternatively,
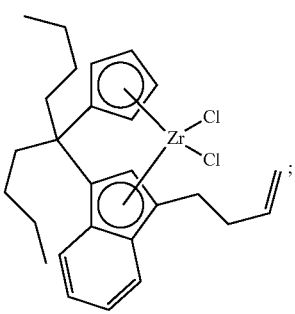

alternatively,

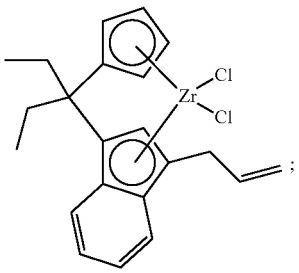

alternatively,

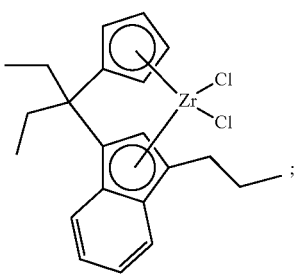

alternatively,

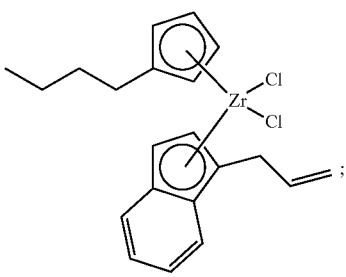

alternatively,

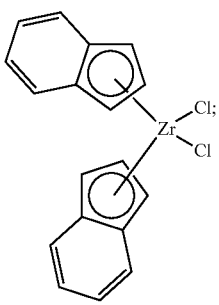

alternatively,

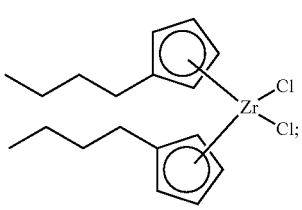

alternatively,

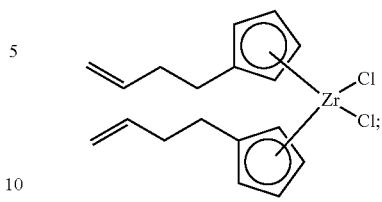

alternatively,

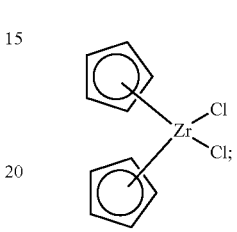

alternatively,

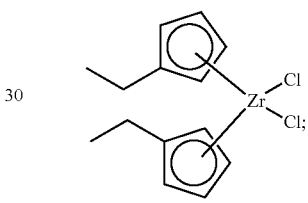

or alternatively,

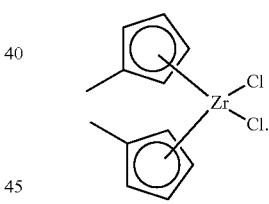

In a non-limiting embodiment where the catalyst system utilizes a metallocene, a first activator, and a second activator, the oligomerization method(s) or method(s) of producing a polyalphaolefin can contact the alpha olefin monomer in any order. In some non-limiting embodiments, the alpha olefin monomer and catalyst system by the steps of (1) contacting the alpha olefin monomer and the second activator to form a first mixture, (2) contacting the first mixture with the first activator to form a second mixture and (3) contacting the second mixture with the metallocene. In other non-limiting embodiments, the alpha olefin monomer and catalyst system can be contacted by the steps of (1) contacting the alpha olefin monomer and the second activator to form a mixture, and (2) simultaneously contacting the first activator and the metallocene with the mixture. In other non-limiting embodiments, the alpha olefin monomer and catalyst system can be contacted by the steps of simultaneously contacting the alpha olefin monomer, the metallocene, the first activator, and the second activator.

In a non-limiting embodiment, the oligomerization method(s) or method(s) of producing a polyalphaolefin can utilize a mole ratio of alpha olefin monomer to metallocene greater than 100:1; alternatively, greater than 1,000:1; alternatively, greater than 10,000:1; or alternatively, greater than 50,000:1. In another non-limiting embodiment, the oligomerization method(s) or method(s) of producing a polyalphaolefin can utilize a mole ratio of alpha olefin monomer to metallocene ranging from 100:1 to 1,000,000,000; alternatively, 1,000:1 to 100,000,000; alternatively, from 10,000:1 to 10,000,000; or alternatively, from 50,000:1 to 5,000,000. Other alpha olefin monomer to metallocene ratios are disclosed herein and can be utilized, without limitation, within the methods described.

In a non-limiting embodiment, the oligomerization method(s) or method(s) of producing a polyalphaolefin can utilize a chemically-treated solid oxide to metal in the metallocene (e.g. Zr in a zirconium metallocene) weight ratio of less than 1,000,000:1; alternatively, less than 100,000:1; alternatively, less than 10,000:1; or alternatively, less than 5,000:1. In another non-limiting embodiment, the oligomerization method(s) or method(s) of producing a polyalphaolefin can utilize a chemically-treated solid oxide to metal in the metallocene (e.g. Zr in a zirconium metallocene) weight ratio ranging from 1:1 to 100,000:1; alternatively, from 10:1 to 10,000:1; alternatively, from 50:1 to 5,000:1; or alternatively, from 100:1 to 1,000:1. Other chemically-treated solid oxide to metallocene ratios are disclosed herein and can be utilized, without limitation, within the methods described.

In a non-limiting embodiment, the oligomerization method(s) or method(s) of producing a polyalphaolefin can utilize a mole ratio of aluminum in the second activator to metal in the metallocene (e.g. Zr in a zirconium metallocene) greater than 0.1:1; alternatively, greater than 1:1; alternatively, greater than 10:1; or alternatively, greater than 50:1. In a non-limiting embodiment, the oligomerization method(s) or method(s) of producing a polyalphaolefin can utilize a mole ratio of aluminum in the second activator to metal in the metallocene (e.g. Zr in a zirconium metallocene) ranging from 0.1:1 to 100,000:1; alternatively, from 1:1 to 10,000:1; alternatively, from 10:1 to 1,000:1; or alternatively, from 50:1 to 500:1. Other aluminum to metal in the metallocene ratios are disclosed herein and can be utilized, without limitation, within the methods described.

In a non-limiting embodiment, the oligomerization method(s) or method(s) of producing a polyalphaolefin can utilize a mole ratio of aluminum-alkyl bonds in the second activator to metal the metallocene (e.g. Zr in a zirconium metallocene) of greater than 0.1:1; alternatively, greater than 0.2:1; alternatively, greater than 1:1; alternatively, greater than 5:1; alternatively, greater than 10:1; alternatively, greater than 50:1; alternatively, greater than 100:1; alternatively, greater than 150:1; or alternatively, greater than 200:1. In a non-limiting embodiment, the oligomerization method(s) or method(s) of producing a polyalphaolefin can utilize a mole ratio of aluminum-alkyl bonds in the second activator to metal the metallocene (e.g. Zr in a zirconium metallocene) ranging from 0.1:1 to 300,000:1; alternatively, from 1:1 to 100,000:1; alternatively, from 10:1 to 10,000:1; alternatively, from 20:1 to 5,000:1; or alternatively, from 50:1 to 1,000:1. Other aluminum-alkyl bonds to metal in the metallocene ratios are disclosed herein and can be utilized, without limitation, within the methods described.

In a non-limiting embodiment, the oligomerization conditions utilized in the oligomerization method(s) or method(s) of producing a polyalphaolefin when forming the oligomer product can comprise an oligomerization temperature from 50° C. to 165° C.; alternatively, from 55° C. to 160° C.; alternatively, from 60° C. to 155° C.; alternatively, from 65° C. to 150° C.; or alternatively, from 70° C. to 145° C.; or alternatively, from 75° C. to 140° C. In a non-limiting embodiment, the oligomerization conditions utilized in the oligomerization method(s) or method(s) of producing a polyalphaolefin when forming the oligomer product can comprise an oligomerization temperature from 70° C. to 90° C.; alternatively, from 90° C. to 120° C.; or alternatively, from 110° C. to 140° C.

In a non-limiting embodiment, the oligomerization conditions utilized in the oligomerization method(s) or method(s) of producing a polyalphaolefin when forming the oligomer product can include performing the oligomerization in an inert atmosphere. In some non-limiting embodiments, an inert atmosphere is an atmosphere substantially free of oxygen; alternatively, substantially free of water when the reaction begins; or alternatively, substantially free of oxygen and substantially free of water when the reaction begins. In an embodiment, the amount of water can be less than 100 ppm; alternatively, less than 75 ppm; alternatively, less than 50 ppm; alternatively, less than 30 ppm; alternatively, less than 25 ppm; alternatively, less than 20 ppm; alternatively, less than 15 ppm; alternatively, less than 10 ppm; alternatively, less than 5 ppm; alternatively, less than 3 ppm; alternatively, less than 2 ppm; alternatively, less than 1 ppm; or alternatively, less than 0.5 ppm. In an embodiment, the amount of $O_2$ can be less than 100 ppm; alternatively, less than 75 ppm; alternatively, less than 50 ppm; alternatively, less than 30 ppm; alternatively, less than 25 ppm; alternatively, less than 20 ppm; alternatively, less than 15 ppm; alternatively, less than 10 ppm; alternatively, less than 5 ppm; alternatively, less than 3 ppm; alternatively, less than 2 ppm; alternatively, less than 1 ppm; or alternatively, less than 0.5 ppm. In some embodiments, the inert atmosphere, can be dry nitrogen; or alternatively, dry argon.

In a non-limiting embodiment, the oligomerization conditions utilized in the oligomerization method(s) or method(s) of producing a polyalphaolefin when forming the oligomer product can comprise performing the oligomerization in the substantial absence of ethylene. In some non-limiting embodiments, the oligomerization conditions for forming the oligomer product can comprise performing the oligomerization with a partial pressure of ethylene less than 10 psig; alternatively, less than 7 psig; alternatively, less than 5 psig; alternatively, less than 4 psig; alternatively, less than 3 psig; alternatively, less than 2 psig; or alternatively, less than 1 psig.

In a non-limiting embodiment, the oligomerization conditions utilized in the oligomerization method(s) or method(s) of producing a polyalphaolefin when forming the oligomer product can comprise performing the oligomerization in the substantial absence of hydrogen. In some non-limiting embodiments, the oligomerization conditions for forming the oligomer product can comprise performing the oligomerization with a partial pressure of hydrogen of less than 10 psig; alternatively, less than 7 psig; alternatively, less than 5 psig; alternatively, less than 4 psig; alternatively, less than 3 psig; alternatively, less than 2 psig; or alternatively, less than 1 psig.

In a non-limiting embodiment, the oligomerization conditions utilized in the oligomerization method(s) or method(s) of producing a polyalphaolefin when forming the oligomer product can comprise performing the oligomerization with a partial pressure of hydrogen. The hydrogen partial pressure in the oligomerization reaction can be any pressure of hydrogen that does not adversely affect the oligomerization reaction. While not intending to be bound by theory, hydrogen can be used in the oligomerization process to control oligomer molecular weight. In some non-limiting embodiments, the oligomerization conditions for forming the oligomer product can comprise performing the oligomerization with a partial pressure of hydrogen of greater than or equal to 5 psig; alternatively, greater than or equal to 10 psig; alternatively, greater than or equal to 50 psig; alternatively, greater than or equal to 100 psig; alternatively, greater than or equal to 200 psig; alternatively, greater than or equal to 300 psig; alternatively, greater than or equal to 400 psig; alternatively, greater than or equal to 500 psig; alternatively, greater than or equal to 750 psig; alternatively, greater than or equal to 1000 psig; alternatively, greater than or equal to 1250 psig; or alternatively, greater than or equal to 1500 psig. In other non-limiting embodiments, the oligomerization conditions utilized in the oligomerization method(s) or method(s) of producing a polyalphaolefin when forming the oligomer product can comprise performing the oligomerization with a partial pressure of hydrogen from 0 psig to 2000 psig; alternatively, from 1 psig to 1500 psig; alternatively, from 5 psig to 1250 psig; alternatively, from 10 psig to 1000 psig; alternatively, from 50 psig to 750 psig; alternatively, from 100 psig to 500 psig; alternatively, from 150 psig to 400 psig; or alternatively, from 200 psig to 300 psig.

In accordance with a further aspect of this disclosure, there are various properties of the oligomer product that can be attained using the oligomerization method disclosed herein. In a non-limiting embodiment, the oligomerization method(s) or method(s) of producing a polyalphaolefin can be characterized by at least 80 weight % of the alpha olefin monomer having been converted to the oligomer product; alternatively, at least 85 weight % of the alpha olefin monomer has been converted to the oligomer product; or alternatively, at least 90 weight % of the alpha olefin monomer has been converted to the oligomer product. In an embodiment, the oligomer product can comprise dimer, trimer, and higher oligomers. In a non-limiting embodiment, the oligomerization method(s) or method(s) of producing a polyalphaolefin can be characterized in that the oligomer product can comprise at least 70 weight % higher oligomers; alternatively, at least 75 weight % higher oligomers; alternatively, at least 77.5 weight % higher oligomers; alternatively, at least 80 weight % higher oligomers; alternatively, at least 82.5 weight % higher oligomers; alternatively, at least 84 weight % higher oligomers; or alternatively, at least 85 weight % higher oligomers.

As disclosed herein and according to any embodiment, the oligomerization method can form an oligomerization reactor effluent comprising the oligomer product, in which the method further comprises separating the oligomerization reactor effluent to provide a heavy oligomer product. In this aspect, at least a portion of the alpha olefin monomer, the dimer, or the trimer can be removed from the oligomerization reactor effluent to form the heavy oligomer product. In a non-limiting embodiment, the oligomerization method(s) or method(s) of producing a polyalphaolefin can be characterized by having a heavy oligomer product comprising less than 0.6 weight % alpha olefin monomer; alternatively, less than 0.5 weight % alpha olefin monomer; alternatively, less than 0.4 weight % alpha olefin monomer; alternatively, less than 0.3 weight % alpha olefin monomer; alternatively, less than 0.2 weight % alpha olefin monomer; or alternatively, less than 0.1 weight % alpha olefin monomer. In a non-limiting embodiment, the oligomerization method(s) or method(s) of producing a polyalphaolefin can be characterized by having a heavy oligomer product comprising less than 2 weight % dimers; alternatively, less than 1.75 weight % dimers; alternatively, less than 1.5 weight % dimers; alternatively, less than 1.25 weight % dimers; alternatively, less than 1 weight % dimers; alternatively, less than 0.9 weight % dimers; alternatively, less than 0.8 weight % dimers; alternatively, less than 0.7 weight % dimers; alternatively, less than 0.6 weight % dimers; alternatively, less than 0.5 weight % dimers; alternatively, less than 0.4 weight % dimers; or alternatively, less than 0.3 weight % dimers. In a non-limiting embodiment, the oligomerization method(s) or method(s) of producing a polyalphaolefin can be characterized by having a heavy oligomer product comprising less than 10 weight % trimers; alternatively, less than 7.5 weight % trimers; alternatively, less than 5 weight % trimers; alternatively, less than 3 weight % trimers; alternatively, less than 2 weight % trimers; alternatively, less than 1.75 weight % trimers; alternatively, less than 1.5 weight % trimers; alternatively, less than 1.25 weight % trimers; alternatively, less than 1 weight % trimers; alternatively, less than 0.9 weight % trimers; alternatively, less than 0.8 weight % trimers; alternatively, less than 0.7 weight % trimers; alternatively, less than 0.6 weight % trimers; alternatively, less than 0.5 weight % trimers; alternatively, less than 0.4 weight % trimers; or alternatively, less than 0.3 weight % trimers. In a non-limiting embodiment, the oligomerization method(s) or method(s) of producing a polyalphaolefin can be characterized by having a heavy oligomer product comprising at least 85 weight % higher oligomers; alternatively, at least 86 weight % higher oligomers; alternatively, at least 87 weight % higher oligomers; alternatively, at least 88 weight % higher oligomers; alternatively, at least 89 weight % higher oligomers; alternatively, at least 90 weight % higher oligomers; alternatively, at least 91 weight % higher oligomers; alternatively, at least 92 weight % higher oligomers; alternatively, at least 93 weight % higher oligomers; alternatively, at least 94 weight % higher oligomers; or alternatively, at least 94 weight % higher oligomers. Other monomer contents, dimer contents, and higher oligomer contents are disclosed herein and can be utilized, without limitation, within the methods described.

In an aspect, the separation utilized to remove at least a portion of the monomer, dimer, and/or trimer from a oligomerization reactor effluent to form a heavy oligomer product can be any separation capable of separating at least a portion of the monomer, dimer, and/or timer from the reactor effluent. In a non-limiting embodiment, the separation can be a distillation. In some embodiment the separation can be a wiped film evaporation. In some non-limiting embodiments, the distillation or wiped film evaporation can be performed at a pressure less than 760 torr; alternatively, less than 600 torr; alternatively, less than 400 torr; alternatively, less than 200 torr; alternatively, less than 100 torr; alternatively, less than 75 torr; alternatively, less than 50 torr; alternatively, less than 40 torr; alternatively, less than 30 torr; alternatively, less than 20 torr; alternatively, less 10 torr; alternatively, less than 5 torr; or alternatively, less than 1 torr. In a non-limiting embodiment, the distillation or wiped film evaporation wiped can be performed by sparging gas an inert gas through the distillation equipment or wiped film evaporator. In an aspect, the sparging gas may be an inert gas. The sparging gas may be nitrogen, helium, argon, or combinations thereof; alternatively, nitrogen; alternatively, helium, or alternatively argon.

As disclosed herein and according to any embodiment, method(s) of producing a polyalphaolefin can produce a polyalphaolefin having a desirable quantity of hydrogenated alpha olefin monomer, hydrogenated dimer, hydrogenated trimer, and/or hydrogenated higher oligomers. In a non-limiting embodiment, the oligomerization method(s) or method(s) of producing a polyalphaolefin can be characterized by having a heavy oligomer product comprising less than 0.6 weight % hydrogenated alpha olefin monomer; alternatively, less than 0.5 weight % hydrogenated alpha olefin monomer; alternatively, less than 0.4 weight % hydrogenated alpha olefin monomer; alternatively, less than 0.3 weight % hydrogenated alpha olefin monomer; alternatively, less than 0.2 weight % hydrogenated alpha olefin monomer; or alternatively, less than 0.1 weight % hydrogenated alpha olefin monomer. In a non-limiting embodiment, the oligomerization method(s) or method(s) of producing a polyalphaolefin can be characterized by having a heavy oligomer product comprising less than 2 weight % hydrogenated dimers; alternatively, less than 1.75 weight % hydrogenated dimers; alternatively, less than 1.5 weight % hydrogenated dimers; alternatively, less than 1.25 weight % hydrogenated dimers; alternatively, less than 1 weight % hydrogenated dimers; alternatively, less than 0.9 weight % hydrogenated dimers; alternatively, less than 0.8 weight % hydrogenated dimers; alternatively, less than 0.7 weight % hydrogenated dimers; alternatively, less than 0.6 weight % hydrogenated dimers; alternatively, less than 0.5 weight % hydrogenated dimers; alternatively, less than 0.4 weight % hydrogenated dimers; or alternatively, less than 0.3 weight % hydrogenated dimers. In a non-limiting embodiment, the oligomerization method(s) or method(s) of producing a polyalphaolefin can be characterized by having a heavy oligomer product comprising less than 10 weight % hydrogenated trimers; alternatively, less than 7.5 weight % hydrogenated trimers; alternatively, less than 5 weight % hydrogenated trimers; alternatively, less than 3 weight % hydrogenated trimers; 2 weight % hydrogenated trimers; alternatively, less than 1.75 weight % hydrogenated trimers; alternatively, less than 1.5 weight % hydrogenated trimers; alternatively, less than 1.25 weight % hydrogenated trimers; alternatively, less than 1 weight % hydrogenated trimers; alternatively, less than 0.9 weight % hydrogenated trimers; alternatively, less than 0.8 weight % hydrogenated trimers; alternatively, less than 0.7 weight % hydrogenated trimers; alternatively, less than 0.6 weight % hydrogenated trimers; alternatively, less than 0.5 weight % hydrogenated trimers; alternatively, less than 0.4 weight % hydrogenated trimers; or alternatively, less than 0.3 weight % hydrogenated trimers. In a non-limiting embodiment, the oligomerization method(s) or method(s) of producing a polyalphaolefin can be characterized by having a heavy oligomer product comprising at least 85 weight % hydrogenated higher oligomers; alternatively, at least 86 weight % hydrogenated higher oligomers; alternatively, at least 87 weight % hydrogenated higher oligomers; alternatively, at least 88 weight % hydrogenated higher oligomers; alternatively, at least 89 weight % hydrogenated higher oligomers; alternatively, at least 90 weight % hydrogenated higher oligomers; alternatively, at least 91 weight % hydrogenated higher oligomers; alternatively, at least 92 weight % hydrogenated higher oligomers; alternatively, at least 93 weight % hydrogenated higher oligomers; alternatively, at least 94 weight % hydrogenated higher oligomers; or alternatively, at least 94 weight % hydrogenated higher oligomers. Other hydrogenated monomer contents, hydrogenated dimer contents, and hydrogenated higher oligomer contents are disclosed herein and can be utilized, without limitation, within the methods described herein.

In an aspect, the oligomer product, the heavy oligomer product, and the polyalphaolefin may have certain desirable properties. In an embodiment, desirable properties can include a certain 100° C. kinematic viscosity, a certain viscosity index, a certain pour point, a certain flash point, a certain fire point, a certain Noack volatility, or any combination thereof; alternatively, a certain 100° C. kinematic viscosity, a certain viscosity index, a certain flash point, a certain fire point, or any combination thereof; alternatively, a certain 100° C. kinematic viscosity, a certain viscosity index, a certain pour point, or any combination thereof; alternatively, a certain flash point, a certain fire point, or any combination thereof; alternatively, a certain 100° C. kinematic viscosity; alternatively, a certain flash point; alternatively, a certain fire point; or alternatively, a certain Noack volatility. Other combination of heavy oligomer product and/or polyalphaolefin properties are readily apparent from the present disclosure.

In a non-limiting embodiment, the oligomerization method(s) or method(s) of producing a polyalphaolefin can be characterized by providing a heavy oligomer product having a 100° C. kinematic viscosity from 25 cSt to 225 cSt; alternatively, from 25 cSt to 55 cSt; alternatively, from 30 cSt to 50 cSt; alternatively, from 32 cSt and 48 cSt; alternatively, from 35 cSt to 45 cSt; alternatively, from 40 cSt to 80 cSt; alternatively, from 45 cSt to 75 cSt; alternatively, from 50 cSt and 70 cSt; alternatively, from 60 cSt to 100 cSt; alternatively, from 65 cSt to 95 cSt; alternatively, from 70 cSt and 90 cSt; alternatively, from 80 cSt to 140 cSt; alternatively, from 80 cSt to 120 cSt; alternatively, from 85 cSt to 115 cSt; alternatively, from 90 cSt and 110 cSt; alternatively, from 100 cSt to 140 cSt; alternatively, from 105 cSt to 135 cSt; alternatively, from 110 cSt and 130 cSt; alternatively, 110 cSt to 190 cSt; alternatively, from 135 cSt to 175 cSt; or alternatively, from 140 cSt and 160. In another non-limiting embodiment, the oligomerization method(s) or method(s) of producing a polyalphaolefin can be characterized by providing a heavy oligomer product having a 100° C. kinematic viscosity from 200 cSt to 300 cSt; alternatively, from 220 cSt to 280 cSt; alternatively, from 235 to 265; alternatively, from 250 cSt to 350 cSt; alternatively, from 270 cSt to 330 cSt; alternatively, 285 cSt to 315 cSt; alternatively, from 300 cSt to 400 cSt; alternatively, from 320 cSt to 380 cSt; alternatively, from 335 to 365; alternatively, from 350 cSt to 450 cSt; alternatively, from 370 cSt to 430 cSt; alternatively, 385 cSt to 415 cSt; alternatively, from 400 cSt to 500 cSt; alternatively, from 420 cSt to 480 cSt; alternatively, from 435 to 465; alternatively, from 450 cSt to 550 cSt; alternatively, from 470 cSt to 530 cSt; alternatively, 485 cSt to 515 cSt; alternatively, from 500 cSt to 700 cSt; alternatively, from 540 cSt to 660 cSt; alternatively, from 570 to 630; alternatively, from 600 cSt to 800 cSt; alternatively, from 640 cSt to 760 cSt; alternatively, 670 cSt to 740 cSt; alternatively, from 700 cSt to 900 cSt; alternatively, from 740 cSt to 860 cSt; alternatively, from 770 to 830; alternatively, from 800 cSt to 1,000 cSt; alternatively, from 840 cSt to 960 cSt; alternatively, 870 cSt to 940 cSt; alternatively, from 900 cSt to 1,100 cSt; alternatively, from 940 cSt to 1,060 cSt; or alternatively, from 970 to 1,030. Thus, a wide range of kinematic viscosities can be achieved with the methods and catalysts of this disclosure by altering the oligomerization conditions, as appreciated by one of ordinary skill. Other heavy oligomer 100° C. kinematic viscosities are disclosed herein and can be utilized, without limitation, within the methods described herein.

In a non-limiting embodiment when the heavy oligomer product is hydrogenated, the oligomerization method(s) or method(s) of producing a polyalphaolefin can be characterized by providing a polyalphaolefin having a 100° C. kinematic viscosity from 25 cSt to 225 cSt; alternatively, from 25 cSt to 55 cSt; alternatively, from 30 cSt to 50 cSt; alternatively, from 32 cSt and 48 cSt; alternatively, from 35 cSt to 45 cSt; alternatively, from 40 cSt to 80 cSt; alternatively, from 45 cSt to 75 cSt; alternatively, from 50 cSt and 70 cSt; alternatively, from 60 cSt to 100 cSt; alternatively, from 65 cSt to 95 cSt; alternatively, from 70 cSt and 90 cSt; alternatively, from 80 cSt to 140 cSt; alternatively, from 80 cSt to 120 cSt; alternatively, from 85 cSt to 115 cSt; alternatively, from 90 cSt and 110 cSt; alternatively, from 100 cSt to 140 cSt; alternatively, from 105 cSt to 135 cSt; alternatively, from 110 cSt and 130 cSt; alternatively, 110 cSt to 190 cSt; alternatively, from 135 cSt to 175 cSt; or alternatively, from 140 cSt and 160. In another non-limiting embodiment when the heavy oligomer product is hydrogenated, the oligomerization method(s) or method(s) of producing a polyalphaolefin can be characterized by providing a polyalphaolefin having a 100° C. kinematic viscosity from 200 cSt to 300 cSt; alternatively, from 220 cSt to 280 cSt; alternatively, from 235 to 265; alternatively, from 250 cSt to 350 cSt; alternatively, from 270 cSt to 330 cSt; alternatively, 285 cSt to 315 cSt; alternatively, from 300 cSt to 400 cSt; alternatively, from 320 cSt to 380 cSt; alternatively, from 335 to 365; alternatively, from 350 cSt to 450 cSt; alternatively, from 370 cSt to 430 cSt; alternatively, 385 cSt to 415 cSt; alternatively, from 400 cSt to 500 cSt; alternatively, from 420 cSt to 480 cSt; alternatively, from 435 to 465; alternatively, from 450 cSt to 550 cSt; alternatively, from 470 cSt to 530 cSt; alternatively, 485 cSt to 515 cSt; alternatively, from 500 cSt to 700 cSt; alternatively, from 540 cSt to 660 cSt; alternatively, from 570 to 630; alternatively, from 600 cSt to 800 cSt; alternatively, from 640 cSt to 760 cSt; alternatively, 670 cSt to 740 cSt; alternatively, from 700 cSt to 900 cSt; alternatively, from 740 cSt to 860 cSt; alternatively, from 770 to 830; alternatively, from 800 cSt to 1,000 cSt; alternatively, from 840 cSt to 960 cSt; alternatively, 870 cSt to 940 cSt; alternatively, from 900 cSt to 1,100 cSt; alternatively, from 940 cSt to 1,060 cSt; or alternatively, from 970 to 1,030. Thus, a wide range of kinematic viscosities can be achieved with the methods and catalysts of this disclosure by altering the oligomerization conditions, as appreciated by one of ordinary skill. Other polyalphaolefin 100° C. kinematic viscosities are disclosed herein and can be utilized, without limitation, within the methods described herein.

In a non-limiting embodiment, the oligomerization method(s) or method(s) of producing a polyalphaolefin can provide a heavy oligomer product and/or a polyalphaolefin having a viscosity index from 150 to 260; alternatively, from 155 to 245; alternatively, from 160 to 230; alternatively, 165 to 220; alternatively, 170 to 220; or alternatively, 175 to 220. Other heavy oligomer and polyalphaolefin viscosity indexes are disclosed herein and can be utilized, without limitation, within the methods described herein.

In a non-limiting embodiment, the oligomerization method(s) or method(s) of producing a polyalphaolefin can provide a heavy oligomer product and/or a polyalphaolefin having a pour point less than 0° C.; alternatively, less than −10° C.; alternatively, less than −20° C.; alternatively, less than −30° C.; alternatively, less than −35° C.; alternatively, less than −40° C.; alternatively, less than −45° C.; alternatively, less than −50° C.; or alternatively, less than −55° C. In another non-limiting embodiment, the oligomerization method(s) or method(s) of producing a polyalphaolefin can provide a heavy oligomer product and/or a polyalphaolefin having a pour point from 0° C. to −100° C.; alternatively, from −10° C. to −95° C.; alternatively, from −20° C. to −90° C.; alternatively, from −30° C. to −90° C.; alternatively, from −35° C. to −90° C.; alternatively, from −40° C. to −90° C.; alternatively, from −45° C. to −90° C.; alternatively, from −50° C. to −85° C.; or alternatively, from −55° C. to −80° C. Other heavy oligomer and polyalphaolefin pour points are disclosed herein and can be utilized, without limitation, within the methods described herein.

In a non-limiting embodiment, the method(s) of producing a polyalphaolefin can provide polyalphaolefin having a Bernoulli index (B (=4[mm][rr]/[mr]$^2$)) of less than 3; alternatively, less than 2.5; alternatively, less than 2; alternatively, less than 1.75; alternatively, less than 1.7; alternatively, less than 1.65; alternatively, less than 1.6; alternatively, less than 1.55; alternatively, less than 1.5; alternatively, less than 1.45; alternatively, less than 1.4; alternatively, less than 1.35; alternatively, less than 1.3; alternatively, less than 1.25; alternatively, less than 1.25; alternatively, less than 1.25; or alternatively, less than 1.15. In a non-limiting embodiment, the method(s) of producing a polyalphaolefin can provide polyalphaolefin having a Bernoulli index (B (=4[mm][rr]/[mr]$^2$)) within a range of 1.4±0.25; alternatively, within a range of 1.4±0.2; alternatively, within a range of 1.4±0.15; alternatively, within a range of 1.4±0.10; alternatively, within a range of 1.3±0.3; alternatively, within a range of 1.3±0.25; alternatively, within a range of 1.3±0.2; alternatively, within a range of 1.3±0.15; alternatively, within a range of 1.4±0.1; alternatively, within a range of 1.2±0.35; alternatively, within a range of 1.2±0.3; alternatively, within a range of 1.2±0.25; alternatively, within a range of 1.2±0.2; alternatively, within a range of 1.2±0.15; alternatively, within a range of 1.1±0.4; alternatively, within a range of 1.1±0.3; alternatively, within a range of 1.1±0.2; or alternatively, within a range of 1.1±0.15. Other polyalphaolefin Bernoulli indexes are disclosed herein and can be utilized, without limitation, within the methods described herein.

In a non-limiting embodiment, the oligomerization method(s) or method(s) of producing a polyalphaolefin can provide polyalphaolefin having a RPVOT as measured by ASTM D2272 in the presence of 0.5 weight % of Naugalube® APAN antioxidant of at least 2,100 minutes; alternatively, at least 2,200 minutes; alternatively, at least 2,300 minutes; or alternatively, at least 2,400 minutes. In another non-limiting embodiment, the oligomerization method(s) or method(s) of producing a polyalphaolefin can provide polyalphaolefin having a RPVOT as measured by ASTM D2272 in the presence of 0.5 weight % of Naugalube® APAN antioxidant of at least 2,000 minutes; alternatively, at least 2,250 minutes; alternatively, at least 2,500 minutes; alternatively, at least 2,750 minutes; or alternatively, at least 3,000 minutes. Other polyalphaolefin RPVOT values are disclosed herein and can be utilized, without limitation, within the methods described herein.

The oligomerizations and/or hydrogenations utilized in the oligomerization method(s) or method(s) of producing a polyalphaolefin of this disclosure can be carried out in the absence of a diluent; or alternatively, can be performed using a diluent, or solvent. Solvents which can be utilized in the oligomerizations and/or hydrogenations utilized in the oligomerization method(s) or method(s) of producing a polyalphaolefin can include, but are not limited to, aliphatic hydrocarbons, aromatic hydrocarbons, halogenated aliphatic hydrocarbons, halogenated aromatic hydrocarbons, and combinations thereof; alternatively, aliphatic hydrocarbons; alternatively, aromatic hydrocarbons; alternatively, halogenated aliphatic hydrocarbons; or alternatively, halogenated aromatic hydrocarbons. Aliphatic hydrocarbons which can be useful as a solvent include $C_3$ to $C_{20}$ aliphatic hydrocarbons; alternatively, $C_3$ to $C_{15}$ aliphatic hydrocarbons; or alternatively, $C_4$ to $C_{10}$ aliphatic hydrocarbons. The aliphatic hydrocarbons can be cyclic or acyclic and/or can be linear or branched, unless otherwise specified. Non-limiting examples of suitable acyclic aliphatic hydrocarbon solvents that can be utilized singly or in any combination include propane, iso-butane, butane, pentane (n-pentane or mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane, and combinations thereof. Non-limiting examples of suitable cyclic aliphatic hydrocarbon solvents include cyclohexane, methyl cyclohexane. Aromatic hydrocarbons which can be useful as a solvent include $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof. Halogenated aliphatic hydrocarbons which can be useful as a solvent include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. The halogenated aliphatic hydrocarbons can be cyclic or acyclic and/or can be linear or branched, unless otherwise specified. Non-limiting examples of suitable halogenated aliphatic hydrocarbons which can be utilized singly of in any combination include methylene chloride, chloroform, carbon tetrachloride, dichloroethane, trichloroethane, and combinations thereof. Halogenated aromatic hydrocarbons which can be useful as a solvent include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons that can be utilized singly or in any combination include chlorobenzene, dichlorobenzene, and combinations thereof.

Selected Embodiments of the Oligomerization Methods

In accordance with one aspect of this disclosure, there is provided an oligomerization method, the oligomerization method comprising:

a) contacting an alpha olefin monomer and a catalyst system, the catalyst system comprising 1) a metallocene having a formula

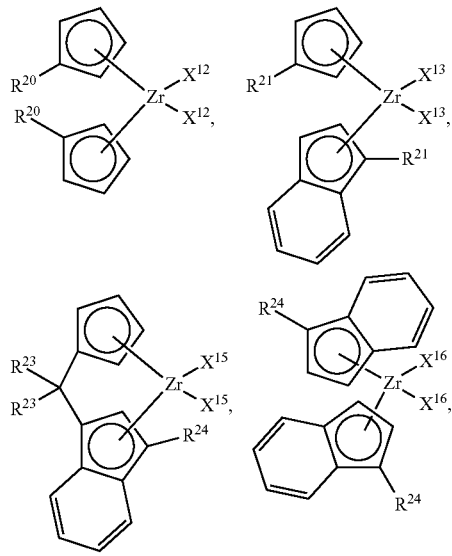

or any combinations thereof, wherein:
i) each $R^{20}$, $R^{21}$, $R^{23}$, and $R^{24}$ is independently a hydrogen, a $C_1$ to $C_{20}$ alkyl group, or a $C_1$ to $C_{20}$ alkenyl group, and
iii) each $X^{12}$, $X^{13}$, $X^{15}$, and $X^{16}$ is independently F, Cl, Br, or I;

2) a first activator comprising a chemically-treated solid oxide comprising fluorided alumina, chlorided alumina, sulfated alumina, fluorided silica-alumina, or any combination thereof; and 3) a second activator comprising an organoaluminum compound having the formula $Al(X^{10})_n(X^{11})_{3-n}$; wherein $X^{10}$ is independently a $C_1$ to $C_{20}$ hydrocarbyl, $X^{11}$ is independently a halide, a hydride, or a $C_1$ to $C_{20}$ hydrocarboxide; and n is a number from 1 to 3; and b) forming an oligomer product under oligomerization conditions.

In a non-limiting embodiment, the metallocenes can comprise, consist essentially of, or consist of:

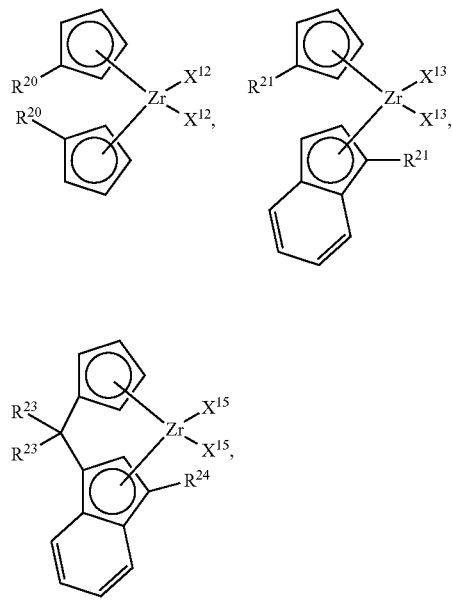

or any combination thereof, wherein:
i) each $R^{20}$, $R^{21}$, and $R^{23}$ is independently a hydrogen, a $C_1$ to $C_{10}$ alkyl group, or a $C_1$ to $C_{10}$ alkenyl group, and
iii) each $X^{12}$, $X^{13}$, and $X^{15}$ is independently Cl or Br.

In another non-limiting embodiment, the metallocene can comprise, consist essentially of, or consist of:

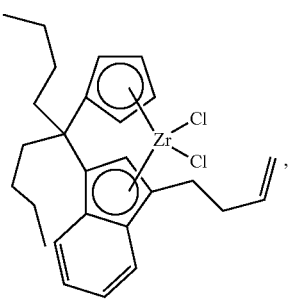

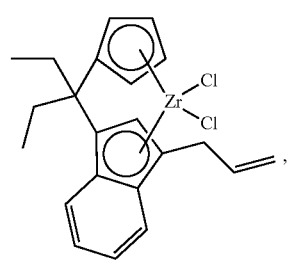

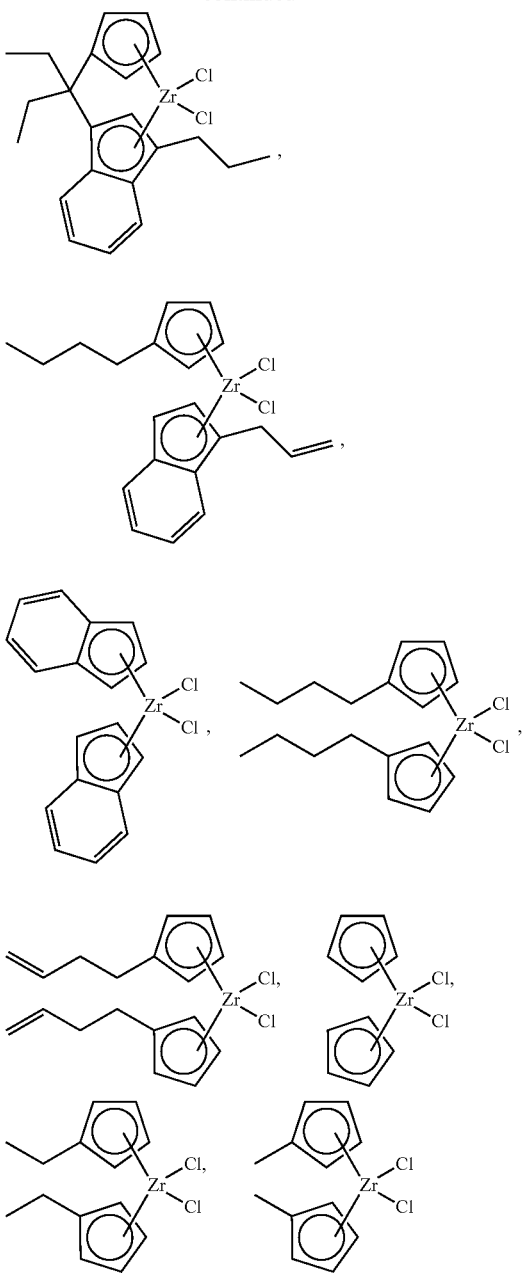

or any combination of these structures.

In a further non-limiting embodiment, the metallocene can comprise, consist essentially of, or consist of:

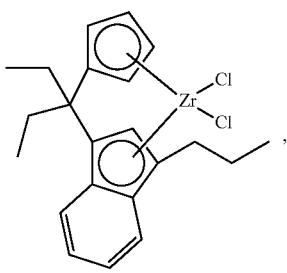

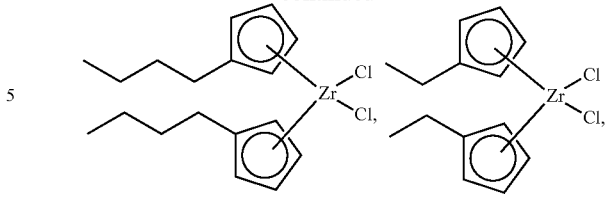

or any combination thereof. Additional embodiments and elements of the oligomerization method and materials produced by the oligomerization method are readily apparent from this disclosure.

In accordance with additional aspects of this disclosure, there is provided an oligomerization method comprising contacting an alpha olefin monomer and a catalyst system under oligomerization conditions and forming an oligomerization reactor effluent comprising an oligomer product, the method further comprising separating the oligomerization reactor effluent to provide a heavy oligomer product, wherein at least a portion of the alpha olefin monomer, the dimer, or the trimer are removed from the oligomerization reactor effluent to form the heavy oligomer product, and wherein:

1) the alpha olefin monomer consists essentially of the $C_8$ normal alpha olefin;
2) the catalyst system comprises
   i) a metallocene having the formula

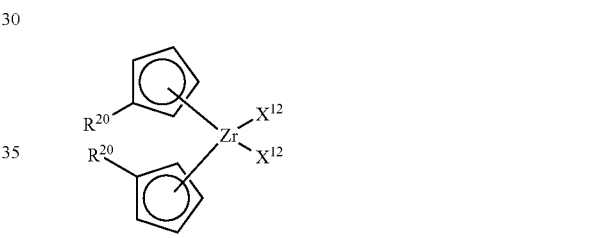

where
(1) each $R^{20}$ is independently a hydrogen, a $C_1$ to $C_{10}$ alkyl group, or a $C_1$ to $C_{10}$ alkenyl group, and
(2) each $X^{12}$ is independently Cl or Br;

ii) a first activator comprising fluorided silica-alumina; and
iii) a second activator comprising a trialkylaluminum; and 3) the oligomerization temperature ranges from 90° C. to 120° C.;
4) the heavy oligomer product has a 100° C. kinematic viscosity from 30 cSt to 50 cSt; and
5) the heavy oligomer product comprises
   i) less than 0.5 weight % alpha olefin monomer;
   ii) less than 1 weight % dimers; and
   iii) at least 88 weight % higher oligomers.

In some non-limiting embodiments, the metallocene can comprise, consist essentially of, or consist of:

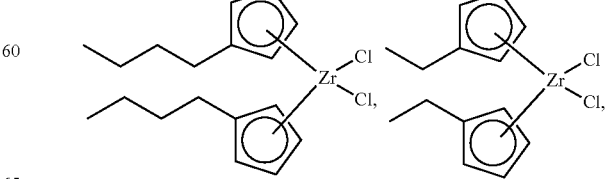

or any combination thereof.

In some embodiments, the heavy oligomer product can have a viscosity index from 150 to 260. In another non-limiting embodiment, the heavy oligomer product is hydrogenated to provide a polyalphaolefin. In other non-limiting embodiments wherein the heavy oligomer product is hydrogenated to provide a polyalphaolefin, the polyalphaolefin can have a pour point from −30° C. to −90° C. In further embodiments wherein the heavy oligomer product is hydrogenated to provide a polyalphaolefin, the polyalphaolefin can have a RPVOT as measured by ASTM D2272 in the presence of 0.5 weight % of Naugalube® APAN antioxidant of at least 2,100 minutes. In yet further non-limiting embodiments wherein the heavy oligomer product is hydrogenated to provide a polyalphaolefin, the polyalphaolefin can have Bernoulli index less 1.65; or alternatively, within a range of 1.4±0.25. In some embodiments, the polyalphaolefin can have no discernable crystallization above −40° C. as determined differential scanning calorimetry using ASTM D 3418. Additional embodiments and elements of the oligomerization method and materials produced by the oligomerization method are readily apparent from this disclosure.

Another aspect of this disclosure provides an oligomerization method comprising contacting an alpha olefin monomer and a catalyst system under oligomerization conditions and forming an oligomerization reactor effluent comprising an oligomer product, the method further comprising separating the oligomerization reactor effluent to provide a heavy oligomer product, wherein at least a portion of the alpha olefin monomer, the dimer, or the trimer are removed from the oligomerization reactor effluent to form the heavy oligomer product, and wherein:

1) the alpha olefin monomer consists essentially of the $C_8$ normal alpha olefin;

2) the catalyst system comprises
i) a metallocene having the formula

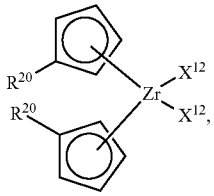

wherein
(1) each $R^{20}$ is independently a hydrogen, a $C_1$ to $C_{10}$ alkyl group, or a $C_1$ to $C_{10}$ alkenyl group, and
(2) each $X^{12}$ is independently Cl or Br;
ii) a first activator comprising fluorided silica-alumina; and
iii) a second activator comprising a trialkylaluminum;

3) the oligomerization temperature ranges from 70° C. to 90° C.;

4) the heavy oligomer product has a 100° C. kinematic viscosity from 80 cSt to 140 cSt; and 5) the heavy oligomer product comprises
i) less than 0.5 weight % alpha olefin monomer;
ii) less than 1 weight % dimers; and
iii) at least 88 weight % higher oligomers.

In some non-limiting embodiments, the metallocene can comprise, consist essentially of, or consist of:

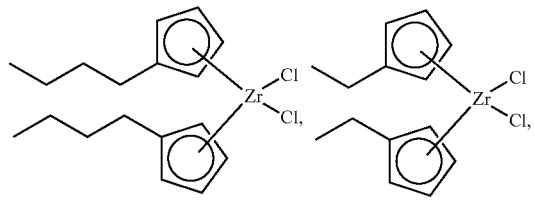

or any combination thereof.

In some embodiments, the heavy oligomer product can have a viscosity index from 150 to 260. In another non-limiting embodiment, the heavy oligomer product is hydrogenated to provide a polyalphaolefin. In other non-limiting embodiments wherein the heavy oligomer product is hydrogenated to provide a polyalphaolefin, the polyalphaolefin can have a pour point from −30° C. to −90° C. In further embodiments wherein the heavy oligomer product is hydrogenated to provide a polyalphaolefin, the polyalphaolefin can have a RPVOT as measured by ASTM D2272 in the presence of 0.5 weight % of Naugalube® APAN antioxidant of at least 2,100 minutes. In yet further non-limiting embodiments wherein the heavy oligomer product is hydrogenated to provide a polyalphaolefin, the polyalphaolefin can have Bernoulli index less 1.65; or alternatively, within a range of 1.1±0.4. In some embodiments, the polyalphaolefin can have no discernable crystallization above −40° C. as determined differential scanning calorimetry using ASTM D 3418. Additional embodiments and elements of the oligomerization method and materials produced by the oligomerization method are readily apparent from this disclosure.

Another aspect of this disclosure provides an oligomerization method comprising contacting an alpha olefin monomer and a catalyst system under oligomerization conditions and forming an oligomerization reactor effluent comprising an oligomer product, the method further comprising separating the oligomerization reactor effluent to provide a heavy oligomer product, wherein at least a portion of the alpha olefin monomer, the dimer, or the trimer are removed from the oligomerization reactor effluent to form the heavy oligomer product, and wherein:

1) the alpha olefin monomer consists essentially of the $C_8$ normal alpha olefin;

2) the catalyst system comprises
i) a metallocene having the formula

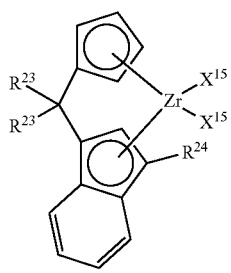

where
(1) each $R^{23}$ and $R^{24}$ is independently a hydrogen, a $C_1$ to $C_{10}$ alkyl group, or a $C_1$ to $C_{10}$ alkenyl group, and
(2) each $X^{15}$ is independently Cl or Br;
ii) a first activator comprising fluorided silica-alumina; and
iii) a second activator comprising trialkylaluminum;

3) the oligomerization temperature ranges from 110° C. to 140° C.;

4) the heavy oligomer product has a 100° C. kinematic viscosity from 80 cSt to 140 cSt; and 5) the heavy oligomer product comprises
   i) less than 0.4 weight % alpha olefin monomer;
   ii) less than 1.5 weight % dimers; and
   iii) at least 88 weight % higher oligomers.

In some non-limiting embodiments, the metallocene can comprise, consist essentially of, or consist of:

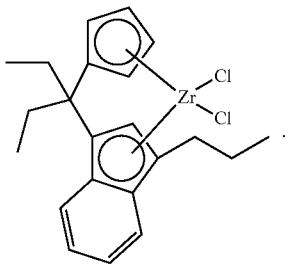

In some embodiments, the heavy oligomer product can have a viscosity index from 150 to 260. In another non-limiting embodiment, the heavy oligomer product is hydrogenated to provide a polyalphaolefin. In other non-limiting embodiments wherein the heavy oligomer product is hydrogenated to provide a polyalphaolefin, the polyalphaolefin can have a pour point from −30° C. to −90° C. In further embodiments wherein the heavy oligomer product is hydrogenated to provide a polyalphaolefin, the polyalphaolefin can have a RPVOT as measured by ASTM D2272 in the presence of 0.5 weight % of Naugalube® APAN antioxidant of at least 2,100 minutes. In yet further non-limiting embodiments wherein the heavy oligomer product is hydrogenated to provide a polyalphaolefin, the polyalphaolefin can have Bernoulli index less 1.65; or alternatively, within a range of 1.1±0.4. In some embodiments, the polyalphaolefin can have no discernable crystallization above −40° C. as determined differential scanning calorimetry using ASTM D 3418. Additional embodiments and elements of the oligomerization method and materials produced by the oligomerization methods are readily apparent from this disclosure.

In another aspect, the method can include a step of blending the polyalphaolefin with at least a second polyalphaolefin. In this aspect of the oligomerization method,
   a) the second polyalphaolefin can have a 100° C. kinematic viscosity at least 10 cSt different than the polyalphaolefin;
   b) the second polyalphaolefin is produced using a different monomer than the polyalphaolefin; or
   c) the second polyalphaolefin has 100° C. kinematic viscosity at least 10 cSt different than the polyalphaolefin and the second polyalphaolefin is produced using a different monomer than the polyalphaolefin.

Reactors

For purposes of the disclosure, the term oligomerization reactor includes any oligomerization reactor or oligomerization reactor system known in the art that is capable of oligomerizing the particular alpha olefin monomers to produce an olefin oligomer product according to the present disclosure. Oligomerization reactors suitable for the present disclosure can comprise at least one raw material feed system, at least one feed system for the catalyst system or catalyst system components, at least one reactor system, at least one oligomer recovery system or any suitable combination thereof. Suitable reactors for the present disclosure can further comprise any one, or combination of, a catalyst system storage system, catalyst system component storage system, a cooling system, a diluent or solvent recycling system, a monomer recycling system, or a control system. Such reactors can comprise continuous take-off and direct recycling of catalyst, diluent, monomer, and oligomer. Generally, continuous processes can comprise the continuous introduction of an alpha olefin monomer, a catalyst, and a diluent into an oligomerization reactor and the continuous removal from this reactor of a suspension comprising alpha olefin oligomer, catalyst system, and the diluent or solvent(s).

Oligomerization reactor systems of the present disclosure can comprise one type of reactor per system or multiple reactor systems comprising two or more types of reactors operated in parallel or in series. Multiple reactor systems can comprise reactors connected together to perform the oligomerization, or reactors that are not connected. The alpha olefin monomer can be oligomerized in one reactor under one set of conditions, and then the reactor effluent comprising alpha olefin oligomers (and potentially the catalyst system and/or unreacted alpha olefin monomer of this first reactor can be transferred to a second reactor for oligomerization under a different set of conditions.

In one aspect of the disclosure, the oligomerization reactor system can comprise at least one loop reactor. Such reactors are known in the art and can comprise vertical or horizontal loops. Such loops can comprise a single loop or a series of loops. Multiple loop reactors can comprise both vertical and horizontal loops. The oligomerization can be performed using the alpha olefin monomer as the liquid carrier, or in the presence of an organic diluent or solvent that can disperse and/or carry the catalyst system components and/or catalyst system. An organic solvent can also be utilized to reduce the viscosity of the reaction mixture (including the alpha olefin oligomers) and allow the reaction mixture to easily flow or be pumped through the process equipment. Solvents are disclosed herein and can be utilized without limitation to disperse and/or carry the catalyst system. Monomer(s), solvent, catalyst system components and/or catalyst system, can be continuously fed to a loop reactor where oligomerization occurs.

In still another aspect of the disclosure, the oligomerization reactor can comprise a tubular reactor. Tubular reactors can have several zones where fresh monomer, the catalyst system, and/or catalyst system components (and/or other components of the oligomerization reaction, e.g. hydrogen) are added. Monomer can be introduced at one zone of the reactor while the catalyst systems, and/or catalyst components (and/or other components of the oligomerization reaction, e.g. hydrogen) can be introduced at another zone of the reactor. Heat and pressure can be employed appropriately to obtain optimal oligomerization reaction conditions.

In another aspect of the disclosure, the oligomerization reactor can comprise a solution oligomerization reactor. During solution oligomerization, the alpha olefin monomer can be contacted with the catalyst system and or catalyst system components by suitable stirring or other means. A carrier comprising an inert organic diluent (if employed) or excess monomer can be employed. If desired, the monomer can be brought in the vapor phase into contact with the catalytic reaction product, in the presence or absence of liquid material. The oligomerization zone is maintained at temperatures and pressures that will result in the formation of a solution of the oligomer product in a reaction medium. Agitation can be employed during oligomerization to obtain better temperature control and to maintain uniform oligomerization mixtures throughout the oligomerization zone. Adequate means are utilized for dissipating the exothermic heat of oligomerization. The oligomerization can be effected in a batch manner, or in a continuous manner. The reactor can comprise a series of at least one separator that employs high pressure and/or low pressure to separate the desired oligomer.

In a further aspect of the disclosure, the oligomerization reactor system can comprise the combination of two or more reactors. Production of oligomers in multiple reactors can include several stages in at least two separate oligomerization reactors interconnected by a transfer device making it possible to transfer the oligomers resulting from the first oligomerization reactor into the second reactor. The desired oligomerization conditions in one of the reactors can be different from the operating conditions of the other reactors. Alternatively, oligomerization in multiple reactors can include the manual transfer of oligomer from one reactor to subsequent reactors for continued oligomerization. Such reactors can include any combination including, but not limited to, any combination of one or more loop reactors, one or more tubular reactors, one or more solution reactors, one or more stirred tank reactors, or one or more autoclave reactors.

In an aspect, the process can include a separation step or multiple separation steps to remove or at least a portion of unreacted monomer, dimer, and/or trimers. In an aspect, the separation step(s) are operated to reduce the amount of monomer, dimer, and/or trimer found in the reactor effluent and/or olefin oligomer product. Desirable monomer, dimer, and/or trimer contents are described herein and can be utilized without limitation to further describe the separation step(s). The separation step(s) can also be utilized to remove the diluent or solvent, if utilized, from the alpha olefin oligomers.

In yet another aspect, the process can include a separation step or multiple separation steps to provide an alpha olefin oligomer product (or oligomer product), or an alpha olefin oligomer product which will produce a polyalphaolefin, having certain desirable properties. One desirable property which can be achieved by utilizing a separation step or steps is 100° C. kinematic viscosity. A second desirable property which can be achieved by utilizing a separation step or steps to achieve a desired flash point. A third desirable property which can be achieved by utilizing a separation step or steps to achieve a desired fire point. A fourth desirable property which can be achieved by utilizing a separation step or steps to achieve a desired Noack volatility. In an embodiment, the separation step(s) can be utilized to remove lower and/or higher molecular weight oligomers to produce an alpha olefin oligomer product, or an alpha olefin oligomer product which will produce a polyalphaolefin, having a desired 100° C. kinematic viscosity, flash point, fire point, and/or Noack volatility. In another embodiment, the separation step(s) can be utilized to produce multiple alpha olefin oligomer products, or multiple alpha olefin oligomer products which will produce polyalphaolefins, having desired 100° C. kinematic viscosities. In a further embodiment, the separation step(s) can be utilized to produce a product having desired 100° C. kinematic viscosity and specified flash point. Desirable 100° C. kinematic viscosities, flash points, and fire points for the alpha olefin oligomer product(s) are described herein and can be utilized without limitation to further describe the separation step(s) olefin oligomer product, heavy oligomer product, and/or polyalphaolefin.

In some embodiments, additives and modifiers are added to the polyalphaolefins in order to provide desired properties or effects. By using the disclosure described herein, PAOs that can be used as lubricants or synthetic oils and the like can be produced at a lower cost, while maintaining most or all of the unique properties of oligomers produced with metallocene catalysts.

All publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed, for example a range of the number of carbon atoms, viscosities, viscosity indices, pour points, Bernoulli indices, temperatures, and the like, it is intended to disclose or claim individually each possible number that such a range could reasonably encompass, including any sub-ranges encompassed therein. For example, when describing a range of the number of carbon atoms, each possible individual integral number and ranges between integral numbers of atoms that the range includes are encompassed therein. Thus, by disclosing a $C_1$ to $C_{10}$ alkyl group or an alkyl group having from 1 to 10 carbon atoms or "up to" 10 carbon atoms, Applicants' intent is to recite that the alkyl group can have 1, 2, 3, 4, 5, 6, 7, 8, 9, or 10 carbon atoms, and these methods of describing such a group are interchangeable. When describing a range of measurements such as viscosity indices, every possible number that such a range could reasonably encompass can, for example, refer to values within the range with one significant digit more than is present in the end points of a range. In this example, a viscosity index between 190 and 200 includes individually viscosity indices of 190, 191, 192, 193, 194, 195, 196, 197, 198, 199, and 200. Applicants' intent is that these two methods of describing the range are interchangeable. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. In this aspect, Applicants' disclosure of a $C_1$ to $C_{10}$ alkyl group is intended to literally encompass a $C_1$ to $C_6$ alkyl, a $C_4$ to $C_8$ alkyl, a $C_2$ to $C_7$ alkyl, a combination of a $C_1$ to $C_3$ and a $C_5$ top $C_7$ alkyl, and so forth. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that are employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

For any particular compound disclosed herein, the general structure presented is also intended to encompasses all conformational isomers and stereoisomers that can arise from a particular set of substituents, unless indicated otherwise. Thus, the general structure encompasses all enantiomers, diastereomers, and other optical isomers whether in enantiomeric or racemic forms, as well as mixtures of stereoisomers, as the context permits or requires. For any particular formula that is presented, any general formula presented also encompasses all conformational isomers, regioisomers, and stereoisomers that can arise from a particular set of substituents.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, may suggest themselves to one of ordinary skill in the art without departing from the spirit of the present invention or the scope of the appended claims.

In the following examples, unless otherwise specified, the syntheses and preparations described therein were carried out under an inert atmosphere such as nitrogen and/or argon. Solvents were purchased from commercial sources and were typically dried prior to use. Unless otherwise specified, reagents were obtained from commercial sources.

General Experimental Procedures
General Procedure for Alpha Olefin Oligomerization Unless specified otherwise, the general procedure used for the alpha olefin oligomerization was as follows. Alpha olefins were purged or sparged using a nitrogen stream for several hours, then were dried over 13× molecular sieves under an inert atmosphere. A heating mantle was used to heat a flask containing the olefin sample to the desired reaction temperature, and stirring was used to maintain uniform temperature and mixing. The flask was relieved to an oil bubbler according to routine safety practices. When using an alkyl aluminum component, the alkyl aluminum component was added to the flask first, followed by a toluene, olefin, or other hydrocarbon solution of the metallocene (typically 0.5-10 mg/ml). Subsequently, the chemically treated solid oxide (solid super acid) activator was then added. The order of addition of these reagents could be varied, but the alkyl aluminum component was typically added first to scavenge any residual moisture in the olefin. Addition of the solid acid catalyst usually resulted in no discernible exotherm, and if an exothermic reaction was observed, the catalyst and activator amounts could be reduced to reduce the initial exotherm to less than 5° C. These slight initial exotherms would typically dissipate after several minutes, and the reaction temperature would drop to the desired set point, where it was maintained for the duration of the reaction. All procedures were carried out under inert atmosphere conditions.

For alpha olefin oligomerization reactions that were conducted under a hydrogen atmosphere, this general procedure was carried out in a Zipperclave™ reactor from Autoclave Engineers at the desired hydrogen pressure. Products were isolated by reducing the reaction temperature, and by adding a few milliliters of water to destroy the residual catalyst. If necessary and/or for ease of filtration, a volatile solvent such as n-pentane was added, and the precipitated catalyst components and the solid acid were removed by filtration. Vacuum distillation was used to remove low molecular weight components and to provide the distilled oligomer product.

Brookfield Viscosity

The −8° C., −20° C., −26° C., and −40° C. Brookfield viscosities of alpha olefin oligomers, hydrogenated oligomers, or commercially available PAO were determined according to ASTM D5133 at the recited temperatures, the results being reported in centiPoise (cP).

Molecular Weights and Molecular Weight Distributions by Gel Permeation Chromatography (GPC) Method Molecular weight averages were obtained using a single-column method with a Polymer Labs PL-gel MIXED-E column. The column packing particle size was 3 microns, and the Column Dimensions were 300 mm×7.5 mm. A refractive index detector was used. A 4-component polystyrene calibration standard with molecular weights 1000, 4000, 20,000, and 50,000 was used, resulting in a quadratic fit to the calibration points with an R-squared value of 0.998. This calibration curve was used to generate the molecular weight data for the reported Examples.

DSC Method

Differential Scanning calorimetry (DSC) analysis was performed on a Perkin-Elmer DSC-7, with a flow rate of 20 cc/min (cubic centimeters per minute) of nitrogen. The temperature program used was as follows:
Hold for 5 min at −60° C.;
Heat from −60° C. to 100° C. at 10° C./min;
Cool from 100° C. to −60° C. at 10° C./min;
Hold at −60° C. for 5 min; and
Heat from −60° C. to 100° C. at 10° C./min.

Sheer Stability

The standard test method for shear stability was determined according to ASTM D6278-07. This ASTM method evaluates the percent viscosity loss for oligomer-containing fluids resulting from oligomer degradation in the high shear nozzle device, in which thermal or oxidative effects are minimized.

KRL Shear Stability

The KRL shear stability (20 hrs) of alpha olefin oligomers, hydrogenated oligomers, or commercially available PAO was determined according to DIN 51350, the results being reported as the percent viscosity loss ratio or percent.

Kinematic Viscosity

The 100° C. kinematic viscosity and the 40° C. kinematic viscosity of alpha olefin oligomers was determined according to ASTM D445 or D742 at temperatures of 100° C. and 40° C., the results being reported in centistokes (cSt).

Viscosity Index

The viscosity index was determined according to procedure ASTM D2270, using the Tables provided therein for viscosity data determined at of 100° C. and 40° C.

Pour Point

Pour point is a measurement of the temperature at which the sample will begin to flow under carefully controlled conditions. Pour point was determined as described in ASTM D 5950 or D97, and the results are reported in degrees Celsius. When lubricant base oils have low pour points, they also are likely to have other good low temperature properties, such as low cloud point, low cold filter plugging point, and low temperature cranking viscosity.

Flash Point

Flash points were determined using the Cleveland Open Cup (COC) method according to ASTM D92, with the results reported in ° C.

Fire Point

Fire points were measured using the Cleveland Open Cup (COC) method according to ASTM D92, with the results reported in ° C.

Noack Volatility Test

Noack volatilities were measure according to ASTM D5800 to determine the evaporative loss of the hydrogenated oligomers or commercially available PAOs under high temperature service conditions, and are reported in weight percent.

The RPVOT Oxidative Stability Test

The RPVOT oxidative stability was determined according to ASTM D2272. This procedure measures the time required to obtain a 25.4 psi pressure drop as oxygen reacts with the hydrogenated oligomers or PAO sample under the designated conditions, the longer time reflecting greater oxidative stability. The samples are oxidized in a stainless steel pressure vessel under an initial pressure, in the presence of 0.5% Naugalube® APAN (alkylated phenyl-α-naphthylamine) antioxidant from Chemtura Corporation, a copper catalyst, and water, at a temperature of about 150° C., in accordance with ASTM D2272 specifications.

Catalyst System Components

Numerous processes to prepare metallocene compounds have been reported that can be used in the preparation of the metallocenes disclosed here. For example, U.S. Pat. Nos. 4,939,217, 5,191,132, 5,210,352, 5,347,026, 5,399,636, 5,401,817, 5,420,320, 5,436,305, 5,451,649, 5,496,781, 5,498,581, 5,541,272, 5,554,795, 5,563,284, 5,565,592, 5,571,880, 5,594,078, 5,631,203, 5,631,335, 5,654,454, 5,668,230, 5,705,579, and 6,509,427 describe such methods, each of which is incorporated by reference herein, in its entirety. Other processes to prepare metallocene compounds have been reported in references such as: Koppl, A. Alt, H. G. J. Mol. Catal. A. 2001, 165, 23; Kajigaeshi, S.; Kadowaki, T.; Nishida, A.; Fujisaki, S. The Chemical Society of Japan, 1986, 59, 97; Alt, H. G.; Jung, M.; Kehr, G. J. Organomet. Chem. 1998, 562, 153-181; and Alt, H. G.; Jung, M. J. Organomet. Chem. 1998, 568, 87-112; each of which is incorporated by reference herein, in its entirety. Further, additional processes to prepare metallocene compounds have been reported in: Journal of Organometallic Chemistry, 1996, 522, 39-54, which is incorporated by reference herein, in its entirety. The following treatises also describe such methods: Wailes, P. C.; Coutts, R. S. P.; Weigold, H. in Organometallic Chemistry of Titanium, Zironium, and Hafnium, Academic; New York, 1974.; Cardin, D. J.; Lappert, M. F.; and Raston, C. L.; Chemistry of Organo-Zirconium and -Hafnium Compounds; Halstead Press; New York, 1986; each of which is incorporated by reference herein, in its entirety.

Metallocene Compounds Used for Catalyst Preparation

Metallocenes utilized in the examples are provided in Table 1, along with a reference designation. These designations are utilized throughout to refer to the metallocenes utilized in the examples.

TABLE 1

Metallocene used in the examples

| Metallocene Designation | Structure |
|---|---|
| A | 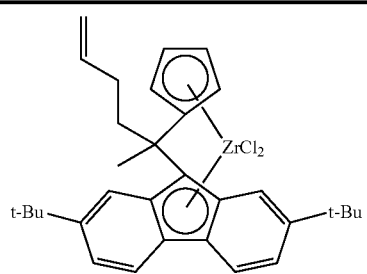 |
| B | 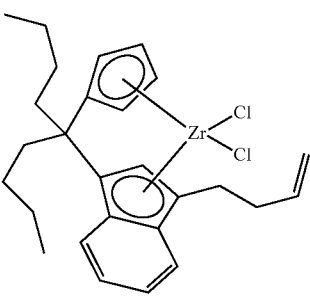 |
| C | 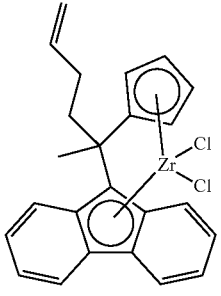 |
| D | 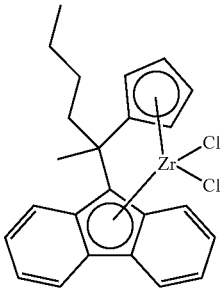 |
| E | 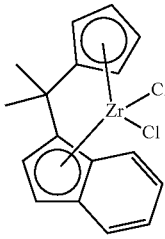 |
| F | 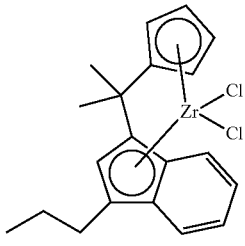 |

TABLE 1-continued

Metallocene used in the examples

| Metallocene Designation | Structure |
|---|---|
| G | (structure) |
| H | (structure) |
| I | (structure) |
| J | (structure) |
| K | (structure) |
| L | (structure) |
| M | (structure) |
| N | (structure) |
| O | (structure) |
| P | (structure) |
| Q | (structure) |

TABLE 1-continued

Metallocene used in the examples

| Metallocene Designation | Structure |
|---|---|
| R | (structure: bis(n-butylcyclopentadienyl) HfCl₂) |
| S | (structure: bis(pentamethylcyclopentadienyl) HfCl₂) |
| T | (structure: bis(ethylcyclopentadienyl) HfCl₂) |
| U | (structure: ansa-bridged zirconocene with indenyl and allyl substituent, ZrCl₂) |
| V | (structure: ansa-bridged zirconocene with cyclopentadienyl and fluorenyl, ZrCl₂) |
| W | (structure: bis(butenylcyclopentadienyl) ZrCl₂) |
| X | (structure: Ph-bridged cyclopentadienyl-fluorenyl ZrCl₂ with allyl substituent) |
| Y | (structure: bis(n-butylcyclopentadienyl) ZrCl₂) |

The modified methyl alumoxane (MMAO) used in the examples is an isobutyl-modified methyl alumoxane is a commercial product of Akzo Nobel having the approximate formula $[(CH_3)_{0.7}(iso\text{-}C_4H_9)_{0.3}AlO]_n$ and is used as a toluene solution.

EXAMPLE 1

Preparation of a Fluorided Silica-Alumina Activator-Support

The silica-alumina used to prepare the fluorided silica-alumina acidic activator-support in this Example was obtained from W.R. Grace as Grade MS13-110, containing 13% alumina, and having a pore volume of about 1.2 cc/g and a surface area of about 400 m²/g. This material was fluorided by impregnation to incipient wetness with a solution containing ammonium bifluoride, in an amount sufficient to equal 10 wt % of the weight of the silica-alumina. This impregnated material was then dried in a vacuum oven for 8 hours at 100° C. The thus-fluorided silica-alumina samples were then calcined as follows. About 10 grams of the fluorided silica-alumina were placed in a 1.75-inch quartz tube fitted with a sintered quartz disk at the bottom. While the fluorided silica-alumina was supported on the disk, dry air was blown up through the disk at the linear rate of about 1.6 to 1.8 standard cubic feet per hour. An electric furnace around the quartz tube was used to increase the temperature of the tube at the rate of about 400° C. per hour to a final temperature of about 450° C. At this temperature, the silica-alumina was allowed to fluidize for three hours in the dry air. Afterward, the silica-alumina was collected and stored under dry nitrogen, and was used without exposure to the atmosphere.

EXAMPLE 2

Preparation of a Chlorided Alumina Activator-Support

Ten mL of Ketjen™ Grade B alumina was calcined in air for three hours at 600° C. After this calcining step, the furnace temperature was lowered to about 400° C., and a nitrogen stream was initiated over the alumina bed, after which 1.0 mL of carbon tetrachloride was injected into the nitrogen stream and evaporated upstream from the alumina bed. This gas phase $CCl_4$ was carried into the bed and there reacted with the alumina to chloride the surface. This process provided the equivalent to about 15.5 mmol of chloride ion per gram of dehydrated alumina. After this chloriding treatment, the resulting alumina was white in color.

EXAMPLE 3

Preparation of a Fluorided Alumina Activator-Support

Alumina can be fluorided in the same manner as described in Example 1 for silica-alumina. The fluorided alumina can then be calcined and collected and stored under dry nitrogen, according to the Example 1 procedure, and then used without exposure to the atmosphere.

EXAMPLE 4

Preparation of Sulfated Alumina Activator-Support

Ketjen™ L alumina, 652 g, was impregnated to just beyond incipient wetness with a solution containing 137 g of $(NH_4)_2SO_4$ dissolved in 1300 mL of water. This mixture was then placed in a vacuum oven and dried overnight at 110° C. under half an atmosphere of vacuum and then calcined in a muffle furnace at 300° C. for 3 hours, then at 450° C. for 3 hours, after which the activated support was screened through an 80 mesh screen. The support was then activated in air at 550° C. for 6 hours, after which the chemically-treated solid oxide was stored under nitrogen until used.

EXAMPLE 5

Preparative Method for High-Viscosity Polyalphaolefins (PAOs) Using Metallocene and MMAO Activator Combinations High-viscosity alpha olefin homooligomers and cooligomers (PAOs) were prepared using various metallocenes and iso-butyl modified methyl aluminoxane (MMAO) as components of the catalyst system, according to the following general method, with reference to the oligomerization runs shown in Table 2.

A Zipperclave™ reactor from Autoclave Engineers was used for any oligomerization reactions requiring hydrogen. The catalyst indicated in Table 2 was dissolved in a small amount of toluene in an NMR tube, which was then sealed and bound to the stirrer shaft of the clean, dry reactor. The reactor was evacuated, then charged with the olefin/MMAO solution. A partial charge of the hydrogen pressure was introduced, and the reactor stirrer was started, resulting in breakage of the NMR tube and catalyst activation. Hydrogen pressure was then increased to the desired reactor pressure, and was fed "on demand" using a TESCOM regulator. Products were isolated by diluting the reaction mixture in pentane and filtering to remove catalyst components, followed by removal of volatiles by distillation and/or evaporation to afford the PAO.

The data in Table 2 illustrate the oligomerization conditions and the alpha olefin oligomer properties that are provided using metallocene and MMAO activator combinations.

TABLE 2

Oligomerization and oligomer data for alpha olefin oligomers (PAOs) prepared using metallocene and MMAO activator combinations.

| Example No. | Catalyst & Amount (mg) | MMAO Al:Zr Ratio | Feed[4] (grams) | $H_2$ (psig) | Ti (° C.) $T_{max}$(° C.) | Conv. (%) | Mn | 100° C. visc. (cSt) | Pour Point (° C.) |
|---|---|---|---|---|---|---|---|---|---|
| 5A | A (7.2) | 1000 | $C_8$ (143), $C_{14}$ (155) | 600 | 41 | 55 | — | 644 | −29 |
| 5B | A (6.0) | 1000 | $C_8$ (286) | 600 | 25 / 51 | — | $M_n$ = 7920 | 986 | −27 |
| 5C | A (3.0) | 1000 | $C_8$ (143) | 75 | 25 | 61 | $M_n$ = 7590 | 1372 | −18 |
| 5D | A (3.0) | 1000 | $C_8$ (143) | 0 | 25 / 25 | 69 | $M_n$ = 9330 | 1119 | −27 |
| 5E | B (5.7) | 1000 | $C_8$ (286) | 600 | 25 / 41 | — | $M_n$ = 7090 | 831 | −24 |
| 5F | B (10.0) | 1000 | $C_8$ (286) | 0 | 25 / 50 | 91 | $M_n$ = 5290 | 582 | −28 |
| 5G | B (8.5) | 1000 | $C_{10}$ (286) | 0 | 25 / 40 | — | $M_n$ = 9840 | 917 | −28 |
| 5H | B (18) | 1000 | $C_{12}$ (286) | 0 | 25 / 40 | — | $M_n$ = 9480 | 437 | −25 |
| 5I | A (6.0) | 1000 | 1-$C_{14}$ (310), 1-$C_4$ (240) | 600 | 25 / 103 | — | $M_n$ = 3700, $M_w$ = 12500 | 529 | 18 |
| 5J | A (4.0) | 1000 | 1-$C_{14}$ (388), 1-$C_4$ (120) | 600 | 25 / unknown | — | $M_n$ = 9980, $M_w$ = 22000 | — | 3 |
| 5K | C (6.3) | 1000 | 1-$C_{14}$ (310), 1-$C_4$ (240) | 0 | 75 / 75 | — | $M_n$ = 21200, $M_w$ = 27300 | — | — |
| 5L | A (3.0) | 1000 | 1-$C_{14}$ (155), 1-$C_4$ (120) | 300 | 25 | — | — | 774 | −31 |
| 5M | A (6.0) | 1000 | 1-$C_{14}$ (155), 1-$C_4$ (115) | 600 | 134 | — | — | — | 21 |
| 5N | A (6.0) | 1000 | 1-$C_{14}$ (155), 1-$C_4$ (125) | 300 | 98 | — | — | — | 6 |
| 5P | A (7.2) | 1000 | 1-$C_{14}$ (155), 1-$C_8$ (143) | 600 | 25 / 41 | — | — | — | −6 |

TABLE 2-continued

Oligomerization and oligomer data for alpha olefin oligomers (PAOs) prepared using metallocene and MMAO activator combinations.

| Example No. | Catalyst & Amount (mg) | MMAO Al:Zr Ratio | Feed[A] (grams) | $H_2$ (psig) | Ti (° C.) $T_{max}$(° C.) | Conv. (%) | Mn | 100° C. visc. (cSt) | Pour Point (° C.) |
|---|---|---|---|---|---|---|---|---|---|
| 5Q | A (6.0) | 1000 | 1-$C_{14}$ (78) 1-$C_8$ (215) | 600 | 25 50 | — | — | — | 6 |
| 5R | A (6.0) | 1000 | 1-$C_{14}$ (39) 1-$C_8$ (250) | 600 | 25 | — | — | — | 0 |
| 5S | A (6.0) | 1000 | 1-$C_{14}$ (271) 1-$C_8$ (36) | 600 | 25 55 | — | $M_n$ = 10200 $M_w$ = 24300 | 469 | −11 |
| 5T | A (6.0) | 1000 | 1-$C_{14}$ (271) 1-$C_8$ (36) | 600 | 25 44 | — | $M_n$ = 11700 $M_w$ = 20500 | — | −3 |
| 5U | A (6.0) | 1000 | 1-$C_{14}$ (271) 1-$C_8$ (36) | 1000 | 25 43 | — | $M_n$ = 12900 $M_w$ = 20800 | — | −9 |

[A]$C_8$, 1-octene; $C_{10}$, 1-decene; $C_{12}$, 1-dodecene; $C_{14}$, 1-tetradecene.

EXAMPLE 6

Preparative Method for High-Viscosity Polyalphaolefins (PAOs) Using Metallocene and Chemically Treated Solid Oxide (SSA) Activator Combinations High-viscosity alpha olefin homooligomers and cooligomers (PAOs) were prepared using various metallocenes and chemically treated solid oxides (solid super acids, SSAs) as components of the catalyst system, according to the following general method, with reference to the polymerization runs shown in Table 3.

The metallocene indicated in Table 3 was dissolved or slurried in the alpha olefin, followed by the addition of TIBA (1M solution in hexanes) at room temperature. The mixture was stirred at room temperature for about 2 minutes. The chemically treated solid oxide (SSA) was then added to above mixture, and the resulting mixture was stirred for the indicated period of time at room temperature, before the oligomerization reaction was quenched. The reactions were observed to be strongly exothermic. In some instances the quenched produced was filtered and then distilled to remove the unreacted monomer and some light oligomers as an overhead fraction. The distillations were performed at 210° C. at 0.1 torr to 1 torr for a time until no additional overhead product was collected plus one hour.

TABLE 3

Oligomerization and oligomer data for polyalphaolefins (PAOs) prepared using metallocene and SSA activator combinations.

| | Oligomerization Conditions | | | | | | Distilled Oligomer Properties | | | | |
|---|---|---|---|---|---|---|---|---|---|---|---|
| Example No. | Metallocene (Amt - mg) | Olefin Amount (grams) | TIBA (mg) | f-SSA[A] (mg) | Olig. T(° C.) | Olig. Time (hours) | % Dimer in Oligomer Product | Oligomer Yield (grams) | 100° C. Visc. (cSt) | Viscosity Index | Pour Pt. (° C.) | Metallocene Prod. (g/g) |
| 7A | B (4.0) | $C_6$ (13.6) | 198 | 250 | 25-28 | 3.5 | — | 12.1 | — | — | — | — |
| 7B | D (3.2) | $C_8$ (14.3) | 198 | 250 | 25-28 | 1.5 | — | 11.1 | — | — | — | — |
| 7C | B (3.75) | C8 (358) | 220 | 260 | 120 | o-n | — | 326 | 124 | 199 | −42 | 86,900 |
| 7D | E (2.86) | C8 (358) | 220 | 260 | 120 | o-n | — | 158 | 159 | 214 | −42 | 55,200 |
| 7E | F (3.16) | C8 (358) | 220 | 520 | 120 | o-n | — | 290 | 132 | 200 | −42 | 91,800 |
| 7F | G (3.15) | C8 (358) | 220 | 260 | 120 | o-n | — | 251 | 156 | 207 | −38 | 79,700 |
| 7G | H (3.13) | C8 (358) | 200 | 450 | 120 | o-n | 4.8% | 44%[C] | 128 | 201 | −41 | 50,200 |
| 7H | I (3.04) | C8 (358) | 200 | 450 | 120 | o-n | 3.5% | 74%[C] | 126 | 199 | −45 | 87,400 |
| 7I | J (3.00) | C8 (358) | 220 | 260 | 115 | o-n | — | 347 | 136 | 210 | −42 | 115,000 |
| 7J | K (12.9) | C8 (358) | 851 | 1030 | 100 | o-n | — | 177[D] | 10.3 | 194 | — | 13,700 |
| 7K | L (12.6) | C8 (358) | 851 | 1030 | 90 | o-n | — | 316[D] | 92.9 | 197 | −42 | 22,000 |
| 7L | M (8.4) | C8 (358) | 851 | 1030 | 90 | o-n | — | 102 | 8.9 | 211 | — | 12,100 |
| 7M | N (11.3) | C8 (358) | 851 | 1030 | 90 | o-n | — | 290 | 22.9 | 169 | −60 | 25,700 |
| 7N | O (2.30) | C8 (358) | 220 | 788 | 105 | o-n | 18.3 | 96%[C] | 44.7 | 175 | −51 | 115,000 |
| 7P | P (0.75) | C8 (358) | 220 | 394 | 75 | o-n | 8.7 | 87%[C] | 104 | 205 | −44 | 414,000 |
| 7Q | Q (2.68) | C8 (358) | 220 | 788 | 110 | o-n | 5.2 | 67%[C] | 61.9 | 186 | −48 | 81,300 |
| 7R | R (2.76) | C8 (358) | 220 | 788 | 120 | o-n | 4.9 | 83%[C] | 101 | — | — | 99,400 |
| 7S | S (3.00) | C8 (358) | 220 | 788 | 90 | o-n | 14.8 | 63%[C] | 8.3 | 157 | −72 | 54,900 |
| 7T | T (2.50) | C8 (358) | 220 | 788 | 110 | o-n | 12.6 | 71%[C] | 42.5 | 181 | −54 | 79,800 |

[A]fSSA, fluorided silica-alumina
[B]o-n—over-night
[C]Percent conversion to oligomers, determined by gas chromatography
[D]Undistilled oligomer yield.

EXAMPLE 7

Viscosity and Pour Point Control using Oligomerization Temperature for 1-Octene Polyalphaolefin Homooligomers (PAOs) Using a Metallocene and Chemically Treated Solid Oxide Combination 1-Octene homooligomers (PAOs) were prepared using a catalyst system a catalyst system of 12.6 mg metallocene L, 1.03 g of fluorided silica-alumina (f-SSA), and 850 mg tri-isobutyl aluminum to oligomerize 360 g 1-octene at a 16 hour oligomerization time. The experiment demonstrates that varying the oligomerization temperature produces a remarkable range of oligomer products. The results of which are shown in Table 4. These batch runs demonstrate that temperature alone can be used to control the product viscosity, and that it is possible to produce high value 100 cSt and/or 40 cSt using the same catalyst system.

Product pour points of these PAO products compared favorably to a commercially available product (ExxonMobil SpectraSyn 100), illustrated in the final column for comparison purposes.

TABLE 4

Oligomerization and oligomer data for polyalphaolefins (PAOs) prepared using the same metallocene and SSA activator, at various temperatures.

| | Example[A,B] | | | | Commercially |
|---|---|---|---|---|---|
| | 7A | 7B | 7C | 7D | Available PAO |
| Oligomerization Temperature | 70° C. | 80° C. | 90° C. | 100° C. | n.a. |
| 100° C. Visc. (cSt) | 157 | 109 | 72 | 24 | 100 |
| 40° C. Visc. (cSt) | 1270 | 901 | 605 | 156 | 1240 |
| Viscosity Index | 242 | 221 | 199 | 187 | 170 |
| Pour point (° C.) | −48 | −48 | −48 | −63 | −30 |
| Conversion (%) | 88 | 88 | 77 | 98 | n.a. |

EXAMPLE 8

Laboratory Scale Synthetic Method for Preparing Olefin Oligomers

The following general procedures were used to produce a number of olefin oligomers on a laboratory scale. These oligomers were then distilled and hydrogenated to produce a PAO. Depending on the particular catalyst and conditions, this general procedure was utilized to prepare the olefin oligomers which were distilled and hydrogenated to provide PAOs having 100° C. kinematic viscosities near 40 cSt and 100 cSt. The specific metallocenes and oligomerization conditions and hydrogenated oligomer characterization data for each run are provided in Table 5. If needed or desired, minor modifications of the procedure detailed in this example were utilized. For example, some metallocenes were added as a slurry in 1-octene, due to their low solubility. Each experiment in Table 2 includes a reference to the patent figure that was generated from that experiment.

Oligomerization Procedure A

An 18-L multi-necked flask was fitted with a heating mantle, an overhead stirrer, and a solid addition funnel charged with fluorided silica-alumina (f-SSA—prepared as described herein). The flask was then purged with nitrogen and dried thoroughly by washing with tri-isobutyl aluminum (TIBA). After removal of the wash TIBA, anhydrous olefin was then charged, via cannula, to the flask. The olefin was then heated to the reaction temperature. The flask was then charged with the tri-isobutylaluminum (TIBA), followed by the metallocene dissolved in a minimal amount of the olefin. The entire quantity f-SSA was then added, with stirring, resulting in a reaction exotherm. The reaction mixture was then heated (or allowed to cool) to the desired reaction temperature and maintained at the desired reaction temperature for the desired reaction time. At the conclusion of the reaction time, the reaction mixture was analyzed by gas chromatography. The results of the gas chromatography analysis are provided in Table 5. The aluminum alkyls were then neutralized with a stoichiometric amount of water (e.g. 1 mole of water per mole of alkyl aluminum bond—approximately 3:1 water:trialkylaluminum). The product was then filtered, distilled, and hydrogenated. Properties of the final hydrogenated products are reported in Table 5.

Oligomerization Procedure B

An 18-L multi-necked flask was fitted with a heating mantle, an overhead stirrer, and a solid addition funnel containing fluorided silica-alumina (f-SSA). The flask was then purged with nitrogen and dried thoroughly by washing with tri-isobutyl aluminum (TIBA). After removal of the wash TIBA, anhydrous olefin was then charged, via cannula, to the flask. The olefin was then heated to the reaction temperature. Once the reaction flask's contents achieved the reaction temperature, tri-isobutylaluminum (TIBA) was charged to the reaction flask. After continued stirring for a few minutes, typically 5-30, the metallocene (dissolved in a minimal amount of the olefin) and f-SSA was simultaneously added to the reaction flask, resulting in a reaction exotherm. The reaction mixture was then heated (or allowed to cool) to the desired reaction temperature and maintained at the desired reaction temperature for the desired reaction time. At the conclusion of the reaction time, the reaction mixture was analyzed by gas chromatography. The results of the gas chromatography analysis are provided in Table 5. The aluminum alkyls were then neutralized with a stoichiometric amount of water. The product was then filtered, distilled, and hydrogenated. Properties of the final hydrogenated products are reported in Table 5.

TABLE 5

Oligomerization process and characterization data for low viscosity and high viscosity PAOs prepared according this disclosure.

| Run Number | 1 | 2 | 3 | 4 | 5 | 6 | 7 | 8 | 9 | 10 | 11 | 12 |
|---|---|---|---|---|---|---|---|---|---|---|---|---|
| Olefin Oligomerization Conditions | | | | | | | | | | | | |
| Oligomerization Method | A | B | B | B | B | B | B | B | B | B | B | B |
| Catalyst | O | N | N | N | J | N | L | I | I | J | J | B |
| mg Catalyst | 230 | 339 | 339 | 373 | 3.0 | 11.3 | 12.6 | 121.9 | 97.5 | 3 | 3 | 15 |
| f-SSA, g | 29.5 | 30.9 | 61.8 | 33.9 | 0.26 | 1.03 | 1.03 | 18.04 | 14.4 | 0.26 | 0.26 | 1.03 |
| TIBA, g | 6.4 | 25.5 | 75.5 | 56.1 | 0.22 | 0.85 | 0.85 | 8.02 | 6.4 | 0.22 | 0.22 | 0.85 |

TABLE 5-continued

Oligomerization process and characterization data for low viscosity and high viscosity PAOs prepared according this disclosure.

| Run Number | 1 | 2 | 3 | 4 | 5 | 6 | 7 | 8 | 9 | 10 | 11 | 12 |
|---|---|---|---|---|---|---|---|---|---|---|---|---|
| Olefin | 1-$C_8$ | 1-$C_8$ | 1-$C_8$ | 1-$C_8$ | 1-$C_{10}$ | 1-$C_8$ | 1-$C_8$ | 1-$C_8$ | 1-$C_8$ | 1-$C_8$ | 1-$C_{10}$ | 1-$C_8$ |
| Olefin feed, g | 11000 | 10000 | 10000 | 10000 | 370 | 358 | 358 | 11000 | 11000 | 358 | 370 | 358 |
| Temperature | 95 | 80 | 80 | 80 | 135 | 80 | 100 | 121 | 121 | 120 | 120 | 121 |
| Olefin Conversion, wt % | 89.0 | 70.0 | 72.0 | 55.0 | — | — | 99 | 73.7 | 57.1 | — | — | 98[A] |
| Final Reaction Mixture Composition | | | | | | | | | | | | |
| Dimer, wt % | 14.4 | — | 9.0 | — | — | — | — | 2.1 | 3.3 | — | — | — |
| Trimer, wt % | 5.4 | — | — | — | — | — | — | — | — | — | — | — |
| Tetramer +, wt % | 69.2 | — | 63.0 | — | — | — | — | 71.6 | 53.8 | — | — | — |
| 1-Olefin in unreacted Monomer, wt % | 63.3 | — | — | — | — | — | — | 87.1 | 92.4 | — | — | — |
| Distilled and Hydrogenated Product Data | | | | | | | | | | | | |
| 100° C. Kinematic Viscosity, cSt | 31.7 | 30.6 | 43.6 | 29.8 | 41 | 43.8 | 37 | 121.5 | 137.5 | 118 | 100.5 | 112.7 |
| 40 C.° Kinematic Viscosity, cSt | 249 | 235.4 | 352 | 226.8 | 289.1 | 360.3 | — | 1256 | — | 1140.1 | 863.6 | — |
| Pour point, ° C. | −54 | −56 | −54 | −56 | −57 | −51 | — | −42 | — | −42 | −45 | −44 |
| Viscosity index, VI | 170 | 171 | 181 | 172 | 197 | 179 | 187 | 196.5 | — | 205 | 212 | 210 |
| Molecular Weight, Mp | — | — | — | — | 4379 | 2601 | — | — | — | 5916 | 6528 | — |
| Figure | 2A | 2A, 3 | — | — | 7A | 7B | 7C | 2B | 2B | 8A | 8B | 8C |

[A]Percent conversion to oligomers, determined by gas chromatography of undistilled oligomers.
Abbreviations: 1-$C_8$, 1-octene; 1-$C_{10}$, 1-decene; Mp,

EXAMPLE 9

PAO Blends

PAO blends having 100° C. kinematic viscosities of 35.0 cSt, 38.8 cSt and 100 cSt were prepared by blending PAOs produced in the runs of Example 8. These PAO blends were prepared as illustrated in Table 6.

Blend B-1 was prepared by mixing the hydrogenated oligomers of Example 8—Run 2, Example 8—Run 3, and Example 8—Run 4 in the quantities indicated in Table 3. Blend B-2 was prepared to have a 100° C. kinematic viscosity near 40 cSt (actual 38.8) by mixing the Blend B-1 and the hydrogenated oligomers of Example 8—Run 8 in the quantities indicated in Table 6. Blend B-3 was prepared to have a 100° C. kinematic viscosity near 100 cSt (actual 99.3) by mixing the Blend B-2 and the hydrogenated oligomers of Example 8—Run 9 in the quantities indicated in Table 6.

TABLE 6

PAO Blends.

| | Blend Number | | |
|---|---|---|---|
| | Blend B-1 | Blend B-2 | Blend B-3 |
| Description | Near 40 cSt Blend | | Near 100 cSt Blend |
| Blend | 42 wt % Example 8 - Run 2 38 wt % Example 8 - Run 3 20 wt % Example 8 Run 4 | 92 wt % Blend B-1 8 wt % Example 8 Run 8 | 74.5 wt % Example 8 Run 9 25.5 wt % B-2 |
| 100° C. Visc, cSt | 35.0 | 38.8 | 99.3 |
| 40° C. Visc, cSt | 280.9 | 318.6 | 992.5 |
| Pour point, ° C. | −53 | −53 | −42 |
| Viscosity index, VI | 172 | 173 | 193 |

Table 7 records the physical and chemical properties of the hydrogenated 1-octene oligomer of PAO Blend B-2 and PAO Blend B-3 reported in Table 6, and compares these properties with commercially available PAO 40 and PAO 100 produced from 1-decene.

TABLE 7

Comparison of the near 40 cSt PAO Blend B2 and near 100 cSt PAO Blend B-3 with commercially available PAO 40 and PAO 100.

| Physical Property | Commercially Available PAO 40 | PAO Blend B-2 | Commercially Available PAO 100 | PAO Blend B-3 |
|---|---|---|---|---|
| Viscosity, Kinematic 100° C. (212° F.) | 40 | 38.8 | 100 | 99.3 |
| Viscosity, Kinematic 40° C. (104° F.) | 395 | 319 | 1231 | 1014 |
| −8° C. Brookfield Viscosity (cP) | 12,150 | 6,566 | 51,403 | 28,435 |

TABLE 7-continued

Comparison of the near 40 cSt PAO Blend B2 and near 100 cSt PAO
Blend B-3 with commercially available PAO 40 and PAO 100.

| Physical Property | Commercially Available PAO 40 | PAO Blend B-2 | Commercially Available PAO 100 | PAO Blend B-3 |
|---|---|---|---|---|
| −20° C. Brookfield Viscosity (cP) | 45,465 | 20,025 | Too viscous to measure | Too viscous to measure |
| −26° C. Brookfield Viscosity (cP) | 102,000 | 35,524 | — | — |
| Viscosity Index | 147 | 173 | 167 | 191 |
| Pour Point, ° C. (° F.) | −36 | −53 | −30 | −42 |
| Flash Point (COC), ° C. (° F.) | 281 | 246 | 283 | 281 |
| Fire Point (COC), ° C. (° F.) | 318 | 287 | 330 | 330 |
| Volatility, Noack, wt % | 2.5 | — | 2.3 | — |
| DSC Crystallization | No | No | Yes, −40° C. | No |
| Specific Gravity | 0.850 | 0.838 | 0.853 | 0.845 |
| Appearance | Clear & Bright | Clear & Bright | Clear & Bright | Clear & Bright |
| Odor | NFO[A] | NFO[A] | NFO[A] | NFO[A] |
| RPVOT, (min) | 1976 | 2375 | 1621 | 2943 |
| Tacticity by $^{13}$C NMR (Catalyst) | Cr—Si | Metallocene Based Catalyst System | Cr—Si | Metallocene Based Catalyst System |
| mm | 29.6% | 32.6% | 25.1% | 40.6% |
| mr | 42.7% | 45.1% | 34.5% | 44.9% |
| rr | 27.7% | 22.3% | 40.4% | 14.5% |

[A]No Foreign Odor.

As seen from the comparative data of Table 7, PAO Blend B-2 and PAO blend B-3 produced from 1-octene have a lower dynamic viscosity at the same temperatures than the commercially available PAO 40 and PAO 100 produced from 1-decene. This trend is also reflected in the lower pour points and higher viscosity indices of PAO Blend B-2 and PAO Blend B-3 produced from 1-octene as compared to commercially available PAO 40 and PAO 100 produced from 1-decene. Although the PAO Blend B-2 produced from 1-octene has lower flash and fire points than the commercially available PAO 40 produced from 1-decene, the PAO Blend B-3 produced from 1-octene has virtually identical flash and fire point as the commercially available PAO 100 produced from 1-decene. PAO Blend B-2 and PAO Blend B-3 produced from 1-octene exhibit lower NOACK volatilities (ASTM D-5800) than the commercially available PAO 40 and PAO 100 produced from 1-decene. The lower NOAK volatilities reflect the lower evaporative loss in high-temperature service, greater utility for reducing wear, reduced emissions, reduced oil consumption, and improved fuel economy of the PAO Blend B-2 and PAO Blend B-3 produced from 1-octene as compared to the commercially available PAO 40 and 100 having similar kinematic viscosities. As discussed, the RPVOT data illustrate the greater oxidative stabilities of the PAO Blend B-2 and PAO Blend B-3 produced from 1-octene as compared to the commercially available PAOs having similar kinematic viscosities.

Figure 2:
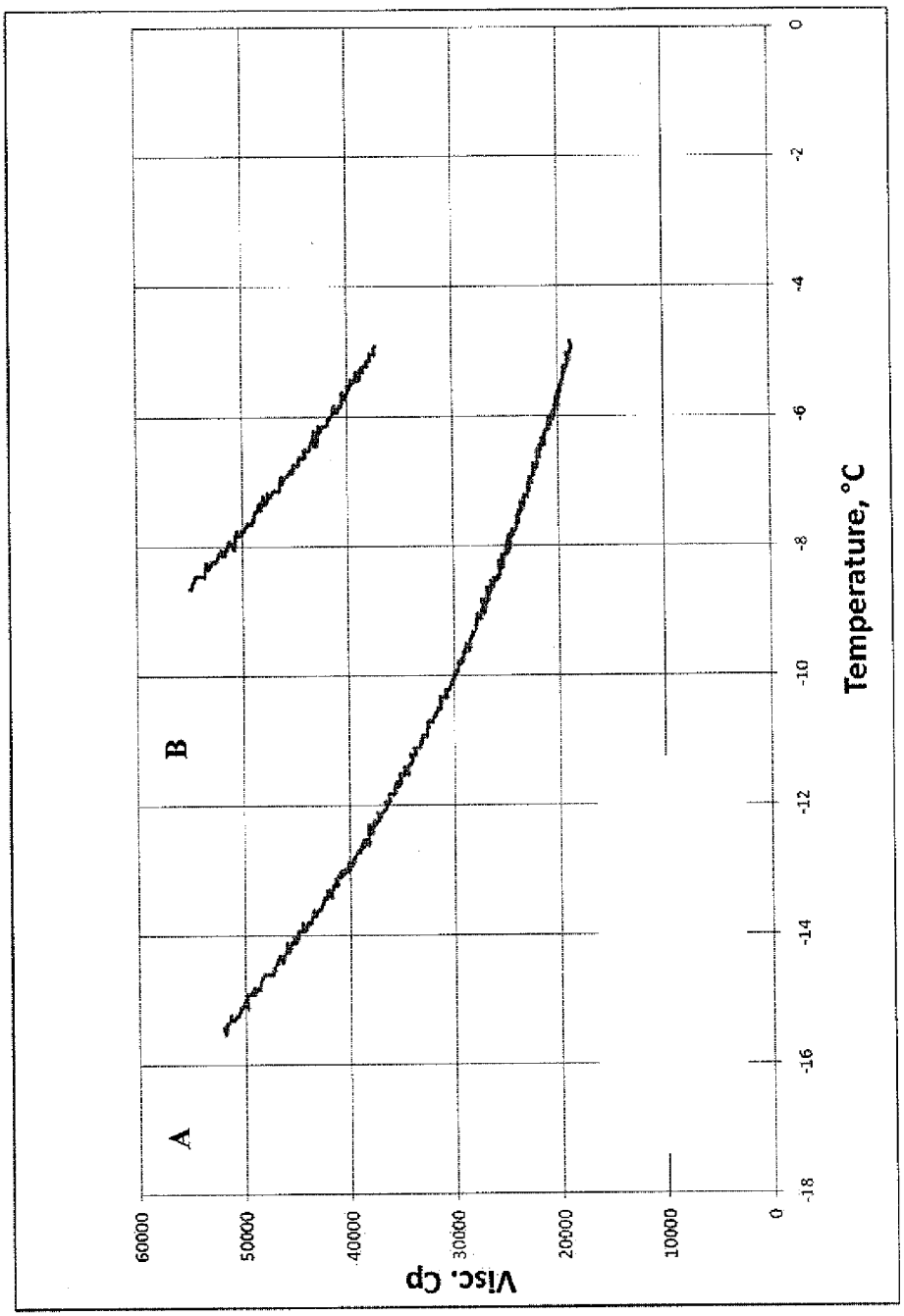
FIG. 2 provides a plot of the scanning Brookfield dynamic viscosity (cP) versus temperature (° C.) of a polyalphaolefin blend of hydrogenated 1-octene oligomers having a 100° C. kinematic viscosity of 99.3 cSt, compared to a commercially available PAO produced from 1-decene having nearly the same kinematic viscosity (PAO 100). Sample identification: A, Blend B-3, blend of hydrogenated 1-octene oligomers having 100° C. kinematic viscosity of 100 cSt; B, commercially available PAO 100. Refer to Tables 6 and 7 for sample preparation and properties.

The changes in dynamic viscosity (cP) as a function of temperature (° C.) of the PAO Blend B-2 and PAO Blend B-3 produced from 1-octene were examined and compared to commercially available PAOs having similar kinematic viscosities. For example, FIG. 1 illustrates a plot of the dynamic viscosity (cP) versus temperature (° C.) of the PAO Blend B-2 produced from 1-octene and prepared according to this disclosure, as compared to a commercially available PAO 40 having a similar kinematic viscosity. Similarly, FIG. 2 illustrates a plot of the dynamic viscosity (cP) versus temperature (° C.) of a PAO Blend B-2 produced from 1-octene and prepared according to this disclosure, as compared to a commercially available PAO 100 having a similar kinematic viscosity. The limited data for the commercially available PAO 100 (line A) results from reaching the torque limit of the acoustic transducer in the Brookfield viscometer. In each case, the PAO Blend B-2 and PAO blend B-3 produced from 1-octene are characterized as having a lower dynamic viscosity as a commercially available PAO produced from 1-decene having similar kinematic viscosities.

Figure 3:
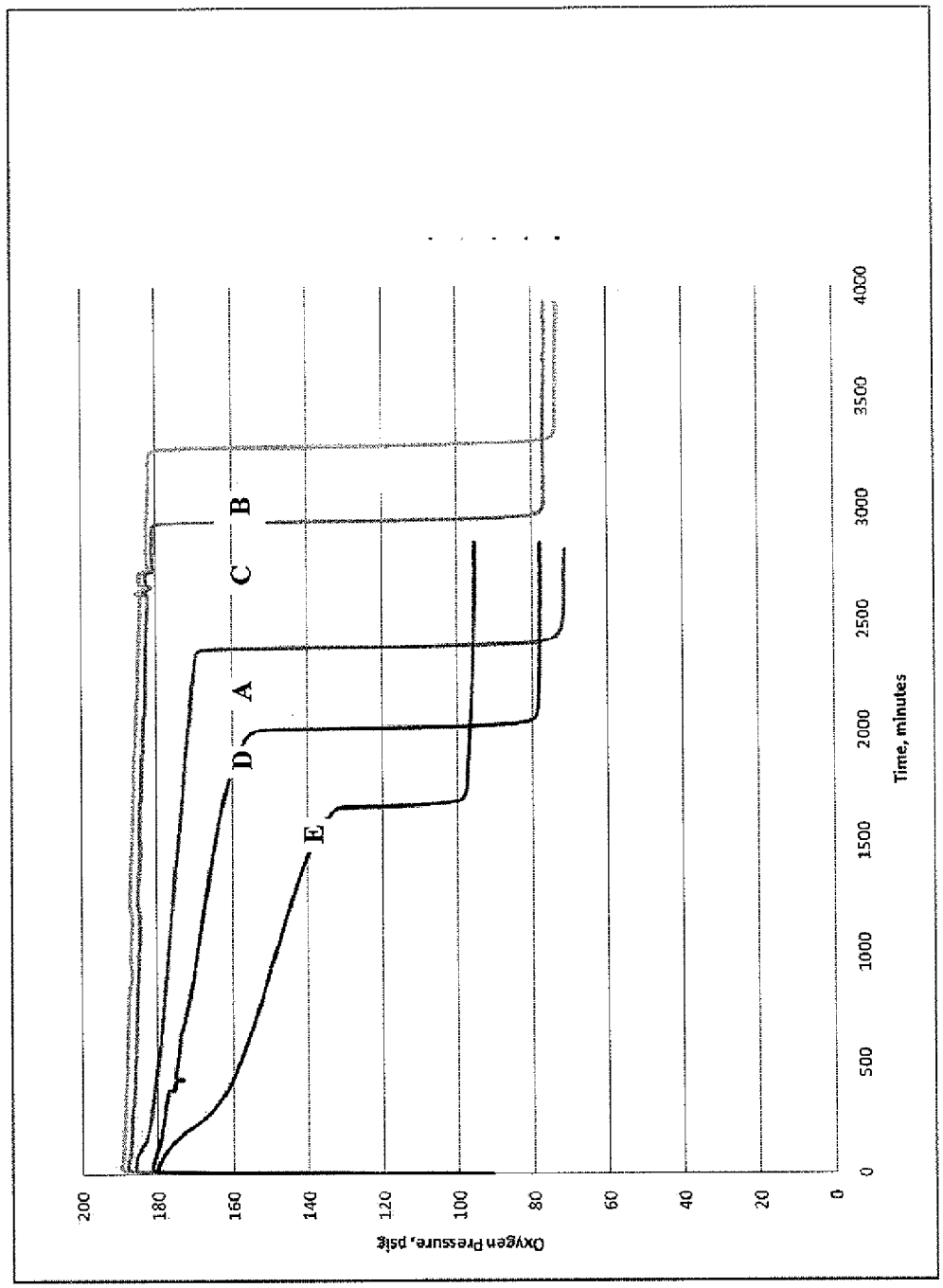
FIG. 3 provides the results of an RPVOT (Rotary Pressure Vessel Oxidation Test) analysis of the oxidation stability of the hydrogenated 1-octene oligomers, measured according to ASTM D2272. The oxidative stability plot of oxygen pressure (psig) versus time (minutes) to illustrate the comparative oxidative stability of hydrogenated 1-octene oligomers prepared using a metallocene and a chemically treated solid oxide catalyst system, as compared to commercial PAOs. Sample identification: A, Blend B-2, blend of hydrogenated 1-octene oligomers having a 100° C. kinematic viscosity of 38.8 cSt; B, hydrogenated 1-octene oligomers having a 100° C. kinematic viscosity of 121 cSt (oligomers hydrogenated at 210° C.); C, hydrogenated 1-octene oligomers having a 100° C. kinematic viscosity of 121 cSt (oligomers hydrogenated at 165° C.); D, commercially available PAO 40 produced from 1-decene; E, commercially available PAO 100 produced from 1-decene. Refer to Tables 6 and 7 for sample preparation and properties.

FIG. 3 provides the results of an RPVOT (Rotary Pressure Vessel Oxidation Test) analysis of the oxidation stability of various PAOs, measured according to ASTM D2272. The oxidative stability plot of oxygen pressure (psig) versus time (minutes) to illustrate the comparative oxidative stability of the PAO Blend B-2 and PAO Blend B-3 prepared from 1-octene using a metallocene and a chemically treated solid oxide catalyst system, as compared to commercially available PAOs prepared from 1-decene having similar 100° C. kinematic viscosities. Sample identification: A, PAO Blend B-2; B, hydrogenated 1-octene oligomers of Example 8—Run 8, hydrogenated at 210° C.; C, hydrogenated 1-octene oligomers of Example 8—Run 8, hydrogenated at 165° C.; D, commercially available PAO 40; E, commercially available PAO 100. Lines A versus D illustrate the differences between the PAOs produced using the catalyst systems and/or methods of this disclosure and commercially available PAO having a similar 100° C. kinematic viscosity. Lines B and C, versus E illustrate the differences between PAOs produced using the catalyst systems and/or methods of this disclosure and commercially available PAO having a similar 100° C. kinematic viscosity.

The RPVOT tests of FIG. 3 RPVOT tests were run in the presence of 0.5% Naugalube® APAN (alkylated phenyl-α-naphthylamine) antioxidant as a standard concentration of antioxidant. The rapid loss of oxygen pressure at the nearly vertical portion of each curve corresponds to antioxidant depletion and rapid oxidation of the sample. Among other things, this figure illustrates the substantially greater oxidative stabilities of the PAOs produced using the catalyst systems and/or methods of this disclosure, as compared to the commercially available PAO having similar or corresponding kinematic viscosities.

Figure 4:
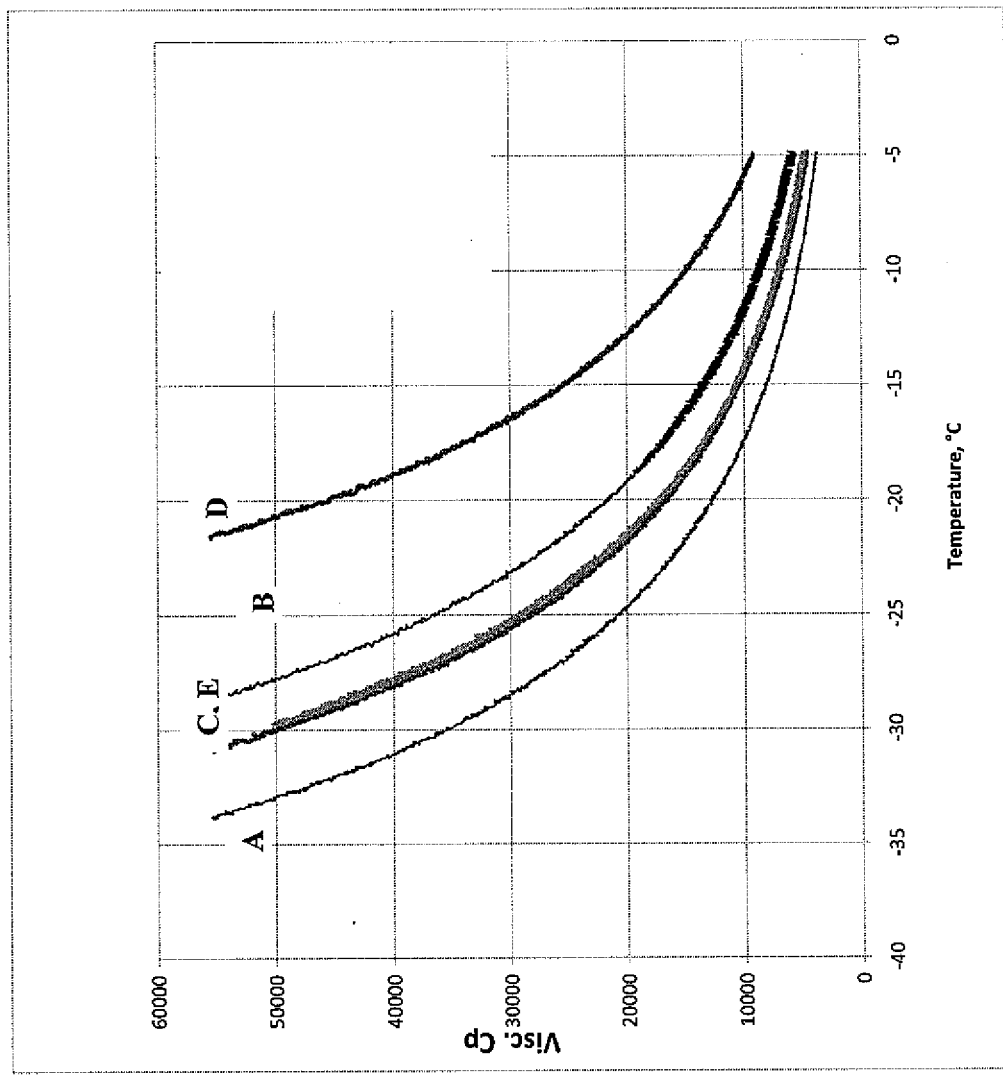
FIG. 4 illustrates the effect of the metallocene of the oligomerization catalyst system on the 100° C. kinematic viscosity of hydrogenated oligomers produced using the oligomerization catalyst system and procedures described herein.
Figure 5:
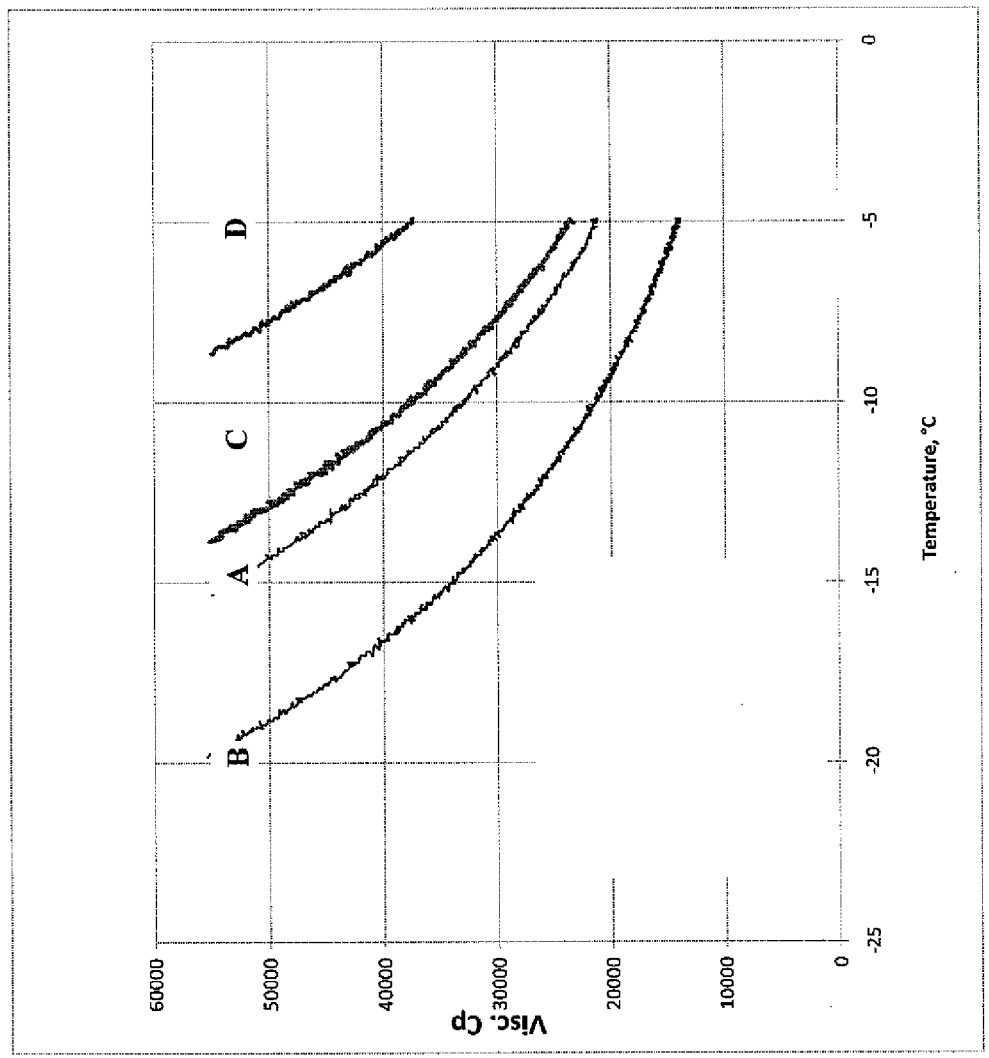
FIG. 5 illustrates the effect of metallocene of the oligomerization catalyst system on the 100° C. kinematic viscosity of hydrogenated oligomers produced using the oligomerization catalyst system and procedures described herein.
Figure 6:
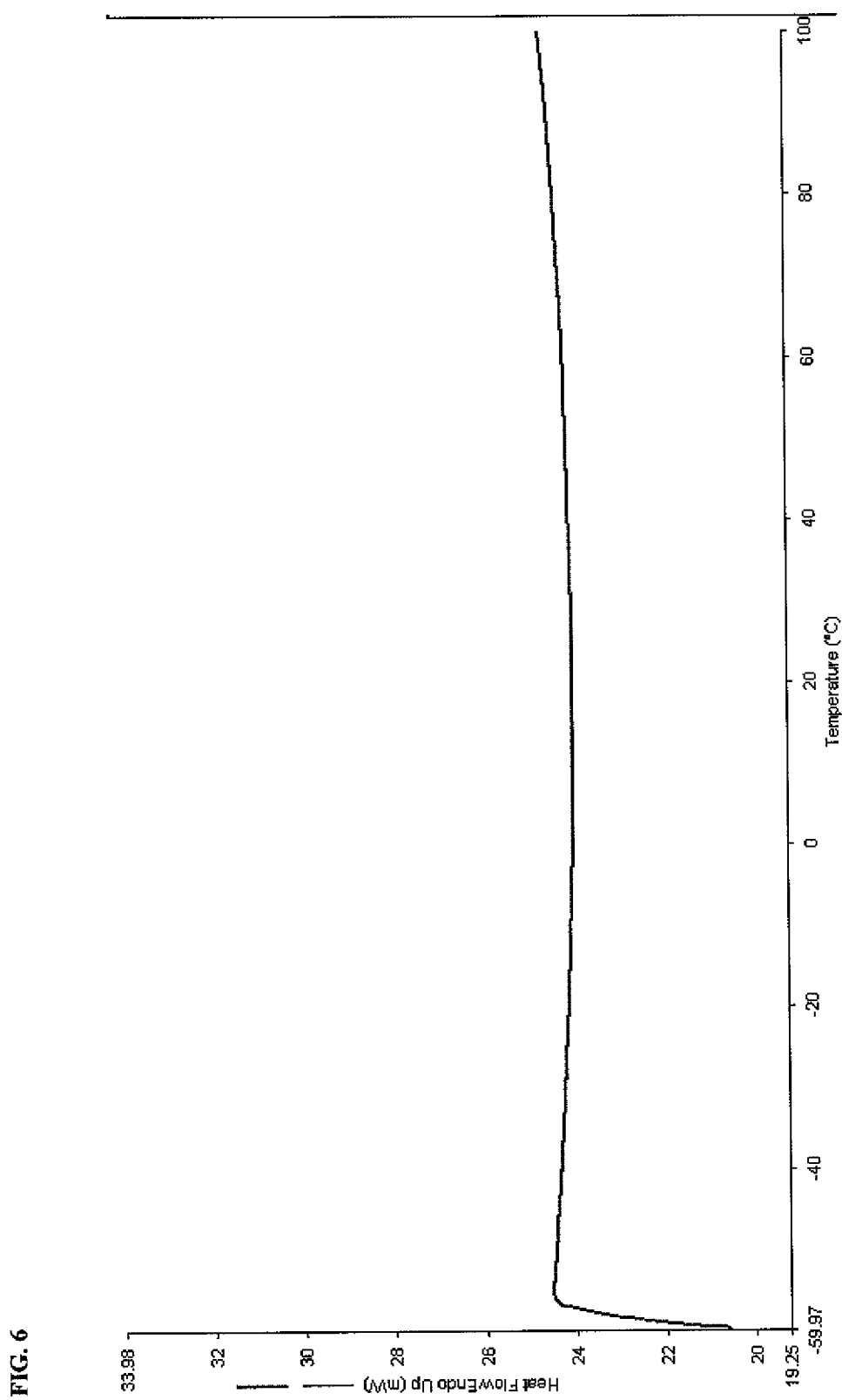
FIG. 6 provides a DSC of PAO produced using 1-octene according to Experiment 8—Run 6. The DSC indicates that there is no discernable crystallization according to the DSC method described herein.
Figure 7:
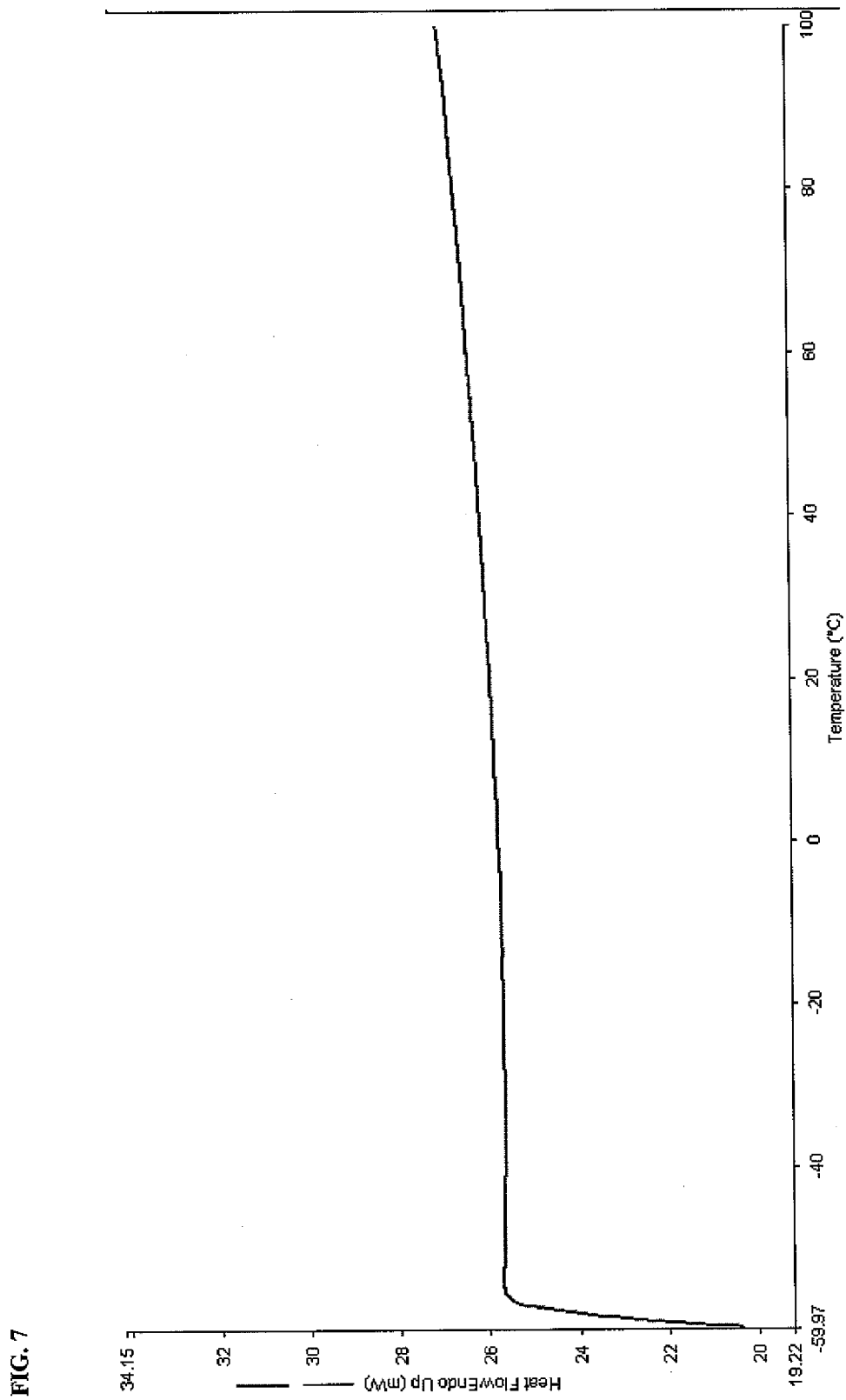
FIG. 7 provides a DSC of PAO produced using 1-decene according to Experiment 8—Run 5. The DSC indicates that there is no discernable crystallization according to the DSC method described herein.
Figure 8:
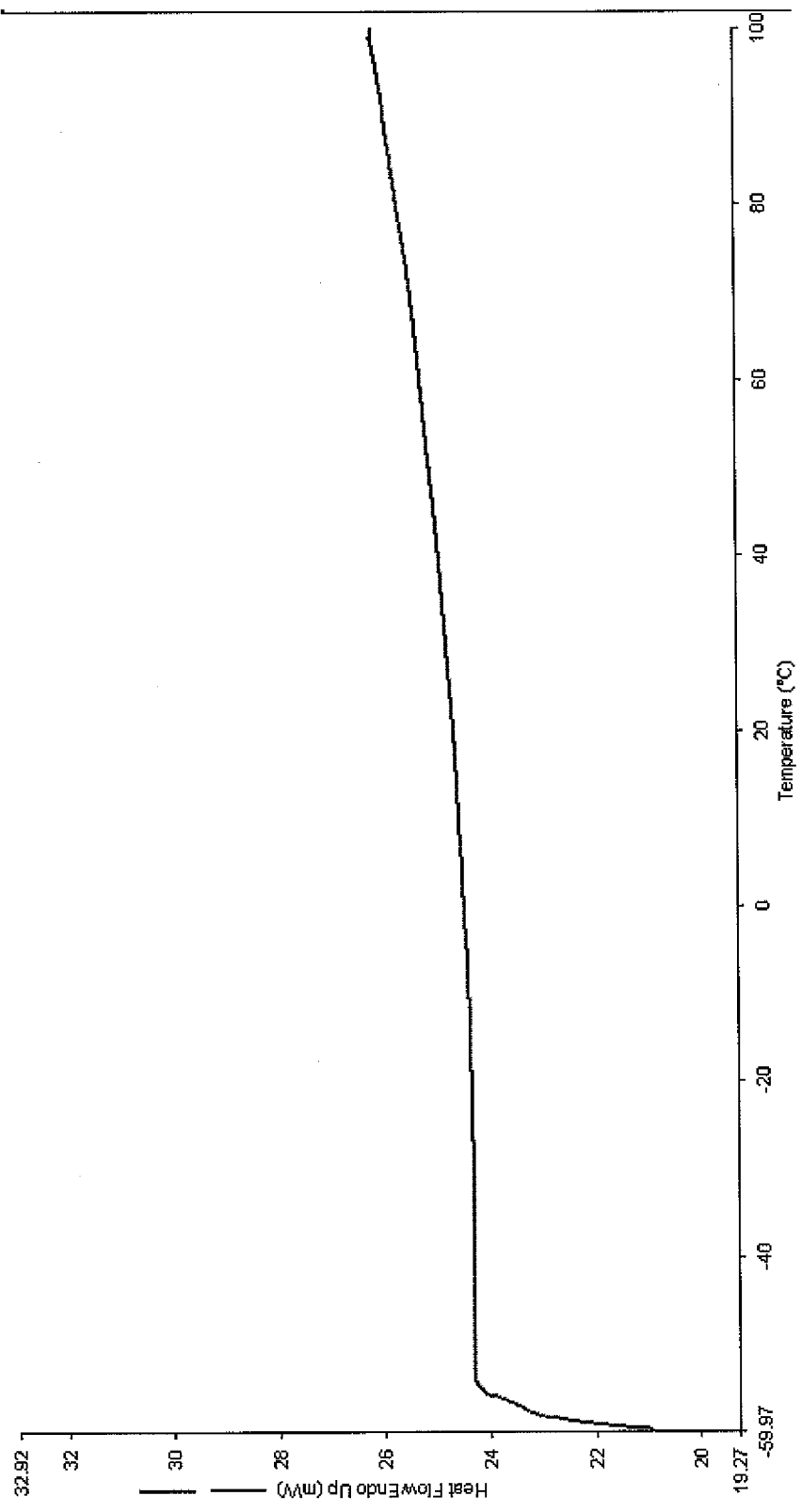
FIG. 8 provides a DSC of PAO produced using 1-octene according to Experiment 8—Run 10. The DSC indicates that there is no discernable crystallization according to the DSC method described herein.
Figure 9:
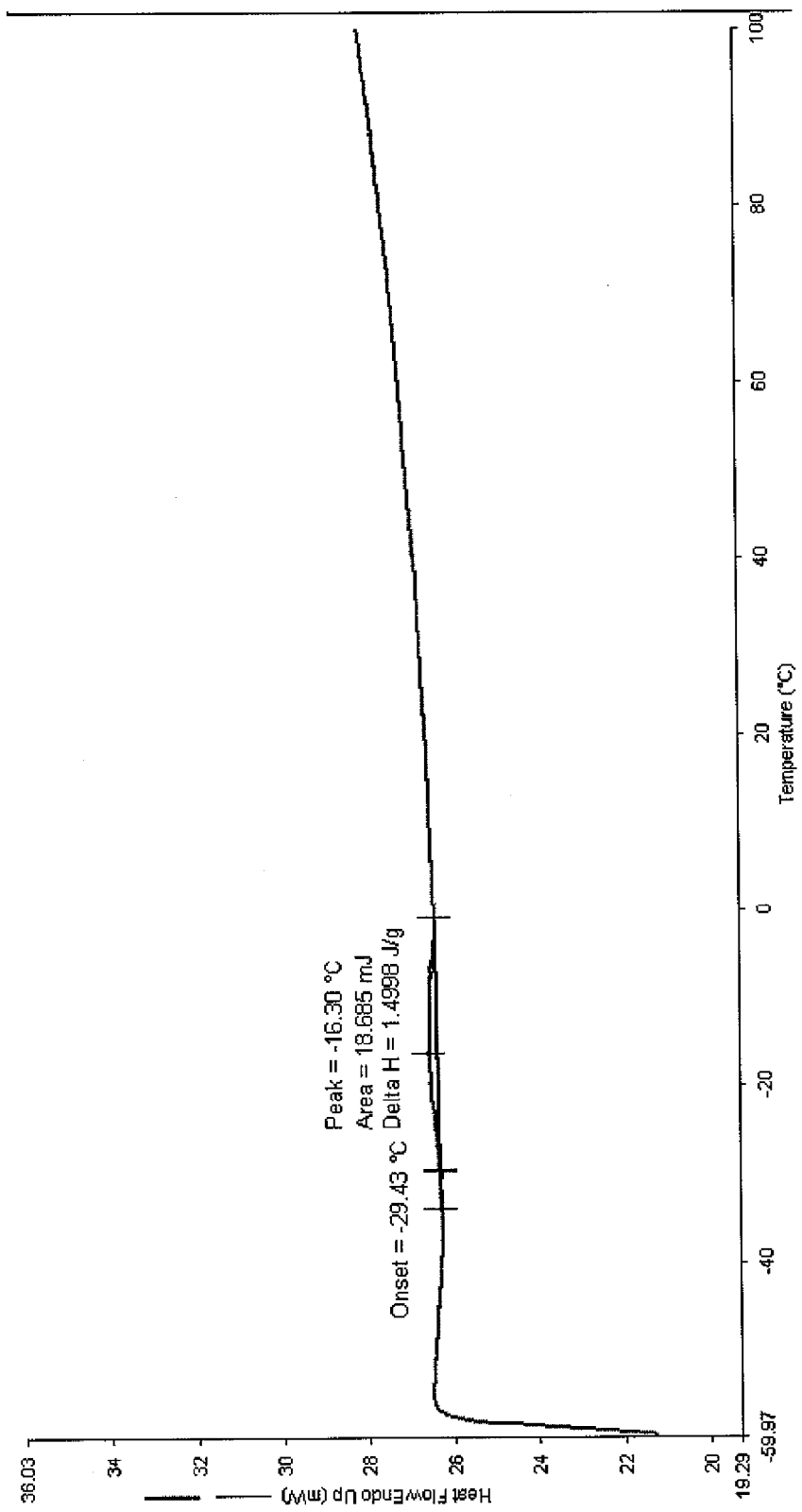
FIG. 9 provides a DSC of PAO produced using 1-decene according to Experiment 8—Run 11. The DSC indicates that there is a small discernable crystallization according to the DSC method described herein.
Figure 10:
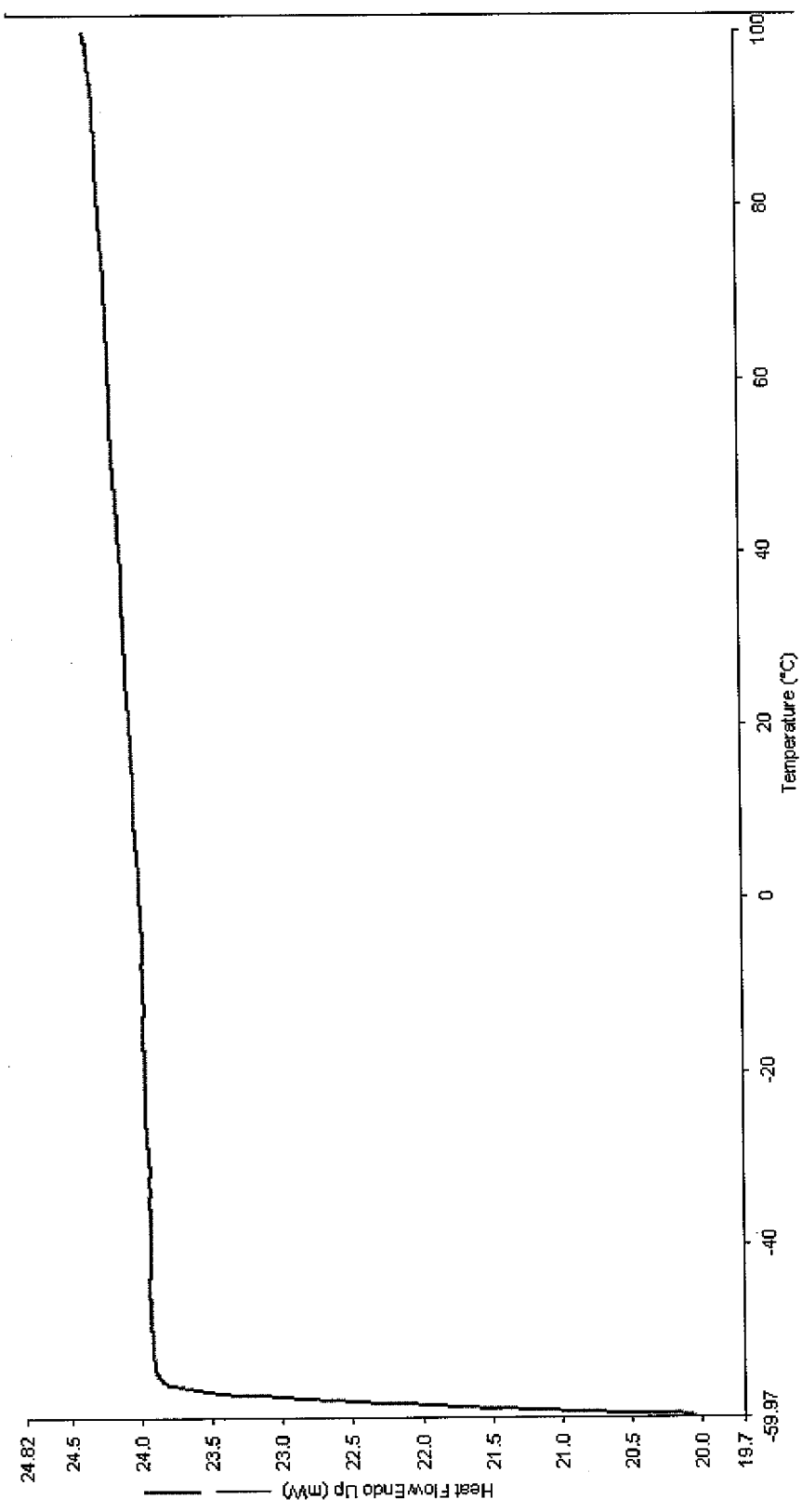
FIG. 10 provides a DSC of PAO produced using 1-octene according to Experiment 8—Run 12. The DSC indicates that there is no discernable crystallization according to the DSC method described herein.
Figure 11:
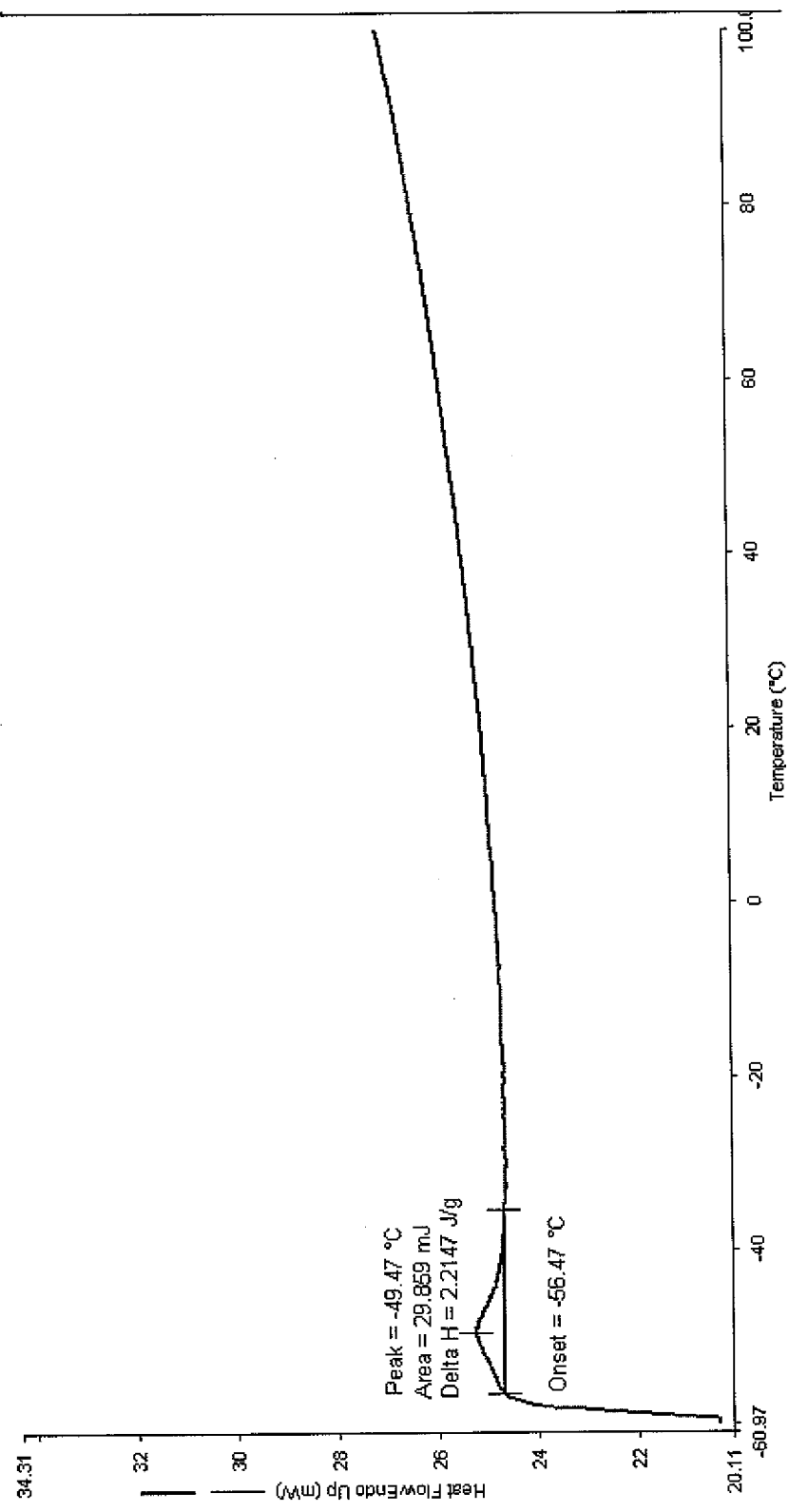
FIG. 11 provides a DSC of a commercial PAO 100. The DSC indicates that there is a discernable crystallization according to the DSC method described herein.

FIG. 4 illustrates the effect of the metallocene of the catalyst system on the dynamic viscosity of the PAOs produced using the catalyst systems and/or methods of this disclosure. Thus, FIG. 4 plots the dynamic viscosity (cP) versus temperature (° C.) of a series of PAOs having similar 100° C. kinematic viscosities using different metallocene catalyst systems, and compares this dynamic viscosity behavior to that of a commercially available 40 cSt polyalphaolefin. The FIG. 4 samples are as follows: A, Example 8—Run 5; B, Example 8—Run 6; C, Example 8—Run 7; D, commercially available PAO 40; E, PAO Blend B-2. Refer to Tables 6 and 7 for sample preparation and properties. Similarly, FIG. 5 plots the dynamic viscosity (cP) versus temperature (° C.) of a series of PAOs having similar 100° C. kinematic viscosities prepared using different metallocene catalyst systems, and compares this dynamic viscosity behavior to that of a commercially available PAO 100 cSt polyalphaolefin. The FIG. 5 samples are as follows: A, Example 8—Run 10; B, Example 8—Run 11; C, Example 8—Run 12; D, commercially available PAO 100. Refer to Tables 6 and 7 for sample preparation and properties.

EXAMPLE 10

Polyalphaolefins (PAOs) Produced from 1-Hexene and/or Dodecene

Olefin oligomers produced from 1-hexene and 1-docedene polyalphaolefins (PAOs) were similarly prepared according to the general procedures outlined in Examples 8 and 9. Selected reaction conditions and homooligomer characterizations are provided in Table 8.

TABLE 8

1-Hexene and 1-docedene olefin oligomers preparation and properties (unhydrogenated).

| | Run No. | | |
|---|---|---|---|
| | 10-A | 10-B | 10-C |
| Olefin | 1-hexene | 1-hexene | 1-dodecene |
| Olefin feed, mL | 500 | 500 | 500 |
| Metallocene | K | G | C |
| Activator | f-SSA | f-SSA | MMAO |
| Activator, g or molar ratio | 2.06 | 0.260 | 1000:1 Al:Zr |
| TIBA, g | 1.7 | 0.220 | 0 |

TABLE 8-continued

1-Hexene and 1-docedene olefin oligomers preparation and properties (unhydrogenated).

| | Run No. | | |
|---|---|---|---|
| | 10-A | 10-B | 10-C |
| Yield (distilled), g | — | 263 | — |
| Temperature, ° C. | 60 | 60 | 25 |
| Temperature, max. ° C. | 65 | — | 40 |
| Conversion to, oligomers, wt % | — | 78% | — |
| 100° C. Kinematic Viscosity, cSt | 228 | 197.4 | 437 |
| 40° C. Kinematic Viscosity, cSt | 4348 | 3545 | 4445 |
| Pour point, ° C. | −42 | −24 | −25 |
| Viscosity index | 170 | 168 | 279 |

EXAMPLE 11

Polyalphaolefins Produced Using a Bis(ethylcyclopentadienyl)zirconium Dichloride/f-SSA Catalyst System An appropriately sized multi-necked flask was fitted with a heating mantle, an overhead stirrer, and a solid addition funnel containing fluorided silica-alumina (f-SSA). The flask is purged with nitrogen and dried thoroughly using a TIBA pre-wash. The olefin was then charged to the flask via cannula. The olefin was heated to the reaction temperature. Once the flask's contents had attained the desired reaction temperature, the alkyl aluminum compound was charged to the reaction flask. After continued stirring for a few minutes, typically 5-30 minutes, bis(ethylcyclopentadienyl)zirconium dichloride dissolved in a minimal amount of olefin reactant was charged to the reactor at the same time as the f-SSA usually resulting in an exotherm. The flask's contents were then allowed to cool to the desired reaction temperature and maintained at the reaction temperature the desired over-night (approximately 16 hours) using a heating mantle. After the reaction time was complete, the aluminum alkyls were neutralized by quenching the reaction with a stoichiometric amount of water. The product is filtered, distilled, and hydrogenated according to procedure provided in Example 8. Table 9 provides information regarding the oligomerization runs and the properties of the hydrogenated oligomers. It is noted that the run using the alumoxane MMAO required more metallocene than the oligomerizations which utilized f-SSA as the activator.

TABLE 9

Olefin Oligomerizations utilizing $(EtCp)_2ZrCl_2$.

| | Run 1 | Run 2 | Run 3 | Run 4 | Run 5 | Run 6 | Run 7 |
|---|---|---|---|---|---|---|---|
| Olefin Oligomerization Conditions | | | | | | | |
| mg $(EtCp)_2ZrCl_2$ | 0.75 | 0.75 | 0.75 | 0.75 | 0.75 | 0.75 | 0.75 |
| mg F-SSA | 394 | 394 | 394 | 394 | 394 | 394 | 394 |
| mg Triisobutylaluminum | 220 | 220 | 220 | 220 | 220 | 220 | 220 |
| MMAO Al:Zr ratio | na | na | na | na | na | na | na |
| g C6 feed | 45 | 107 | 201 | — | — | — | — |
| g C14 feed | 313 | 251 | 157 | — | — | — | — |
| g C8 feed | — | — | — | 358 | 358 | 358 | 358 |
| g C10 feed | — | — | — | — | — | — | — |
| g C12 feed | — | — | — | — | — | — | — |
| C14/C6 molar ratio | 3.0 | 1.0 | 0.33 | na | na | na | na |
| Temperature | 70 | 65 | 65 | 70 | 72 | 75 | 80 |
| T max. | 70 | 66 | 66 | 71 | 74 | 76 | 82 |
| Final Reaction Mixture Data | | | | | | | |
| C6 Conv. % | 83.4 | 79.5 | 85.8 | — | — | — | — |
| C14 Conv. % | 68.9 | 65.5 | 77.5 | — | — | — | — |

TABLE 9-continued

Olefin Oligomerizations utilizing (EtCp)₂ZrCl₂.

| | | | | | | | |
|---|---|---|---|---|---|---|---|
| Total Conv. % | 70.6 | 69.7 | 82.1 | 81.4 | 88.9 | 86.8 | 89.5 |
| Rel % dimer | n.d. | n.d. | n.d. | 7.1 | 7.3 | 8.7 | 11.5 |
| Reactivity ratio C14/C6 | 0.83 | 0.83 | 0.9 | — | — | — | — |

Catalyst System Productivity Data

| | | | | | | | |
|---|---|---|---|---|---|---|---|
| Productivity (g oligomer/g metallocene) | 337,000 | 333,000 | 392,000 | 38,900 | 424,000 | 414,000 | 427,000 |
| Productivity (g oligomer/mmol metallocene) | 117,000 | 116,000 | 137,000 | 135,000 | 147,000 | 144,000 | 149,000 |

Hydrogenated Oligomer Properties

| | | | | | | | |
|---|---|---|---|---|---|---|---|
| 100° C. Kinematic Viscosity (cSt) | 84.0 | 115.0 | 153 | 146 | 130 | 104 | 61.2 |
| 40° C. Kinematic Viscosity (cSt) | 666 | 1062 | 1894 | 1487 | 1151 | 965 | 512 |
| Pour Pt (° C.) | −10 | −20 | −34 | −42 | −42 | −44 | −47 |
| Viscosity Index | 213 | 210 | 191 | 210 | 222 | 205 | 192 |

| | Run 8 | Run 9 | Run 10 | Run 11 | Run 12 |
|---|---|---|---|---|---|

Olefin Oligomerization Conditions

| | Run 8 | Run 9 | Run 10 | Run 11 | Run 12 |
|---|---|---|---|---|---|
| mg (EtCp)₂ZrCl₂ | 0.75 | 0.75 | 0.75 | 0.75 | 2.0 |
| mg F-SSA | 394 | 394 | 394 | 394 | — |
| mg Triisobutylaluminum | 220 | 220 | 220 | 220 | — |
| MMAO Al:Zr ratio | na | na | na | na | 1000 |
| g C6 feed | — | — | — | — | — |
| g C14 feed | — | — | — | — | — |
| g C8 feed | 358 | 358 | 358 | — | 358 |
| g C10 feed | — | — | — | — | — |
| g C12 feed | — | — | — | 358 | — |
| C14/C6 molar ratio | na | na | na | na | na |
| Temperature | 82 | 85 | 75 | 75 | 80 |
| T max. | 84 | 88 | 75 | 77 | 83 |

Final Reaction Mixture Data

| | Run 8 | Run 9 | Run 10 | Run 11 | Run 12 |
|---|---|---|---|---|---|
| C6 Conv. % | — | — | — | — | — |
| C14 Conv. % | — | — | — | — | — |
| Total Conv. % | 89.6 | 92.0 | 82.5 | 81.3 | 73.0 |
| Rel % dimer | 10.9 | 16.2 | 9.4 | n.d. | 19.2 |
| Reactivity ratio C14/C6 | — | — | — | — | — |

Catalyst System Productivity Data

| | Run 8 | Run 9 | Run 10 | Run 11 | Run 12 |
|---|---|---|---|---|---|
| Productivity (g oligomer/g metallocene) | 428,000 | 439,000 | 394,000 | 388,000 | 131,000 |
| Productivity (g oligomer/mmol metallocene) | 149,000 | 150,000 | 137,000 | 135,000 | 45,500 |

Hydrogenated Oligomer Properties

| | Run 8 | Run 9 | Run 10 | Run 11 | Run 12 |
|---|---|---|---|---|---|
| 100° C. Kinematic Viscosity (cSt) | 64 | 30.1 | 66.8 | 54.3 | 12.3 |
| 40° C. Kinematic Viscosity (cSt) | 556 | 222 | 498 | 365 | 75 |
| Pour Pt (° C.) | −47 | −54 | −50 | −26 | −65 |
| Viscosity Index | 189 | 177 | 211 | 216 | 162 |

EXAMPLE 12

Pilot Plant Method for Preparing a Polyalphaolefin Having a 100° C. Kinematic Viscosity of Approximately 40 cSt Several batches of a 1-octene oligomer which when distilled and hydrogenated would have a 100° C. kinematic viscosity of approximately 40 cSt were prepared utilizing the following procedure. Oligomerization data for each oligomerization reaction batch is presented in Table 10.

Under a dry nitrogen atmosphere, a 1,000-pound sample of dried 1-octene (dried with activated AZ-300 alumina) was charged to a pilot plant batch reactor that had been pre-dried by contacting with tri-isobutyl aluminum (TIBA). The 1-octene sample was heated to temperature 5 to 10° C. lower than the desired reaction temperature, with stirring. The reactor was then charged with a 10% solution of tri-isobutyl aluminum in hexane. This mixture was then stirred for 20 minutes, after which the powdered fluorided silica-alumina (f-SSA) and the $(\eta^5\text{-n-BuCp})_2\text{ZrCl}_2$ (compound H) dissolved in a minimal quantity of 1-octene was simultaneously added to the 1-octene/TIBA mixture. An exotherm was observed, after which the reaction mixture was controlled to the desired reaction temperature for the desired time (typically when the conversion of 1-octene to tetramers or higher oligomers was deemed by gas chromatography to be within a range of about 60%-75%). After this time, the reaction mixture was cooled about 50° C. The reaction mixture was then transferred to a catalyst deactivation tank where the catalyst composition was quenched with water, typically about 4 ounces. This deactivated oligomer mixture was then stirred for at least one hour, as the oligomer mixture was allowed to cool to ambient temperature. The deactivated reaction mixture was then filtered to remove the deactivated catalyst system. Specific reaction information for each oligomerization batch is presented in Table 10.

The deactivated and filtered oligomerization product mixture was then transferred to one or two distillation set-ups and vacuum distilled to remove a majority of the unreacted monomer and dimer overhead. The distillation bottoms were then stored in drums. Table 11 provides information for each distillation of reaction 1-octene oligomerization batch.

TABLE 10

Pilot plant oligomerization data for olefin oligomers of Example 12.

| | Oligomerization Run No. | | | | |
|---|---|---|---|---|---|
| | O-1 | O-2 | O-3 | O-4 | O-5 |
| 1-Octene (lbs) | 1000 | 1000 | 1000 | 1000 | 1000 |
| Triisobutylaluminum (lbs of 10%, by weight, solution) | 9.3 | 9.2 | 9.25 | 9.2 | 9.35 |
| $(\eta^5\text{-n-BuCp})_2\text{ZrCl}_2$ (grams) | 5.8 | 5.8 | 5.8 | 5.8 | 5.8 |
| f-SSA (lbs) | 4.1 | 3.92 | 3.88 | 4.1 | 4.0 |
| Temperature at $(\eta^5\text{-n-BuCp})_2\text{ZrCl}_2$ Addition (° C.) | 101 | 102 | 100 | 99 | 100 |
| Maximum Temperature of Exotherm (° C.) | 111 | 111 | 108 | 110 | 110 |
| Oligomerization Temp (° C.) | 105 | 108 | 108 | 110 | 110 |
| Oligomerization Time (Hours) | 4.75 | 4.5 | 7.2 | 4.0 | 4.7 |
| Total Conversion, Process End (%)† | 74.25 | 74.37 | 73.48 | 72.08 | 69.99 |
| Monomer (%) | 9.46 | 5.87 | 9.32 | 7.25 | 4.36 |
| Dimer (%) | 11.86 | 14.16 | 11.84 | 14.59 | 17.99 |
| Trimer (%) | 4.43 | 5.60 | 5.36 | 6.08 | 7.66 |

†Conversion is the percent of 1-octene converted to tetramer or higher oligomers.

TABLE 11

Distillation Data for the Distillation of the 1-Octene Oligomers Produced in Example 12.

| Distillation Batch No. | D-1a | D-1b | D-2 | D-3a | D-3b | D-4, 5a | D-4, 5b | D-4, 5c | D-4, 5d |
|---|---|---|---|---|---|---|---|---|---|
| Oligomer Source | O-1 | O-1 | O-2 | O-3 | O-3 | O-4 + O-5 | O-4 + O-5 | O-4 + O-5 | O-4 + O-5 |
| Monomer (%) | 0 | 0 | 0 | 0.01 | 0 | 0.50 | 0.61 | 0.35 | 0 |
| Dimer (%) | 0.73 | 0.46 | 0.14 | 0.60 | 1.27 | 0.45 | 0.58 | 0.88 | 0.51 |
| Trimer (%) | 5.04 | 4.34 | 5.75 | 7.29 | 6.36 | 7.26 | 5.16 | 7.05 | 8.55 |
| Distillation Bottoms Wt (lbs.) | 162.6 | 606.8 | 543 | 308.8 | 488.2 | 304.2 | 501.6 | 296.6 | 549.4 |
| Flash Point (° C.) | 257 | 258 | 248 | 234 | 262 | 248 | 261 | — | 261 |
| Fire Point (° C.) | 298 | 299 | 297 | 291 | 294 | 278 | 292 | — | 294 |
| 100° C. Viscosity (cSt) | 44.23 | 44.23 | 37.18 | 34.71 | 36.85 | 30.94 | 34.03 | 32.20 | 32.61 |
| 40° C. Viscosity (cSt) | 381.1 | 380.2 | 307.8 | 279.8 | 304.3 | 243.1 | 277.0 | — | 261.1 |
| Viscosity Index (VI) | 173 | 173 | 170 | 171 | 170 | 169 | 169 | — | 169 |

The distilled oligomers were then hydrogenated by charging various quantities of the distilled oligomer product to a reactor with approximately 60 pounds of the supported nickel catalyst (HTC NI 500 RP, from Johnson Matthey). The oligomers were hydrogenated at about 180° C. and 430 psig to 500 psig of hydrogen to a bromine index of less than 200. The hydrogenated product was then filtered to remove the hydrogenation catalyst and stored in drums. Table 12 provides information regarding the quantity and specific distilled oligomer batches utilized for each hydrogenation run along with properties of the hydrogenated oligomer batch. Chart 1 provides a flowsheet showing the fate of the oligomers throughout oligomerization (O), distillation (D), and hydrogenation (H).

TABLE 12

Hydrogenation data for distilled oligomers D-1a, D-1b, D-2, D-3a, D-3b, D-4, D-5a, D-5b, D-5c, and D-5d of Example 12.

| | Hydrogenation No. | | | |
|---|---|---|---|---|
| | H-1 | H-2 | H-3 | H-4 |
| Distillation Batch Charge to Hydrogenation (lbs.) | D-1a (162.6) D-1b (606.8) D-3b (273.1) | D-2 (422.4) D-3a (308.0) D-3b (213.4) D-4,5d (85.0) | D-2 (116) D-4,5a (299) D-4,5d (456.8) | D-4,5b (496.2) D-4,5c (296.6) |
| Amt of Hydrogenated PAO (lbs.) | 861 | 918.2 | 833.4 | 700 |
| 100° C. Viscosity (cSt) | 42.1 | 36.9 | 33.573 | 34.345 |

CHART 1

Sample fate throughout oligomerization (O), distillation (D), hydrogenation (H), and blending (B).

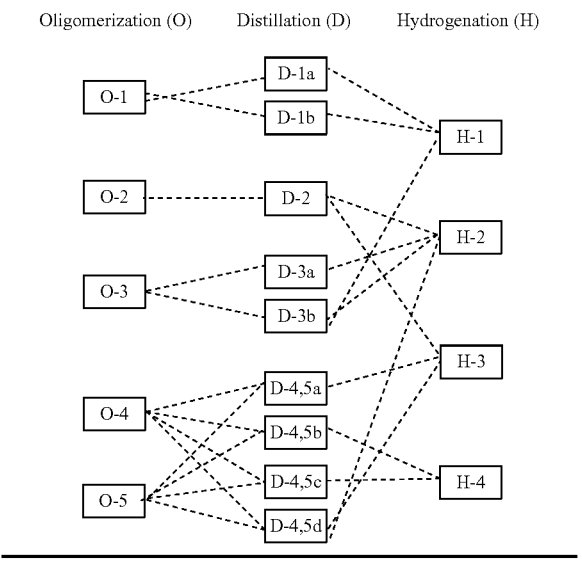

EXAMPLE 13

Pilot Plant Method for Preparing Polyalphaolefin (HVPAO), Nominally 100 cSt

Several batches of a 1-octene oligomer which when distilled and hydrogenated would have a 100° C. kinematic viscosity of approximately 100 cSt were prepared utilizing the following procedure. Oligomerization data for each oligomerization reaction batch is presented in Table 13.

Under a dry nitrogen atmosphere, a 1,000-pound sample of dried 1-octene (dried with activated AZ-300 alumina) was charged to a pilot plant batch reactor that had been pre-dried by contacting with tri-isobutyl aluminum. The 1-octene sample was heated to temperature 5 to 10° C. lower than the desired reaction temperature, with stirring. The reactor was then charged with a 10% solution (in hexane) of tri-isobutyl aluminum. This mixture was then stirred for 20 minutes, after which the powdered fluorided silica-alumina (f-SSA) and the $(\eta^5\text{-n-BuCp})_2\text{ZrCl}_2$ (compound H), dissolved in a minimal quantity 1-octene, of was added to the 1-octene-TIBA mixture. An exotherm was observed, after which the reaction mixture was then controlled at the desired reaction temperature for the desired reaction time (typically, when the conversion of 1-octene to tetramers or higher oligomers was deemed by gas chromatography to be within a range of about 60%-75%). After this time, the reaction mixture was cooled about 50° C. The reaction mixture was then transferred to a catalyst deactivation tank where the catalyst composition was quenched with water, typically about 4 ounces. This mixture was then stirred for at least one hour as the mixture was allowed to cool to ambient temperature. The deactivated reaction mixture was then filtered to remove the deactivated catalyst system. Specific reaction information for each batch is presented in Table 13.

TABLE 13

Pilot plant oligomerization data for olefin oligomers of Example 13.

| | Oligomerization Run No. | | | | |
|---|---|---|---|---|---|
| | O-6 | O-7 | O-8 | O-9 | O-10 |
| 1-Octene (lbs) | 1000 | 1000 | 1000 | 1000 | 1000 |
| Triisobutylaluminum (lbs of 10%, by weight, solution) | 10.3 | 9.2 | 9.2 | 9.3 | 9.2 |
| $(\eta^5\text{-n-BuCp})_2\text{ZrCl}_2$ (grams) | 5.8 | 5.8 | 5.8 | 5.8 | 5.8 |
| f-SSA (lbs) | 4.06 | 3.84 | 3.88 | 4.02 | 3.52 |
| Temperature at $(\eta^5\text{-n-BuCp})_2\text{ZrCl}_2$ Addition (° C.) | 85 | 81 | 79 | 80 | 81 |
| Maximum Temperature of Exotherm (° C.) | 88 | 89 | 87 | 86 | 86 |
| Oligomerization Temp (° C.) | 88 | 85 | 86 | 85 | 86 |
| Oligomerization Time (Hours) | 4.12 | 7.9 | 8.72 | 5.3 | 7.33 |
| Total Conversion, Process End (%)† | 60.7 | 85.8 | 78.8 | 84.2 | 84.1 |
| Monomer (%) | 27.4 | 6.2 | 10.0 | 8.9 | 7.3 |
| Dimer (%) | 9.3 | 5.8 | 8.6 | 5.0 | 6.4 |
| Trimer (%) | 2.6 | 2.2 | 2.6 | 1.9 | 2.2 |

†Conversion is the percent of 1-octene converted to tetramer or higher oligomers.

The deactivated and filtered oligomerization product mixture was then transferred to one or two distillation set-ups and vacuum distilled to remove a majority of the unreacted monomer and dimer overhead. The distillation bottoms were then stored in drums. Table 14 provides information for each distillation of reaction 1-octene oligomerization batch.

TABLE 14

Distillation Data for the Distillation of the 1-Octene Oligomers Produced in Example 13.

| Distillation Batch No. | D-6 | D-7 | D-8 | D-9 | D-10 | D-11 | D-12 |
|---|---|---|---|---|---|---|---|
| Oligomer Source | O-6 | O-7 | O-8 | O-6, O-7, O-8 | O-9 | O-10 | O-9, O-10 |
| Monomer (%) | 0 | 0 | 0 | 0 | 0 | 0 | 0 |
| Dimer (%) | 0.4 | 0.2 | 0.4 | 0.1 | 0 | 0.8 | 1.5 |
| Trimer (%) | 4.7 | 2.2 | 2.3 | 0.9 | 1.4 | 1.8 | 5.4 |
| Distillation Bottoms Wt (lbs.) | 334.8 | 480.2 | 533.4 | 335.2 | 563.0 | 584.2 | 589.4 |
| Flash Point (° C.) | 266 | 299 | 259 | 291 | 292 | 285 | — |
| Fire Point (° C.) | 317 | 334 | 315 | 332 | 333 | 326 | — |
| 100° C. Viscosity (cSt) | 86.08 | 113.5 | 114.4 | 132.92 | 153.78 | 104.62 | 131.77 |
| 40° C. Viscosity (cSt) | — | 1347.7 | 1066.4 | 1451.8 | 1594.7 | 1509.3 | — |
| Viscosity Index (VI) | — | 205 | 205 | 221 | 215 | 201 | — |

The distilled oligomers were then hydrogenated by charging various quantities of the distilled oligomer product to a reactor with approximately 60 pounds of the supported nickel catalyst (HTC NI 500 RP, from Johnson Matthey). The oligomers were hydrogenated at about 180° C. and 420 psig to 440 psig of hydrogen. The hydrogenated product was then filtered to remove the hydrogenation catalyst and stored in drums. Table 15 provides information regarding the quantity and specific distilled oligomer batches utilized for each hydrogenation run along with properties of the hydrogenated oligomer batch.

TABLE 15

Hydrogenation data for olefin oligomer of Example 13.

| | Hydrogenation No. | | | |
|---|---|---|---|---|
| | H-5 | H-6 | H-7 | H-8 |
| Distillation Batch Charge to Hydrogenation (lbs.) | D-6 (332.2) D-7 (476.2) D-8 (216.6) | D-8 (406.0) D-9 (332.4) D-10 (61.6) | D-10 (499.2) D-11 (353.2) | D-11 (225.0) D-12 (585.4) |
| Amt of Hydrogenated PAO (lbs.) | 882.8 | 900.0 | 852.4 | 810.4 |
| 100° C. Viscosity (cSt) | 115 | 134.9 | 149.5 | 140.4 |
| 40° C. Viscosity (cSt) | 1204 | 1430 | 1618 | 1504 |
| Viscosity Index | 195 | 201 | 204 | 202 |
| Pour Point (° C.) | −42 | — | — | — |
| Flash Point (° C.) | 266 | — | — | — |
| Fire Point (° C.) | 300 | — | — | — |

EXAMPLE 14

Blending Different Viscosity PAOs Produced from 1-Octene

Quantities of the hydrogenated oligomers produced in Examples 12 and 13 were blended to produce PAOs having 100° C. kinematic viscosities of approximately 40 cSt or 100 cSt. Table 16 provides information regarding the identity and quantities of the hydrogenated oligomers (PAOs) blended and the final properties of the blended PAO.

TABLE 16

Blend data for Hydrogenated 1-Octene Oligomers Produced in Example 12

| | Blend No. | |
|---|---|---|
| | B-4 | B-5 |
| Hydrogenated PAO Sources (lbs.) | H-1 (854.2) H-2 (715.8) H-3 (94.8) H-4 (105.6) H-5 (59.2) | B-4 (29.6) H-4 (93) H-5 (817.8) |
| 100° C. Viscosity (cSt) | 40.1 | 100.6 |
| 40° C. Viscosity (cSt) | 342.3 | 1007 |
| Viscosity Index | 169.7 | 193 |

EXAMPLE 15

Pilot Plant Method for Preparing a Polyalphaolefin Having a 100° C. Kinematic Viscosity of Approximately 100 cSt Under a dry nitrogen atmosphere, a 994-pound sample of dried 1-octene (dried with activated AZ-300 alumina) was charged to a pilot plant batch reactor that had been pre-dried by contacting with tri-isobutyl aluminum (TIBA). The 1-octene sample was heated to 70° C., with stirring. The reactor was then charged with 4.4 lbs of a 10% solution of triisobutyl aluminum in hexane (lbs TIBA) and 2.7 lbs of a 12.6% solution of triisobutyl aluminum in hexane. This mixture was then stirred for 5 minutes, after which 717 grams of powdered fluorided silica-alumina (f-SSA) and 1.2 grams of $(\eta^5\text{-ethylCp})_2\text{ZrCl}_2$ (compound P) dissolved in a minimal quantity of 1-octene was simultaneously added to the 1-octene/TIBA mixture. An exotherm was observed, after which the reaction mixture was controlled to 75° C. for 8.33 hours. The reaction mixture was the cooled about 50° C. The reaction mixture was then transferred to a catalyst deactivation tank where the catalyst composition was quenched with water, approximately 4 ounces. This deactivated oligomer mixture was then stirred for at least one hour, as the oligomer mixture was allowed to cool to ambient temperature. The deactivated reaction mixture was then filtered to remove the deactivated catalyst system. GC analysis of the reactor effluent showed it to contain 14.1 weight percent monomer, 7.6 weight percent dimer, 2.3 and weight percent trimer. The conversion of 1-octene to higher oligomer was thus 76% percent.

The deactivated and filtered oligomerization product mixture was then transferred to a distillation set-up and vacuum distilled to remove a majority of the unreacted monomer and dimer overhead. The distillation bottoms were then stored in drums. GC analysis of the hydrogenation reactor effluent indicated that the distilled oligomer contained 0 weight percent monomer, 0.6 weight percent dimer, 3.2 weight percent trimer, and 96.2 weight percent higher oligomers. Further analysis of the distilled oligomer indicated that the distilled oligomer had a 100° C. kinematic viscosity of 97.4 cSt.

The distilled oligomers were then hydrogenated by charging 530.4 lbs of the distilled oligomer product to a reactor with approximately 80 pounds of the supported nickel catalyst (HTC NI 500 RP, from Johnson Matthey). The oligomers were hydrogenated at about 180° C. and 440 psig of hydrogen. The hydrogenated product was then filtered to remove the hydrogenation catalyst and stored in drums. Analysis of the distilled oligomer indicated that the distilled oligomer had a 100° C. kinematic viscosity of 105.3 cSt, a 40° C. kinematic viscosity of 1066 cSt, and a viscosity index of 194.

EXAMPLE 16

Control of PAO Viscosity and Pour Point with Oligomerization Temperature for 1-Octene Homooligomers (PAOs)

1-Octene homooligomers (PAOs) were prepared according to the general procedure of Examples 8 or 9, using metallocene L (shown below) in combination with fluorided silica-alumina (f-SSA), using different reaction temperatures for each run. The results of these runs are shown in Table 17.

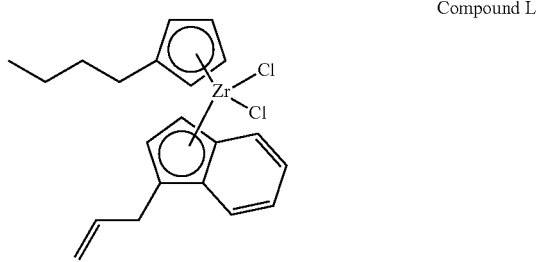

Compound L

Each oligomerization run was conducted using 360 g of 1-octene, 12.6 mg of metallocene compound F, 850 mg of TIBAL (triisobutyl aluminum), 1.03 g solid f-SSA, and a 16-hour run time. By using the same metallocene-activator—support catalyst system and varying only the oligomerization temperature, a remarkable range of PAO products was produced, Table 18. These batch runs demonstrate that temperature alone can be used to control the product viscosities of a PAO with this metallocene/SSA catalyst system and method, and that it is possible to produce an oligomer distribution which when hydrogenated can be provide 100 cSt and/or 40 cSt PAO's without blending. As illustrated in Table 17, product pour points less than those of commercially available PAO 40 and PAO 100.

TABLE 17

Oligomerization and oligomer data for polyalphaolefins (PAOs) of 1-octene, using the same metallocene and activator, at various temperatures.

| Run No. | 1 | 2 | 3 | 4 | Commercially Available 100 | Commercially Available 40 |
|---|---|---|---|---|---|---|
| Oligomerization Temperature | 80° C. | 90° C. | 100° C. | 110° C. | — | — |
| 100° C. Viscosity, cSt | 172 | 93 | 37 | 10 | 100 | 39 |
| 40° C. Viscosity, cSt | 1773 | 873 | 277 | 150 | 1240 | 396 |
| Viscosity Index (VI) | 217 | 197 | 175 | 193 | 170 | 147 |
| Pour point (° C.) | −42 | −42 | −57 | −76 | −30 | −36 |
| Conversion to Oligomers (%) | 88 | 77 | 98 | 98 | n.a. | n.a. |

EXAMPLE 17

Other Metallocene Catalyst Systems for Inventive Polyalphaolefins (PAOs)

Some additional representative, non-limiting examples of specific metallocene-based catalyst systems are illustrated in Table 18, as representative of this disclosure. These representative combinations can be used according to the examples and generally according to this disclosure, and are provided as non-limiting combinations.

TABLE 18

Examples of specific metallocene-based catalyst systems for preparing the inventive PAOs.

| Example Number | Metallocene | Solid Oxide Activator | Co-Catalyst and/or Aluminum Akyl[4] |
|---|---|---|---|
| 17-B | 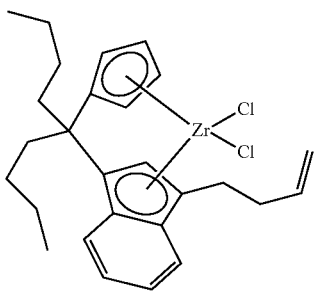 | fluorided silica-alumina (f-SSA), chlorided alumina, or sulfated alumina | TIBA, TEA, TMA, MAO, MMAO, or TBA |
| 17-D | 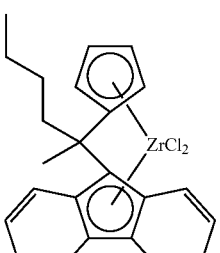 | fluorided silica-alumina (f-SSA), chlorided alumina, or sulfated alumina | TIBA, TEA, TMA, MAO, MMAO, or TBA |

TABLE 18-continued

Examples of specific metallocene-based catalyst systems for preparing the inventive PAOs.

| Example Number | Metallocene | Solid Oxide Activator | Co-Catalyst and/or Aluminum Akyl[4] |
|---|---|---|---|
| 17-I | | fluorided silica-alumina (f-SSA), chlorided alumina, or sulfated alumina | TIBA, TEA, TMA, MAO, MMAO, or TBA |
| 17-J | | fluorided silica-alumina (f-SSA), chlorided alumina, or sulfated alumina | TIBA, TEA, TMA, MAO, MMAO, or TBA |
| 17-L | | fluorided silica-alumina (f-SSA), chlorided alumina, or sulfated alumina | TIBA, TEA, TMA, MAO, MMAO, or TBA |
| 17-M | | fluorided silica-alumina (f-SSA), chlorided alumina, or sulfated alumina | TIBA, TEA, TMA, MAO, MMAO, or TBA |
| 17-N | | fluorided silica-alumina (f-SSA), chlorided alumina, or sulfated alumina | TIBA, TEA, TMA, MAO, MMAO, or TBA |
| 17-O | | fluorided silica-alumina (f-SSA), chlorided alumina, or sulfated alumina | TIBA, TEA, TMA, MAO, MMAO, or TBA |

TABLE 18-continued

Examples of specific metallocene-based catalyst systems for preparing the inventive PAOs.

| Example Number | Metallocene | Solid Oxide Activator | Co-Catalyst and/or Aluminum Akyl[A] |
|---|---|---|---|
| 17-P | | fluorided silica-alumina (f-SSA), chlorided alumina, or sulfated alumina | TIBA, TEA, TMA, MAO, MMAO, or TBA |
| 17-U | | fluorided silica-alumina (f-SSA), chlorided alumina, or sulfated alumina | TIBA, TEA, TMA, MAO, MMAO, or TBA |
| 17-V | | fluorided silica-alumina (f-SSA), chlorided alumina, or sulfated alumina | TIBA, TEA, TMA, MAO, MMAO, or TBA |
| 17-W | | fluorided silica-alumina (f-SSA), chlorided alumina, or sulfated alumina | TIBA, TEA, TMA, MAO, MMAO, or TBA |
| 17-X | | fluorided silica-alumina (f-SSA), chlorided alumina, or sulfated alumina | TIBA, TEA, TMA, MAO, MMAO, or TBA |
| 17-Y | | fluorided silica-alumina (f-SSA), chlorided alumina, or sulfated alumina | TIBA, TEA, TMA, MAO, MMAO, or TBA |

[A]Abbreviations: TIBA, triisobutyl aluminum; TEA, triethyl aluminum; TMA, trimethyl aluminum; MAO, methylaluminoxane; MMAO, isobutyl-modified methylaluminoxane; TBA, tri-n-butyl aluminum

What is claimed:

1. A composition comprising a polyalphaolefin, the polyalphaolefin being produced from a $C_6$ to $C_{16}$ normal alpha olefin comprising at least 82.5 weight percent of a $C_8$ normal alpha olefin, the polyalphaolefin comprising:
   a) less than 1 weight % saturated alpha olefin monomer;
   b) less than 3 weight % saturated dimers; and
   c) greater than 80 weight % saturated higher oligomers
   and having
      i) a 100° C. kinematic viscosity of at least 25 cSt;
      ii) a viscosity index greater than 160;
      iii) a pour point less than −35° C.; and
      iv) no discernable crystallization as determined by differential scanning calorimetry using ASTM D 3418.

2. The composition of claim 1, wherein the polyalphaolefin comprises:
   a) less than 0.5 weight % saturated alpha olefin monomer;
   b) less than 1 weight % saturated dimers; and
   c) at least 88 weight % saturated higher oligomers.

3. The composition of claim 1, wherein the polyalphaolefin has a kinematic viscosity from 25 cSt to 225 cSt.

4. The composition of claim 1, wherein the polyalphaolefin has RPVOT as measured by ASTM D2272 in the presence of 0.5 weight % of an antioxidant of at least 2,000, wherein the antioxidant contains at least 90 weight % N-(dodecylphenyl)naphthalen-1-amine and from greater than 5 weight % to less than 10 weight % N-1-naphthylaniline.

5. The composition of claim 1, wherein the $C_6$ to $C_{16}$ normal alpha olefin comprises at least 90 weight percent of the $C_8$ normal alpha olefin.

6. The composition of claim 5, wherein the polyalphaolefin comprises:
   a) less than 0.5 weight % saturated alpha olefin monomer;
   b) less than 1 weight % saturated dimers; and
   c) at least 88 weight % saturated higher oligomers;
   and wherein
   i) the 100° C. kinematic viscosity ranges from 30 cSt to 50 cSt;
   ii) the viscosity index is greater than 160; and
   iii) the pour point is less than −40° C.

7. The composition of claim 5, wherein the polyalphaolefin comprises:
   a) less than 0.5 weight % saturated alpha olefin monomer;
   b) less than 1 weight % saturated dimers; and
   c) at least 88 weight % saturated higher oligomers; and
   and wherein
   i) the 100° C. kinematic viscosity ranges from 80 cSt to 140 cSt;
   ii) the viscosity index is greater than 160; and
   iii) the pour point is less than −35° C.

8. The composition of claim 5, wherein the polyalphaolefin has a Bernoulli index less than 1.65.

9. A composition comprising a polyalphaolefin, the polyalphaolefin being produced from a $C_6$ to $C_{16}$ normal alpha olefin comprising at least 80 weight percent of a $C_8$ normal alpha olefin, the polyalphaolefin comprising:
   a) less than 1 weight % saturated alpha olefin monomer;
   b) less than 3 weight % saturated dimers; and
   c) greater than 80 weight % saturated higher oligomers
   and having
      i) a 100° C. kinematic viscosity of at least 25 cSt;
      ii) a viscosity index greater than 150; and
      iii) a pour point less than 0° C.; and
      iv. a Bernoulli index less than 1.65.

10. A composition comprising an alpha olefin oligomer product, the alpha olefin oligomer product being produced from a $C_6$ to $C_{16}$ normal alpha olefin comprising at least 90 weight percent of a $C_8$ normal alpha olefin, the alpha olefin oligomer product comprising:
   a) less than 1 weight % residual alpha olefin monomer;
   b) less than 3 weight % dimers; and
   c) greater than 80 weight % higher oligomers;
   and having
   i) a 100° C. kinematic viscosity of at least 25 cSt; and
   ii) a viscosity index greater than 170.

11. The composition of claim 10, wherein the alpha olefin oligomer product comprises:
   a) less than 0.5 weight % residual alpha olefin monomer;
   b) less than 1 weight % dimers; and
   c) greater than 88 weight % higher oligomers; and
   wherein the alpha olefin oligomer product has
   i) a 100° C. kinematic viscosity from 30 cSt to 50 cSt; and
   ii) a viscosity index greater than 170.

12. The composition of claim 10, wherein the alpha olefin oligomer product comprises:
   a) less than 0.5 weight % residual alpha olefin monomer;
   b) less than 1 weight % dimers; and
   c) greater than 80 weight % higher oligomers;
   and having
   i) a 100° C. kinematic viscosity from 80 cSt to 140 cSt; and
   ii) a viscosity index greater than 175.

13. The composition of claim 9, wherein the polyalphaolefin has no discernible crystallization as determined by differential scanning calorimetry using ASTM D 3418.

14. The composition of claim 9, wherein:
   i) the 100° C. kinematic viscosity ranges from 40 cSt to 80 cSt;
   ii) the viscosity index ranges from 170 to 220; and
   iii) the pour point ranges from −30° C. to −90° C.

15. The composition of claim 9, wherein:
   i) the 100° C. kinematic viscosity ranges from 80 cSt to 120 cSt;
   ii) the viscosity index ranges from 170 to 220; and
   iii) the pour point ranges from −30° C. to −90° C.

16. The composition of claim 9, wherein:
   i) the 100° C. kinematic viscosity ranges from 130 cSt to 170 cSt;
   ii) the viscosity index ranges from 170 to 220; and
   iii) the pour point ranges from −30° C. to −90° C.

17. The composition of claim 10, wherein:
   i) the 100° C. kinematic viscosity ranges from 40 cSt to 80 cSt; and
   ii) the viscosity index ranges from 175 to 220.

18. The composition of claim 10, wherein:
   i) the 100° C. kinematic viscosity ranges from 80 cSt to 120 cSt; and
   ii) the viscosity index ranges from 175 to 220.

19. The composition of claim 10, wherein:
   i) the 100° C. kinematic viscosity ranges from 130 cSt to 170 cSt; and
   ii) the viscosity index ranges from 175 to 220.

* * * * *